US010138254B2

(12) United States Patent
Cerezo-Galvez et al.

(10) Patent No.: US 10,138,254 B2
(45) Date of Patent: Nov. 27, 2018

(54) BICYCLIC COMPOUNDS AS PEST CONTROL AGENTS

(71) Applicant: BAYER CROPSCIENCE AKTIENGESELLSCHAFT, Monheim am Rhein (DE)

(72) Inventors: Silvia Cerezo-Galvez, Langenfeld (DE); Alexander Arlt, Köln (DE); Thomas Bretschneider, Lohmar (DE); Reiner Fischer, Monheim (DE); Martin Füßlein, Düsseldorf (DE); Peter Jeschke, Bergisch Gladbach (DE); Arnd Voerste, Köln (DE); Kerstin Ilg, Köln (DE); Olga Malsam, Rösrath (DE); Peter Lösel, Leverkusen (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 15/531,548

(22) PCT Filed: Nov. 30, 2015

(86) PCT No.: PCT/EP2015/078062
§ 371 (c)(1),
(2) Date: May 30, 2017

(87) PCT Pub. No.: WO2016/087373
PCT Pub. Date: Jun. 9, 2016

(65) Prior Publication Data
US 2017/0355714 A1 Dec. 14, 2017

(30) Foreign Application Priority Data

Dec. 2, 2014 (EP) .................................... 14195946

(51) Int. Cl.
*C07D 513/04* (2006.01)
*A01N 43/90* (2006.01)
(52) U.S. Cl.
CPC ........... *C07D 513/04* (2013.01); *A01N 43/90* (2013.01)
(58) Field of Classification Search
CPC .................................................. C07D 513/04
See application file for complete search history.

(56) References Cited

U.S. PATENT DOCUMENTS 4,038,396 A 7/1977 Shen et al.

FOREIGN PATENT DOCUMENTS

| DE | 2330109 A1 | 1/1974 |
| WO | 2012/000896 A2 | 1/2012 |
| WO | 2012/102387 A1 | 8/2012 |
| WO | 2014/104407 A1 | 7/2014 |
| WO | 2014/125651 A1 | 8/2014 |
| WO | 2015/038503 A1 | 3/2015 |

OTHER PUBLICATIONS

STN Chemical Database entry for 2-(3-pyridinyl)-Oxazolo[4,5-b]pyridin-6-amine, RN 1483796-70-8, SR Chemical Catalog Supplier: Aurora Fine Chemicals ED Entered STN: Nov. 29, 2013.*
Online: "http://web.archive.org/web/20070630171813/http://www.enamine.net/index.php?option=com_content&task=view&id=22&menuid=51&PHPSESSID=64a4f248f69d671a413f487bb62c4d90" dated Jun. 30, 2007, accessed Apr. 1, 2015.*
Online "http://web.archive.org/web/20070406205858/http://www.aurorafinechemicals.com/english/order.html" dated Apr. 6, 2007, accessed Feb. 19, 2015.*
Thomas A. Magee "Insecticidal Substituted 2-Butanone O-(Methylaminocarbonyl)oximes" Journal of Agricultural and Food Chemistry 1977, 25, 1376-1382.*
Kurtz, et. al. "Novel Insecticidal Oxathiolane and Oxathiane Oxime Carbamates" Journal of Agricultural and Food Chemistry 1987, 35, 106-114.*
Henrick et. al. "Ovicidal Activity and Its Relation to Chemical Structure for the Two-spotted Spider Mite (*Tetranychus urticae* Koch) in a New Class of Miticides Containing the Cyclopropyl Group" Journal of Agricultural and Food Chemistry 1976, 24, 1023-1029.*
Dekeyser et. al. "Synthesis and Miticidal and Insecticidal Activities of 4-(2-Fluoroethyl)-5,6-dihydro-4H-1,3,4—oxadiazines" Journal of Agricultural and Food Chemistry 1993, 41, 1329-1331.*
Pasteris "Discovery of oxathiapiprolin, a new oomycete fungicide that targets an oxysterol binding protein" Bioorganic & Medicinal Chemistry 24 (2016) 354-361.*
Pozharskii et. al. Heterocycles in Life and Society Wiley, 1997, pp. 1-6.*
Pitt "Heteroaromatic Rings of the Future" J. Med. Chem. 2009, 52, 2952-2963.*
Database Registry Chemical Abstracts Service, Columbus, OH, Nov. 24, 2013, XP002737643.
Garnier, Ethel et al., "New Access to Oxazolopyridines via Hydroxyamidine Derivatives; Application to Quinolines", Synthesis, Sep. 18, 2003, No. 13, pp. 2033-2040.
International Search Report of International Patent Application No. PCT/EP2015/078062 dated Jan. 28, 2016.

* cited by examiner

*Primary Examiner* — David K O'Dell
(74) *Attorney, Agent, or Firm* — McBee Moore Woodward & Vanik IP, LLC

(57) ABSTRACT

The present application relates to novel bicyclic compounds, to their use for controlling animal pests and to processes and intermediates for their preparation.

18 Claims, No Drawings

BICYCLIC COMPOUNDS AS PEST CONTROL AGENTS

CROSS-REFERENCE TO RELATED APPLICATIONS

This application is a National Stage entry of International Application No. PCT/EP2015/078062, filed Nov. 30, 2015, which claims priority to European Patent Application No. 14195946.0, filed Dec. 2, 2014.

BACKGROUND

Field of the Invention

The present application relates to novel bicyclic compounds, to compositions comprising these compounds, to their use for controlling animal pests and to processes and intermediates for their preparation.

Description of Related Art

Recently, bicyclic compounds having insecticidal properties have been disclosed (WO 2015/038503 A1).

WO 2012/102387 A1 describes heterocyclic compounds which can be used particularly as insecticides and acaricides.

Synthesis 2003, (13), 2033-2040 reports a new route to oxazolopyridines via hydroxyamidine derivatives.

U.S. Pat. No. 4,038,396 and DE 2 330 109 A1 describe synthesis and use of oxazolopyridines and thiazolopyridines as antiinflammatory, analgesic and antipyretic substances.

Modern crop protection compositions have to meet many demands, for example in relation to extent, persistence and spectrum of their action and possible use. Questions of toxicity and of combinability with other active ingredients or formulation auxiliaries play a role, as does the question of the cost and complexity involved in the synthesis of an active ingredient. In addition, resistances can occur. For all these reasons alone, the search for novel crop protection compositions cannot be considered complete, and there is a constant need for novel compounds having improved properties compared to the known compounds, at least in relation to individual aspects.

SUMMARY

It was an object of the present invention to provide compounds which widen the spectrum of the pesticides under various aspects.

The object, and further objects which are not stated explicitly but can be discerned or derived from the connections discussed herein, are achieved by compounds of the formula (I)

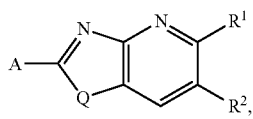

(I)

in which
A is an A radical from the group of (A-b) to (A-f)

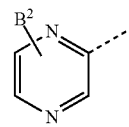

(A-b)

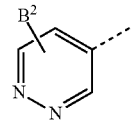

(A-c)

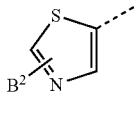

(A-d)

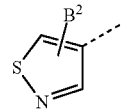

(A-e)

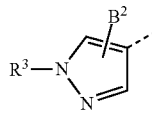

(A-f)

in which the broken line denotes the bond to the carbon atom of the bicyclic system of the formula (I) and $B^2$ is a radical from the group of hydrogen, halogen, cyano, nitro, alkyl, haloalkyl, alkoxy, haloalkoxy and in each case optionally substituted cycloalkyl and cycloalkenyl, Q is oxygen or sulphur, $R^1$ is a radical from the group of hydrogen, alkyl, alkoxy and cyano, $R^2$ a) is a B radical from the group of

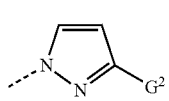

(B-1)

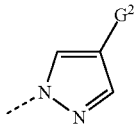

(B-2)

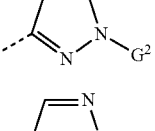

(B-3)

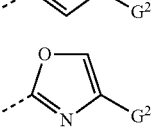

(B-4)

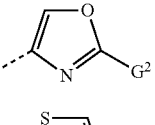

(B-5)

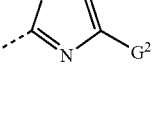

(B-6)

(B-7)

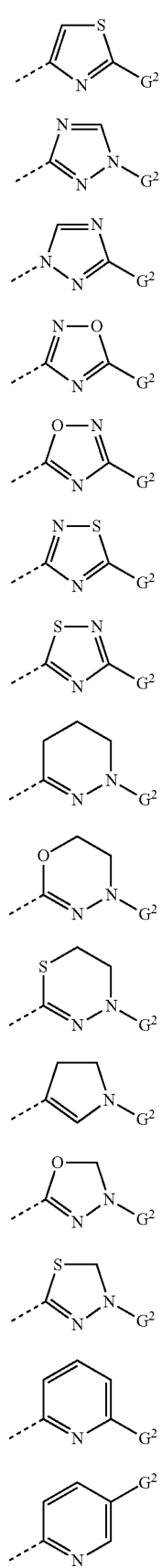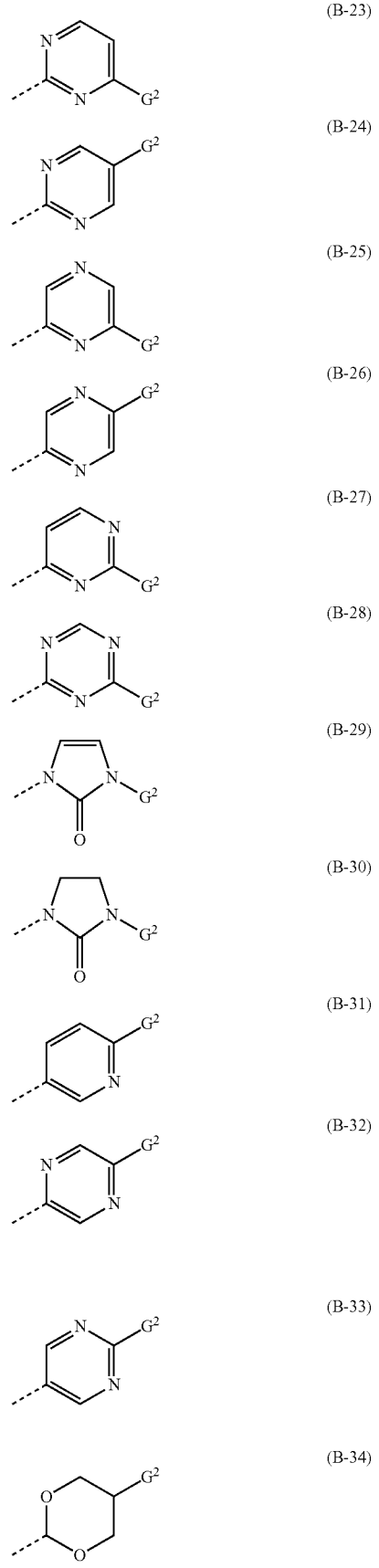

-continued (B-35) 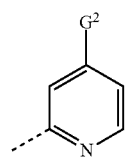

(B-36) 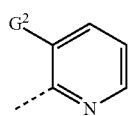

(B-37) 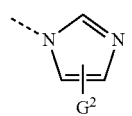

(B-38) 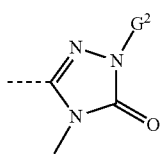

(B-39) 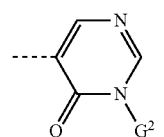

(B-40) 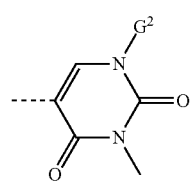

(B-41) 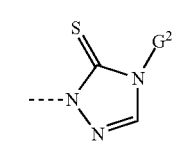

(B-42) 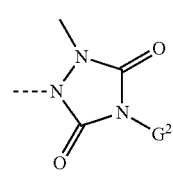

(B-43) 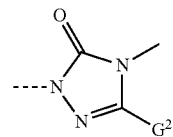

(B-44) 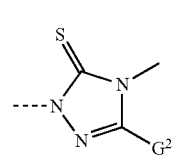

-continued (B-45) 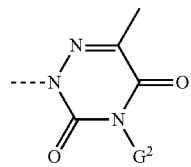

(B-46) 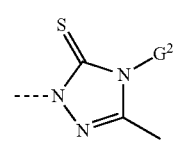

(B-47) 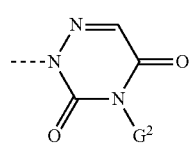

in which the broken line denotes the bond to the carbon atom of the bicyclic system of the formula (I), or $R^2$ b) is a radical from the group of (D-1) to (D-3)

(D-1) 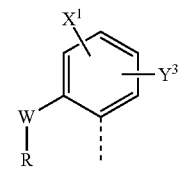

(D-2) 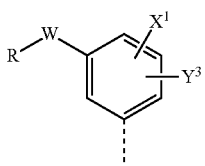

(D-3) 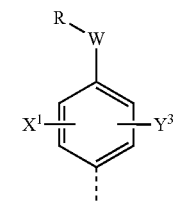

in which the broken line denotes the bond to the carbon atom of the bicyclic system of the formula (I), or $R^2$ c) is a radical of the formula

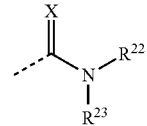

in which the broken line denotes the bond to the carbon atom of the bicyclic system of the formula (I), or $R^2$ d) is a radical of the formula

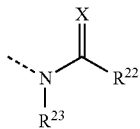

in which the broken line denotes the bond to the carbon atom of the bicyclic system of the formula (I), or $R^2$ e) is an F radical from the group of (F-1) to (F-11)

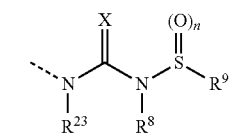 (F-1)

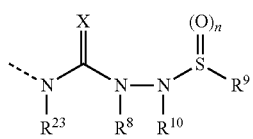 (F-2)

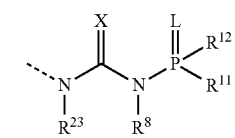 (F-3)

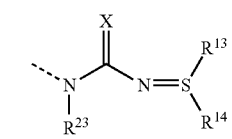 (F-4)

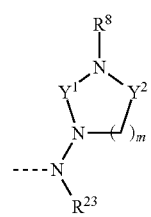 (F-5)

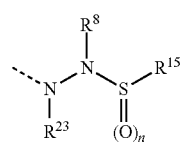 (F-6)

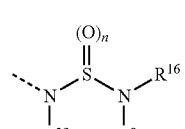 (F-7)

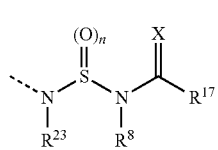 (F-8)

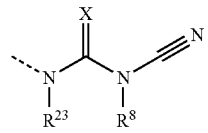 (F-9)

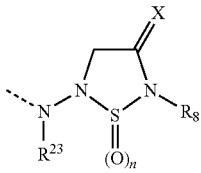 (F-10)

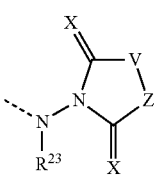 (F-11)

in which the broken line denotes the bond to the carbon atom of the bicyclic system of the formula (I), or $R^2$ f) is a radical of the formula

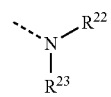

in which the broken line denotes the bond to the carbon atom of the bicyclic system of the formula (I), or $R^2$ g) is optionally substituted phenyl,
in which
$G^2$ is hydrogen or a radical from the group of halogen, nitro, amino, cyano, alkylamino, haloalkylamino, dialkylamino, alkyl, haloalkyl, saturated or unsaturated cycloalkyl which is optionally substituted and optionally interrupted by one or more heteroatoms, cycloalkylalkyl, alkoxy, haloalkoxy, alkoxyalkyl, halogenated alkoxyalkyl, alkylthioalkyl, alkylsulphinylalkyl, alkylsulphonyl alkyl, bis(alkoxy)alkyl, bis(haloalkoxy)alkyl, alkoxy(alkylsulphanyl)alkyl, alkoxy(alkylsulphinyl)alkyl, alkoxy(alkylsulphonyl)alkyl, bis(alkylsulphanyl)alkyl, bis(haloalkylsulphanyl)alkyl, bis(hydroxyalkylsulphanyl)alkyl, alkoxycarbonyl, alkoxycarbonylalkyl, alpha-hydroxyiminoalkoxycarbonyl alkyl, alpha-alkoxyiminoalkoxycarbonylalkyl, $C(X^2)NR^3R^4$, $NR^6R^7$, alkylthio, alkylsulphinyl, alkylsulphonyl, haloalkylthio, haloalkylsulphinyl, haloalkylsulphonyl, the heterocyclyl radicals dioxanyl, dioxolanyl, dioxepanyl, dioxocanyl, oxathianyl, oxathiolanyl, oxathiepanyl, oxathiocanyl, dithianyl, dithiolanyl, dithiepanyl, dithiocanyl, oxathianyl oxide, oxathiolanyl oxide, oxathiepanyl oxide, oxathiocanyl oxide, oxathianyl dioxide, oxathiolanyl dioxide, oxathiepanyl dioxide, oxathiocanyl dioxide, morpholinyl, triazolinonyl, oxazolinyl, dihydrooxadiazinyl, dihydrodioxazinyl, dihydrooxazolyl, dihydrooxazinyl and pyrazolinonyl (which for their part may in turn be substituted by alkyl, haloalkyl, alkoxy and alkoxyalkyl), phenyl (which for its part may in turn be substituted by halogen, cyano, nitro, alkyl and haloalkyl), the heteroaryl radicals pyridyl, pyridyl N-oxide, pyrimidyl, imidazolyl, pyrazolyl, oxazolyl, thiazolyl, furanyl, thienyl, triazolyl, tetrazolyl, oxadiazolyl, thiadiazolyl, pyrazinyl, triazinyl, tetrazinyl and isoquinolinyl (which for their part may in turn be substituted by halogen, nitro, alkyl, haloalkyl, alkoxy, haloalkoxy, alkoxyalkyl, alkylthio, alkylthioalkyl and cycloalkyl) and the heteroarylalkyl radicals triazolylalkyl, pyridylalkyl, pyrimidylalkyl and oxadiazolylalkyl (which for their part may in turn be substituted by halogen and alkyl), or $G^2$ is a C radical from the group of (C-1) to (C-9)

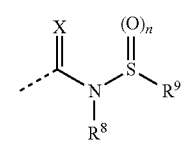
(C-1)

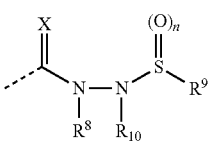
(C-2)

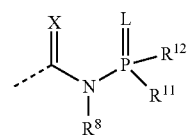
(C-3)

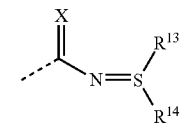
(C-4)

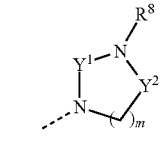
(C-5)

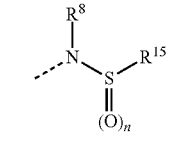
(C-6)

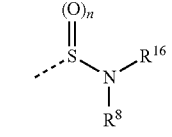
(C-7)

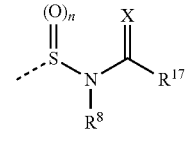
(C-8)

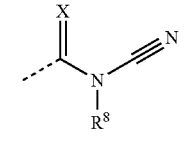
(C-9)

in which the broken line denotes the bond to the B radicals,

X is oxygen or sulphur, $X^1$ is a radical from the group of hydrogen, halogen, cyano, nitro, alkyl, haloalkyl, cycloalkyl, alkoxy and haloalkoxy, $X^2$ is oxygen, sulphur, $NR^5$ or NOH, L is oxygen or sulphur, V—Z is $R^{24}CH$—$CHR^{25}$ or $R^{24}C$=$CR^{25}$, n is 1 or 2, m is 1, 2, 3 or 4, R is $NR^{18}R^{19}$, or is an in each case optionally substituted radical from the group of alkyl, alkenyl, alkynyl, alkoxyalkyl, alkyl-S-alkyl, alkyl-S(O)-alkyl, alkyl-S(O)$_2$-alkyl, $R^{18}$—CO-alkyl, $NR^{18}R^{19}$—CO-alkyl, cycloalkyl, cycloalkenyl, cycloalkylalkyl, cycloalkenylalkyl, heterocyclyl, heterocyclylalkyl, phenyl, phenylalkyl, hetaryl and hetarylalkyl, $R^3$ is hydrogen or alkyl, $R^4$ is a radical from the group of hydrogen, alkyl, haloalkyl, cyanoalkyl, alkynyl, cycloalkyl, cycloalkylalkyl, alkoxyalkyl, alkoxycarbonyl, alkoxycarbonylalkyl, alkylthioalkyl, alkylsulphinylalkyl, alkylsulphonylalkyl, aryl, arylalkyl and hetarylalkyl, $R^5$ is a radical from the group of hydrogen, alkyl, haloalkyl, cyanoalkyl, alkynyl, cycloalkyl, cycloalkylalkyl, alkoxyalkyl, alkoxycarbonyl, alkoxycarbonylalkyl, alkylthioalkyl, aryl, arylalkyl and hetarylalkyl, or $R^3$ and $R^4$ together with the nitrogen atom to which they are bonded form a ring which may contain one or more further heteroatoms from the group of nitrogen, oxygen and sulphur, or $R^3$ and $R^5$ together with the nitrogen atoms to which they are bonded form a ring, $R^6$ is hydrogen or alkyl, $R^7$ is a radical from the group of hydrogen, alkyl, haloalkyl, cyanoalkyl, alkynyl, cycloalkyl, cycloalkylalkyl, alkoxy, haloalkoxy, alkoxyalkyl, alkylthioalkyl, alkylsulphinylalkyl, alkylsulphonylalkyl, alkoxycarbonyl, alkoxycarbonylalkyl, alkylthioalkyl, aryl, arylalkyl and hetarylalkyl, or $R^6$ and $R^7$ together with the nitrogen atom to which they are bonded form a ring which may contain one or more further heteroatoms from the group of nitrogen, oxygen and sulphur, $R^8$ is a radical from the group of hydrogen, alkyl, haloalkyl, cyanoalkyl, alkoxy, haloalkoxy, alkenyl, alkoxyalkyl, in each case optionally halogen-substituted alkylcarbonyl and alkylsulphonyl, optionally halogen-substituted alkoxycarbonyl, and optionally halogen-, alkyl-, alkoxy-, haloalkyl- and cyano-substituted cycloalkylcarbonyl, or a cation, or an optionally alkyl- or arylalkyl-substituted ammonium ion, $R^9$ is a radical from the group of in each case optionally substituted alkyl, alkenyl and alkynyl, in each case optionally substituted cycloalkyl, cycloalkylalkyl and cycloalkenyl, in which the rings may contain at least one heteroatom from the group of sulphur, oxygen (where oxygen atoms must not be directly adjacent to one another) and nitrogen, in each case optionally substituted aryl, heteroaryl, arylalkyl and heteroarylalkyl and an optionally substituted amino group, $R^8$ and $R^9$ in the (C-1) and (F-1) radicals, together with the N—S(O)n group to which they are bonded, may also form a saturated or unsaturated and optionally substituted 4- to 8-membered ring which may contain one or more further heteroatoms from the group of sulphur, oxygen (where oxygen atoms must not be directly adjacent to one another) and nitrogen and/or at least one carbonyl group, $R^{10}$ is hydrogen or alkyl, $R^8$ and $R^{10}$ in the (C-2) and (F-2) radicals, together with the nitrogen atoms to which they are bonded, may also be a saturated or unsaturated and optionally substituted 4- to 8-membered ring which may contain at least one further heteroatom from the group of sulphur, oxygen (where oxygen atoms must not be directly adjacent to one another) and nitrogen and/or at least one carbonyl group, $R^9$ and $R^{10}$ in the (C-2) and (F-2) radicals, together with the N—S(O)n group to which they are bonded, may also form a saturated or unsaturated and optionally substituted 4- to 8-membered ring which may contain one or more further heteroatoms from the group of sulphur, oxygen (where oxygen atoms must not be directly adjacent to one another) and nitrogen and/or at least one carbonyl group, $R^{11}$ is an in each case optionally substituted radical from the group of alkyl, alkenyl, alkynyl, alkoxy, alkenyloxy, alkynyloxy, cycloalkyl, cycloalkyloxy, cycloalkenyloxy, cycloalkylalkoxy, alkylthio, alkenylthio, phenoxy, phenylthio, benzyloxy, benzylthio, heteroaryloxy, heteroarylthio, heteroarylalkoxy and heteroarylalkylthio, $R^{12}$ is an in each case optionally substituted radical from the group of alkyl, alkenyl, alkynyl, alkoxy, alkenyloxy, alkynyloxy, cycloalkyl, cycloalkyloxy, cycloalkenyloxy, cycloalkylalkoxy, alkylthio, alkenylthio, phenoxy, phenylthio, benzyloxy, benzylthio, heteroaryloxy, heteroarylthio, heteroarylalkoxy and heteroarylalkylthio, $R^{11}$ and $R^{12}$ in the (C-3) and (F-3) radicals, together with the phosphorus atom to which they are bonded, may also form a saturated or unsaturated and optionally substituted 5- to 7-membered ring which may contain one or two heteroatoms from the group of oxygen (where oxygen atoms must not be directly adjacent to one another) and sulphur, $R^{13}$ is an in each case optionally substituted radical from the group of alkyl, alkenyl, alkynyl, phenyl and phenylalkyl, $R^{14}$ is an in each case optionally substituted radical from the group of alkyl, alkenyl, alkynyl, phenyl and phenylalkyl, $R^{15}$ is a radical from the group of in each case optionally substituted alkyl, alkenyl and alkynyl, in each case optionally substituted cycloalkyl, cycloalkylalkyl and cycloalkenyl, in which the rings may contain at least one heteroatom from the group of sulphur, oxygen (where oxygen atoms must not be directly adjacent to one another) and nitrogen, in each case optionally substituted aryl, heteroaryl, arylalkyl and heteroarylalkyl and an optionally substituted amino group, $R^8$ and $R^{15}$ in the (C-6) and (F-6) radicals, together with the N—S(O)n group to which they are bonded, may also form a saturated or unsaturated and optionally substituted 4- to 8-membered ring which may contain one or more further heteroatoms from the group of sulphur, oxygen (where oxygen atoms must not be directly adjacent to one another) and nitrogen and/or at least one carbonyl group, $R^{16}$ is a radical from the group of hydrogen, in each case optionally substituted alkyl, alkoxy, alkenyl and alkynyl, in each case optionally substituted cycloalkyl, cycloalkylalkyl and cycloalkenyl, in which the rings may contain at least one heteroatom from the group of sulphur, oxygen (where oxygen atoms must not be directly adjacent to one another) and nitrogen, in each case optionally substituted aryl, arylalkyl and heteroarylalkyl and an optionally substituted amino group, $R^8$ and $R^{16}$ in the (C-7) and (F-7) radicals, together with the nitrogen atom to which they are bonded, may also form a saturated or unsaturated and optionally substituted 4- to 8-membered ring which may contain one or more further heteroatoms from the group of sulphur, oxygen (where oxygen atoms must not be directly adjacent to one another) and nitrogen and/or at least one carbonyl group, $R^{17}$ is a radical from the group of in each case optionally substituted alkyl, alkoxy, alkenyl and alkynyl, in each case optionally substituted cycloalkyl, cycloalkylalkyl and cycloalkenyl, in which the rings may contain at least one heteroatom from the group of sulphur, oxygen (where oxygen atoms must not be directly adjacent to one another) and nitrogen, in each case optionally substituted aryl, heteroaryl, arylalkyl and heteroarylalkyl and an optionally substituted amino group, $R^8$ and $R^{17}$ in the (C-8) and (F-8) radicals, together with the N—C(X) group to which they are bonded, may also form a saturated or unsaturated and optionally substituted 4- to 8-membered ring which may contain one or more further heteroatoms from the group of sulphur, oxygen (where oxygen atoms must not be directly adjacent to one another) and nitrogen and/or at least one carbonyl group, $R^{18}$ is a radical from the group of hydrogen, hydroxy, in each case optionally substituted alkyl, alkoxy, alkoxyalkyl, alkylthioalkyl, alkylsulphinylalkyl, alkylsulphonylalkyl, alkylcarbonyl, alkoxycarbonyl, alkenyl and alkynyl, in each case optionally substituted cycloalkyl, cycloalkylalkyl, cycloalkenyl and cycloalkenylalkyl, in which the rings may contain at least one heteroatom from the group of sulphur, oxygen (where oxygen atoms must not be directly adjacent to one another) and nitrogen, in each case optionally substituted aryl, arylalkyl, heteroaryl and heteroarylalkyl and an optionally substituted amino group, $R^{19}$ is a radical from the group of hydrogen, is an alkali metal or alkaline earth metal ion or is an ammonium ion which is optionally mono- to tetrasubstituted by $C_1$-$C_4$-alkyl or is an in each case optionally halogen- or cyano-substituted radical from the group of alkyl, alkoxy, alkoxyalkyl, alkylthioalkyl, alkylsulphinylalkyl and alkylsulphonylalkyl, $Y^1$ and $Y^2$ are independently C=O or $S(O)_2$, $Y^3$ is a radical from the group of hydrogen, halogen, cyano, alkyl, cycloalkyl, haloalkyl, alkoxy, haloalkoxy and $NR^{20}R^{21}$, W is a radical from the group of O, S, SO and $SO_2$, $R^{22}$ is a radical from the group of hydrogen, alkyl, haloalkyl, cyanoalkyl, alkenyl, haloalkenyl, alkynyl, haloalkynyl, alkoxy, haloalkoxy, optionally halogen-substituted alkoxyalkyl, optionally halogen-substituted bis(alkoxy) alkyl, optionally halogen-substituted alkylsulphanylalkyl, optionally halogen-substituted alkylcarbonylalkyl, optionally halogen-substituted alkylsulphinylalkyl, optionally halogen-substituted alkylsulphonylalkyl, dialkylaminosulphanylalkyl, dialkylaminosulphinylalkyl, dialkylaminosulphonylalkyl, optionally halogen-substituted alkoxycarbonyl, optionally halogen-substituted alkoxycarbonylalkyl, optionally halogen-substituted alkynyloxy, optionally halogen-substituted alkynyloxycarbonyl, dialkylaminocarbonyl, N-alkyl-N-cycloalkylaminocarbonyl, dialkylaminocarbonylalkyl, N-alkyl-N-cycloalkylaminocarbonylalkyl, heterocyclylcarbonylalkyl, alkylsulphanyl, haloalkylsulphanyl, alkylsulphinyl, haloalkylsulphinyl, alkylsulphonyl, haloalkylsulphonyl, cycloalkyl optionally substituted by halogen, cyano, nitro, alkyl, cycloalkyl, haloalkyl, alkoxy, haloalkoxy, alkoxycarbonyl, haloalkoxycarbonyl or hetaryl (which for its part may optionally be substituted by alkyl or halogen), cycloalkylcarbonyl optionally substituted by halogen, cyano, nitro, alkyl, haloalkyl, cycloalkyl, alkoxy, haloalkoxy, alkoxycarbonyl, haloalkoxycarbonyl or hetaryl (which for its part may optionally be substituted by alkyl or halogen), cycloalkylalkyl optionally substituted by halogen, cyano, nitro, alkyl, haloalkyl, cycloalkyl, alkoxy, haloalkoxy, alkoxycarbonyl, haloalkoxycarbonyl or hetaryl (which for its part may optionally be substituted by alkyl or halogen), optionally substituted heterocyclyl, heterocyclylalkyl optionally substituted by halogen, cyano (including in the alkyl moiety), nitro, hydroxyl, alkyl, haloalkyl, cycloalkyl (which is optionally substituted), alkoxy, haloalkoxy, alkylthio, haloalkylthio, alkylsulphinyl, alkylsulphonyl, haloalkylsulphinyl, haloalkylsulphonyl, amino, alkylamino, dialkylamino, alkylcarbonylamino, alkoxycarbonylamino, alkoxyalkyl, haloalkoxyalkyl, alkenyl, alkynyl, cycloalkylalkyl, alkylcarbonyl, alkoxycarbonyl or aminocarbonyl, aryl optionally substituted by halogen, cyano, nitro, hydroxyl, amino, alkyl, haloalkyl, cycloalkyl (which is optionally substituted), alkoxy or haloalkoxy, arylalkyl optionally substituted by halogen, cyano (including in the alkyl moiety), nitro, hydroxyl, amino, alkyl, cycloalkyl (which is optionally substituted), haloalkyl, alkoxy or haloalkoxy, hetarylalkyl optionally substituted by halogen, cyano (including in the alkyl moiety), nitro, hydroxyl, alkyl, haloalkyl, cycloalkyl (which is optionally substituted), alkoxy, haloalkoxy, alkylthio, haloalkylthio, alkylsulphinyl, alkylsulphonyl, haloalkylsulphinyl, haloalkylsulphonyl, amino, alkylamino, dialkylamino, alkylcarbonylamino, alkoxycarbonylamino, alkoxyalkyl, haloalkoxyalkyl, alkenyl, alkynyl, cycloalkylalkyl, alkylcarbonyl, alkoxycarbonyl or aminocarbonyl, or $R^{22}$ is a D radical from the group of (D-1) to (D-3)

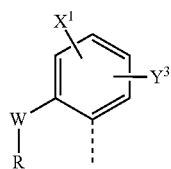

(D-1)

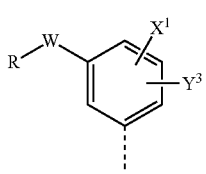

(D-2)

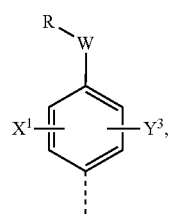

(D-3)

is an E radical from the group of (E-1) to (E-11)

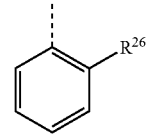

E-1

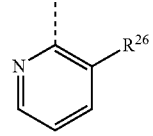

E-2

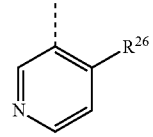

E-3

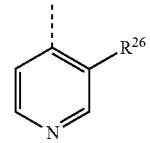

E-4

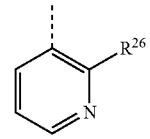

E-5

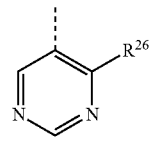

E-6

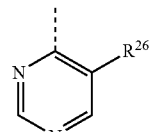

E-7

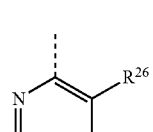

E-8

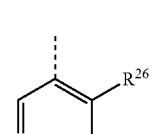

E-9

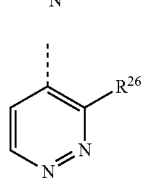

E-10

-continued
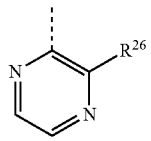
E-11
and (E-18) to (E-51)
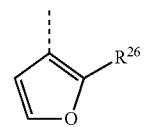
E-18
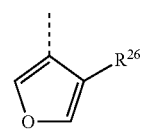
E-19
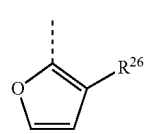
E-20
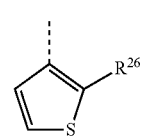
E-21
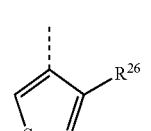
E-22
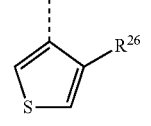
E-23
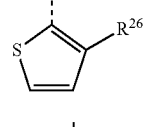
E-24
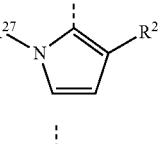
E-25
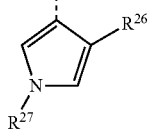
E-26
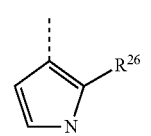
E-27
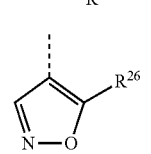
-continued
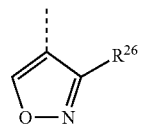
E-28
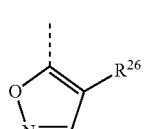
E-29
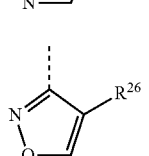
E-30
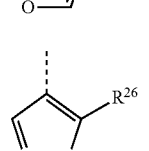
E-31
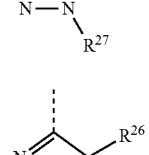
E-32
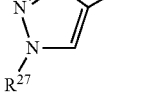
E-33
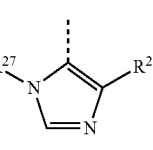
E-34
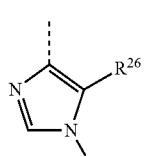
E-35
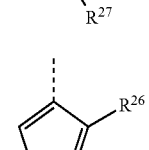
E-36
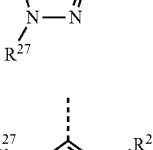
E-37

E-38 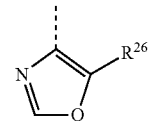

E-39 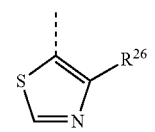

E-40 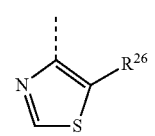

E-41 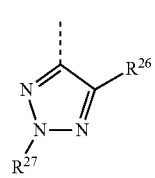

E-42 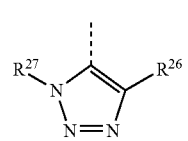

E-43 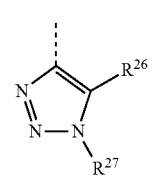

E-44 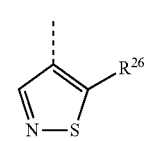

E-45 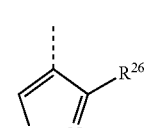

E-46 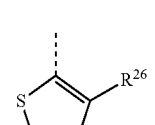

E-47 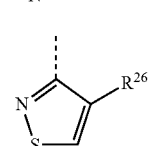

E-48 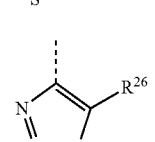

E-49 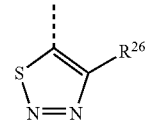

E-50 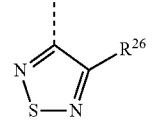

E-51 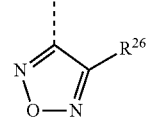

or
in the case $R^2$=d),
$R^{22}$ is also an E radical from the group of E-12 to E-17

E-12 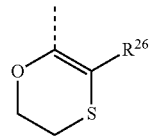

E-13 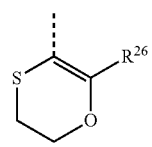

E-14 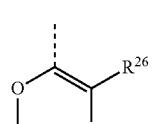

E-15 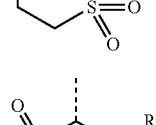

E-16 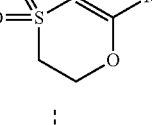

E-17 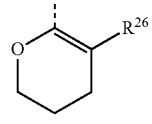

$R^{20}$ is a radical from the group of hydrogen, halogen, cyano, nitro, amino, hydroxy and in each case optionally substituted alkyl, alkenyl, alkynyl, cycloalkyl, cycloalkylalkyl, alkoxy, alkenyloxy, alkynyloxy, cycloalkyloxy, alkylcarbonyloxy, alkenylcarbonyloxy, alkynylcarbonyloxy, cycloalkylcarbonyloxy, alkoxycarbonyloxy, alkylsulphonyloxy, alkylamino, alkenylamino, alkynylamino, cycloalkylamino, alkylthio, haloalkylthio, alkenylthio, alkynylthio, cycloalkylthio, alkylsulphinyl, alkylsulphonyl, alkylcarbonyl, alkoxyiminoalkyl, alkoxycarbonyl, aminocarbonyl, alkylaminocarbonyl, dialkylaminocarbonyl, aminothiocarbonyl, alkylaminosulphonyl, alkylsulphonylamino, alkylcarbonylamino, alkenylcarbonylamino, alkynylcarbonylamino, cycloalkylcarbonylamino, alkoxycarbonylamino, alkylthiocarbonylamino, bicycloalkyl, aryl, aryloxy, heteroaryl and heteroaryloxy, where the substituents are independently of one another selected from halogen, cyano, nitro, hydroxy, amino, alkyl and haloalkyl, $R^{21}$ is a radical from the group of hydrogen, alkyl, cycloalkyl, haloalkyl, alkenyl, alkynyl, cycloalkylalkyl, cyanoalkyl, alkylcarbonyl, alkenylcarbonyl, haloalkylcarbonyl, haloalkenylcarbonyl, alkoxyalkyl, alkoxycarbonyl, alkylsulphonyl and haloalkylsulphonyl, $R^{23}$ is a radical from the group of hydrogen, alkyl, alkenyl, alkynyl, cycloalkyl, cycloalkenyl, alkoxy, alkenyloxy, alkynyloxy, cycloalkyloxy, alkylthioalkyl, alkenylthioalkyl, cyanoalkyl and alkoxyalkyl, or, when $R^2$=c) or f), $R^{22}$ and $R^{23}$ together with the nitrogen atom to which they are bonded form a ring which may contain one or more further heteroatoms from the group of nitrogen, oxygen and sulphur, and $R^{24}$ is hydrogen or an in each case optionally substituted radical from the group of alkyl, alkenyl, alkynyl, phenyl and phenylalkyl and $R^{25}$ is hydrogen or an in each case optionally substituted radical from the group of alkyl, alkenyl, alkynyl, phenyl and phenylalkyl, $R^{27}$ is hydrogen or alkyl and $R^{26}$ is a radical from the group of hydrogen, alkyl, haloalkyl, alkenyl, alkynyl, cycloalkyl, cycloalkylalkyl, alkoxyalkyl, alkylsulphanyl, haloalkylsulphanyl, alkylsulphinyl, haloalkylsulphinyl, alkylsulphonyl, alkylthioalkyl, alkylsulphinylalkyl, alkylsulphonylalkyl and cyano alkyl and compounds of the formula (I)
in which
A is the A radical

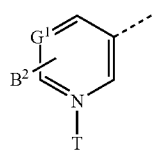
(A-a)

in which the broken line denotes the bond to the carbon atom of the bicyclic system of the formula (I) and $G^1$ is N or C—$B^1$, $B^1$ is a radical from the group of hydrogen, halogen, cyano, nitro, alkyl, haloalkyl, alkoxy, haloalkoxy and in each case optionally substituted cycloalkyl and cycloalkenyl, $B^2$ is a radical from the group of hydrogen, halogen, cyano, nitro, alkyl, haloalkyl, alkoxy, haloalkoxy and in each case optionally substituted cycloalkyl and cycloalkenyl, T is oxygen or an electron pair, Q is oxygen or sulphur, $R^1$ is a radical from the group of hydrogen, alkyl, alkoxy and cyano, $R^2$ a) is a B radical from the group of

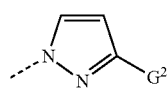
(B-1)

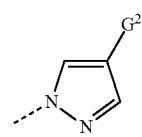
(B-2)

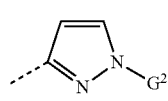
(B-3)

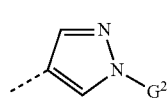
(B-4)

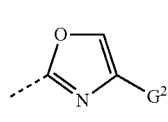
(B-5)

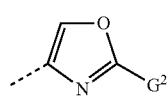
(B-6)

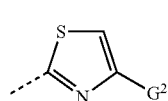
(B-7)

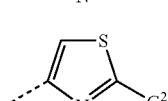
(B-8)

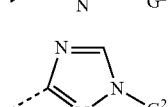
(B-9)

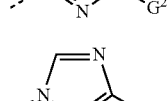
(B-10)

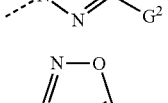
(B-11)

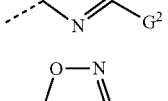
(B-12)

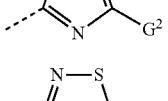
(B-13)

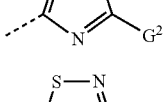
(B-14)

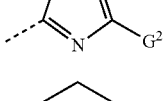
(B-15)

-continued
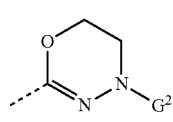
(B-16)
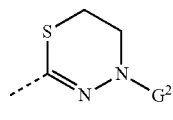
(B-17)
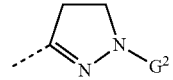
(B-18)
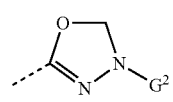
(B-19)
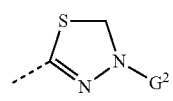
(B-20)
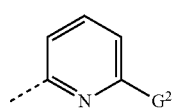
(B-21)
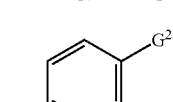
(B-22)
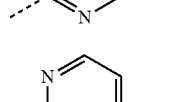
(B-23)
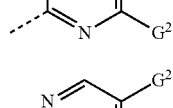
(B-24)
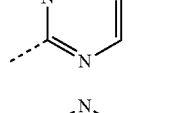
(B-25)
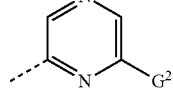
(B-26)
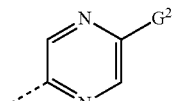
(B-27)
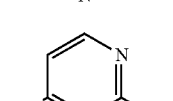
(B-28)
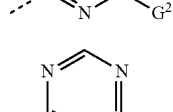
(B-29)
-continued
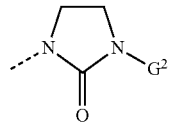
(B-30)
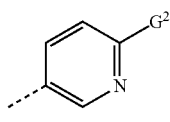
(B-31)
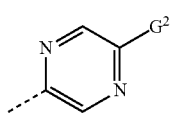
(B-32)
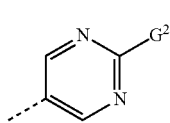
(B-33)
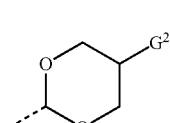
(B-34)
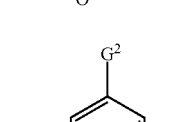
(B-35)
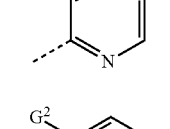
(B-36)
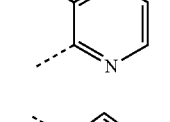
(B-37)
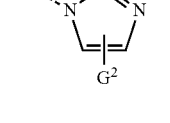
(B-38)
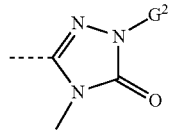
(B-39)
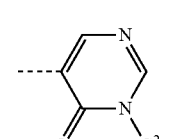
(B-40)

-continued (B-41) 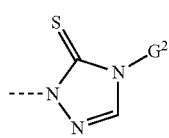

(B-42) 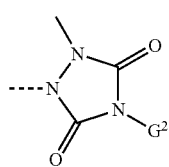

(B-43) 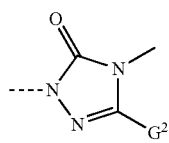

(B-44) 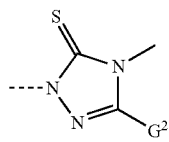

(B-45) 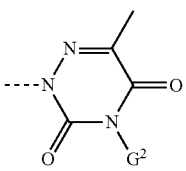

(B-46) 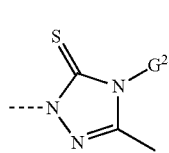

(B-47) 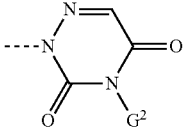

in which the broken line denotes the bond to the carbon atom of the bicyclic system of the formula (I), or R² c) is a radical of the formula

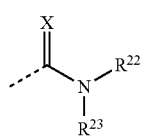

in which the broken line denotes the bond to the carbon atom of the bicyclic system of the formula (I), or R² d) is a radical of the formula

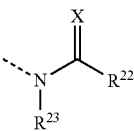

in which the broken line denotes the bond to the carbon atom of the bicyclic system of the formula (I), or R² e) is an F radical from the group of (F-2) 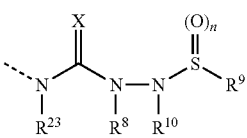

(F-3) 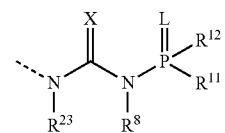

(F-4) 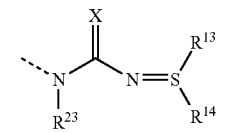

(F-5) 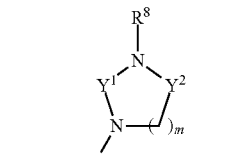

(F-6) 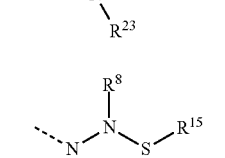

(F-7) 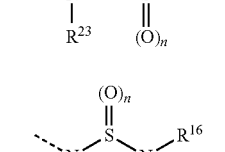

(F-8) 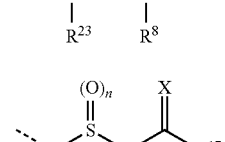

(F-9) 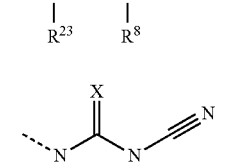

(F-10)

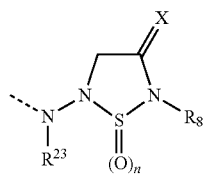

(F-11)

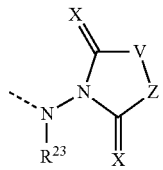

in which the broken line denotes the bond to the carbon atom of the bicyclic system of the formula (I), or $R^2$ f) is a radical of the formula

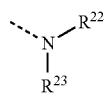

in which the broken line denotes the bond to the carbon atom of the bicyclic system of the formula (I), in which $G^2$ is hydrogen or a radical from the group of halogen, nitro, amino, cyano, alkylamino, haloalkylamino, dialkylamino, alkyl, haloalkyl, saturated or unsaturated cycloalkyl which is optionally substituted and optionally interrupted by one or more heteroatoms, cycloalkylalkyl, alkoxy, haloalkoxy, alkoxyalkyl, halogenated alkoxyalkyl, alkylthioalkyl, alkylsulphinylalkyl, alkylsulphonylalkyl, bis (alkoxy)alkyl, bis(haloalkoxy)alkyl, alkoxy(alkylsulphanyl)alkyl, alkoxy(alkylsulphinyl)alkyl, alkoxy(alkylsulphonyl)alkyl, bis(alkylsulphanyl)alkyl, bis(haloalkylsulphanyl)alkyl, bis(hydroxyalkylsulphanyl) alkyl, alkoxycarbonyl, alkoxycarbonylalkyl, alpha-hydroxyiminoalkoxycarbonylalkyl, alpha-alkoxyiminoalkoxycarbonylalkyl, $C(X^2)NR^3R^4$, $NR^6R^7$, alkylthio, alkylsulphinyl, alkylsulphonyl, haloalkylthio, haloalkylsulphinyl, haloalkylsulphonyl, the heterocyclyl radicals dioxanyl, dioxolanyl, dioxepanyl, dioxocanyl, oxathianyl, oxathiolanyl, oxathiepanyl, oxathiocanyl, dithianyl, dithiolanyl, dithiepanyl, dithiocanyl, oxathianyl oxide, oxathiolanyl oxide, oxathiepanyl oxide, oxathiocanyl oxide, oxathianyl dioxide, oxathiolanyl dioxide, oxathiepanyl dioxide, oxathiocanyl dioxide, morpholinyl, triazolinonyl, oxazolinyl, dihydrooxadiazinyl, dihydrodioxazinyl, dihydrooxazolyl, dihydrooxazinyl and pyrazolinonyl (which for their part may in turn be substituted by alkyl, haloalkyl, alkoxy and alkoxyalkyl), phenyl (which for its part may in turn be substituted by halogen, cyano, nitro, alkyl and haloalkyl), the heteroaryl radicals pyridyl, pyridyl N-oxide, pyrimidyl, imidazolyl, pyrazolyl, oxazolyl, thiazolyl, furanyl, thienyl, triazolyl, tetrazolyl, oxadiazolyl, thiadiazolyl, pyrazinyl, triazinyl, tetrazinyl and isoquinolinyl (which for their part may in turn be substituted by halogen, nitro, alkyl, haloalkyl, alkoxy, haloalkoxy, alkoxyalkyl, alkylthio, alkylthioalkyl and cycloalkyl) and the heteroarylalkyl radicals triazolylalkyl, pyridylalkyl, pyrimidylalkyl and oxadiazolylalkyl (which for their part may in turn be substituted by halogen and alkyl), or $G^2$ is a C radical from the group of (C-1) to (C-9)

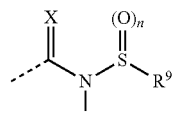
(C-1)

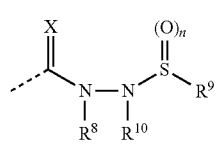
(C-2)

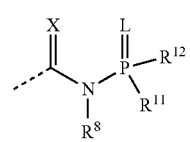
(C-3)

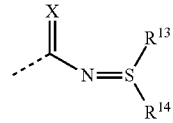
(C-4)

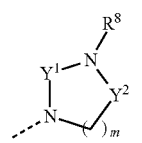
(C-5)

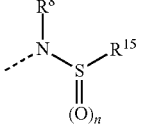
(C-6)

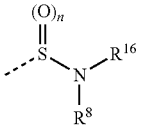
(C-7)

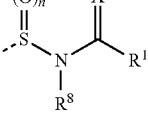
(C-8)

(C-9)

in which the broken line denotes the bond to the B radicals,

X is oxygen or sulphur, $X^1$ is a radical from the group of hydrogen, halogen, cyano, nitro, alkyl, haloalkyl, cycloalkyl, alkoxy and haloalkoxy, $X^2$ is oxygen, sulphur, $NR^5$ or NOH, L is oxygen or sulphur, V—Z is $R^{24}CH$—$CHR^{25}$ or $R^{24}C$=$CR^{25}$, n is 1 or 2, m is 1, 2, 3 or 4, R is $NR^{18}R^{19}$, or is an in each case optionally substituted radical from the group of alkyl, alkenyl, alkynyl, alkoxyalkyl, alkyl-S-alkyl, alkyl-S(O)-alkyl, alkyl-S(O)$_2$-alkyl, $R^{18}$—CO-alkyl, $NR^{18}R^{19}$—CO-alkyl, cycloalkyl, cycloalkenyl, cycloalkylalkyl, cycloalkenylalkyl, heterocyclyl, heterocyclylalkyl, phenyl, phenylalkyl, hetaryl and hetarylalkyl, $R^3$ is hydrogen or alkyl, $R^4$ is a radical from the group of hydrogen, alkyl, haloalkyl, cyanoalkyl, alkynyl, cycloalkyl, cycloalkylalkyl, alkoxyalkyl, alkoxycarbonyl, alkoxycarbonylalkyl, alkylthioalkyl, alkylsulphinylalkyl, alkylsulphonylalkyl, aryl, arylalkyl and hetarylalkyl, $R^5$ is a radical from the group of hydrogen, alkyl, haloalkyl, cyanoalkyl, alkynyl, cycloalkyl, cycloalkylalkyl, alkoxyalkyl, alkoxycarbonyl, alkoxycarbonylalkyl, alkylthioalkyl, aryl, arylalkyl and hetarylalkyl, or $R^3$ and $R^4$ together with the nitrogen atom to which they are bonded form a ring which may contain one or more further heteroatoms from the group of nitrogen, oxygen and sulphur, or $R^3$ and $R^5$ together with the nitrogen atoms to which they are bonded form a ring, $R^6$ is hydrogen or alkyl, $R^7$ is a radical from the group of hydrogen, alkyl, haloalkyl, cyanoalkyl, alkynyl, cycloalkyl, cycloalkylalkyl, alkoxy, haloalkoxy, alkoxyalkyl, alkylthioalkyl, alkylsulphinylalkyl, alkylsulphonylalkyl, alkoxycarbonyl, alkoxycarbonylalkyl, alkylthioalkyl, aryl, arylalkyl and hetarylalkyl, or $R^6$ and $R^7$ together with the nitrogen atom to which they are bonded form a ring which may contain one or more further heteroatoms from the group of nitrogen, oxygen and sulphur, $R^8$ is a radical from the group of hydrogen, alkyl, haloalkyl, cyanoalkyl, alkoxy, haloalkoxy, alkenyl, alkoxyalkyl, in each case optionally halogen-substituted alkylcarbonyl and alkylsulphonyl, optionally halogen-substituted alkoxycarbonyl, and optionally halogen-, alkyl-, alkoxy-, haloalkyl- and cyano-substituted cycloalkylcarbonyl, or a cation, or an optionally alkyl- or arylalkyl-substituted ammonium ion, $R^9$ is a radical from the group of in each case optionally substituted alkyl, alkenyl and alkynyl, in each case optionally substituted cycloalkyl, cycloalkylalkyl and cycloalkenyl, in which the rings may contain at least one heteroatom from the group of sulphur, oxygen (where oxygen atoms must not be directly adjacent to one another) and nitrogen, in each case optionally substituted aryl, heteroaryl, arylalkyl and heteroarylalkyl and an optionally substituted amino group, $R^8$ and $R^9$ in the (C-1) radical, together with the N—S(O)n group to which they are bonded, may also form a saturated or unsaturated and optionally substituted 4- to 8-membered ring which may contain one or more further heteroatoms from the group of sulphur, oxygen (where oxygen atoms must not be directly adjacent to one another) and nitrogen and/or at least one carbonyl group, $R^{10}$ is hydrogen or alkyl, $R^8$ and $R^{10}$ in the (C-2) and (F-2) radicals, together with the nitrogen atoms to which they are bonded, may also be a saturated or unsaturated and optionally substituted 4- to 8-membered ring which may contain at least one further heteroatom from the group of sulphur, oxygen (where oxygen atoms must not be directly adjacent to one another) and nitrogen and/or at least one carbonyl group, $R^9$ and $R^{10}$ in the (C-2) and (F-2) radicals, together with the N—S(O)n group to which they are bonded, may also form a saturated or unsaturated and optionally substituted 4- to 8-membered ring which may contain one or more further heteroatoms from the group of sulphur, oxygen (where oxygen atoms must not be directly adjacent to one another) and nitrogen and/or at least one carbonyl group, $R^{11}$ is an in each case optionally substituted radical from the group of alkyl, alkenyl, alkynyl, alkoxy, alkenyloxy, alkynyloxy, cycloalkyl, cycloalkyloxy, cycloalkenyloxy, cycloalkylalkoxy, alkylthio, alkenylthio, phenoxy, phenylthio, benzyloxy, benzylthio, heteroaryloxy, heteroarylthio, heteroarylalkoxy and heteroarylalkylthio, $R^{12}$ is an in each case optionally substituted radical from the group of alkyl, alkenyl, alkynyl, alkoxy, alkenyloxy, alkynyloxy, cycloalkyl, cycloalkyloxy, cycloalkenyloxy, cycloalkylalkoxy, alkylthio, alkenylthio, phenoxy, phenylthio, benzyloxy, benzylthio, heteroaryloxy, heteroarylthio, heteroarylalkoxy and heteroarylalkylthio, $R^{11}$ and $R^{12}$ in the (C-3) and (F-3) radicals, together with the phosphorus atom to which they are bonded, may also form a saturated or unsaturated and optionally substituted 5- to 7-membered ring which may contain one or two heteroatoms from the group of oxygen (where oxygen atoms must not be directly adjacent to one another) and sulphur, $R^{13}$ is an in each case optionally substituted radical from the group of alkyl, alkenyl, alkynyl, phenyl and phenylalkyl, $R^{14}$ is an in each case optionally substituted radical from the group of alkyl, alkenyl, alkynyl, phenyl and phenylalkyl, $R^{15}$ is a radical from the group of in each case optionally substituted alkyl, alkenyl and alkynyl, in each case optionally substituted cycloalkyl, cycloalkylalkyl and cycloalkenyl, in which the rings may contain at least one heteroatom from the group of sulphur, oxygen (where oxygen atoms must not be directly adjacent to one another) and nitrogen, in each case optionally substituted aryl, heteroaryl, arylalkyl and heteroarylalkyl and an optionally substituted amino group, $R^8$ and $R^{15}$ in the (C-6) and (F-6) radicals, together with the N—S(O)n group to which they are bonded, may also form a saturated or unsaturated and optionally substituted 4- to 8-membered ring which may contain one or more further heteroatoms from the group of sulphur, oxygen (where oxygen atoms must not be directly adjacent to one another) and nitrogen and/or at least one carbonyl group, $R^{16}$ is a radical from the group of hydrogen, in each case optionally substituted alkyl, alkoxy, alkenyl and alkynyl, in each case optionally substituted cycloalkyl, cycloalkylalkyl and cycloalkenyl, in which the rings may contain at least one heteroatom from the group of sulphur, oxygen (where oxygen atoms must not be directly adjacent to one another) and nitrogen, in each case optionally substituted aryl, heteroaryl, arylalkyl and heteroarylalkyl and an optionally substituted amino group, $R^8$ and $R^{16}$ in the (C-7) and (F-7) radicals, together with the nitrogen atom to which they are bonded, may also form a saturated or unsaturated and optionally substituted 4- to 8-membered ring which may contain one or more further heteroatoms from the group of sulphur, oxygen (where oxygen atoms must not be directly adjacent to one another) and nitrogen and/or at least one carbonyl group, $R^{17}$ is a radical from the group of in each case optionally substituted alkyl, alkoxy, alkenyl and alkynyl, in each case optionally substituted cycloalkyl, cycloalkylalkyl and cycloalkenyl, in which the rings may contain at least one heteroatom from the group of sulphur, oxygen (where oxygen atoms must not be directly adjacent to one another) and nitrogen, in each case optionally substituted aryl, heteroaryl, arylalkyl and heteroarylalkyl and an optionally substituted amino group, $R^8$ and $R^{17}$ in the (C-8) and (F-8) radicals, together with the N—C(X) group to which they are bonded, may also form a saturated or unsaturated and optionally substituted 4- to 8-membered ring which may contain one or more further heteroatoms from the group of sulphur, oxygen (where oxygen atoms must not be directly adjacent to one another) and nitrogen and/or at least one carbonyl group, $R^{18}$ is a radical from the group of hydrogen, hydroxy, in each case optionally substituted alkyl, alkoxy, alkoxyalkyl, alkylthioalkyl, alkylsulphinylalkyl, alkylsulphonylalkyl, alkylcarbonyl, alkoxycarbonyl, alkenyl and alkynyl, in each case optionally substituted cycloalkyl, cycloalkylalkyl, cycloalkenyl and cycloalkenylalkyl, in which the rings may contain at least one heteroatom from the group of sulphur, oxygen (where oxygen atoms must not be directly adjacent to one another) and nitrogen, in each case optionally substituted aryl, arylalkyl, heteroaryl and heteroarylalkyl and an optionally substituted amino group, $R^{19}$ is a radical from the group of hydrogen, is an alkali metal or alkaline earth metal ion or is an ammonium ion which is optionally mono- to tetrasubstituted by $C_1$-$C_4$-alkyl or is an in each case optionally halogen- or cyano-substituted radical from the group of alkyl, alkoxy, alkoxyalkyl, alkylthioalkyl, alkylsulphinylalkyl and alkylsulphonylalkyl, $Y^1$ and $Y^2$ are independently C=O or $S(O)_2$, $Y^3$ is a radical from the group of hydrogen, halogen, cyano, alkyl, cycloalkyl, haloalkyl, alkoxy, haloalkoxy and $NR^{20}R^{21}$, W is a radical from the group of S, SO and $SO_2$, and in the case that $R^2$ is f)

$R^{22}$ is a radical from the group of hydrogen, alkyl, haloalkyl, cyanoalkyl, alkenyl, haloalkenyl, alkynyl, haloalkynyl, alkoxy, haloalkoxy, optionally halogen-substituted alkoxyalkyl, optionally halogen-substituted bis(alkoxy) alkyl, optionally halogen-substituted alkylsulphanylalkyl, optionally halogen-substituted alkylcarbonylalkyl, optionally halogen-substituted alkylsulphinylalkyl, optionally halogen-substituted alkylsulphonylalkyl, dialkylaminosulphanylalkyl, dialkylaminosulphinylalkyl, dialkylaminosulphonylalkyl, optionally halogen-substituted alkoxycarbonylalkyl, optionally halogen-substituted alkynyloxy, dialkylaminocarbonylalkyl, N-alkyl-N-cycloalkylaminocarbonylalkyl, heterocyclylcarbonylalkyl, alkylsulphanyl, haloalkylsulphanyl, alkylsulphinyl, haloalkylsulphinyl, alkylsulphonyl, haloalkylsulphonyl, cycloalkyl optionally substituted by halogen, cyano, nitro, alkyl, cycloalkyl, haloalkyl, alkoxy, haloalkoxy, alkoxycarbonyl, haloalkoxycarbonyl or hetaryl (which for its part may optionally be substituted by alkyl or halogen), cycloalkylalkyl optionally substituted by halogen, cyano, nitro, alkyl, haloalkyl, cycloalkyl, alkoxy, haloalkoxy, alkoxycarbonyl, haloalkoxycarbonyl or hetaryl (which for its part may optionally be substituted by alkyl or halogen), optionally substituted heterocyclyl, heterocyclylalkyl optionally substituted by halogen, cyano (including in the alkyl moiety), nitro, hydroxyl, alkyl, haloalkyl, cycloalkyl (which is optionally substituted), alkoxy, haloalkoxy, alkylthio, haloalkylthio, alkylsulphinyl, alkylsulphonyl, haloalkylsulphinyl, haloalkylsulphonyl, amino, alkylamino, dialkylamino, alkylcarbonylamino, alkoxycarbonylamino, alkoxyalkyl, haloalkoxyalkyl, alkenyl, alkynyl, cycloalkylalkyl, alkylcarbonyl, alkoxycarbonyl or aminocarbonyl, aryl optionally substituted by halogen, cyano, nitro, hydroxyl, amino, alkyl, haloalkyl, cycloalkyl (which is optionally substituted), alkoxy or haloalkoxy, arylalkyl optionally substituted by halogen, cyano (including in the alkyl moiety), nitro, hydroxyl, amino, alkyl, cycloalkyl (which is optionally substituted), haloalkyl, alkoxy or haloalkoxy, hetarylalkyl optionally substituted by halogen, cyano (including in the alkyl moiety), nitro, hydroxyl, alkyl, haloalkyl, cycloalkyl (which is optionally substituted), alkoxy, haloalkoxy, alkylthio, haloalkylthio, alkylsulphinyl, alkylsulphonyl, haloalkylsulphinyl, haloalkylsulphonyl, amino, alkylamino, dialkylamino, alkylcarbonylamino, alkoxycarbonylamino, alkoxyalkyl, haloalkoxyalkyl, alkenyl, alkynyl, cycloalkylalkyl, alkylcarbonyl, alkoxycarbonyl or aminocarbonyl, and in the case that $R^2$ is c), d) or f)

$R^{22}$ is a D radical from the group of (D-1) to (D-3)

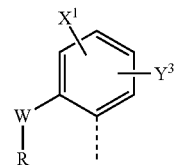
(D-1)

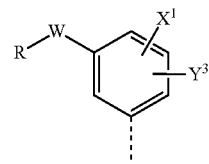
(D-2)

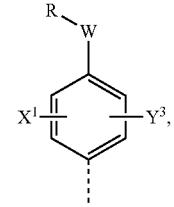
(D-3)

is an E radical from the group of (E-1) to (E-11)

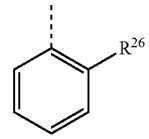
E-1

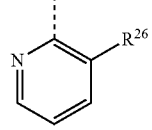
E-2

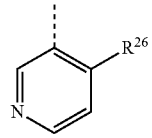
E-3

-continued
E-4
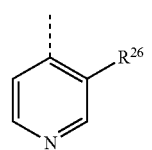
E-5
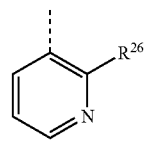
E-6
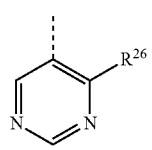
E-7
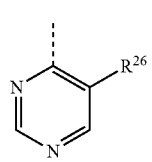
E-8
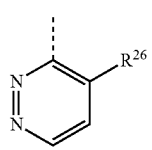
E-9
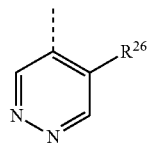
E-10
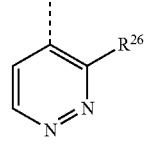
E-11
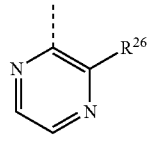
E-18
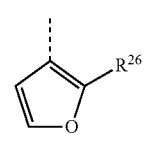
E-19
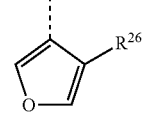
-continued
E-20
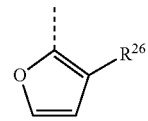
E-21
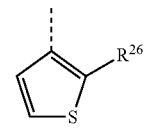
E-22
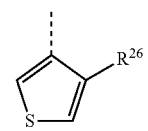
E-23
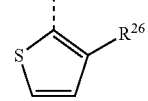
E-24
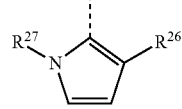
E-25
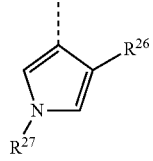
E-26
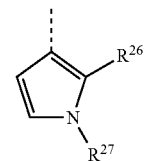
E-27
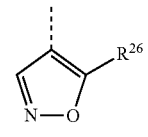
E-28
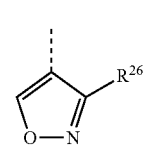
E-29
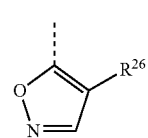
E-30
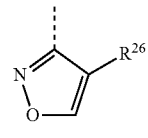
and (E-18) to (E-51)

E-31 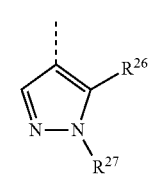
E-32 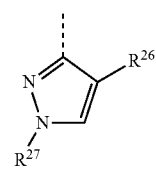
E-33 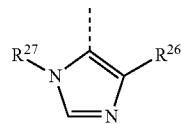
E-34 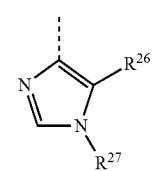
E-35 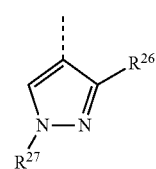
E-36 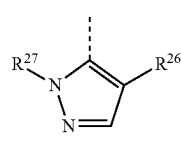
E-37 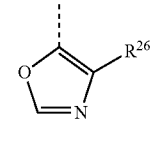
E-38 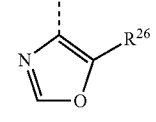
E-39 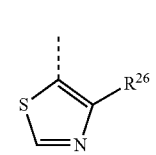
E-40 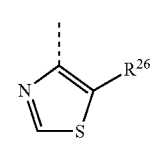
E-41 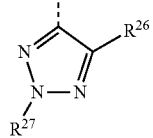
E-42 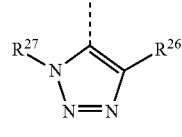
E-43 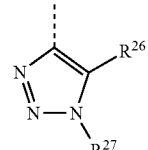
E-44 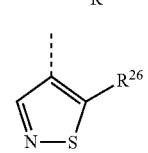
E-45 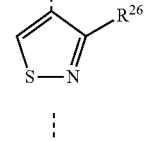
E-46 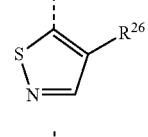
E-47 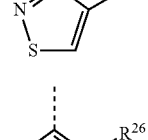
E-48 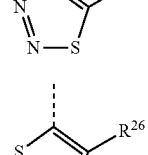
E-49 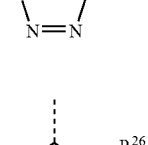
E-50 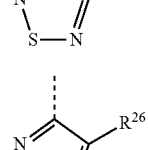
E-51 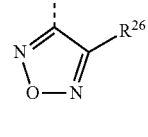

or
in the case R²=d),
R²² is also an E radical from the group of E-12 to E-17

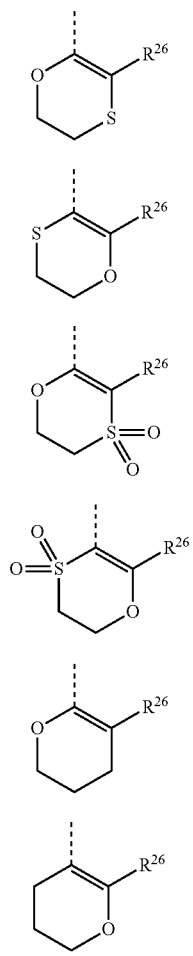

E-12

E-13

E-14

E-15

E-16

E-17

R²⁰ is a radical from the group of hydrogen, halogen, cyano, nitro, amino, hydroxy and in each case optionally substituted alkyl, alkenyl, alkynyl, cycloalkyl, cycloalkylalkyl, alkoxy, alkenyloxy, alkynyloxy, cycloalkyloxy, alkylcarbonyloxy, alkenylcarbonyloxy, alkynylcarbonyloxy, cycloalkylcarbonyloxy, alkoxycarbonyloxy, alkylsulphonyloxy, alkylamino, alkenylamino, alkynylamino, cycloalkylamino, alkylthio, haloalkylthio, alkenylthio, alkynylthio, cycloalkylthio, alkylsulphinyl, alkylsulphonyl, alkylcarbonyl, alkoxyiminoalkyl, alkoxycarbonyl, aminocarbonyl, alkylaminocarbonyl, dialkylaminocarbonyl, aminothiocarbonyl, alkylaminosulphonyl, alkylsulphonylamino, alkylcarbonylamino, alkenylcarbonylamino, alkynylcarbonylamino, cycloalkylcarbonylamino, alkoxycarbonylamino, alkylthiocarbonylamino, bicycloalkyl, aryl, aryloxy, heteroaryl and heteroaryloxy, where the substituents are independently of one another selected from halogen, cyano, nitro, hydroxy, amino, alkyl and haloalkyl, R²¹ is a radical from the group of hydrogen, alkyl, cycloalkyl, haloalkyl, alkenyl, alkynyl, cycloalkylalkyl, cyanoalkyl, alkylcarbonyl, alkenylcarbonyl, haloalkylcarbonyl, haloalkenylcarbonyl, alkoxyalkyl, alkoxycarbonyl, alkylsulphonyl and haloalkylsulphonyl, R²³ is a radical from the group of hydrogen, alkyl, alkenyl, alkynyl, cycloalkyl, cycloalkenyl, alkoxy, alkenyloxy, alkynyloxy, cycloalkyloxy, alkylthioalkyl, alkenylthioalkyl, cyanoalkyl and alkoxyalkyl, or, when R²=f), R²² and R²³ together with the nitrogen atom to which they are bonded form a ring which may contain one or more further heteroatoms from the group of nitrogen, oxygen and sulphur, and R²⁴ is hydrogen or an in each case optionally substituted radical from the group of alkyl, alkenyl, alkynyl, phenyl and phenylalkyl and R²⁵ is hydrogen or an in each case optionally substituted radical from the group of alkyl, alkenyl, alkynyl, phenyl and phenylalkyl, R²⁷ is hydrogen or alkyl and R²⁶ is a radical from the group of hydrogen, alkyl, haloalkyl, alkenyl, alkynyl, cycloalkyl, cycloalkylalkyl, alkoxyalkyl, alkylsulphanyl, haloalkylsulphanyl, alkylsulphinyl, haloalkylsulphinyl, alkylsulphonyl, alkylthioalkyl, alkylsulphinylalkyl, alkylsulphonylalkyl and cyanoalkyl.

It has been additionally found that the compounds of the formula (I) and also the compounds listed in Table 1 which are not covered by the formula (I) have good efficacy as pesticides, for example against arthropods and especially insects, and additionally generally have very good compatibility with plants, especially crop plants, and/or have favourable toxicological and/or favourable environmentally relevant properties.

Area of preference (1): Preference is given to compounds of the formula (I) in which A is an A radical from the group of (A-b) and (A-f)

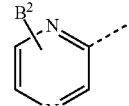

(A-b)

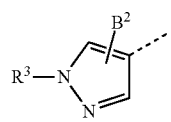

(A-f)

in which the broken line denotes the bond to the carbon atom of the bicyclic system of the formula (I) and B² is a radical from the group of hydrogen, halogen, $C_1$-$C_6$-alkyl and $C_1$-$C_4$-haloalkyl, Q is sulphur, R¹ is a radical from the group of hydrogen, $C_1$-$C_6$-alkyl and $C_1$-$C_6$-alkoxy, R² a) is a B radical from the group of

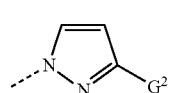

(B-1)

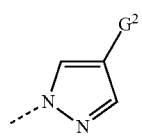

(B-2)

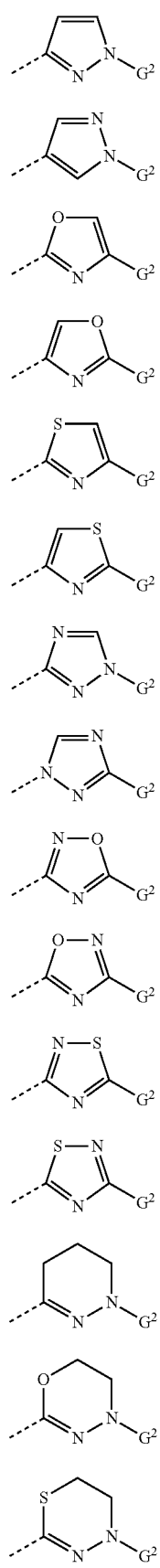
(B-3)
(B-4)
(B-5)
(B-6)
(B-7)
(B-8)
(B-9)
(B-10)
(B-11)
(B-12)
(B-13)
(B-14)
(B-15)
(B-16)
(B-17)
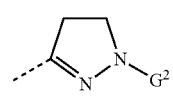 (B-18)
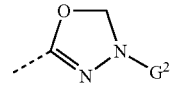 (B-19)
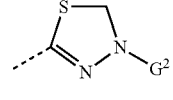 (B-20)
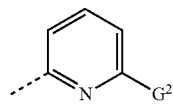 (B-21)
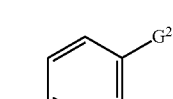 (B-22)
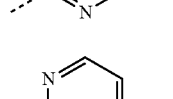 (B-23)
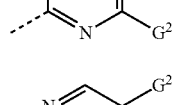 (B-24)
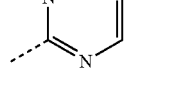 (B-25)
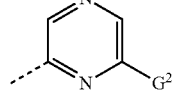 (B-26)
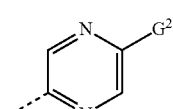 (B-27)
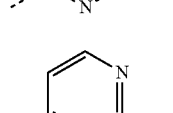 (B-28)
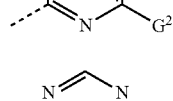 (B-29)
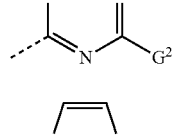 (B-30)

(B-31) 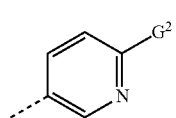
(B-32) 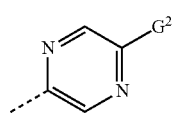
(B-33) 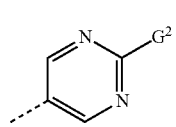
(B-34) 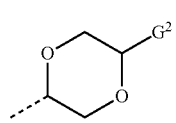
(B-35) 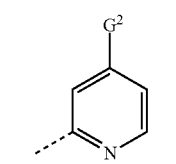
(B-36) 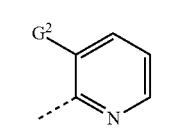
(B-37) 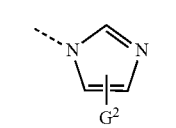
(B-38) 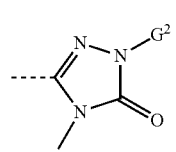
(B-39) 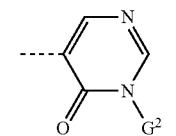
(B-40) 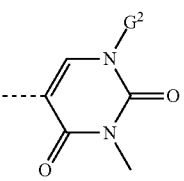
(B-41) 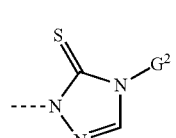
(B-42) 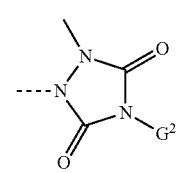
(B-43) 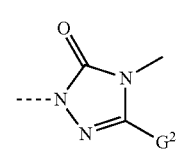
(B-44) 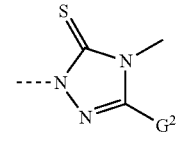
(B-45) 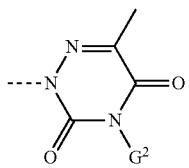
(B-46) 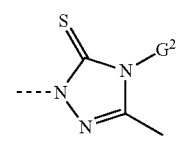
(B-47) 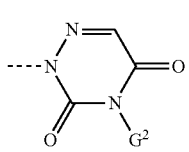
in which the broken line denotes the bond to the carbon atom of the bicyclic system of the formula (I), or
$R^2$ b) is a D radical from the group of (D-1) to (D-3)
(D-1) 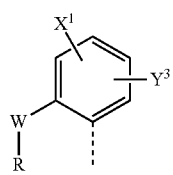
(D-2) 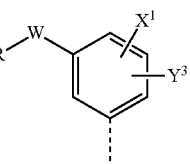

-continued

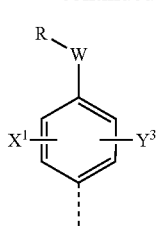 (D-3)

in which the broken line denotes the bond to the carbon atom of the bicyclic system of the formula (I), or
R² c) is a radical of the formula

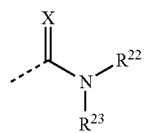

in which the broken line denotes the bond to the carbon atom of the bicyclic system of the formula (I), or
R² d) is a radical of the formula

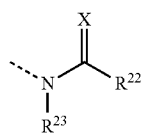

in which the broken line denotes the bond to the carbon atom of the bicyclic system of the formula (I), or
R² e) is an F radical from the group of (F-1), (F-8), (F-10) and (F-11)

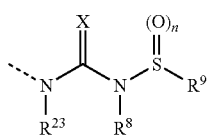 (F-1)

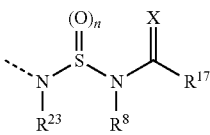 (F-8)

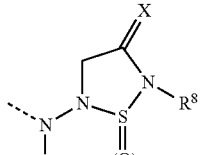 (F-10)

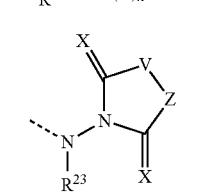 (F-11)

in which the broken line denotes the bond to the carbon atom of the bicyclic system of the formula (I), or
R² f) is a radical of the formula

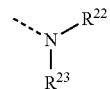

in which the broken line denotes the bond to the carbon atom of the bicyclic system of the formula (I), or
R² g) is a radical of the formula

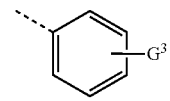

in which the broken line denotes the bond to the carbon atom of the bicyclic system of the formula (I),
in which
$G^2$ is hydrogen or a radical from the group of halogen, nitro, amino, cyano, $C_1$-$C_4$-alkylamino, halo-$C_1$-$C_4$-alkylamino, di-($C_1$-$C_4$-alkyl)amino, $C_1$-$C_4$-alkyl, halo-$C_1$-$C_4$-alkyl, $C_3$-$C_6$-cycloalkyl, $C_3$-$C_6$-cycloalkenyl, $C_3$-$C_6$-cycloalkyl-$C_1$-$C_4$-alkyl, $C_1$-$C_4$-alkoxy, halo-$C_1$-$C_4$-alkoxy, $C_1$-$C_4$-alkoxy-$C_1$-$C_4$-alkyl, halogenated $C_1$-$C_4$-alkoxy-$C_1$-$C_4$-alkyl, bis($C_1$-$C_4$-alkoxy)-$C_1$-$C_4$-alkyl, bis(halo-$C_1$-$C_4$-alkoxy)-$C_1$-$C_4$-alkyl, $C_1$-$C_4$-alkoxy-($C_1$-$C_4$-alkylsulphanyl)-$C_1$-$C_4$-alkyl, $C_1$-$C_4$-alkoxy-($C_1$-$C_4$-alkylsulphinyl)-$C_1$-$C_4$-alkyl, $C_1$-$C_4$-alkoxy-($C_1$-$C_4$-alkylsulphonyl)-$C_1$-$C_4$-alkyl, bis($C_1$-$C_4$-alkylsulphanyl)-$C_1$-$C_4$-alkyl, bis(halo-$C_1$-$C_4$-alkylsulphanyl)-$C_1$-$C_4$-alkyl, bis(hydroxy-$C_1$-$C_4$-alkylsulphanyl)-$C_1$-$C_4$-alkyl, $C_1$-$C_4$-alkoxycarbonyl, $C_1$-$C_4$-alkoxycarbonyl-$C_1$-$C_4$-alkyl, alpha-hydroxyimino-$C_1$-$C_4$-alkoxycarbonyl-$C_1$-$C_4$-alkyl, alpha-$C_1$-$C_4$-alkoxyimino-$C_1$-$C_4$-alkoxycarbonyl-$C_1$-$C_4$-alkyl, $C(X^2)NR^3R^4$, $NR^6R^7$, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, the heterocyclyl radicals dioxanyl, dioxolanyl, dioxepanyl, dioxocanyl, oxathianyl, oxathiolanyl, oxathiepanyl, oxathiocanyl, dithianyl, dithiolanyl, dithiepanyl, dithiocanyl, oxathianyl oxide, oxathiolanyl oxide, oxathiepanyl oxide, oxathiocanyl oxide, oxathianyl dioxide, oxathiolanyl dioxide, oxathiepanyl dioxide, oxathiocanyl dioxide, morpholinyl, triazolinonyl, oxazolinyl, dihydrooxadiazinyl, dihydrodioxazinyl, dihydrooxazolyl, dihydrooxazinyl and pyrazolinonyl (which for their part may in turn be substituted by $C_1$-$C_4$-alkyl, halo-$C_1$-$C_4$-alkyl, $C_1$-$C_4$-alkoxy and $C_1$-$C_4$-alkoxy-$C_1$-$C_4$-alkyl), phenyl (which for its part may in turn be substituted by halogen, cyano, nitro, $C_1$-$C_4$-alkyl and halo-$C_1$-$C_4$-alkyl), the heteroaryl radicals pyridyl, pyridyl N-oxide, pyrimidyl, imidazolyl, pyrazolyl, oxazolyl, thiazolyl, furanyl, thienyl, triazolyl, tetrazolyl, oxadiazolyl, thiadiazolyl, pyrazinyl, triazinyl, tetrazinyl and isoquinolinyl (which for their part may in turn be substituted by halogen, nitro, $C_1$-$C_4$-alkyl, halo-$C_1$-$C_4$-alkyl, $C_1$-$C_4$-alkoxy, halo-$C_1$-$C_4$-alkoxy, $C_1$-$C_4$-alkoxy-$C_1$-$C_4$-alkyl, $C_1$-$C_4$-alkylthio, $C_1$-$C_4$-alkylthio-$C_1$-$C_4$-alkyl and $C_3$-$C_6$-cycloalkyl) and the heteroaryl-$C_1$-$C_4$-alkyl radicals triazolyl-$C_1$-$C_4$-alkyl, pyridyl-$C_1$-$C_4$-alkyl, pyrimidyl-$C_1$-$C_4$-alkyl and oxadiazolyl-$C_1$-$C_4$-alkyl (which for their part may in turn be substituted by halogen and $C_1$-$C_4$-alkyl), or G² is a radical from the group of (C-1) and (C-6) to (C-9)

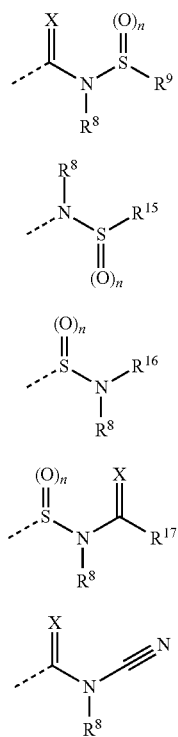

in which the broken line denotes the bond to the radicals (B-1) to (B-37),

G³ is a radical from the group of hydrogen, halogen, alkyl and haloalkyl,

X is oxygen or sulphur,

X¹ is a radical from the group of hydrogen, halogen, cyano, nitro, $C_1$-$C_6$-alkyl, $C_1$-$C_6$-haloalkyl, $C_3$-$C_6$-cycloalkyl, $C_1$-$C_6$-alkoxy and $C_1$-$C_6$-haloalkoxy, X² is oxygen, sulphur, NR⁵ or NOH, V—Z is $R^{24}$CH—CHR²⁵ or $R^{24}$C═CR²⁵, n is 1 or 2, R is NR¹⁸R¹⁹ or is in each case optionally halogen-, oxygen- (leads to C═O) or cyano-substituted $C_1$-$C_6$-alkyl, $C_3$-$C_6$-alkenyl, $C_3$-$C_6$-alkynyl, $C_1$-$C_6$-alkoxy-$C_1$-$C_4$-alkyl, $C_1$-$C_6$-alkyl-S—$C_1$-$C_4$-alkyl, $C_1$-$C_6$-alkyl-S(O)—$C_1$-$C_4$-alkyl, $C_1$-$C_6$-alkyl-S(O)₂—$C_1$-$C_4$-alkyl, is R¹⁸—CO—$C_1$-$C_4$-alkyl, is NR¹⁸R¹⁹—CO—$C_1$-$C_4$-alkyl, is optionally mono- or di-oxygen- (leads to C═O), —$C_1$-$C_4$-alkyl-, —$C_3$-$C_8$-cycloalkyl-, —$C_1$-$C_4$-alkoxy- and —$C_1$-$C_4$-haloalkyl-substituted $C_3$-$C_6$-cycloalkyl, is optionally mono- or di-oxygen- (leads to C═O), —$C_1$-$C_4$-alkyl-, —$C_3$-$C_6$-cycloalkyl-, —$C_1$-$C_4$-alkoxy- and —$C_1$-$C_4$-haloalkyl-substituted $C_3$-$C_8$-cycloalkenyl, is optionally mono- or di-oxygen- (leads to C═O), —$C_1$-$C_4$-alkyl-, —$C_3$-$C_6$-cycloalkyl-, —$C_1$-$C_4$-alkoxy- and —$C_1$-$C_4$-haloalkyl-substituted $C_3$-$C_6$-cycloalkyl-$C_1$-$C_4$-alkyl, is optionally mono- or di-oxygen- (leads to C═O), —$C_1$-$C_4$-alkyl-, —$C_3$-$C_6$-cycloalkyl-, —$C_1$-$C_4$-alkoxy- and —$C_1$-$C_4$-haloalkyl-substituted $C_3$-$C_6$-cycloalkenyl-$C_1$-$C_4$-alkyl, is optionally mono- or di-oxygen- (leads to C═O), —$C_1$-$C_4$-alkyl-, —$C_3$-$C_6$-cycloalkyl-, —$C_1$-$C_4$-alkoxy- and —$C_1$-$C_4$-haloalkyl-substituted heterocyclyl, is optionally mono- or di-oxygen- (leads to C═O), —$C_1$-$C_4$-alkyl-, —$C_3$-$C_6$-cycloalkyl-, —$C_1$-$C_4$-alkoxy- and —$C_1$-$C_4$-haloalkyl-substituted heterocyclyl-$C_1$-$C_4$-alkyl or is in each case optionally mono- to tri-halogen-, -cyano-, —$C_1$-$C_4$-alkyl-, —$C_1$-$C_4$-haloalkyl-, —$C_3$-$C_6$-cycloalkyl-, —$C_1$-$C_4$-alkoxy- or —$C_1$-$C_4$-haloalkoxy-substituted phenyl, phenyl-$C_1$-$C_4$-alkyl, hetaryl and hetaryl-$C_1$-$C_4$-alkyl, R³ is hydrogen or $C_1$-$C_6$-alkyl, R⁴ is a radical from the group of hydrogen, $C_1$-$C_4$-alkyl, halo-$C_1$-$C_4$-alkyl, cyano-$C_1$-$C_4$-alkyl, $C_2$-$C_4$-alkynyl, $C_3$-$C_6$-cycloalkyl, $C_3$-$C_6$-cycloalkyl-$C_1$-$C_4$-alkyl, $C_1$-$C_4$-alkoxy-$C_1$-$C_4$-alkyl, $C_1$-$C_4$-alkoxycarbonyl, $C_1$-$C_4$-alkoxycarbonyl-$C_1$-$C_4$-alkyl, $C_1$-$C_4$-alkylthio-$C_1$-$C_4$-alkyl, aryl, aryl-$C_1$-$C_4$-alkyl and hetaryl-$C_1$-$C_4$-alkyl, R⁵ is a radical from the group of hydrogen, $C_1$-$C_4$-alkyl, halo-$C_1$-$C_4$-alkyl, cyano-$C_1$-$C_4$-alkyl, $C_2$-$C_4$-alkynyl, $C_3$-$C_6$-cycloalkyl, $C_3$-$C_6$-cycloalkyl-$C_1$-$C_4$-alkyl, $C_1$-$C_4$-alkoxy-$C_1$-$C_4$-alkyl, $C_1$-$C_4$-alkoxycarbonyl, $C_1$-$C_4$-alkoxycarbonyl-$C_1$-$C_4$-alkyl, $C_1$-$C_4$-alkylthio-$C_1$-$C_4$-alkyl, aryl, aryl-$C_1$-$C_4$-alkyl and hetaryl-$C_1$-$C_4$-alkyl, or R³ and R⁴ together with the nitrogen atom to which they are bonded form a 4- to 7-membered ring which may contain one or two further heteroatoms from the group of nitrogen, oxygen and sulphur (where oxygen and sulphur atoms must not be directly adjacent to one another), R⁶ is hydrogen or $C_1$-$C_4$-alkyl, R⁷ is a radical from the group of hydrogen, $C_1$-$C_4$-alkyl, halo-$C_1$-$C_4$-alkyl, cyano-$C_1$-$C_4$-alkyl, $C_2$-$C_4$-alkynyl, $C_3$-$C_6$-cycloalkyl, $C_3$-$C_4$-cycloalkyl-$C_1$-$C_4$-alkyl, $C_1$-$C_4$-alkoxy, halo-$C_1$-$C_4$-alkoxy, $C_1$-$C_4$-alkoxy-$C_1$-$C_4$-alkyl, $C_1$-$C_4$-alkoxycarbonyl, $C_1$-$C_4$-alkoxycarbonyl-$C_1$-$C_4$-alkyl, $C_1$-$C_4$-alkylthio-$C_1$-$C_4$-alkyl, aryl, aryl-$C_1$-$C_4$-alkyl or hetaryl-$C_1$-$C_4$-alkyl, or R⁶ and R⁷ together with the nitrogen atom to which they are bonded form a 4- to 7-membered ring which may contain one or two further heteroatoms from the group of nitrogen, oxygen and sulphur (where oxygen and sulphur atoms must not be directly adjacent to one another), R⁸ is a radical from the group of hydrogen, $C_1$-$C_6$-alkyl, $C_1$-$C_6$-haloalkyl, cyano-$C_1$-$C_6$-alkyl, $C_1$-$C_6$-alkoxy, $C_1$-$C_6$-haloalkoxy, $C_2$-$C_6$-alkenyl, $C_1$-$C_6$-alkoxy-$C_1$-$C_6$-alkyl, in each case optionally halogen-substituted $C_1$-$C_6$-alkylcarbonyl and $C_1$-$C_6$-alkylsulphonyl, optionally halogen-substituted $C_1$-$C_6$-alkoxycarbonyl and optionally halogen-, $C_1$-$C_6$-alkyl-, $C_1$-$C_6$-alkoxy-, $C_1$-$C_6$-haloalkyl- and cyano-substituted $C_3$-$C_6$-cycloalkylcarbonyl, or is a cation or an optionally $C_1$-$C_6$-alkyl- or aryl-$C_1$-$C_6$-alkyl-substituted ammonium ion, R⁹ is a radical from the group of in each case optionally halogen-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-haloalkylsulphinyl-, $C_1$-$C_6$-alkylsulphonyl- and $C_1$-$C_6$-haloalkylsulphonyl-substituted $C_1$-$C_6$-alkyl, $C_2$-$C_6$-alkenyl and $C_2$-$C_6$-alkynyl, in each case optionally halogen-, $C_1$-$C_6$-alkyl-, $C_1$-$C_6$-haloalkyl-, $C_1$-$C_6$-alkoxy- or $C_1$-$C_6$-haloalkoxy-substituted $C_3$-$C_6$-cycloalkyl, $C_3$-$C_6$-cycloalkyl-$C_1$-$C_6$-alkyl and $C_3$-$C_6$-cycloalkenyl, in which one ring member may be replaced by a heteroatom from the group of sulphur, oxygen (where oxygen atoms must not be directly adjacent to one another) and nitrogen (and in this case are especially

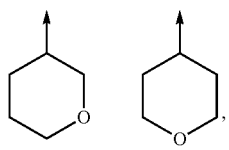

where the arrow in each case denotes the bond to the sulphur atom in the (C-1) radical and in the (F-1) radical), in each case optionally halogen-, cyano- (including in the alkyl moiety), nitro-, $C_1$-$C_6$-alkyl-, $C_1$-$C_6$-haloalkyl-, $C_3$-$C_6$-cycloalkyl-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-haloalkylsulphinyl-, $C_1$-$C_6$-alkylsulphonyl-, $C_1$-$C_6$-haloalkylsulphonyl-, amino-, $C_1$-$C_6$-alkylamino-, di($C_1$-$C_6$-alkyl)amino-, $C_1$-$C_6$-alkylcarbonylamino-, $C_1$-$C_6$-alkoxycarbonylamino-, $C_1$-$C_6$-alkoxy-$C_1$-$C_6$-alkyl-, $C_1$-$C_6$-haloalkoxy-$C_1$-$C_6$-alkyl-, $C_2$-$C_6$-alkenyl-, $C_2$-$C_6$-alkynyl-, $C_3$-$C_6$-cycloalkyl-$C_1$-$C_6$-alkyl-, $C_1$-$C_6$-alkylcarbonyl-, $C_1$-$C_6$-alkoxycarbonyl- or aminocarbonyl-substituted aryl, heteroaryl, aryl-$C_1$-$C_6$-alkyl, heteroaryl-$C_1$-$C_6$-alkyl, or is NR'R" in which R' and R" are independently a radical from the group of hydrogen, $C_1$-$C_6$-alkyl, $C_1$-$C_6$-haloalkyl, $C_3$-$C_6$-cycloalkyl, $C_1$-$C_6$-alkoxy, $C_1$-$C_6$-alkylcarbonyl and $C_1$-$C_6$-alkoxycarbonyl, or $R^8$ and $R^9$ in the (C-1) radical and in the (F-1) radical, together with the N—S(O)$_n$ group to which they are bonded, may also form a saturated or unsaturated and optionally halogen-, $C_1$-$C_6$-alkyl-, $C_1$-$C_6$-haloalkyl-, $C_1$-$C_6$-alkoxy-, $C_1$-$C_6$-haloalkoxy-substituted 5- to 7-membered ring which may contain one or two heteroatoms from the group of sulphur, oxygen (where oxygen atoms must not be directly adjacent to one another) and nitrogen and/or at least one and preferably one carbonyl group; in particular, $R^8$ and $R^9$ together with the N—S(O)$_n$ group to which they are bonded may be a radical from the group of

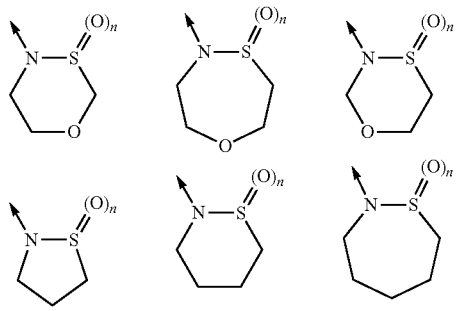

(in which the arrow in each case denotes the bond to the C(X) group), $R^{15}$ is a radical from the group of in each case optionally methyl-, cyano-, carbamoyl-substituted $C_1$-$C_6$-alkyl, $C_2$-$C_6$-alkenyl and $C_2$-$C_6$-alkynyl, in each case optionally methyl-, trifluoromethyl-, halogen-, cyano- or carbamoyl-substituted $C_3$-$C_6$-cycloalkyl, $C_3$-$C_6$-cycloalkyl-$C_1$-$C_2$-alkyl and $C_3$-$C_6$-cycloalkenyl, in which the rings may contain at least one heteroatom from the group of sulphur, oxygen (where oxygen atoms must not be directly adjacent to one another) and nitrogen, in each case optionally $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-haloalkylsulphinyl-, $C_1$-$C_4$-haloalkylsulphonyl-, $C_1$-$C_4$-alkylamino-, di-($C_1$-$C_4$-alkyl)amino-, halogen-, nitro- or cyano-substituted aryl, heteroaryl, aryl-$C_1$-$C_4$-alkyl and heteroaryl-$C_1$-$C_2$-alkyl and an optionally $C_1$-$C_4$-alkyl-, $C_1$-$C_4$-alkylcarbonyl-, $C_1$-$C_4$-alkyl-$C_1$-$C_4$-alkoxycarbonyl- or $C_1$-$C_4$-alkylsulphonyl-substituted amino group, $R^8$ and $R^{15}$ in the (C-6) radical, together with the N—S(O)n group to which they are bonded, may also form a saturated or unsaturated and optionally substituted 4- to 8-membered ring which may contain one or two further heteroatoms from the group of sulphur, oxygen (where oxygen and sulphur atoms must not be directly adjacent to one another) and nitrogen and/or at least one carbonyl group, $R^{16}$ is a radical from the group of hydrogen, in each case optionally methyl-, cyano-, carbamoyl- or carboxyl-substituted $C_1$-$C_6$-alkyl, $C_1$-$C_6$-alkoxy, $C_2$-$C_4$-alkenyl and $C_2$-$C_4$-alkynyl, in each case optionally halogen-, cyano-, nitro-, $C_1$-$C_6$-alkyl-, $C_1$-$C_6$-haloalkyl-, $C_3$-$C_6$-cycloalkyl-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-haloalkylsulphinyl-, $C_1$-$C_6$-alkylsulphonyl-, $C_1$-$C_6$-haloalkylsulphonyl-, amino-, $C_1$-$C_6$-alkylamino-, di-($C_1$-$C_6$-alkyl)amino-, $C_1$-$C_6$-alkylcarbonylamino-, $C_1$-$C_6$-alkoxycarbonylamino-, $C_2$-$C_6$-alkenyl-, $C_2$-$C_6$-alkynyl- or $C_1$-$C_6$-alkylcarbonyl-substituted $C_3$-$C_6$-cycloalkyl, $C_3$-$C_6$-cycloalkyl-$C_1$-$C_4$-alkyl and $C_3$-$C_6$-cycloalkenyl in which the rings may contain at least one heteroatom from the group of sulphur, oxygen (where oxygen atoms must not be directly adjacent to one another) and nitrogen, in each case optionally halogen-, cyano-, nitro-, $C_1$-$C_6$-alkyl-, $C_1$-$C_6$-haloalkyl-, $C_3$-$C_6$-cycloalkyl-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-haloalkylsulphinyl-, $C_1$-$C_6$-alkylsulphonyl-, $C_1$-$C_6$-haloalkylsulphonyl-, amino-, $C_1$-$C_6$-alkylamino-, di-($C_1$-$C_6$-alkyl)amino-, $C_1$-$C_6$-alkylcarbonylamino-, $C_1$-$C_6$-alkoxycarbonylamino-, $C_2$-$C_6$-alkenyl-, $C_2$-$C_6$-alkynyl- or $C_1$-$C_6$-alkylcarbonyl-substituted aryl, heteroaryl, aryl-$C_1$-$C_2$-alkyl and heteroaryl-$C_1$-$C_2$-alkyl and an optionally $C_1$-$C_6$-alkyl-, $C_1$-$C_6$-haloalkyl-, $C_3$-$C_6$-cycloalkyl-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-haloalkylsulphinyl-, $C_1$-$C_6$-alkylsulphonyl-, $C_1$-$C_6$-haloalkylsulphonyl-, $C_2$-$C_6$-alkenyl-, $C_2$-$C_6$-alkynyl- or $C_1$-$C_6$-alkylcarbonyl-substituted amino group, $R^{17}$ is a radical from the group of in each case optionally halogen-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-haloalkylsulphinyl-, $C_1$-$C_6$-alkylsulphonyl- or $C_1$-$C_6$-haloalkylsulphonyl-substituted $C_1$-$C_6$-alkyl, $C_1$-$C_6$-alkoxy, $C_2$-$C_6$-alkenyl and $C_2$-$C_6$-alkynyl, in each case optionally halogen-, $C_1$-$C_6$-alkyl-, $C_1$-$C_6$-haloalkyl-, $C_1$-$C_6$-alkoxy- or $C_1$-$C_6$-haloalkoxy-substituted $C_3$-$C_6$-cycloalkyl, $C_3$-$C_6$-cycloalkyl-$C_1$-$C_6$-alkyl, $C_3$-$C_6$-cycloalkenyl, N-pyrrolidinyl, N-piperidinyl, N-morpholinyl, N-thiomorpholinyl, N-thiomorpholinyl 1-oxide, N-thiomorpholinyl 1,1-dioxide, N-piperazinyl, N-1-methylpiperazinyl and N-2-oxo-1-methylpiperazinyl, in each case optionally halogen-, cyano- (including in the alkyl moiety), nitro-, $C_1$-$C_6$-alkyl-, $C_1$-$C_6$-haloalkyl-, $C_3$-$C_6$-cycloalkyl-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-haloalkylsulphinyl-, $C_1$-$C_6$-alkylsulphonyl-, $C_1$-$C_6$-haloalkylsulphonyl-, amino-, $C_1$-$C_6$-alkylamino-, di($C_1$-$C_6$-alkyl)amino-, $C_1$-$C_6$-alkylcarbonylamino-, $C_1$-$C_6$-alkoxycarbonylamino-, $C_1$-$C_6$-alkoxy-$C_1$-$C_6$-alkyl-, $C_1$-$C_6$-haloalkoxy-$C_1$-$C_6$-alkyl-, $C_2$-$C_6$-alkenyl-, $C_2$-$C_6$-alkynyl-, $C_3$-$C_6$-cycloalkyl-$C_1$-$C_6$-alkyl-, $C_1$-$C_6$-alkylcarbonyl-, $C_1$-$C_6$-alkoxycarbonyl- or aminocarbonyl-substituted aryl, heteroaryl, aryl-$C_1$-$C_6$-alkyl, heteroaryl-$C_1$-$C_6$-alkyl and NR'R'' in which R' and R'' are each independently a radical from the group of hydrogen, $C_1$-$C_6$-alkyl, $C_1$-$C_6$-haloalkyl, $C_3$-$C_6$-cycloalkyl, $C_1$-$C_6$-alkoxy, $C_1$-$C_6$-alkylcarbonyl and $C_1$-$C_6$-alkoxycarbonyl, $R^8$ and $R^{17}$ in the (C-8) radical and in the (F-8) radical, together with the N—C(X) group to which they are bonded, may also form a saturated or unsaturated and optionally halogen-, $C_1$-$C_6$-alkyl-, $C_1$-$C_6$-haloalkyl-, $C_1$-$C_6$-alkoxy-, $C_1$-$C_6$-haloalkoxy-substituted 5- to 7-membered ring which may contain one or two further heteroatoms from the group of sulphur, oxygen (where oxygen atoms must not be directly adjacent to one another) and nitrogen and/or one carbonyl group; $R^8$ and $R^{17}$ together with the N—C(X) group to which they are bonded may especially be a radical from the group of

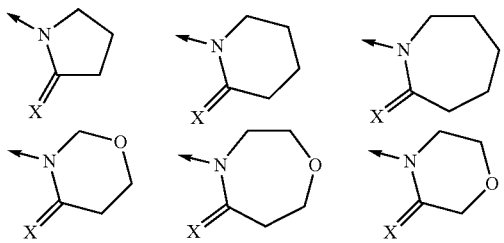

(where the arrow in each case denotes the bond to the sulphur atom in the (C-8) radical and in the (F-8) radical), $R^{18}$ is a radical from the group of hydrogen, hydroxyl, in each case optionally mono- or poly-halogen-substituted or mono- or di-cyano-substituted $C_1$-$C_6$-alkyl, $C_1$-$C_6$-alkoxy, $C_1$-$C_6$-alkoxy-$C_1$-$C_4$-alkyl, $C_1$-$C_6$-alkyl-S—$C_1$-$C_4$-alkyl, $C_1$-$C_6$-alkyl-S(O)—$C_1$-$C_4$-alkyl, $C_1$-$C_6$-alkyl-S(O)$_2$—$C_1$-$C_4$-alkyl, $C_1$-$C_6$-alkylcarbonyl, $C_1$-$C_6$-alkoxycarbonyl, $C_3$-$C_6$-cycloalkyl, $C_3$-$C_6$-cycloalkenyl, $C_3$-$C_6$-cycloalkyl-$C_1$-$C_3$-alkyl, $C_3$-$C_6$-cycloalkenyl-$C_1$-$C_3$-alkyl, heterocyclyl, heterocyclyl-$C_1$-$C_3$-alkyl and in each case optionally mono- to tetra-$C_1$-$C_4$-alkyl-, —$C_1$-$C_4$-haloalkyl-, —$C_1$-$C_4$-alkoxy-, —$C_1$-$C_4$-haloalkoxy-, —$C_3$-$C_6$-cycloalkyl-, -halogen- or -cyano-substituted phenyl, phenyl-$C_1$-$C_3$-alkyl, hetaryl and hetaryl-$C_1$-$C_3$-alkyl, $R^{19}$ is hydrogen, an alkali metal or alkaline earth metal ion or an optionally mono- to tetra-$C_1$-$C_4$-alkyl-substituted ammonium ion or an in each case optionally mono- or poly-halogen-substituted or mono- or di-cyano-substituted radical from the group of $C_1$-$C_4$-alkyl, $C_1$-$C_4$-alkoxy, $C_1$-$C_4$-alkoxy-$C_1$-$C_4$-alkyl, $C_1$-$C_4$-alkyl-S—$C_1$-$C_4$-alkyl, $C_1$-$C_4$-alkyl-S(O)—$C_1$-$C_4$-alkyl and $C_1$-$C_4$-alkyl-S(O)$_2$—$C_1$-$C_4$-alkyl, $Y^3$ is a radical from the group of hydrogen, halogen, cyano, $C_1$-$C_6$-alkyl, $C_1$-$C_6$-haloalkyl, $C_3$-$C_6$-cycloalkyl, $C_1$-$C_6$-alkoxy, $C_1$-$C_6$-haloalkoxy and $NR^{20}R^{21}$, W is a radical from the group of O, S, SO and $SO_2$, $R^{22}$ is a radical from the group of hydrogen, $C_1$-$C_6$-alkyl, $C_2$-$C_6$-haloalkyl, cyano-$C_1$-$C_6$-alkyl, $C_2$-$C_4$-alkenyl, $C_2$-$C_4$-haloalkenyl, $C_2$-$C_4$-alkynyl, $C_2$-$C_4$-haloalkynyl, $C_1$-$C_6$-alkoxy, $C_1$-$C_6$-haloalkoxy, optionally halogen-substituted $C_1$-$C_6$-alkoxy-$C_1$-$C_6$-alkyl, optionally halogen-substituted bis($C_1$-$C_6$-alkoxy)-$C_1$-$C_6$-alkyl, optionally halogen-substituted $C_1$-$C_6$-alkylsulphanyl-$C_1$-$C_6$-alkyl, optionally halogen-substituted $C_1$-$C_4$-alkylcarbonyl-$C_1$-$C_4$-alkyl, optionally halogen-substituted $C_1$-$C_6$-alkylsulphinyl-$C_1$-$C_6$-alkyl, optionally halogen-substituted $C_1$-$C_6$-alkyl sulphonyl-$C_1$-$C_6$-alkyl, di-($C_1$-$C_6$-alkyl)aminosulphanyl-$C_1$-$C_6$-alkyl, di-($C_1$-$C_6$-alkyl)aminosulphinyl-$C_1$-$C_6$-alkyl, di-($C_1$-$C_6$-alkyl)aminosulphonyl-$C_1$-$C_6$-alkyl, optionally halogen-substituted $C_1$-$C_6$-alkoxycarbonyl, optionally halogen-substituted $C_1$-$C_6$-alkoxycarbonyl-$C_1$-$C_6$-alkyl, optionally halogen-substituted $C_2$-$C_4$-alkynyloxy, optionally halogen-substituted $C_2$-$C_4$-alkynyloxycarbonyl, di-($C_1$-$C_6$-alkyl)-aminocarbonyl, N—$C_1$-$C_6$-alkyl-N—$C_3$-$C_6$-cycloalkylaminocarbonyl, di-($C_1$-$C_6$-alkyl)-aminocarbonyl-$C_1$-$C_6$-alkyl, N—$C_1$-$C_6$-alkyl-N—$C_3$-$C_6$-cycloalkylaminocarbonyl-$C_1$-$C_6$-alkyl, heterocyclylcarbonyl-$C_1$-$C_6$-alkyl, $C_1$-$C_6$-alkylsulphanyl, $C_1$-$C_6$-haloalkylsulphanyl, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, $C_3$-$C_6$-cycloalkyl optionally substituted by halogen, cyano, nitro, $C_1$-$C_6$-alkyl, $C_1$-$C_6$-haloalkyl, $C_3$-$C_6$-cycloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl or hetaryl (which for its part is optionally substituted by $C_1$-$C_6$-alkyl or halogen), $C_3$-$C_6$-cycloalkylcarbonyl optionally substituted by halogen, cyano, nitro, $C_1$-$C_6$-alkyl, $C_1$-$C_6$-haloalkyl, $C_3$-$C_6$-cycloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl or hetaryl (which for its part is optionally substituted by $C_1$-$C_6$-alkyl or halogen), $C_3$-$C_6$-cycloalkyl-$C_1$-$C_6$-alkyl optionally substituted by halogen, cyano, nitro, $C_1$-$C_6$-alkyl, $C_1$-$C_6$-haloalkyl, $C_3$-$C_6$-cycloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl or hetaryl (which for its part is optionally substituted by $C_1$-$C_6$-alkyl or halogen), heterocyclyl-$C_1$-$C_6$-alkyl optionally substituted by halogen, cyano (including in the $C_1$-$C_6$-alkyl moiety of heterocyclyl-$C_1$-$C_6$-alkyl), nitro, hydroxyl, $C_1$-$C_6$-alkyl, $C_1$-$C_6$-haloalkyl, $C_3$-$C_6$-cycloalkyl (which is optionally substituted by halogen, cyano, $C_1$-$C_6$-alkyl and $C_3$-$C_6$-cycloalkyl), $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulphinyl, $C_1$-$C_6$-alkylsulphonyl, $C_1$-$C_6$-haloalkylsulphinyl, $C_1$-$C_6$-haloalkylsulphonyl, amino, $C_1$-$C_6$-alkylamino, di-($C_1$-$C_6$-alkyl)amino, $C_1$-$C_6$-alkylcarbonylamino, $C_1$-$C_6$-alkoxycarbonylamino, $C_1$-$C_6$-alkoxy-$C_1$-$C_6$-alkyl, $C_1$-$C_6$-haloalkoxy-$C_1$-$C_6$-alkyl, $C_2$-$C_6$-alkenyl, $C_2$-$C_6$-alkynyl, $C_3$-$C_6$-cycloalkyl-$C_1$-$C_6$-alkyl, $C_1$-$C_6$-alkylcarbonyl, $C_1$-$C_6$-alkoxycarbonyl or aminocarbonyl, aryl optionally substituted by halogen, cyano, nitro, hydroxyl, amino, $C_1$-$C_6$-alkyl, $C_1$-$C_6$-haloalkyl, $C_3$-$C_6$-cycloalkyl (which is optionally substituted by halogen, cyano, $C_1$-$C_6$-alkyl and $C_3$-$C_6$-cycloalkyl), $C_1$-$C_6$-alkoxy or $C_1$-$C_6$-haloalkoxy, aryl-$C_1$-$C_6$-alkyl optionally substituted by halogen, cyano (including in the $C_1$-$C_6$-alkyl moiety of aryl-$C_1$-$C_6$-alkyl), nitro, hydroxyl, amino, $C_1$-$C_6$-alkyl, $C_1$-$C_6$-haloalkyl, $C_3$-$C_6$-cycloalkyl (which is optionally substituted by halogen, cyano, $C_1$-$C_6$-alkyl and $C_3$-$C_6$-cycloalkyl), $C_1$-$C_6$-alkoxy or $C_1$-$C_6$-haloalkoxy, hetaryl-$C_1$-$C_6$-alkyl optionally substituted by halogen, cyano (including in the $C_1$-$C_6$-alkyl moiety of hetaryl-$C_1$-$C_6$-alkyl), nitro, hydroxyl, $C_1$-$C_6$-alkyl, $C_1$-$C_6$-haloalkyl, $C_3$-$C_6$-cycloalkyl (which is optionally substituted by halogen, cyano, $C_1$-$C_6$-alkyl and $C_3$-$C_6$-cycloalkyl), $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulphinyl, $C_1$-$C_6$-alkylsulphonyl, $C_1$-$C_6$-haloalkylsulphinyl, $C_1$-$C_6$-haloalkylsulphonyl, amino, $C_1$-$C_6$-alkylamino, di-($C_1$-$C_6$-alkyl)amino, $C_1$-$C_6$-alkylcarbonylamino, $C_1$-$C_6$-alkoxycarbonylamino, $C_1$-$C_6$-alkoxy-$C_1$-$C_6$-alkyl, $C_1$-$C_6$-haloalkoxy-$C_1$-$C_6$-alkyl, $C_2$-$C_6$-alkenyl, $C_2$-$C_6$-alkynyl, $C_3$-$C_6$-cycloalkyl-$C_1$-$C_6$-alkyl, $C_1$-$C_6$-alkylcarbonyl, $C_1$-$C_6$-alkoxycarbonyl or aminocarbonyl, or $R^{22}$ is a D radical from the group of (D-1) to (D-3)

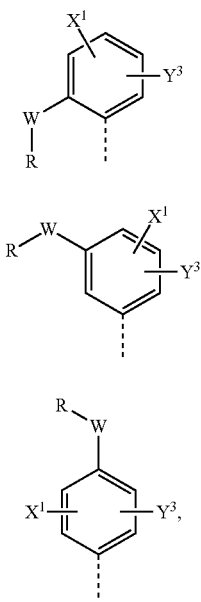

(D-1)

(D-2)

(D-3)

is an E radical from the group of (E-1) to (E-11)

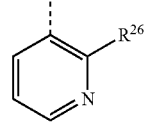

E-1

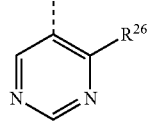

E-2

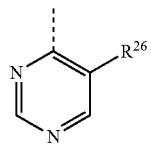

E-3

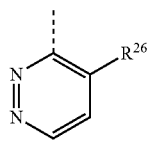

E-4

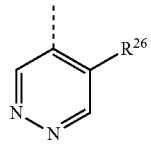

E-5

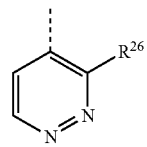

E-6

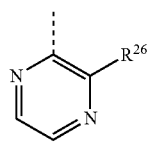

E-7

E-8

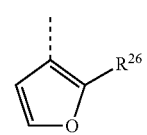

E-9

E-10

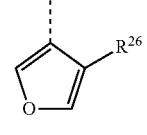

E-11 and (E-18) to (E-51)

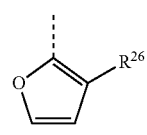

E-18

E-19

E-20

E-21 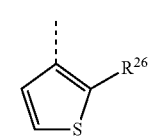
E-22 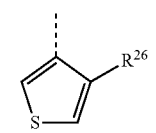
E-23 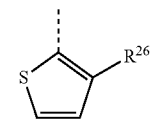
E-24 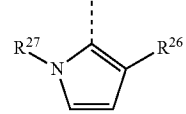
E-25 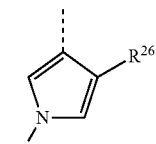
E-26 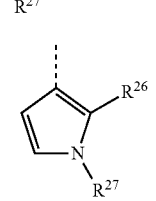
E-27 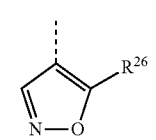
E-28 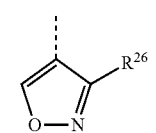
E-29 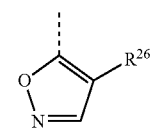
E-30 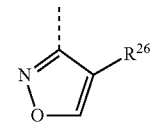
E-31 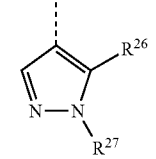
E-32 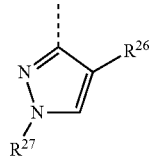
E-33 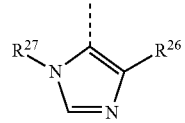
E-34 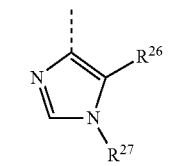
E-35 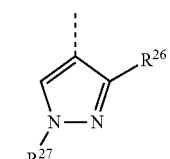
E-36 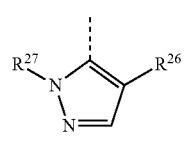
E-37 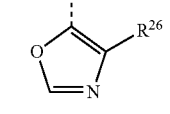
E-38 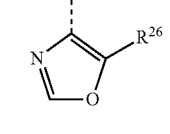
E-39 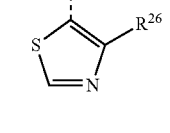
E-40
E-41

-continued

E-42
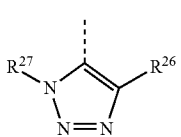

E-43
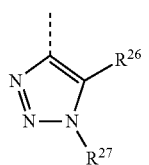

E-44
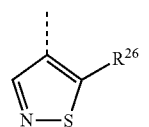

E-45
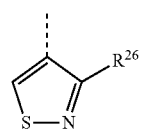

E-46
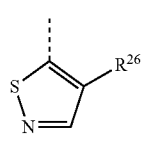

E-47
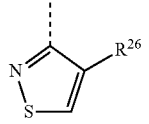

E-48
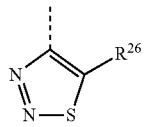

E-49
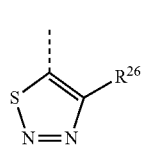

E-50
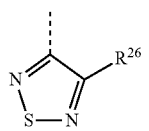

E-51
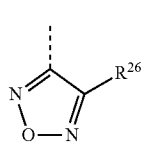

or in the case $R^2$=d),
$R^{22}$ is also an E radical from the group of E-12 to E-17

E-12
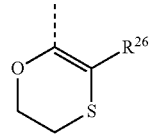

E-13
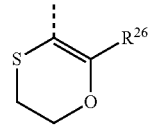

E-14
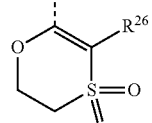

E-15
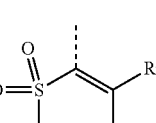

E-16
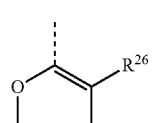

E-17
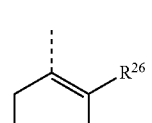

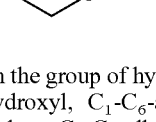

$R^{20}$ is a radical from the group of hydrogen, halogen, cyano, nitro, amino, hydroxyl, $C_1$-$C_6$-alkyl, $C_1$-$C_6$-haloalkyl, cyano-$C_1$-$C_6$-alkyl, $C_2$-$C_6$-alkenyl, $C_2$-$C_6$-alkynyl, $C_3$-$C_6$-cycloalkyl (which is optionally substituted by halogen, cyano, $C_1$-$C_4$-alkyl and $C_3$-$C_6$-cycloalkyl), $C_3$-$C_6$-cycloalkyl-$C_1$-$C_6$-alkyl, $C_1$-$C_6$-alkoxy, $C_1$-$C_6$-haloalkoxy, $C_3$-$C_6$-alkenyloxy, $C_3$-$C_6$-alkynyloxy, $C_3$-$C_6$-cycloalkyloxy, $C_1$-$C_6$-alkylcarbonyloxy, $C_2$-$C_6$-alkenylcarbonyloxy, $C_2$-$C_6$-alkynylcarbonyloxy, $C_3$-$C_6$-cycloalkylcarbonyloxy, $C_1$-$C_6$-alkoxycarbonyloxy, $C_1$-$C_6$-alkylsulphonyloxy, $C_1$-$C_6$-alkylamino, $C_3$-$C_6$-alkenylamino, $C_3$-$C_6$-alkynylamino, $C_3$-$C_6$-cycloalkylamino, $C_1$-$C_6$-alkylthio, $C_1$-$C_6$-haloalkylthio, $C_3$-$C_6$-alkenylthio, $C_3$-$C_6$-alkynylthio, $C_3$-$C_6$-cycloalkylthio, $C_1$-$C_6$-alkylsulphinyl, $C_1$-$C_6$-alkylsulphonyl, $C_1$-$C_6$-alkylcarbonyl, $C_1$-$C_6$-alkoxyimino-$C_1$-$C_6$-alkyl, $C_1$-$C_6$-alkoxycarbonyl, aminocarbonyl, $C_1$-$C_6$-alkyl aminocarbonyl, di-($C_1$-$C_6$-alkyl)aminocarbonyl, aminothiocarbonyl, $C_1$-$C_6$-alkylaminosulphonyl, $C_1$-$C_6$-alkyl sulphonylamino, $C_1$-$C_6$-alkylcarbonylamino, $C_1$-$C_6$-alkylthiocarbonylamino, and phenyl, phenoxy, pyridinyl and pyridinyloxy each optionally substituted by a radical from the group of halogen, cyano, nitro, amino, hydroxyl, $C_1$-$C_6$-alkyl and $C_1$-$C_6$-haloalkyl, $R^{21}$ is a radical from the group of hydrogen, $C_1$-$C_6$-alkyl, $C_3$-$C_6$-cycloalkyl, $C_1$-$C_6$-haloalkyl, $C_3$-$C_6$-alkenyl, $C_2$-$C_6$-alkynyl, $C_3$-$C_6$-cycloalkyl-$C_1$-$C_6$-alkyl, cyano-$C_1$-$C_6$-alkyl, $C_1$-$C_6$-alkylcarbonyl, $C_2$-$C_6$-alkenylcarbonyl, $C_1$-$C_6$-haloalkylcarbonyl, $C_2$-$C_6$-haloalkenylcarbonyl, $C_1$-$C_6$-alkoxy-$C_1$-$C_6$-alkyl, $C_1$-$C_6$-alkoxycarbonyl, $C_1$-$C_6$-alkylsulphonyl and $C_1$-$C_6$-haloalkylsulphonyl, $R^{23}$ is a radical from the group of hydrogen, $C_1$-$C_6$-alkyl, $C_2$-$C_4$-alkenyl, $C_2$-$C_4$-alkynyl, $C_3$-$C_6$-cycloalkyl, $C_3$-$C_6$-cycloalkenyl, $C_1$-$C_6$-alkoxy, $C_2$-$C_6$-alkenyloxy, $C_2$-$C_6$-alkynyloxy, $C_3$-$C_6$-cycloalkyloxy, $C_1$-$C_4$-alkylthio-$C_1$-$C_4$-alkyl, $C_2$-$C_4$-alkenylthio-$C_1$-$C_4$-alkyl, cyano-$C_1$-$C_4$-alkyl, $C_1$-$C_4$-alkoxy-$C_1$-$C_4$-alkyl, or, when $R^2$=c) or f), $R^{22}$ and $R^{23}$ together with the nitrogen atom to which they are bonded form a saturated ring which may contain one or two further heteroatoms from the group of nitrogen, oxygen and sulphur, and $R^{24}$ is hydrogen or an in each case optionally halogen- or cyano-substituted radical from the group of $C_1$-$C_4$-alkyl, $C_2$-$C_6$-alkenyl, $C_2$-$C_6$-alkynyl, phenyl and phenyl-$C_1$-$C_2$-alkyl, $R^{25}$ is hydrogen or an in each case optionally halogen- or cyano-substituted radical from the group of $C_1$-$C_4$-alkyl, $C_2$-$C_6$-alkenyl, $C_2$-$C_6$-alkynyl, phenyl and phenyl-$C_1$-$C_2$-alkyl, $R^{27}$ is hydrogen or $C_1$-$C_4$-alkyl and $R^{26}$ is a radical from the group of hydrogen, $C_1$-$C_4$-alkyl, $C_1$-$C_4$-haloalkyl, $C_2$-$C_4$-alkenyl, $C_2$-$C_4$-alkynyl, $C_3$-$C_6$-cycloalkyl, $C_3$-$C_6$-cycloalkyl-$C_1$-$C_4$-alkyl, $C_1$-$C_4$-alkoxy-$C_1$-$C_2$-alkyl, $C_1$-$C_6$-alkylsulphanyl, $C_1$-$C_6$-haloalkylsulphanyl $C_1$-$C_6$-alkylsulphinyl, $C_1$-$C_6$-haloalkylsulphinyl, $C_1$-$C_6$-alkylsulphonyl, $C_1$-$C_4$-alkylthio-$C_1$-$C_2$-alkyl, $C_1$-$C_4$-alkylsulphinyl-$C_1$-$C_2$-alkyl, $C_1$-$C_4$-alkylsulphonyl-$C_1$-$C_2$-alkyl and cyano-$C_1$-$C_4$-alkyl and compounds of the formula (I) in which A is the A radical

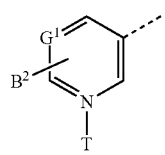

(A-a)

in which the broken line denotes the bond to the carbon atom of the bicyclic system of the formula (I) and $G^1$ is N or C—$B^1$, $B^1$ is a radical from the group of hydrogen, halogen, $C_1$-$C_6$-alkyl and $C_1$-$C_4$-haloalkyl, $B^2$ is a radical from the group of hydrogen, halogen, $C_1$-$C_6$-alkyl and $C_1$-$C_4$-haloalkyl, T is oxygen or an electron pair, Q is sulphur, $R^1$ is a radical from the group of hydrogen, $C_1$-$C_6$-alkyl and $C_1$-$C_6$-alkoxy, $R^2$ a) is a B radical from the group of

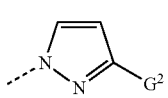

(B-1)

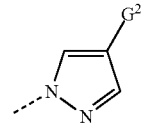

(B-2)

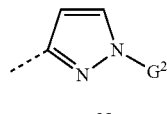

(B-3)

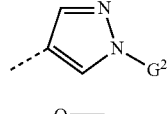

(B-4)

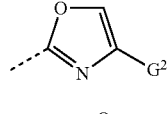

(B-5)

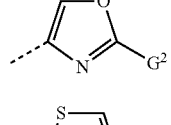

(B-6)

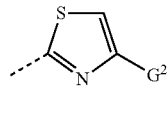

(B-7)

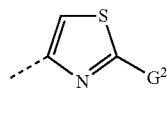

(B-8)

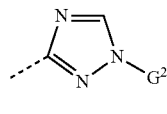

(B-9)

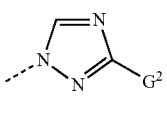

(B-10)

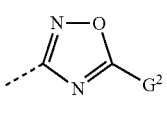

(B-11)

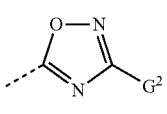

(B-12)

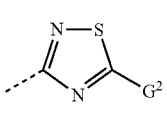

(B-13)

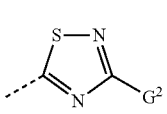

(B-14)

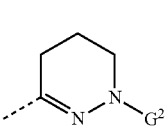

(B-15)

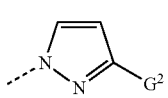

(B-16)

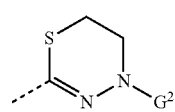 (B-17)
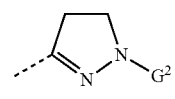 (B-18)
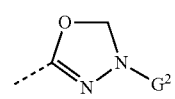 (B-19)
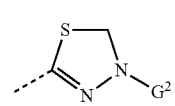 (B-20)
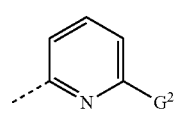 (B-21)
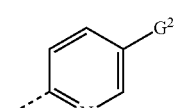 (B-22)
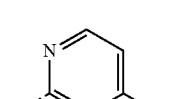 (B-23)
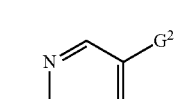 (B-24)
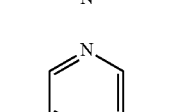 (B-25)
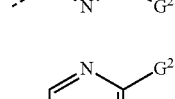 (B-26)
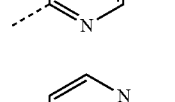 (B-27)
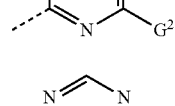 (B-28)
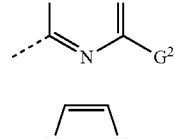 (B-29)
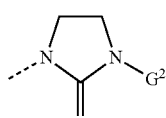 (B-30)
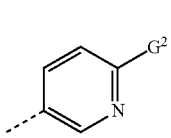 (B-31)
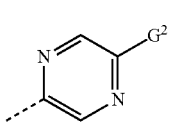 (B-32)
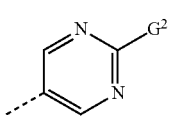 (B-33)
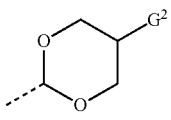 (B-34)
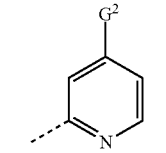 (B-35)
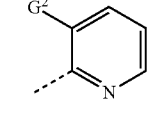 (B-36)
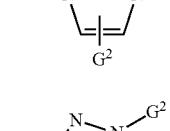 (B-37)
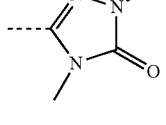 (B-38)
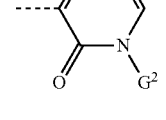 (B-39)
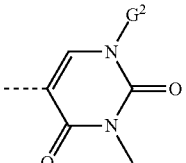 (B-40)

-continued (B-41)
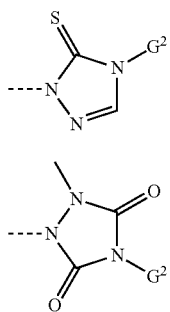

(B-42)
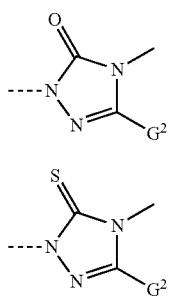

(B-43)
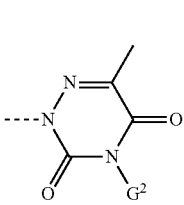

(B-44)
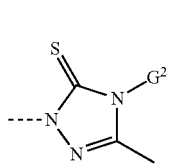

(B-45)
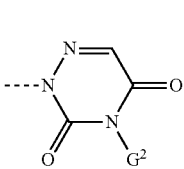

(B-46)
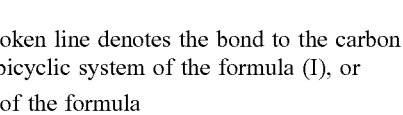

(B-47)
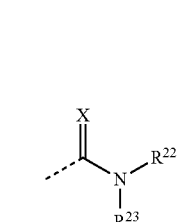

in which the broken line denotes the bond to the carbon atom of the bicyclic system of the formula (I), or $R^2$ c) is a radical of the formula

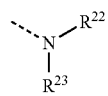

in which the broken line denotes the bond to the carbon atom of the bicyclic system of the formula (I), or $R^2$ d) is a radical of the formula

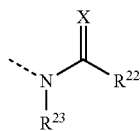

in which the broken line denotes the bond to the carbon atom of the bicyclic system of the formula (I), or $R^2$ e) is an F radical from the group of (F-8), (F-10) and (F-11)

(F-8)
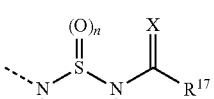

(F-10)
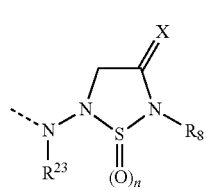

(F-11)
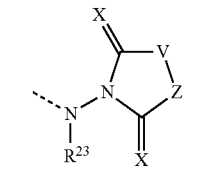

in which the broken line denotes the bond to the carbon atom of the bicyclic system of the formula (I), or $R^2$ f) is a radical of the formula

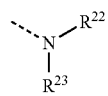

in which the broken line denotes the bond to the carbon atom of the bicyclic system of the formula (I), in which $G^2$ is hydrogen or a radical from the group of halogen, nitro, amino, cyano, $C_1$-$C_4$-alkylamino, halo-$C_1$-$C_4$-alkylamino, di-($C_1$-$C_4$-alkyl)amino, $C_1$-$C_4$-alkyl, halo-$C_1$-$C_4$-alkyl, $C_3$-$C_6$-cycloalkyl, $C_3$-$C_6$-cycloalkenyl, $C_3$-$C_6$-cycloalkyl-$C_1$-$C_4$-alkyl, $C_1$-$C_4$-alkoxy, halo-$C_1$-$C_4$-alkoxy, $C_1$-$C_4$-alkoxy-$C_1$-$C_4$-alkyl, halogenated $C_1$-$C_4$-alkoxy-$C_1$-$C_4$-alkyl, bis($C_1$-$C_4$-alkoxy)-$C_1$-$C_4$-alkyl, bis(halo-$C_1$-$C_4$-alkoxy)-$C_1$-$C_4$-alkyl, $C_1$-$C_4$-alkoxy-($C_1$-$C_4$-alkylsulphanyl)-$C_1$-$C_4$-alkyl, $C_1$-$C_4$-alkoxy-($C_1$-$C_4$-alkylsulphinyl)-$C_1$-$C_4$-alkyl, $C_1$-$C_4$-alkoxy-($C_1$-$C_4$-alkylsulphonyl)-$C_1$-$C_4$-alkyl, bis($C_1$-$C_4$-alkylsulphanyl)-$C_1$-$C_4$-alkyl, bis(halo-$C_1$-$C_4$-alkylsulphanyl)-$C_1$-$C_4$-alkyl, bis(hydroxy-$C_1$-$C_4$-alkylsulphanyl)-$C_1$-$C_4$-alkyl, $C_1$-$C_4$-alkoxycarbonyl, $C_1$-$C_4$-alkoxycarbonyl-$C_1$-$C_4$-alkyl, alpha-hydroxyimino-$C_1$-$C_4$-alkoxycarbonyl-$C_1$-$C_4$-alkyl, alpha-$C_1$-$C_4$-alkoxyimino-$C_1$-$C_4$-alkoxycarbonyl-$C_1$-$C_4$-alkyl, $C(X^2)NR^3R^4$, $NR^6R^7$, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, the heterocyclyl radicals dioxanyl, dioxolanyl, dioxepanyl, dioxocanyl, oxathianyl, oxathiolanyl, oxathiepanyl, oxathiocanyl, dithianyl, dithiolanyl, dithiepanyl, dithiocanyl, oxathianyl oxide, oxathiolanyl oxide, oxathiepanyl oxide, oxathiocanyl oxide, oxathianyl dioxide, oxathiolanyl dioxide, oxathiepanyl dioxide, oxathiocanyl dioxide, morpholinyl, triazolinonyl, oxazolinyl, dihydrooxadiazinyl, dihydrodioxazinyl, dihydrooxazolyl, dihydrooxazinyl and pyrazolinonyl (which for their part may in turn be substituted by $C_1$-$C_4$-alkyl, halo-$C_1$-$C_4$-alkyl, $C_1$-$C_4$-alkoxy and $C_1$-$C_4$-alkoxy-$C_1$-$C_4$-alkyl), phenyl (which for its part may in turn be substituted by halogen, cyano, nitro, $C_1$-$C_4$-alkyl and halo-$C_1$-$C_4$-alkyl), the heteroaryl radicals pyridyl, pyridyl N-oxide, pyrimidyl, imidazolyl, pyrazolyl, oxazolyl, thiazolyl, furanyl, thienyl, triazolyl, tetrazolyl, oxadiazolyl, thiadiazolyl, pyrazinyl, triazinyl, tetrazinyl and isoquinolinyl (which for their part may in turn be substituted by halogen, nitro, $C_1$-$C_4$-alkyl, halo-$C_1$-$C_4$-alkyl, $C_1$-$C_4$-alkoxy, halo-$C_1$-$C_4$-alkoxy, $C_1$-$C_4$-alkoxy-$C_1$-$C_4$-alkyl, $C_1$-$C_4$-alkylthio, $C_1$-$C_4$-alkylthio-$C_1$-$C_4$-alkyl and $C_3$-$C_6$-cycloalkyl) and the heteroaryl-$C_1$-$C_4$-alkyl radicals triazolyl-$C_1$-$C_4$-alkyl, pyridyl-$C_1$-$C_4$-alkyl, pyrimidyl-$C_1$-$C_4$-alkyl and oxadiazolyl-$C_1$-$C_4$-alkyl (which for their part may in turn be substituted by halogen and $C_1$-$C_4$-alkyl), or $G^2$ is a C radical from the group of (C-1) and (C-6) to (C-9)

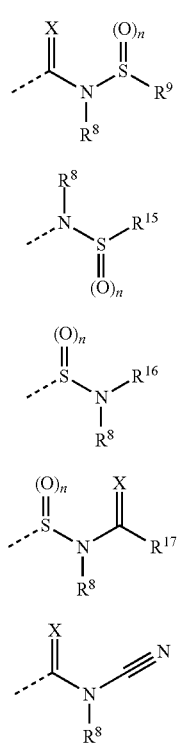

in which the broken line denotes the bond to the B radicals,

X is oxygen or sulphur, $X^1$ is a radical from the group of hydrogen, halogen, cyano, nitro, $C_1$-$C_6$-alkyl, $C_1$-$C_6$-haloalkyl, $C_3$-$C_6$-cycloalkyl, $C_1$-$C_6$-alkoxy and $C_1$-$C_6$-haloalkoxy, $X^2$ is oxygen, sulphur, $NR^5$ or NOH, V—Z is $R^{24}$CH—$CHR^{25}$ or $R^{24}$C=$CR^{25}$, n is 1 or 2, R is $NR^{18}R^{19}$ or is in each case optionally halogen-, oxygen- (leads to C=O) or cyano-substituted $C_1$-$C_6$-alkyl, $C_3$-$C_6$-alkenyl, $C_3$-$C_6$-alkynyl, $C_1$-$C_6$-alkoxy-$C_1$-$C_4$-alkyl, $C_1$-$C_6$-alkyl-S—$C_1$-$C_4$-alkyl, $C_1$-$C_6$-alkyl-S(O)—$C_1$-$C_4$-alkyl, $C_1$-$C_6$-alkyl-S(O)$_2$—$C_1$-$C_4$-alkyl, is $R^{18}$—CO—$C_1$-$C_4$-alkyl, is $NR^{18}R^{19}$—CO—$C_1$-$C_4$-alkyl, is optionally mono- or di-oxygen- (leads to C=O), —$C_1$-$C_4$-alkyl-, —$C_3$-$C_8$-cycloalkyl-, —$C_1$-$C_4$-alkoxy- and —$C_1$-$C_4$-haloalkyl-substituted $C_3$-$C_6$-cycloalkyl, is optionally mono- or di-oxygen- (leads to C=O), —$C_1$-$C_4$-alkyl-, —$C_3$-$C_6$-cycloalkyl-, —$C_1$-$C_4$-alkoxy- and —$C_1$-$C_4$-haloalkyl-substituted $C_3$-$C_8$-cycloalkenyl, is optionally mono- or di-oxygen- (leads to C=O), —$C_1$-$C_4$-alkyl-, —$C_3$-$C_6$-cycloalkyl-, —$C_1$-$C_4$-alkoxy- and —$C_1$-$C_4$-haloalkyl-substituted $C_3$-$C_6$-cycloalkyl-$C_1$-$C_4$-alkyl, is optionally mono- or di-oxygen- (leads to C=O), —$C_1$-$C_4$-alkyl-, —$C_3$-$C_6$-cycloalkyl-, —$C_1$-$C_4$-alkoxy- and —$C_1$-$C_4$-haloalkyl-substituted $C_3$-$C_6$-cycloalkenyl-$C_1$-$C_4$-alkyl, is optionally mono- or di-oxygen- (leads to C=O), —$C_1$-$C_4$-alkyl-, —$C_3$-$C_6$-cycloalkyl-, —$C_1$-$C_4$-alkoxy- and —$C_1$-$C_4$-haloalkyl-substituted heterocyclyl, is optionally mono- or di-oxygen- (leads to C=O), —$C_1$-$C_4$-alkyl-, —$C_3$-$C_6$-cycloalkyl-, —$C_1$-$C_4$-alkoxy- and —$C_1$-$C_4$-haloalkyl-substituted heterocyclyl-$C_1$-$C_4$-alkyl or is in each case optionally mono- to tri-halogen-, -cyano-, —$C_1$-$C_4$-alkyl-, —$C_1$-$C_4$-haloalkyl-, —$C_3$-$C_6$-cycloalkyl-, —$C_1$-$C_4$-alkoxy- or —$C_1$-$C_4$-haloalkoxy-substituted phenyl, phenyl-$C_1$-$C_4$-alkyl, hetaryl and hetaryl-$C_1$-$C_4$-alkyl, $R^3$ is hydrogen or $C_1$-$C_6$-alkyl, $R^4$ is a radical from the group of hydrogen, $C_1$-$C_4$-alkyl, halo-$C_1$-$C_4$-alkyl, cyano-$C_1$-$C_4$-alkyl, $C_2$-$C_4$-alkynyl, $C_3$-$C_6$-cycloalkyl, $C_3$-$C_6$-cycloalkyl-$C_1$-$C_4$-alkyl, $C_1$-$C_4$-alkoxy-$C_1$-$C_4$-alkyl, $C_1$-$C_4$-alkoxycarbonyl, $C_1$-$C_4$-alkoxycarbonyl-$C_1$-$C_4$-alkyl, $C_1$-$C_4$-alkylthio-$C_1$-$C_4$-alkyl, aryl, aryl-$C_1$-$C_4$-alkyl and hetaryl-$C_1$-$C_4$-alkyl, $R^5$ is a radical from the group of hydrogen, $C_1$-$C_4$-alkyl, halo-$C_1$-$C_4$-alkyl, cyano-$C_1$-$C_4$-alkyl, $C_2$-$C_4$-alkynyl, $C_3$-$C_6$-cycloalkyl, $C_3$-$C_6$-cycloalkyl-$C_1$-$C_4$-alkyl, $C_1$-$C_4$-alkoxy-$C_1$-$C_4$-alkyl, $C_1$-$C_4$-alkoxycarbonyl, $C_1$-$C_4$-alkoxycarbonyl-$C_1$-$C_4$-alkyl, $C_1$-$C_4$-alkylthio-$C_1$-$C_4$-alkyl, aryl, aryl-$C_1$-$C_4$-alkyl and hetaryl-$C_1$-$C_4$-alkyl, or $R^3$ and $R^4$ together with the nitrogen atom to which they are bonded form a 4- to 7-membered ring which may contain one or two further heteroatoms from the group of nitrogen, oxygen and sulphur (where oxygen and sulphur atoms must not be directly adjacent to one another), $R^6$ is hydrogen or $C_1$-$C_4$-alkyl, $R^7$ is a radical from the group of hydrogen, $C_1$-$C_4$-alkyl, halo-$C_1$-$C_4$-alkyl, cyano-$C_1$-$C_4$-alkyl, $C_2$-$C_4$-alkynyl, $C_3$-$C_6$-cycloalkyl, $C_3$-$C_4$-cycloalkyl-$C_1$-$C_4$-alkyl, $C_1$-$C_4$-alkoxy, halo-$C_1$-$C_4$-alkoxy, $C_1$-$C_4$-alkoxy-$C_1$-$C_4$-alkyl, $C_1$-$C_4$-alkoxycarbonyl, $C_1$-$C_4$-alkoxycarbonyl-$C_1$-$C_4$-alkyl, $C_1$-$C_4$-alkylthio-$C_1$-$C_4$-alkyl, aryl, aryl-$C_1$-$C_4$-alkyl or hetaryl-$C_1$-$C_4$-alkyl, or $R^6$ and $R^7$ together with the nitrogen atom to which they are bonded form a 4- to 7-membered ring which may contain one or two further heteroatoms from the group of nitrogen, oxygen and sulphur (where oxygen and sulphur atoms must not be directly adjacent to one another), $R^8$ is a radical from the group of hydrogen, $C_1$-$C_6$-alkyl, $C_1$-$C_6$-haloalkyl, cyano-$C_1$-$C_6$-alkyl, $C_1$-$C_6$-alkoxy, $C_1$-$C_6$-haloalkoxy, $C_2$-$C_6$-alkenyl, $C_1$-$C_6$-alkoxy-$C_1$-$C_6$-alkyl, in each case optionally halogen-substituted $C_1$-$C_6$-alkylcarbonyl and $C_1$-$C_6$-alkylsulphonyl, optionally halogen-substituted $C_1$-$C_6$-alkoxycarbonyl and optionally halogen-, $C_1$-$C_6$-alkyl-, $C_1$-$C_6$-alkoxy-, $C_1$-$C_6$-haloalkyland cyano-substituted $C_3$-$C_6$-cycloalkylcarbonyl, or is a cation or an optionally $C_1$-$C_6$-alkyl- or aryl-$C_1$-$C_6$-alkyl-substituted ammonium ion, $R^9$ is a radical from the group of in each case optionally halogen-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-haloalkylsulphinyl-, $C_1$-$C_6$-alkylsulphonyl- and $C_1$-$C_6$-haloalkylsulphonyl-substituted $C_1$-$C_6$-alkyl, $C_2$-$C_6$-alkenyl and $C_2$-$C_6$-alkynyl, in each case optionally halogen-, $C_1$-$C_6$-alkyl-, $C_1$-$C_6$-haloalkyl-, $C_1$-$C_6$-alkoxy- or $C_1$-$C_6$-haloalkoxy-substituted $C_3$-$C_6$-cycloalkyl, $C_3$-$C_6$-cycloalkyl-$C_1$-$C_6$-alkyl and $C_3$-$C_6$-cycloalkenyl, in which one ring member may be replaced by a heteroatom from the group of sulphur, oxygen (where oxygen atoms must not be directly adjacent to one another) and nitrogen (and in this case are especially

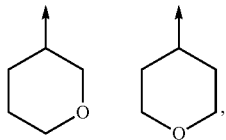

where the arrow in each case denotes the bond to the sulphur atom in the (C-1) radical), in each case optionally halogen-, cyano- (including in the alkyl moiety), nitro-, $C_1$-$C_6$-alkyl-, $C_1$-$C_6$-haloalkyl-, $C_3$-$C_6$-cycloalkyl-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-haloalkylsulphinyl-, $C_1$-$C_6$-alkylsulphonyl-, $C_1$-$C_6$-haloalkylsulphonyl-, amino-, $C_1$-$C_6$-alkyl amino-, di($C_1$-$C_6$-alkyl)amino-, $C_1$-$C_6$-alkylcarbonylamino-, $C_1$-$C_6$-alkoxycarbonylamino-, $C_1$-$C_6$-alkoxy-$C_1$-$C_6$-alkyl-, $C_1$-$C_6$-haloalkoxy-$C_1$-$C_6$-alkyl-, $C_2$-$C_6$-alkenyl-, $C_2$-$C_6$-alkynyl-, $C_3$-$C_6$-cycloalkyl-$C_1$-$C_6$-alkyl-, $C_1$-$C_6$-alkylcarbonyl-, $C_1$-$C_6$-alkoxycarbonyl- or aminocarbonyl-substituted aryl, heteroaryl, aryl-$C_1$-$C_6$-alkyl, heteroaryl-$C_1$-$C_6$-alkyl, or is NR'R" in which R' and R" are independently a radical from the group of hydrogen, $C_1$-$C_6$-alkyl, $C_1$-$C_6$-haloalkyl, $C_3$-$C_6$-cycloalkyl, $C_1$-$C_6$-alkoxy, $C_1$-$C_6$-alkylcarbonyl and $C_1$-$C_6$-alkoxycarbonyl, $R^8$ and $R^9$ in the (C-1) radical, together with the N—S(O)$_n$ group to which they are bonded, may also form a saturated or unsaturated and optionally halogen-, $C_1$-$C_6$-alkyl-, $C_1$-$C_6$-haloalkyl-, $C_1$-$C_6$-alkoxy-, $C_1$-$C_6$-haloalkoxy-substituted 5- to 7-membered ring which may contain one or two heteroatoms from the group of sulphur, oxygen (where oxygen atoms must not be directly adjacent to one another) and nitrogen and/or at least one and preferably one carbonyl group; $R^8$ and $R^9$ together with the N—S(O)$_n$ group to which they are bonded may especially be a radical from the group of

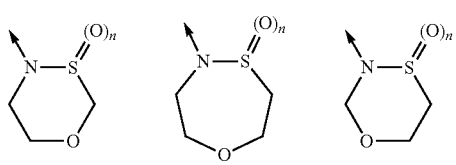

-continued

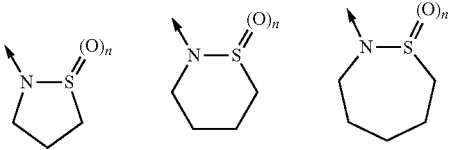

(in which the arrow in each case denotes the bond to the C(X) group), $R^{15}$ is a radical from the group of in each case optionally methyl-, cyano-, carbamoyl-substituted $C_1$-$C_6$-alkyl, $C_2$-$C_6$-alkenyl and $C_2$-$C_6$-alkynyl, in each case optionally methyl-, trifluoromethyl-, halogen-, cyano- or carbamoyl-substituted $C_3$-$C_6$-cycloalkyl, $C_3$-$C_6$-cycloalkyl-$C_1$-$C_2$-alkyl and $C_3$-$C_6$-cycloalkenyl, in which the rings may contain at least one heteroatom from the group of sulphur, oxygen (where oxygen atoms must not be directly adjacent to one another) and nitrogen, in each case optionally $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-haloalkylsulphinyl-, $C_1$-$C_4$-haloalkylsulphonyl-, $C_1$-$C_4$-alkyl amino-, di-($C_1$-$C_4$-alkyl)amino-, halogen-, nitro- or cyano-substituted aryl, heteroaryl, aryl-$C_1$-$C_4$-alkyl and heteroaryl-$C_1$-$C_2$-alkyl and an optionally $C_1$-$C_4$-alkyl-, $C_1$-$C_4$-alkylcarbonyl-, $C_1$-$C_4$-alkyl-$C_1$-$C_4$-alkoxycarbonyl- or $C_1$-$C_4$-alkylsulphonyl-substituted amino group, $R^8$ and $R^{15}$ in the (C-6) radical, together with the N—S(O)n group to which they are bonded, may also form a saturated or unsaturated and optionally substituted 4- to 8-membered ring which may contain one or two further heteroatoms from the group of sulphur, oxygen (where oxygen and sulphur atoms must not be directly adjacent to one another) and nitrogen and/or at least one carbonyl group, $R^{16}$ is a radical from the group of hydrogen, in each case optionally methyl-, cyano-, carbamoyl- or carboxyl-substituted $C_1$-$C_6$-alkyl, $C_1$-$C_6$-alkoxy, $C_2$-$C_4$-alkenyl and $C_2$-$C_4$-alkynyl, in each case optionally halogen-, cyano-, nitro-, $C_1$-$C_6$-alkyl-, $C_1$-$C_6$-haloalkyl-, $C_3$-$C_6$-cycloalkyl-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-haloalkylsulphinyl-, $C_1$-$C_6$-alkylsulphonyl-, $C_1$-$C_6$-haloalkylsulphonyl-, amino-, $C_1$-$C_6$-alkylamino-, di-($C_1$-$C_6$-alkyl)amino-, $C_1$-$C_6$-alkylcarbonylamino-, $C_1$-$C_6$-alkoxycarbonylamino-, $C_2$-$C_6$-alkenyl-, $C_2$-$C_6$-alkynyl- or $C_1$-$C_6$-alkylcarbonyl-substituted $C_3$-$C_6$-cycloalkyl, $C_3$-$C_6$-cycloalkyl-$C_1$-$C_4$-alkyl and $C_3$-$C_6$-cycloalkenyl in which the rings may contain at least one heteroatom from the group of sulphur, oxygen (where oxygen atoms must not be directly adjacent to one another) and nitrogen, in each case optionally halogen-, cyano-, nitro-, $C_1$-$C_6$-alkyl-, $C_1$-$C_6$-haloalkyl-, $C_3$-$C_6$-cycloalkyl-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-haloalkylsulphinyl-, $C_1$-$C_6$-alkylsulphonyl-, $C_1$-$C_6$-haloalkylsulphonyl-, amino-, $C_1$-$C_6$-alkylamino-, di-($C_1$-$C_6$-alkyl)amino-, $C_1$-$C_6$-alkylcarbonylamino-, $C_1$-$C_6$-alkoxycarbonylamino-, $C_2$-$C_6$-alkenyl-, $C_2$-$C_6$-alkynyl- or $C_1$-$C_6$-alkylcarbonyl-substituted aryl, heteroaryl, aryl-$C_1$-$C_2$-alkyl and heteroaryl-$C_1$-$C_2$-alkyl and an optionally $C_1$-$C_6$-alkyl-, $C_1$-$C_6$-haloalkyl-, $C_3$-$C_6$-cycloalkyl-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-haloalkylsulphinyl-, $C_1$-$C_6$-alkylsulphonyl-, $C_1$-$C_6$-haloalkylsulphonyl-, $C_2$-$C_6$-alkenyl-, $C_2$-$C_6$-alkynyl- or $C_1$-$C_6$-alkylcarbonyl-substituted amino group, $R^{17}$ is a radical from the group of in each case optionally halogen-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-haloalkylsulphinyl-, $C_1$-$C_6$-alkylsulphonyl- or $C_1$-$C_6$-haloalkylsulphonyl-substituted $C_1$-$C_6$-alkyl, $C_1$-$C_6$-alkoxy, $C_2$-$C_6$-alkenyl and $C_2$-$C_6$-alkynyl, in each case optionally halogen-, $C_1$-$C_6$-alkyl-, $C_1$-$C_6$-haloalkyl-, $C_1$-$C_6$-alkoxy- or $C_1$-$C_6$-haloalkoxy-substituted $C_3$-$C_6$-cycloalkyl, $C_3$-$C_6$-cycloalkyl-$C_1$-$C_6$-alkyl, $C_3$-$C_6$-cycloalkenyl, N-pyrrolidinyl, N-piperidinyl, N-morpholinyl, N-thiomorpholinyl, N-thiomorpholinyl 1-oxide, N-thiomorpholinyl 1,1-dioxide, N-piperazinyl, N-1-methylpiperazinyl and N-2-oxo-1-methylpiperazinyl, in each case optionally halogen-, cyano- (including in the alkyl moiety), nitro-, $C_1$-$C_6$-alkyl-, $C_1$-$C_6$-haloalkyl-, $C_3$-$C_6$-cycloalkyl-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-haloalkylsulphinyl-, $C_1$-$C_6$-alkylsulphonyl-, $C_1$-$C_6$-haloalkylsulphonyl-, amino-, $C_1$-$C_6$-alkylamino-, di($C_1$-$C_6$-alkyl)amino-, $C_1$-$C_6$-alkylcarbonylamino-, $C_1$-$C_6$-alkoxycarbonylamino-, $C_1$-$C_6$-alkoxy-$C_1$-$C_6$-alkyl-, $C_1$-$C_6$-haloalkoxy-$C_1$-$C_6$-alkyl-, $C_2$-$C_6$-alkenyl-, $C_2$-$C_6$-alkynyl-, $C_3$-$C_6$-cycloalkyl-$C_1$-$C_6$-alkyl-, $C_1$-$C_6$-alkylcarbonyl-, $C_1$-$C_6$-alkoxycarbonyl- or aminocarbonyl-substituted aryl, heteroaryl, aryl-$C_1$-$C_6$-alkyl, heteroaryl-$C_1$-$C_6$-alkyl and NR'R" in which R' and R" are each independently a radical from the group of hydrogen, $C_1$-$C_6$-alkyl, $C_1$-$C_6$-haloalkyl, $C_3$-$C_6$-cycloalkyl, $C_1$-$C_6$-alkoxy, $C_1$-$C_6$-alkylcarbonyl and $C_1$-$C_6$-alkoxycarbonyl, $R^8$ and $R^{17}$ in the (C-8) radical and in the (F-8) radical, together with the N—C(X) group to which they are bonded, may also form a saturated or unsaturated and optionally halogen-, $C_1$-$C_6$-alkyl-, $C_1$-$C_6$-haloalkyl-, $C_1$-$C_6$-alkoxy-, $C_1$-$C_6$-haloalkoxy-substituted 5- to 7-membered ring which may contain one or two further heteroatoms from the group of sulphur, oxygen (where oxygen atoms must not be directly adjacent to one another) and nitrogen and/or one carbonyl group; $R^8$ and $R^{17}$ together with the N—C(X) group to which they are bonded may especially be a radical from the group of

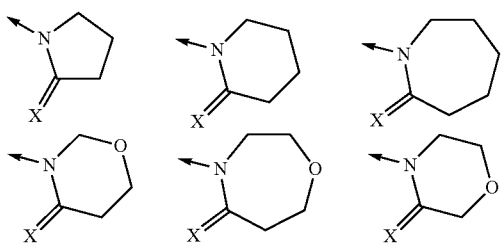

(where the arrow in each case denotes the bond to the sulphur atom in the (C-8) radical and in the (F-8) radical), $R^{18}$ is a radical from the group of hydrogen, hydroxyl, in each case optionally mono- or poly-halogen-substituted or mono- or di-cyano-substituted $C_1$-$C_6$-alkyl, $C_1$-$C_6$-alkoxy, $C_1$-$C_6$-alkoxy-$C_1$-$C_4$-alkyl, $C_1$-$C_6$-alkyl-S—$C_1$-$C_4$-alkyl, $C_1$-$C_6$-alkyl-S(O)—$C_1$-$C_4$-alkyl, $C_1$-$C_6$-alkyl-S(O)$_2$—$C_1$-$C_4$-alkyl, $C_1$-$C_6$-alkylcarbonyl, $C_1$-$C_6$-alkoxycarbonyl, $C_3$-$C_6$-cycloalkyl, $C_3$-$C_6$-cycloalkenyl, $C_3$-$C_6$-cycloalkyl-$C_1$-$C_3$-alkyl, $C_3$-$C_6$-cycloalkenyl-$C_1$-$C_3$-alkyl, heterocyclyl, heterocyclyl-$C_1$-$C_3$-alkyl and in each case optionally mono- to tetra-$C_1$-$C_4$-alkyl-, —$C_1$-$C_4$-haloalkyl-, —$C_1$-$C_4$-alkoxy-, —$C_1$-$C_4$-haloalkoxy-, —$C_3$-$C_6$-cycloalkyl-, -halogen- or -cyano-substituted phenyl, phenyl-$C_1$-$C_3$-alkyl, hetaryl and hetaryl-$C_1$-$C_3$-alkyl, $R^{19}$ is hydrogen, an alkali metal or alkaline earth metal ion or an optionally mono- to tetra-$C_1$-$C_4$-alkyl-substituted ammonium ion or an in each case optionally mono- or poly-halogen-substituted or mono- or di-cyano-substituted radical from the group of $C_1$-$C_4$-alkyl, $C_1$-$C_4$-alkoxy, $C_1$-$C_4$-alkoxy-$C_1$-$C_4$-alkyl, $C_1$-$C_4$-alkyl-S—$C_1$-$C_4$-alkyl, $C_1$-$C_4$-alkyl-S(O)—$C_1$-$C_4$-alkyl and $C_1$-$C_4$-alkyl-S(O)$_2$—$C_1$-$C_4$-alkyl, $Y^3$ is a radical from the group of hydrogen, halogen, cyano, $C_1$-$C_6$-alkyl, $C_1$-$C_6$-haloalkyl, $C_3$-$C_6$-cycloalkyl, $C_1$-$C_6$-alkoxy, $C_1$-$C_6$-haloalkoxy and NR$^{20}$R$^{21}$, W is a radical from the group of S, SO and SO$_2$, and in the case that $R^2$ is f)

$R^{22}$ is a radical from the group of hydrogen, $C_1$-$C_6$-alkyl, $C_2$-$C_6$-haloalkyl, cyano-$C_1$-$C_6$-alkyl, $C_2$-$C_4$-alkenyl, $C_2$-$C_4$-haloalkenyl, $C_2$-$C_4$-alkynyl, $C_2$-$C_4$-haloalkynyl, $C_1$-$C_6$-alkoxy, $C_1$-$C_6$-haloalkoxy, optionally halogen-substituted $C_1$-$C_6$-alkoxy-$C_1$-$C_6$-alkyl, optionally halogen-substituted bis($C_1$-$C_6$-alkoxy)-$C_1$-$C_6$-alkyl, optionally halogen-substituted $C_1$-$C_6$-alkylsulphanyl-$C_1$-$C_6$-alkyl, optionally halogen-substituted $C_1$-$C_4$-alkylcarbonyl-$C_1$-$C_4$-alkyl, optionally halogen-substituted $C_1$-$C_6$-alkylsulphinyl-$C_1$-$C_6$-alkyl, optionally halogen-substituted $C_1$-$C_6$-alkyl sulphonyl-$C_1$-$C_6$-alkyl, di-($C_1$-$C_6$-alkyl)aminosulphanyl-$C_1$-$C_6$-alkyl, di-($C_1$-$C_6$-alkyl)amino sulphinyl-$C_1$-$C_6$-alkyl, di-($C_1$-$C_6$-alkyl)aminosulphonyl-$C_1$-$C_6$-alkyl, optionally halogen-substituted $C_1$-$C_6$-alkoxycarbonyl-$C_1$-$C_6$-alkyl, optionally halogen-substituted $C_2$-$C_4$-alkynyloxy, di-($C_1$-$C_6$-alkyl)aminocarbonyl-$C_1$-$C_6$-alkyl, N—$C_1$-$C_6$-alkyl-N—$C_3$-$C_6$-cycloalkylaminocarbonyl-$C_1$-$C_6$-alkyl, heterocyclylcarbonyl-$C_1$-$C_6$-alkyl, $C_1$-$C_6$-alkylsulphanyl, $C_1$-$C_6$-haloalkylsulphanyl, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, $C_3$-$C_6$-cycloalkyl optionally substituted by halogen, cyano, nitro, $C_1$-$C_6$-alkyl, $C_1$-$C_6$-haloalkyl, $C_3$-$C_6$-cycloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl or hetaryl (which for its part is optionally substituted by $C_1$-$C_6$-alkyl or halogen), $C_3$-$C_6$-cycloalkyl-$C_1$-$C_6$-alkyl optionally substituted by halogen, cyano, nitro, $C_1$-$C_6$-alkyl, $C_1$-$C_6$-haloalkyl, $C_3$-$C_6$-cycloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl or hetaryl (which for its part is optionally substituted by $C_1$-$C_6$-alkyl or halogen), heterocyclyl-$C_1$-$C_6$-alkyl optionally substituted by halogen, cyano (including in the $C_1$-$C_6$-alkyl moiety of heterocyclyl-$C_1$-$C_6$-alkyl), nitro, hydroxyl, $C_1$-$C_6$-alkyl, $C_1$-$C_6$-haloalkyl, $C_3$-$C_6$-cycloalkyl (which is optionally substituted by halogen, cyano, $C_1$-$C_6$-alkyl and $C_3$-$C_6$-cycloalkyl), $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulphinyl, $C_1$-$C_6$-alkylsulphonyl, $C_1$-$C_6$-haloalkylsulphinyl, $C_1$-$C_6$-haloalkylsulphonyl, amino, $C_1$-$C_6$-alkylamino, di-($C_1$-$C_6$-alkyl)amino, $C_1$-$C_6$-alkylcarbonylamino, $C_1$-$C_6$-alkoxycarbonylamino, $C_1$-$C_6$-alkoxy-$C_1$-$C_6$-alkyl, $C_1$-$C_6$-haloalkoxy-$C_1$-$C_6$-alkyl, $C_2$-$C_6$-alkenyl, $C_2$-$C_6$-alkynyl, $C_3$-$C_6$-cycloalkyl-$C_1$-$C_6$-alkyl, $C_1$-$C_6$-alkylcarbonyl, $C_1$-$C_6$-alkoxycarbonyl or aminocarbonyl, aryl optionally substituted by halogen, cyano, nitro, hydroxyl, amino, $C_1$-$C_6$-alkyl, $C_1$-$C_6$-haloalkyl, $C_3$-$C_6$-cycloalkyl (which is optionally substituted by halogen, cyano, $C_1$-$C_6$-alkyl and $C_3$-$C_6$-cycloalkyl), $C_1$-$C_6$-alkoxy or $C_1$-$C_6$-haloalkoxy, aryl-$C_1$-$C_6$-alkyl optionally substituted by halogen, cyano (including in the $C_1$-$C_6$-alkyl moiety of aryl-$C_1$-$C_6$-alkyl), nitro, hydroxyl, amino, $C_1$-$C_6$-alkyl, $C_1$-$C_6$-haloalkyl, $C_3$-$C_6$-cycloalkyl (which is optionally substituted by halogen, cyano, $C_1$-$C_6$-alkyl and $C_3$-$C_6$-cycloalkyl), $C_1$-$C_6$-alkoxy or $C_1$-$C_6$-haloalkoxy, hetaryl-$C_1$-$C_6$-alkyl optionally substituted by halogen, cyano (including in the $C_1$-$C_6$-alkyl moiety of hetaryl-$C_1$-$C_6$-alkyl), nitro, hydroxyl, $C_1$-$C_6$-alkyl, $C_1$-$C_6$-haloalkyl, $C_3$-$C_6$-cycloalkyl (which is optionally substituted by halogen, cyano, $C_1$-$C_6$-alkyl and $C_3$-$C_6$-cycloalkyl), $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulphinyl, $C_1$-$C_6$-alkylsulphonyl, $C_1$-$C_6$-haloalkylsulphinyl, $C_1$-$C_6$-haloalkylsulphonyl, amino, $C_1$-$C_6$-alkylamino, di-($C_1$-$C_6$-alkyl)amino, $C_1$-$C_6$-alkylcarbonylamino, $C_1$-$C_6$-alkoxycarbonylamino, $C_1$-$C_6$-alkoxy-$C_1$-$C_6$-alkyl, $C_1$-$C_6$-haloalkoxy-$C_1$-$C_6$-alkyl, $C_2$-$C_6$-alkenyl, $C_2$-$C_6$-alkynyl, $C_3$-$C_6$-cycloalkyl-$C_1$-$C_6$-alkyl, $C_1$-$C_6$-alkylcarbonyl, $C_1$-$C_6$-alkoxycarbonyl or aminocarbonyl, and in the case that $R^2$ is c), d) or f)

$R^{22}$ is a D radical from the group of (D-1) to (D-3)

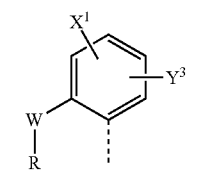
(D-1)

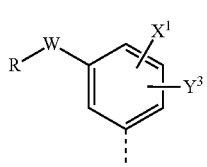
(D-2)

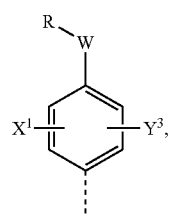
(D-3)

is an E radical from the group of (E-1) to (E-11)

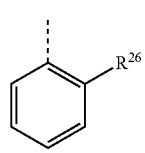
E-1

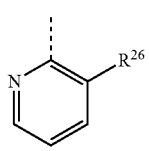
E-2

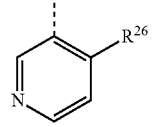
E-3

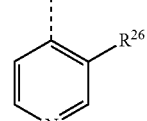
E-4

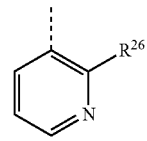
E-5

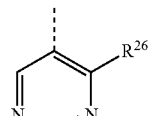
E-6

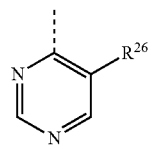
E-7

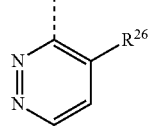
E-8

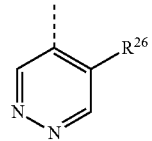
E-9

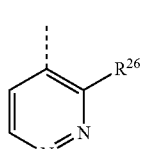
E-10

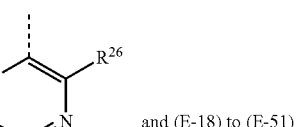
E-11 and (E-18) to (E-51)

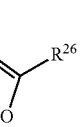
E-18

| | | |
|---|---|---|
| E-19 | 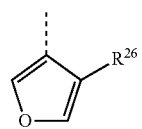 | E-30 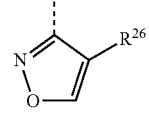 |
| E-20 | 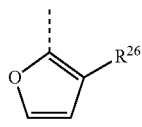 | E-31 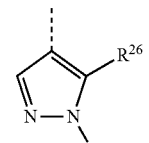 |
| E-21 | 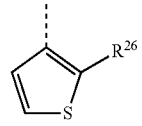 | E-32 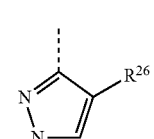 |
| E-22 | 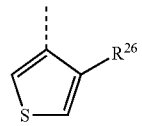 | E-33 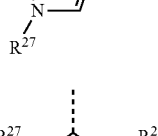 |
| E-23 | 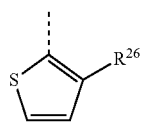 | E-34 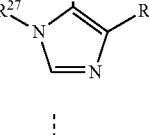 |
| E-24 | 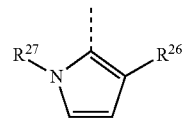 | E-35 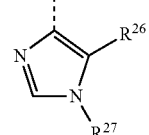 |
| E-25 | 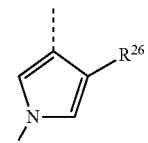 | E-36 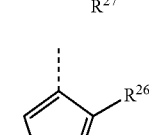 |
| E-26 | 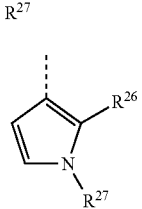 | E-37 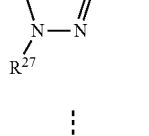 |
| E-27 | 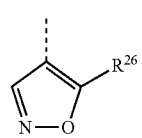 | |
| E-28 | 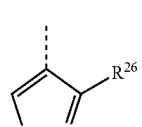 | E-38 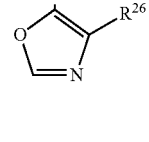 |
| E-29 | 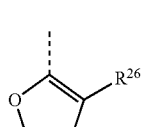 | E-39 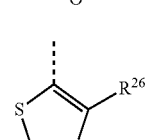 |

-continued

E-40 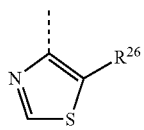

E-41 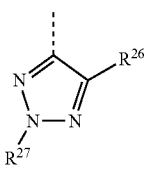

E-42 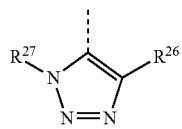

E-43 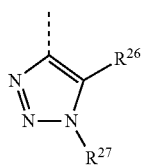

E-44 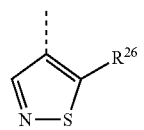

E-45 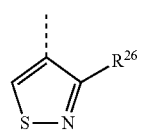

E-46 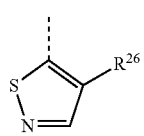

E-47 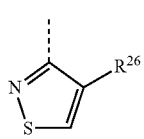

E-48 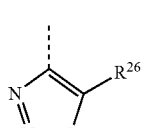

E-49 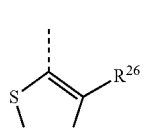

E-50 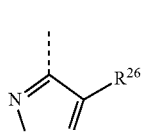

-continued

E-51 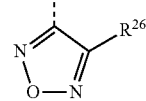

or in the case that $R^2$=d)
$R^{22}$ is also an E radical from the group of E-12 to E-17

E-12 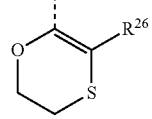

E-13 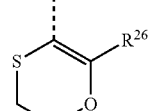

E-14 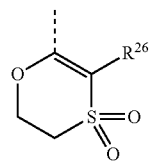

E-15 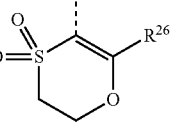

E-16 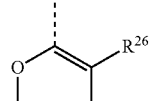

E-17 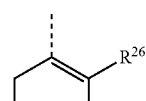

$R^{20}$ is a radical from the group of hydrogen, halogen, cyano, nitro, amino, hydroxyl, $C_1$-$C_6$-alkyl, $C_1$-$C_6$-haloalkyl, cyano-$C_1$-$C_6$-alkyl, $C_2$-$C_6$-alkenyl, $C_2$-$C_6$-alkynyl, $C_3$-$C_6$-cycloalkyl (which is optionally substituted by halogen, cyano, $C_1$-$C_4$-alkyl and $C_3$-$C_6$-cycloalkyl), $C_3$-$C_6$-cycloalkyl-$C_1$-$C_6$-alkyl, $C_1$-$C_6$-alkoxy, $C_1$-$C_6$-haloalkoxy, $C_3$-$C_6$-alkenyloxy, $C_3$-$C_6$-alkynyloxy, $C_3$-$C_6$-cycloalkyloxy, $C_1$-$C_6$-alkylcarbonyloxy, $C_2$-$C_6$-alkenylcarbonyloxy, $C_2$-$C_6$-alkynylcarbonyloxy, $C_3$-$C_6$-cycloalkylcarbonyloxy, $C_1$-$C_6$-alkoxycarbonyloxy, $C_1$-$C_6$-alkylsulphonyloxy, $C_1$-$C_6$-alkylamino, $C_3$-$C_6$-alkenylamino, $C_3$-$C_6$-alkynylamino, $C_3$-$C_6$-cycloalkylamino, $C_1$-$C_6$-alkylthio, $C_1$-$C_6$-haloalkylthio, $C_3$-$C_6$-alkenylthio, $C_3$-$C_6$-alkynylthio, $C_3$-$C_6$-cycloalkylthio, $C_1$-$C_6$-alkylsulphinyl, $C_1$-$C_6$-alkylsulphonyl, $C_1$-$C_6$-alkylcarbonyl, $C_1$-$C_6$-alkoxyimino-$C_1$-$C_6$-alkyl, $C_1$-$C_6$-alkoxycarbonyl, aminocarbonyl, $C_1$-$C_6$-alkyl aminocarbonyl, di-(C₁-C₆-alkyl)aminocarbonyl, aminothiocarbonyl, C₁-C₆-alkylaminosulphonyl, C₁-C₆-alkyl sulphonylamino, C₁-C₆-alkylcarbonylamino, C₁-C₆-alkylthiocarbonylamino, and phenyl, phenoxy, pyridinyl and pyridinyloxy each optionally substituted by a radical from the group of halogen, cyano, nitro, amino, hydroxyl, C₁-C₆-alkyl and C₁-C₆-haloalkyl, R²¹ is a radical from the group of hydrogen, C₁-C₆-alkyl, C₃-C₆-cycloalkyl, C₁-C₆-haloalkyl, C₃-C₆-alkenyl, C₂-C₆-alkynyl, C₃-C₆-cycloalkyl-C₁-C₆-alkyl, cyano-C₁-C₆-alkyl, C₁-C₆-alkylcarbonyl, C₂-C₆-alkenylcarbonyl, C₁-C₆-haloalkylcarbonyl, C₂-C₆-haloalkenylcarbonyl, C₁-C₆-alkoxy-C₁-C₆-alkyl, C₁-C₆-alkoxycarbonyl, C₁-C₆-alkylsulphonyl and C₁-C₆-haloalkylsulphonyl, R²³ is a radical from the group of hydrogen, C₁-C₆-alkyl, C₂-C₄-alkenyl, C₂-C₄-alkynyl, C₃-C₆-cycloalkyl, C₃-C₆-cycloalkenyl, C₁-C₆-alkoxy, C₂-C₆-alkenyloxy, C₂-C₆-alkynyloxy, C₃-C₆-cycloalkyloxy, C₁-C₄-alkylthio-C₁-C₄-alkyl, C₂-C₄-alkenylthio-C₁-C₄-alkyl, cyano-C₁-C₄-alkyl, C₁-C₄-alkoxy-C₁-C₄-alkyl, or, when R²=f), R²² and R²³ together with the nitrogen atom to which they are bonded form a saturated ring which may contain one or two further heteroatoms from the group of nitrogen, oxygen and sulphur, and R²⁴ is hydrogen or an in each case optionally halogen- or cyano-substituted radical from the group of C₁-C₄-alkyl, C₂-C₆-alkenyl, C₂-C₆-alkynyl, phenyl and phenyl-C₁-C₂-alkyl, R²⁵ is hydrogen or an in each case optionally halogen- or cyano-substituted radical from the group of C₁-C₄-alkyl, C₂-C₆-alkenyl, C₂-C₆-alkynyl, phenyl and phenyl-C₁-C₂-alkyl, R²⁷ is hydrogen or C₁-C₄-alkyl and R²⁶ is a radical from the group of hydrogen, C₁-C₄-alkyl, C₁-C₄-haloalkyl, C₂-C₄-alkenyl, C₂-C₄-alkynyl, C₃-C₆-cycloalkyl, C₃-C₆-cycloalkyl-C₁-C₄-alkyl, C₁-C₄-alkoxy-C₁-C₂-alkyl, C₁-C₆-alkylsulphanyl, C₁-C₆-haloalkylsulphanyl C₁-C₆-alkylsulphinyl, C₁-C₆-haloalkylsulphinyl, C₁-C₆-alkylsulphonyl, C₁-C₄-alkylthio-C₁-C₂-alkyl, C₁-C₄-alkylsulphinyl-C₁-C₂-alkyl, C₁-C₄-alkylsulphonyl-C₁-C₂-alkyl and cyano-C₁-C₂-alkyl.

Area of preference (2): Particular preference is given to compounds of the formula (I) in which A is an A radical from the group of (A-b) and (A-f)

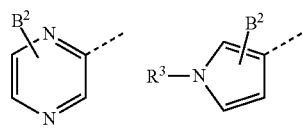

(A-b) (A-f)

in which the broken line denotes the bond to the carbon atom of the bicyclic system of the formula (I), B² is a radical from the group of hydrogen, halogen, C₁-C₆-alkyl and C₁-C₄-haloalkyl, Q is sulphur, R¹ is a radical from the group of hydrogen, C₁-C₄-alkyl and C₁-C₄-alkoxy, R² a) is a B radical from the group of

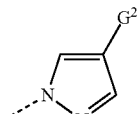
(B-2)

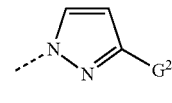
(B-1)

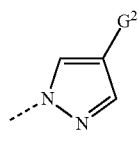
(B-2)

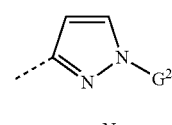
(B-3)

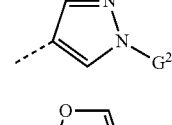
(B-4)

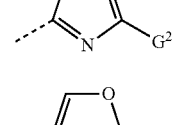
(B-5)

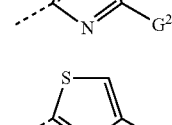
(B-6)

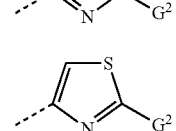
(B-7)

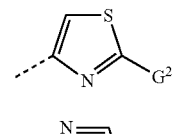
(B-8)

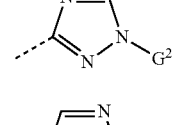
(B-9)

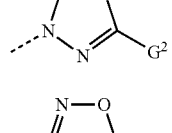
(B-10)

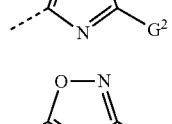
(B-11)

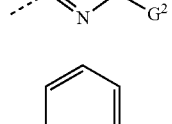
(B-12)

(B-21)

-continued
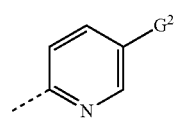 (B-22)
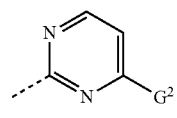 (B-23)
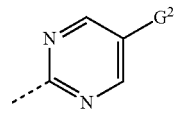 (B-24)
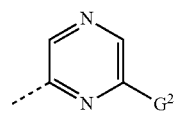 (B-25)
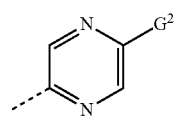 (B-26)
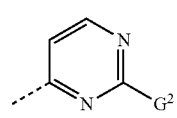 (B-27)
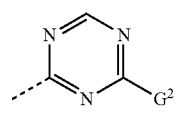 (B-28)
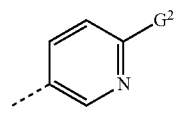 (B-31)
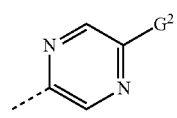 (B-32)
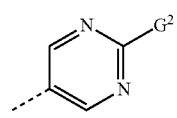 (B-33)
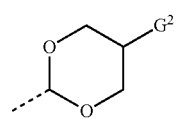 (B-34)
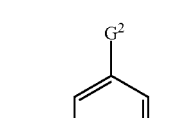 (B-35)
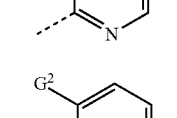 (B-36)
-continued
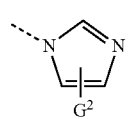 (B-37)
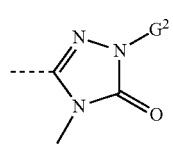 (B-38)
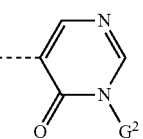 (B-39)
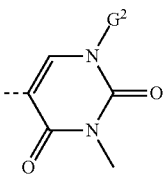 (B-40)
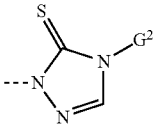 (B-41)
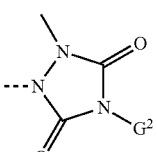 (B-42)
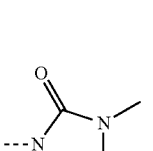 (B-43)
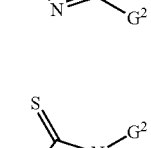 (B-44)
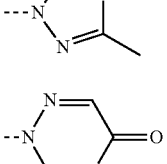 (B-45)
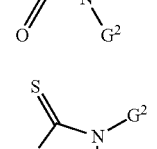 (B-46)

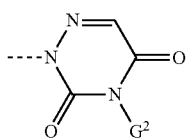
(B-47)

in which the broken line denotes the bond to the carbon atom of the bicyclic system of the formula (I), or $R^2$ b) is a D radical from the group of (D-1) to (D-3)

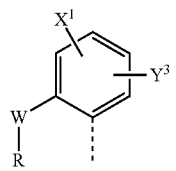
(D-1)

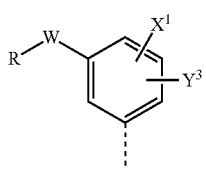
(D-2)

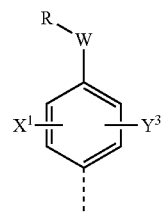
(D-3)

in which the broken line denotes the bond to the carbon atom of the bicyclic system of the formula (I), or $R^2$ c) is a radical of the formula

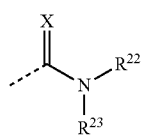

in which the broken line denotes the bond to the carbon atom of the bicyclic system of the formula (I), or $R^2$ d) is a radical of the formula

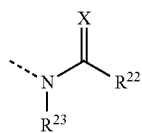

in which the broken line denotes the bond to the carbon atom of the bicyclic system of the formula (I), or $R^2$ e) is a radical from the group of (F-1), (F-8) and (F-10)

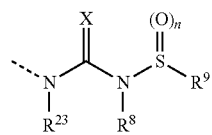
(F-1)

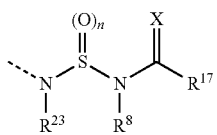
(F-8)

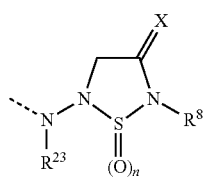
(F-10)

in which the broken line denotes the bond to the carbon atom in the formula (I), or $R^2$ f) is a radical of the formula

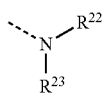

in which the broken line denotes the bond to the carbon atom of the bicyclic system of the formula (I), or $R^2$ g) is a radical of the formula in which the broken line denotes the bond to the carbon atom of the bicyclic system of the formula (I), in which $G^2$ is hydrogen or a radical from the group of halogen, nitro, amino, cyano, $C_1$-$C_4$-alkylamino, halo-$C_1$-$C_4$-alkylamino, di-($C_1$-$C_4$-alkyl)amino, $C_1$-$C_4$-alkyl, halo-$C_1$-$C_4$-alkyl, $C_1$-$C_4$-alkoxy, halo-$C_1$-$C_4$-alkoxy, $C_1$-$C_4$-alkoxy-$C_1$-$C_4$-alkyl, halogenated $C_1$-$C_4$-alkoxy-$C_1$-$C_4$-alkyl, bis($C_1$-$C_4$-alkoxy)-$C_1$-$C_4$-alkyl, bis(halo-$C_1$-$C_4$-alkoxy)-$C_1$-$C_4$-alkyl, $C_1$-$C_4$-alkoxy-($C_1$-$C_4$-alkylsulphanyl)-$C_1$-$C_4$-alkyl, $C_1$-$C_4$-alkoxy-($C_1$-$C_4$-alkylsulphinyl)-$C_1$-$C_4$-alkyl, $C_1$-$C_4$-alkoxy-($C_1$-$C_4$-alkylsulphonyl)-$C_1$-$C_4$-alkyl, bis($C_1$-$C_4$-alkylsulphanyl)-$C_1$-$C_4$-alkyl, bis(halo-$C_1$-$C_4$-alkylsulphanyl)-$C_1$-$C_4$-alkyl, bis(hydroxy-$C_1$-$C_4$-alkylsulphanyl)-$C_1$-$C_4$-alkyl, $C_1$-$C_4$-alkoxycarbonyl, $C_1$-$C_4$-alkoxycarbonyl-$C_1$-$C_4$-alkyl, $C(X^2)NR^3R^4$, $NR^6R^7$, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, the heterocyclyl radicals dioxanyl, dioxolanyl, dioxepanyl, dioxocanyl, oxathianyl, oxathiolanyl, oxathiepanyl, oxathiocanyl, dithianyl, dithiolanyl, dithiepanyl, dithiocanyl, oxathianyl oxide, oxathiolanyl oxide, oxathiepanyl oxide, oxathiocanyl oxide, oxathianyl dioxide, oxathiolanyl dioxide, oxathiepanyl dioxide, oxathiocanyl dioxide, morpholinyl, triazolinonyl, oxazolinyl, dihydrooxadiazinyl, dihydrodioxazinyl, dihydrooxazolyl, dihydrooxazinyl and pyrazolinonyl (which for their part may in turn be substituted by $C_1$-$C_4$-alkyl, halo-$C_1$-$C_4$-alkyl, $C_1$-$C_4$-alkoxy and $C_1$-$C_4$-alkoxy-$C_1$-$C_4$-alkyl), phenyl (which for its part may in turn be substituted by halogen, cyano, nitro, $C_1$-$C_4$-alkyl and halo-$C_1$-$C_4$-alkyl), the heteroaryl radicals pyridyl, pyridyl N-oxide, pyrimidyl, imidazolyl, pyrazolyl, oxazolyl, thiazolyl, furanyl, thienyl, triazolyl, tetrazolyl, oxadiazolyl, thiadiazolyl, pyrazinyl, triazinyl, tetrazinyl and isoquinolinyl (which for their part may in turn be substituted by halogen, nitro, $C_1$-$C_4$-alkyl, halo-$C_1$-$C_4$-alkyl, $C_1$-$C_4$-alkoxy, halo-$C_1$-$C_4$-alkoxy, $C_1$-$C_4$-alkoxy-$C_1$-$C_4$-alkyl, $C_1$-$C_4$-alkylthio, $C_1$-$C_4$-alkylthio-$C_1$-$C_4$-alkyl and $C_3$-$C_6$-cycloalkyl) and the heteroaryl-$C_1$-$C_4$-alkyl radicals triazolyl-$C_1$-$C_4$-alkyl, pyridyl-$C_1$-$C_4$-alkyl, pyrimidyl-$C_1$-$C_4$-alkyl and oxadiazolyl-$C_1$-$C_4$-alkyl (which for their part may in turn be substituted by halogen and $C_1$-$C_4$-alkyl),
or $G^2$ is a C radical from the group of (C-1), (C-6) and (C-9)

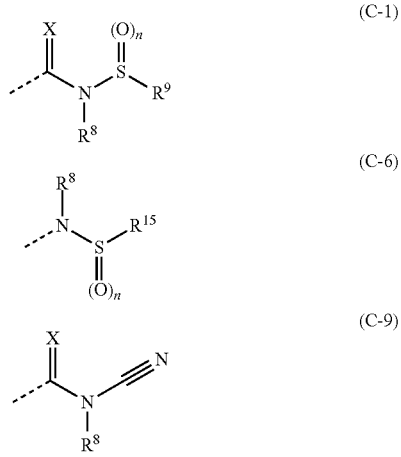

in which the broken line denotes the bond to the B radicals, $G^3$ is a radical from the group of hydrogen, halogen, $C_1$-$C_6$-alkyl and $C_1$-$C_6$-haloalkyl, X is oxygen, $X^1$ is a radical from the group of hydrogen, fluorine, chlorine, bromine, iodine, cyano, nitro, $C_1$-$C_4$-alkyl, $C_1$-$C_4$-haloalkyl, $C_3$-$C_6$-cycloalkyl, $C_1$-$C_4$-alkoxy and $C_1$-$C_4$-haloalkoxy, $X^2$ is oxygen, sulphur, $NR^5$ or NOH, n is 2, R is $NR^{18}R^{19}$ or is in each case optionally mono- to hepta-halogen-substituted, mono- or di-oxygen-substituted (leads to C=O) or mono- or di-cyano-substituted $C_1$-$C_6$-alkyl, $C_3$-$C_6$-alkenyl, $C_3$-$C_6$-alkynyl, $C_1$-$C_4$-alkoxy-$C_1$-$C_3$-alkyl, $C_1$-$C_4$-alkyl-S—$C_1$-$C_3$-alkyl, $C_1$-$C_4$-alkyl-S(O)—$C_1$-$C_3$-alkyl, $C_1$-$C_4$-alkyl-S(O)$_2$—$C_1$-$C_3$-alkyl, is $R^{18}$—CO—$C_1$-$C_2$-alkyl, is $NR^{18}R^{19}$—CO—$C_1$-$C_2$-alkyl, is optionally mono- or di-oxygen- (leads to C=O), —$C_1$-$C_4$-alkyl-, —$C_3$-$C_6$-cycloalkyl-, —$C_1$-$C_4$-alkoxy- and —$C_1$-$C_4$-haloalkyl-substituted $C_3$-$C_6$-cycloalkyl, is optionally mono- or di-oxygen- (leads to C=O), —$C_1$-$C_4$-alkyl-, —$C_3$-$C_6$-cycloalkyl-, —$C_1$-$C_4$-alkoxy- and —$C_1$-$C_4$-haloalkyl-substituted $C_3$-$C_8$-cycloalkenyl, is optionally mono- or di-oxygen- (leads to C=O), —$C_1$-$C_4$-alkyl-, —$C_3$-$C_6$-cycloalkyl-, —$C_1$-$C_4$-alkoxy- and —$C_1$-$C_4$-haloalkyl-substituted $C_3$-$C_6$-cycloalkyl-$C_1$-$C_4$-alkyl, is optionally mono- or di-oxygen- (leads to C=O), —$C_1$-$C_4$-alkyl-, —$C_3$-$C_6$-cycloalkyl-, —$C_1$-$C_4$-alkoxy- and —$C_1$-$C_4$-haloalkyl-substituted $C_3$-$C_6$-cycloalkenyl-$C_1$-$C_4$-alkyl, is optionally mono- or di-oxygen- (leads to C=O), —$C_1$-$C_4$-alkyl-, —$C_3$-$C_6$-cycloalkyl-, —$C_1$-$C_4$-alkoxy- and —$C_1$-$C_4$-haloalkyl-substituted heterocyclyl, is optionally mono- or di-oxygen- (leads to C=O), —$C_1$-$C_4$-alkyl-, —$C_3$-$C_6$-cycloalkyl-, —$C_1$-$C_4$-alkoxy- and —$C_1$-$C_4$-haloalkyl-substituted heterocyclyl-$C_1$-$C_4$-alkyl or is in each case optionally mono- to tri-halogen-, -cyano-, —$C_1$-$C_4$-alkyl-, —$C_1$-$C_4$-haloalkyl-, —$C_3$-$C_6$-cycloalkyl-, —$C_1$-$C_4$-alkoxy- or —$C_1$-$C_4$-haloalkoxy-substituted phenyl, phenyl-$C_1$-$C_4$-alkyl, hetaryl and hetaryl-$C_1$-$C_4$-alkyl, $R^3$ is $C_1$-$C_4$-alkyl, $R^4$ is a radical from the group of hydrogen, $C_1$-$C_4$-alkyl, halo-$C_1$-$C_4$-alkyl, cyano-$C_1$-$C_4$-alkyl, $C_2$-$C_4$-alkynyl, $C_3$-$C_6$-cycloalkyl, $C_3$-$C_6$-cycloalkyl-$C_1$-$C_4$-alkyl, $C_1$-$C_4$-alkoxy-$C_1$-$C_4$-alkyl, $C_1$-$C_4$-alkoxycarbonyl, $C_1$-$C_4$-alkoxycarbonyl-$C_1$-$C_4$-alkyl and $C_1$-$C_4$-alkylthio-$C_1$-$C_4$-alkyl, $R^5$ is a radical from the group of hydrogen, $C_1$-$C_4$-alkyl, halo-$C_1$-$C_4$-alkyl, cyano-$C_1$-$C_4$-alkyl, $C_2$-$C_4$-alkynyl, $C_3$-$C_6$-cycloalkyl, $C_3$-$C_6$-cycloalkyl-$C_1$-$C_4$-alkyl, $C_1$-$C_4$-alkoxy-$C_1$-$C_4$-alkyl, $C_1$-$C_4$-alkoxycarbonyl, $C_1$-$C_4$-alkoxycarbonyl-$C_1$-$C_4$-alkyl and $C_1$-$C_4$-alkylthio-$C_1$-$C_4$-alkyl, $R^6$ is hydrogen or $C_1$-$C_4$-alkyl, $R^7$ is a radical from the group of hydrogen, $C_1$-$C_4$-alkyl, halo-$C_1$-$C_4$-alkyl, cyano-$C_1$-$C_4$-alkyl, $C_2$-$C_4$-alkynyl, $C_1$-$C_4$-alkoxy, halo-$C_1$-$C_4$-alkoxy, $C_1$-$C_4$-alkoxy-$C_1$-$C_4$-alkyl, $C_1$-$C_4$-alkoxycarbonyl, $C_1$-$C_4$-alkoxycarbonyl-$C_1$-$C_4$-alkyl, $C_1$-$C_4$-alkylthio-$C_1$-$C_4$-alkyl, aryl-$C_1$-$C_4$-alkyl or hetaryl-$C_1$-$C_4$-alkyl, or $R^6$ and $R^7$ together with the nitrogen atom to which they are bonded form a 4- to 7-membered ring which may contain one or two further heteroatoms from the group of nitrogen, oxygen and sulphur (where oxygen and sulphur atoms must not be directly adjacent to one another), $R^8$ is a radical from the group of hydrogen, $C_1$-$C_6$-alkyl, $C_1$-$C_6$-haloalkyl, cyano-$C_1$-$C_6$-alkyl, $C_1$-$C_6$-alkoxy, $C_1$-$C_6$-haloalkoxy, $C_2$-$C_6$-alkenyl, $C_1$-$C_6$-alkoxy-$C_1$-$C_6$-alkyl, in each case optionally halogen-substituted $C_1$-$C_6$-alkylcarbonyl and $C_1$-$C_6$-alkylsulphonyl, optionally halogen-substituted $C_1$-$C_6$-alkoxycarbonyl and optionally halogen-, $C_1$-$C_6$-alkyl-, $C_1$-$C_6$-alkoxy-, $C_1$-$C_6$-haloalkyl- and cyano-substituted $C_3$-$C_6$-cycloalkylcarbonyl, or is a cation or an optionally $C_1$-$C_6$-alkyl- or aryl-$C_1$-$C_6$-alkyl-substituted ammonium ion, $R^9$ is a radical from the group of in each case optionally halogen-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-haloalkylsulphinyl-, $C_1$-$C_4$-alkylsulphonyl- and $C_1$-$C_4$-haloalkylsulphonyl-substituted $C_1$-$C_4$-alkyl, $C_2$-$C_4$-alkenyl and $C_2$-$C_4$-alkynyl, in each case optionally halogen-, $C_1$-$C_4$-alkyl-, $C_1$-$C_4$-haloalkyl-, $C_1$-$C_4$-alkoxy-, $C_1$-$C_4$-haloalkoxy-substituted $C_3$-$C_6$-cycloalkyl, $C_3$-$C_6$-cycloalkyl-$C_1$-$C_4$-alkyl and $C_3$-$C_4$-cycloalkenyl, in which one or two ring members may each be replaced by a heteroatom from the group of sulphur, oxygen (where oxygen atoms must not be directly adjacent to one another) and nitrogen (and in this case is especially

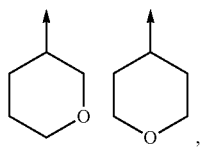

where the arrow in each case denotes the bond to the sulphur atom in the (C-1) radical and in the (F-1) radical), in each case optionally halogen-, cyano- (including in the alkyl moiety), nitro-, $C_1$-$C_4$-alkyl-, $C_1$-$C_4$-haloalkyl-, $C_3$-$C_6$-cycloalkyl-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-haloalkylsulphinyl-, $C_1$-$C_4$-alkyl sulphonyl-, $C_1$-$C_4$-haloalkylsulphonyl-, amino-, $C_1$-$C_4$-alkyl amino-, di($C_1$-$C_4$-alkyl)amino-, $C_1$-$C_4$-alkylcarbonylamino-, $C_1$-$C_4$-alkoxycarbonylamino-, $C_1$-$C_4$-alkoxy-$C_1$-$C_4$-alkyl-, $C_1$-$C_4$-haloalkoxy-$C_1$-$C_4$-alkyl-, $C_2$-$C_4$-alkenyl-, $C_2$-$C_4$-alkynyl-, $C_3$-$C_6$-cycloalkyl-$C_1$-$C_4$-alkyl-, $C_1$-$C_4$-alkylcarbonyl-, $C_1$-$C_4$-alkoxycarbonyl- or aminocarbonyl-substituted aryl, heteroaryl, aryl-$C_1$-$C_4$-alkyl and heteroaryl-$C_1$-$C_4$-alkyl, or is NR'R" in which R' and R" are independently a radical from the group of hydrogen and $C_1$-$C_4$-alkyl, or $R^8$ and $R^9$ in the (C-1) radical and in the (F-1) radical, together with the N—S(O)n group to which they are bonded, may also form a saturated or unsaturated and optionally halogen-, $C_1$-$C_6$-alkyl-, $C_1$-$C_6$-haloalkyl-, $C_1$-$C_6$-alkoxy-, $C_1$-$C_6$-haloalkoxy-substituted 5- to 7-membered ring which may contain one or two heteroatoms from the group of sulphur, oxygen (where oxygen atoms must not be directly adjacent to one another) and nitrogen and/or at least one and preferably exactly one carbonyl group; $R^8$ and $R^9$ together with the N—S(O)n group to which they are bonded may especially be a radical from the group of

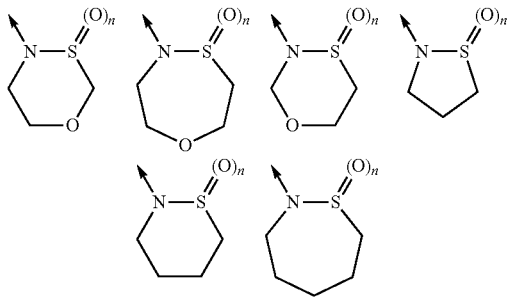

(in which the arrow in each case denotes the bond to the C(X) group), $R^{15}$ is a radical from the group of in each case optionally methyl-substituted $C_1$-$C_6$-alkyl, $C_2$-$C_6$-alkenyl and $C_2$-$C_6$-alkynyl and in each case optionally methyl-, halogen-, cyano- or carbamoyl-substituted $C_3$-$C_6$-cycloalkyl, $C_3$-$C_6$-cycloalkyl-$C_1$-$C_2$-alkyl and $C_3$-$C_6$-cycloalkenyl, $R^8$ and $R^{15}$ in the (C-6) radical, together with the N—S(O)n group to which they are bonded, may also form a saturated or unsaturated and optionally substituted 4- to 8-membered ring which may contain one or two further heteroatoms from the group of sulphur, oxygen (where oxygen and sulphur atoms must not be directly adjacent to one another) and nitrogen and/or at least one carbonyl group, $R^{17}$ is a radical from the group of optionally halogen-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-haloalkylsulphinyl-, $C_1$-$C_4$-alkylsulphonyl- and $C_1$-$C_4$-haloalkylsulphonyl-substituted $C_1$-$C_4$-alkyl, $C_2$-$C_4$-alkenyl and $C_2$-$C_4$-alkynyl, in each case optionally halogen-, $C_1$-$C_4$-alkyl-, $C_1$-$C_4$-haloalkyl-, $C_1$-$C_4$-alkoxy-, $C_1$-$C_4$-haloalkoxy-substituted $C_3$-$C_6$-cycloalkyl, $C_3$-$C_6$-cycloalkyl-$C_1$-$C_4$-alkyl, $C_3$-$C_4$-cycloalkenyl, N-pyrrolidinyl, N-piperidinyl, N-morpholinyl, N-thiomorpholinyl, N-thiomorpholinyl 1-oxide, N-thiomorpholinyl 1,1-dioxide, N-piperazinyl, N-1-methylpiperazinyl and N-2-oxo-1-methylpiperazinyl, in each case optionally halogen-, cyano- (including in the alkyl moiety), nitro-, $C_1$-$C_4$-alkyl-, $C_1$-$C_4$-haloalkyl-, $C_3$-$C_6$-cycloalkyl-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-haloalkylsulphinyl-, $C_1$-$C_4$-alkylsulphonyl-, $C_1$-$C_4$-haloalkylsulphonyl-, amino-, $C_1$-$C_4$-alkylamino-, di-($C_1$-$C_4$-alkyl)amino-, $C_1$-$C_4$-alkylcarbonylamino-, $C_1$-$C_4$-alkoxycarbonylamino-, $C_1$-$C_4$-alkoxy-$C_1$-$C_4$-alkyl-, $C_1$-$C_4$-haloalkoxy-$C_1$-$C_4$-alkyl-, $C_2$-$C_4$-alkenyl-, $C_2$-$C_4$-alkynyl-, $C_3$-$C_6$-cycloalkyl-$C_1$-$C_4$-alkyl-, $C_1$-$C_4$-alkylcarbonyl-, $C_1$-$C_4$-alkoxycarbonyl- or aminocarbonyl-substituted aryl, heteroaryl, aryl-$C_1$-$C_4$-alkyl and heteroaryl-$C_1$-$C_4$-alkyl, or is NR'R" in which R' and R" are independently a radical from the group of hydrogen and $C_1$-$C_4$-alkyl, $R^{18}$ is a radical from the group of hydrogen, hydroxyl, in each case optionally mono- or poly-halogen-substituted or mono- or di-cyano-substituted $C_1$-$C_4$-alkyl, $C_1$-$C_4$-alkoxy, $C_1$-$C_4$-alkoxy-$C_1$-$C_4$-alkyl, $C_1$-$C_4$-alkyl-S—$C_1$-$C_3$-alkyl, $C_1$-$C_4$-alkyl-S(O)—$C_1$-$C_3$-alkyl, $C_1$-$C_4$-alkyl-S(O)$_2$—$C_1$-$C_3$-alkyl, $C_1$-$C_4$-alkylcarbonyl, $C_1$-$C_4$-alkoxycarbonyl, $C_3$-$C_6$-cycloalkyl, $C_3$-$C_6$-cycloalkyl-$C_1$-$C_3$-alkyl, heterocyclyl, heterocyclyl-$C_1$-$C_3$-alkyl and in each case optionally mono- to tri-$C_1$-$C_4$-alkyl-, —$C_1$-$C_3$-haloalkyl-, —$C_1$-$C_3$-alkoxy-, —$C_1$-$C_3$-haloalkoxy-, -cyclopropyl-, -fluorine-, -chlorine-, -bromine- or -cyano-substituted phenyl, benzyl, pyridyl, pyrimidyl, thiazolyl, oxazolyl, pyrazolyl, thienyl, furanyl, pyridinylmethyl and thiazolylmethyl, $R^{19}$ is hydrogen, is an alkali metal or alkaline earth metal ion, or is an optionally mono- to tetra-$C_1$-$C_4$-alkyl-substituted ammonium ion or an in each case optionally mono- or poly-halogen-substituted or mono- or di-cyano-substituted radical from the group of $C_1$-$C_4$-alkyl, $C_1$-$C_4$-alkoxy, $C_1$-$C_4$-alkoxy-$C_1$-$C_2$-alkyl, $C_1$-$C_4$-alkyl-S—$C_1$-$C_2$-alkyl, $C_1$-$C_4$-alkyl-S(O)—$C_1$-$C_2$-alkyl and $C_1$-$C_4$-alkyl-S(O)$_2$—$C_1$-$C_2$-alkyl, $Y^3$ is a radical from the group of hydrogen, fluorine, chlorine, bromine, iodine, cyano, $C_1$-$C_4$-alkyl, $C_1$-$C_4$-haloalkyl, $C_3$-$C_6$-cycloalkyl, $C_1$-$C_4$-alkoxy and $C_1$-$C_4$-haloalkoxy, W is a radical from the group of S, SO and SO$_2$, $R^{22}$ is a radical from the group of hydrogen, $C_1$-$C_4$-alkyl, $C_2$-$C_4$-haloalkyl, cyano-$C_1$-$C_4$-alkyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkoxy, $C_1$-$C_4$-haloalkoxy, optionally halogen-substituted $C_1$-$C_2$-alkoxy-$C_1$-$C_4$-alkyl, optionally halogen-substituted bis($C_1$-$C_2$-alkoxy)-$C_1$-$C_4$-alkyl, optionally halogen-substituted $C_1$-$C_4$-alkylsulphanyl-$C_1$-$C_4$-alkyl, optionally halogen-substituted $C_1$-$C_4$-alkylcarbonyl-$C_1$-$C_4$-alkyl, optionally halogen-substituted $C_1$-$C_4$-alkylsulphinyl-$C_1$-$C_4$-alkyl, optionally halogen-substituted $C_1$-$C_4$-alkylsulphonyl-$C_1$-$C_4$-alkyl, di-($C_1$-$C_4$-alkyl)aminosulphanyl-$C_1$-$C_4$-alkyl, di-($C_1$-$C_4$-alkyl)aminosulphinyl-$C_1$-$C_4$-alkyl, di-($C_1$-$C_4$-alkyl)aminosulphonyl-$C_1$-$C_4$-alkyl, optionally halogen-substituted $C_1$-$C_4$-alkoxycarbonyl, optionally halogen-substituted $C_1$-$C_4$-alkoxycarbonyl-$C_1$-$C_4$-alkyl, optionally halogen-substituted $C_2$-$C_4$-alkynyloxy, optionally halogen-substituted $C_2$-$C_4$-alkynyloxycarbonyl, di-($C_1$-$C_4$-alkyl)-aminocarbonyl, N—$C_1$-$C_4$-alkyl-N—$C_3$-$C_6$-cycloalkylaminocarbonyl, di-($C_1$-$C_4$-alkyl)-aminocarbonyl-$C_1$-$C_4$-alkyl, N—$C_1$-$C_4$-alkyl-N—$C_3$-$C_6$-cycloalkylaminocarbonyl-$C_1$-$C_4$-alkyl, heterocyclylcarbonyl-$C_1$-$C_4$-alkyl, $C_1$-$C_4$-alkylsulphanyl, $C_1$-$C_4$-haloalkylsulphanyl, $C_1$-$C_4$-alkylsulphinyl, $C_1$-$C_4$-haloalkylsulphinyl, $C_1$-$C_4$-alkylsulphonyl, $C_1$-$C_4$-haloalkylsulphonyl, $C_3$-$C_6$-cycloalkyl optionally substituted by halogen, cyano, nitro, $C_1$-$C_4$-alkyl, $C_1$-$C_4$-haloalkyl, $C_3$-$C_6$-cycloalkyl, $C_1$-$C_4$-alkoxy, $C_1$-$C_4$-haloalkoxy, $C_1$-$C_4$-alkoxycarbonyl, $C_1$-$C_4$-haloalkoxycarbonyl or pyridyl (which for its part is optionally substituted by $C_1$-$C_4$-alkyl or halogen), $C_3$-$C_6$-cycloalkylcarbonyl optionally substituted by halogen, cyano, nitro, $C_1$-$C_4$-alkyl, $C_1$-$C_4$-haloalkyl, $C_3$-$C_6$-cycloalkyl, $C_1$-$C_4$-alkoxy, $C_1$-$C_4$-haloalkoxy, $C_1$-$C_4$-alkoxycarbonyl, $C_1$-$C_4$-haloalkoxycarbonyl or pyridyl (which for its part is optionally substituted by $C_1$-$C_4$-alkyl or halogen), $C_3$-$C_6$-cycloalkyl-$C_1$-$C_4$-alkyl optionally substituted by halogen, cyano, nitro, $C_1$-$C_4$-alkyl, $C_1$-$C_4$-haloalkyl, $C_3$-$C_6$-cycloalkyl, $C_1$-$C_4$-alkoxy, $C_1$-$C_4$-haloalkoxy, $C_1$-$C_4$-alkoxycarbonyl, $C_1$-$C_4$-haloalkoxycarbonyl, pyridyl, pyrimidyl, pyrazanyl, pyridazinyl, thiazolyl, isothiazolyl, thiadiazolyl, oxazolyl, isoxazolyl, oxadiazolyl, pyrazolyl, triazinyl or triazolyl (where the hetaryls mentioned for their part are optionally substituted by $C_1$-$C_4$-alkyl or halogen), heterocyclyl-$C_1$-$C_4$-alkyl optionally substituted by halogen, cyano (including in the $C_1$-$C_4$-alkyl moiety of heterocyclyl-$C_1$-$C_4$-alkyl), nitro, hydroxyl, $C_1$-$C_4$-alkyl, $C_1$-$C_4$-haloalkyl, $C_3$-$C_6$-cycloalkyl (which is optionally substituted by halogen, cyano, $C_1$-$C_4$-alkyl and $C_3$-$C_6$-cycloalkyl), $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulphinyl, $C_1$-$C_4$-alkylsulphonyl, $C_1$-$C_4$-haloalkylsulphinyl, $C_1$-$C_4$-haloalkylsulphonyl, amino, $C_1$-$C_4$-alkylamino, di-($C_1$-$C_4$-alkyl)amino, $C_1$-$C_4$-alkylcarbonylamino, $C_1$-$C_4$-alkoxycarbonylamino, $C_1$-$C_4$-alkoxy-$C_1$-$C_4$-alkyl, $C_1$-$C_4$-haloalkoxy-$C_1$-$C_4$-alkyl, $C_2$-$C_4$-alkenyl, $C_2$-$C_4$-alkynyl, $C_3$-$C_6$-cycloalkyl-$C_1$-$C_4$-alkyl, $C_1$-$C_4$-alkylcarbonyl, $C_1$-$C_4$-alkoxycarbonyl or aminocarbonyl, aryl optionally substituted by halogen, cyano, nitro, hydroxyl, amino, $C_1$-$C_4$-alkyl, $C_1$-$C_4$-haloalkyl, $C_3$-$C_6$-cycloalkyl (which is optionally substituted by halogen, cyano, $C_1$-$C_4$-alkyl and $C_3$-$C_6$-cycloalkyl), $C_1$-$C_4$-alkoxy or $C_1$-$C_4$-haloalkoxy, aryl-$C_1$-$C_4$-alkyl optionally substituted by halogen, cyano (including in the $C_1$-$C_4$-alkyl moiety of aryl-$C_1$-$C_4$-alkyl), nitro, hydroxyl, amino, $C_1$-$C_4$-alkyl, $C_1$-$C_4$-haloalkyl, $C_3$-$C_6$-cycloalkyl (which is optionally substituted by halogen, cyano, $C_1$-$C_4$-alkyl and $C_3$-$C_6$-cycloalkyl), $C_1$-$C_4$-alkoxy or $C_1$-$C_4$-haloalkoxy, hetaryl-$C_1$-$C_4$-alkyl optionally substituted by halogen, cyano (including in the $C_1$-$C_4$-alkyl moiety of hetaryl-$C_1$-$C_4$-alkyl), nitro, hydroxyl, $C_1$-$C_4$-alkyl, $C_1$-$C_4$-haloalkyl, $C_3$-$C_6$-cycloalkyl (which is optionally substituted by halogen, cyano, $C_1$-$C_4$-alkyl and $C_3$-$C_6$-cycloalkyl), $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulphinyl, $C_1$-$C_4$-alkylsulphonyl, $C_1$-$C_4$-haloalkylsulphinyl, $C_1$-$C_4$-haloalkylsulphonyl, amino, $C_1$-$C_4$-alkylamino, di-($C_1$-$C_4$-alkyl) amino, $C_1$-$C_4$-alkylcarbonylamino, $C_1$-$C_4$-alkoxycarbonylamino, $C_1$-$C_4$-alkoxy-$C_1$-$C_4$-alkyl, $C_1$-$C_4$-haloalkoxy-$C_1$-$C_4$-alkyl, $C_2$-$C_4$-alkenyl, $C_2$-$C_4$-alkynyl, $C_3$-$C_6$-cycloalkyl-$C_1$-$C_4$-alkyl, $C_1$-$C_4$-alkylcarbonyl, $C_1$-$C_4$-alkoxycarbonyl or aminocarbonyl, or $R^{22}$ is one of the following D radicals:

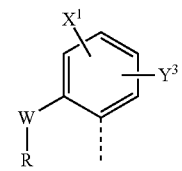
(D-1)

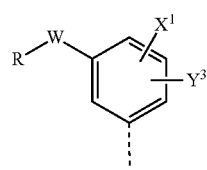
(D-2)

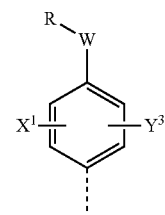
(D-3)

or one of the following E radicals:

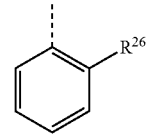
E-1

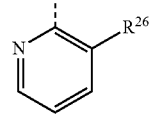
E-2

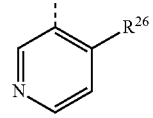
E-3

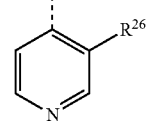
E-4

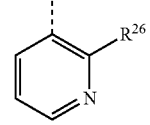
E-5

-continued

E-6 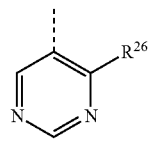

E-10 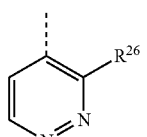

E-11 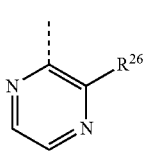

E-18 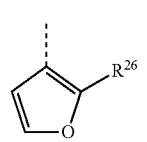

E-21 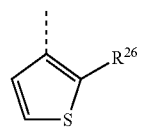

E-23 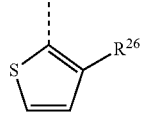

E-25 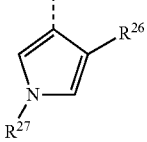

E-27 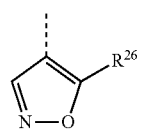

E-31 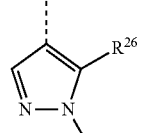

E-35 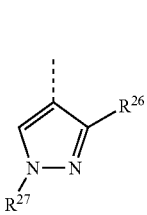

-continued

E-36 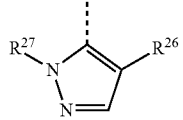

E-39 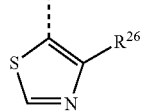

E-44 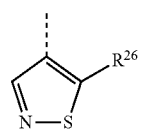

E-49 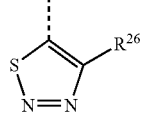

E-51 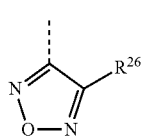

or in the case that $R^2$=d)

$R^{22}$ is also the radical

E-13 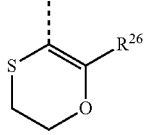

$R^{23}$ is a radical from the group of hydrogen, $C_1$-$C_6$-alkyl, $C_2$-$C_4$-alkenyl, $C_2$-$C_4$-alkynyl, $C_3$-$C_6$-cycloalkyl, $C_3$-$C_6$-cycloalkenyl, $C_1$-$C_6$-alkoxy, $C_2$-$C_6$-alkenyloxy, $C_2$-$C_6$-alkynyloxy, $C_3$-$C_6$-cycloalkyloxy, $C_1$-$C_4$-alkylthio-$C_1$-$C_4$-alkyl, $C_2$-$C_4$-alkenylthio-$C_1$-$C_4$-alkyl, cyano-$C_1$-$C_4$-alkyl and $C_1$-$C_4$-alkoxy-$C_1$-$C_4$-alkyl, or, when $R^2$=c) or f), $R^{22}$ and $R^{23}$ together with the nitrogen atom to which they are bonded form a saturated four- to six-membered ring which may contain one further heteroatom from the group of nitrogen, oxygen and sulphur, $R^{27}$ is hydrogen or $C_1$-$C_4$-alkyl and $R^{26}$ is a radical from the group of hydrogen, $C_1$-$C_4$-alkyl, $C_1$-$C_4$-haloalkyl, $C_2$-$C_4$-alkenyl, $C_2$-$C_4$-alkynyl, $C_3$-$C_6$-cycloalkyl, $C_3$-$C_6$-cycloalkyl-$C_1$-$C_4$-alkyl, $C_1$-$C_4$-alkoxy-$C_1$-$C_2$-alkyl, $C_1$-$C_4$-alkylsulphanyl, $C_1$-$C_4$-haloalkylsulphanyl, $C_1$-$C_4$-alkylsulphinyl, $C_1$-$C_4$-haloalkylsulphinyl, $C_1$-$C_4$-alkylsulphonyl, $C_1$-$C_4$-alkylthio-$C_1$-$C_2$-alkyl, $C_1$-$C_4$-alkylsulphinyl-$C_1$-$C_2$-alkyl, $C_1$-$C_4$-alkylsulphonyl-$C_1$-$C_2$-alkyl and cyano-$C_1$-$C_4$-alkyl and compounds of the formula (I) in which A is the A radical from the group of (A-a)

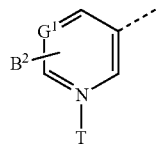 (A-a)

in which the broken line denotes the bond to the carbon atom of the bicyclic system of the formula (I), $G^1$ is N or C—$B^1$, $B^1$ is a radical from the group of hydrogen, halogen, $C_1$-$C_6$-alkyl and $C_1$-$C_4$-haloalkyl, $B^2$ is a radical from the group of hydrogen, halogen, $C_1$-$C_6$-alkyl and $C_1$-$C_4$-haloalkyl, T is oxygen or an electron pair, Q is sulphur, $R^1$ is a radical from the group of hydrogen, $C_1$-$C_4$-alkyl and $C_1$-$C_4$-alkoxy, $R^2$ a) is a B radical from the group of

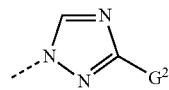 (B-1)

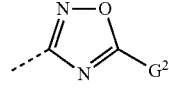 (B-2)

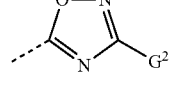 (B-3)

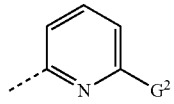 (B-4)

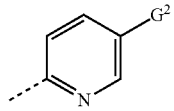 (B-5)

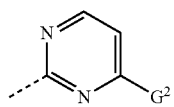 (B-6)

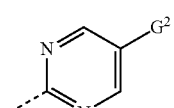 (B-7)

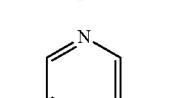 (B-8)

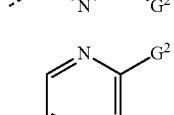 (B-9)

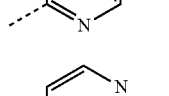 (B-10)

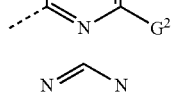 (B-11)

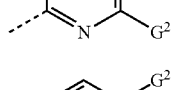 (B-12)

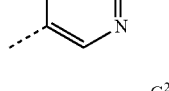 (B-21)

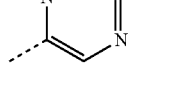 (B-22)

(B-23)

(B-24)

(B-25)

(B-26)

(B-27)

(B-28)

(B-31)

(B-32)

(B-33)

-continued (B-34) 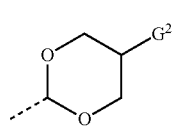

(B-35) 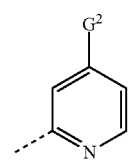

(B-36) 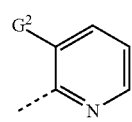

(B-37) 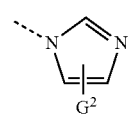

(B-38) 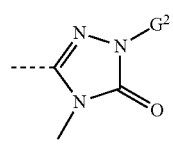

(B-39) 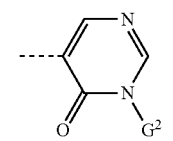

(B-40) 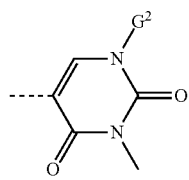

(B-41) 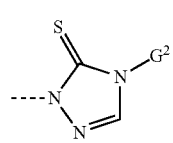

(B-42) 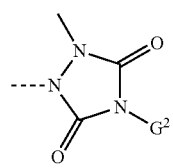

(B-43) 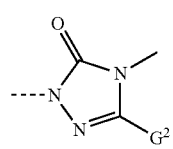

(B-44) 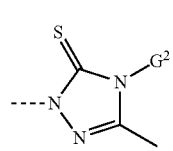

-continued (B-45) 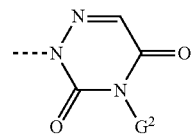

(B-46) 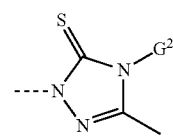

(B-47) 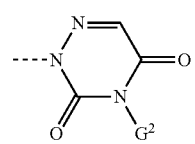

in which the broken line denotes the bond to the carbon atom in the formula (I), or $R^2$ c) is a radical of the formula

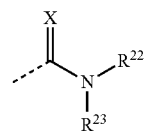

in which the broken line denotes the bond to the carbon atom of the bicyclic system of the formula (I), or $R^2$ d) is a radical of the formula

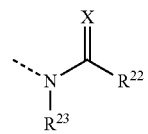

in which the broken line denotes the bond to the carbon atom in the formula (I), or $R^2$ e) is a radical from the group of (F-8) and (F-10)

(F-8) 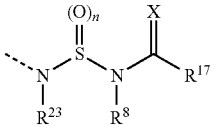

(F-10) 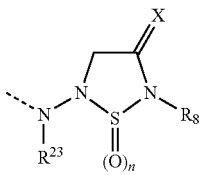

in which the broken line denotes the bond to the carbon atom in the formula (I), or $R^2$ f) is a radical of the formula

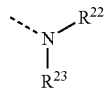

in which the broken line denotes the bond to the carbon atom of the bicyclic system of the formula (I), $G^2$ is hydrogen or a radical from the group of halogen, nitro, amino, cyano, $C_1$-$C_4$-alkylamino, halo-$C_1$-$C_4$-alkylamino, di-($C_1$-$C_4$-alkyl)amino, $C_1$-$C_4$-alkyl, halo-$C_1$-$C_4$-alkyl, $C_1$-$C_4$-alkoxy, halo-$C_1$-$C_4$-alkoxy, $C_1$-$C_4$-alkoxy-$C_1$-$C_4$-alkyl, halogenated $C_1$-$C_4$-alkoxy-$C_1$-$C_4$-alkyl, bis($C_1$-$C_4$-alkoxy)-$C_1$-$C_4$-alkyl, bis(halo-$C_1$-$C_4$-alkoxy)-$C_1$-$C_4$-alkyl, $C_1$-$C_4$-alkoxy-($C_1$-$C_4$-alkylsulphanyl)-$C_1$-$C_4$-alkyl, $C_1$-$C_4$-alkoxy-($C_1$-$C_4$-alkylsulphinyl)-$C_1$-$C_4$-alkyl, $C_1$-$C_4$-alkoxy-($C_1$-$C_4$-alkylsulphonyl)-$C_1$-$C_4$-alkyl, bis($C_1$-$C_4$-alkylsulphanyl)-$C_1$-$C_4$-alkyl, bis(halo-$C_1$-$C_4$-alkylsulphanyl)-$C_1$-$C_4$-alkyl, bis(hydroxy-$C_1$-$C_4$-alkylsulphanyl)-$C_1$-$C_4$-alkyl, $C_1$-$C_4$-alkoxycarbonyl, $C_1$-$C_4$-alkoxycarbonyl-$C_1$-$C_4$-alkyl, $C(X^2)NR^3R^4$, $NR^6R^7$, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, the heterocyclyl radicals dioxanyl, dioxolanyl, dioxepanyl, dioxocanyl, oxathianyl, oxathiolanyl, oxathiepanyl, oxathiocanyl, dithianyl, dithiolanyl, dithiepanyl, dithiocanyl, oxathianyl oxide, oxathiolanyl oxide, oxathiepanyl oxide, oxathiocanyl oxide, oxathianyl dioxide, oxathiolanyl dioxide, oxathiepanyl dioxide, oxathiocanyl dioxide, morpholinyl, triazolinonyl, oxazolinyl, dihydrooxadiazinyl, dihydrodioxazinyl, dihydrooxazolyl, dihydrooxazinyl and pyrazolinonyl (which for their part may in turn be substituted by $C_1$-$C_4$-alkyl, halo-$C_1$-$C_4$-alkyl, $C_1$-$C_4$-alkoxy and $C_1$-$C_4$-alkoxy-$C_1$-$C_4$-alkyl), phenyl (which for its part may in turn be substituted by halogen, cyano, nitro, $C_1$-$C_4$-alkyl and halo-$C_1$-$C_4$-alkyl), the heteroaryl radicals pyridyl, pyridyl N-oxide, pyrimidyl, imidazolyl, pyrazolyl, oxazolyl, thiazolyl, furanyl, thienyl, triazolyl, tetrazolyl, oxadiazolyl, thiadiazolyl, pyrazinyl, triazinyl, tetrazinyl and isoquinolinyl (which for their part may in turn be substituted by halogen, nitro, $C_1$-$C_4$-alkyl, halo-$C_1$-$C_4$-alkyl, $C_1$-$C_4$-alkoxy, halo-$C_1$-$C_4$-alkoxy, $C_1$-$C_4$-alkoxy-$C_1$-$C_4$-alkyl, $C_1$-$C_4$-alkylthio, $C_1$-$C_4$-alkylthio-$C_1$-$C_4$-alkyl and $C_3$-$C_6$-cycloalkyl) and the heteroaryl-$C_1$-$C_4$-alkyl radicals triazolyl-$C_1$-$C_4$-alkyl, pyridyl-$C_1$-$C_4$-alkyl, pyrimidyl-$C_1$-$C_4$-alkyl and oxadiazolyl-$C_1$-$C_4$-alkyl (which for their part may in turn be substituted by halogen and $C_1$-$C_4$-alkyl), or $G^2$ is a C radical from the group of (C-1), (C-6) and (C-9)

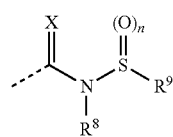
(C-1)

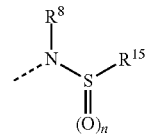
(C-6)

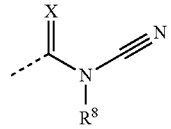
(C-9)

in which the broken line denotes the bond to the B radicals,

X is oxygen, $X^1$ is a radical from the group of hydrogen, fluorine, chlorine, bromine, iodine, cyano, nitro, $C_1$-$C_4$-alkyl, $C_1$-$C_4$-haloalkyl, $C_3$-$C_6$-cycloalkyl, $C_1$-$C_4$-alkoxy and $C_1$-$C_4$-haloalkoxy, $X^2$ is oxygen, sulphur, $NR^5$ or NOH, n is 2, R is $NR^{18}R^{19}$ or is in each case optionally mono- to hepta-halogen-substituted, mono- or di-oxygen-substituted (leads to C=O) or mono- or di-cyano-substituted $C_1$-$C_6$-alkyl, $C_3$-$C_6$-alkenyl, $C_3$-$C_6$-alkynyl, $C_1$-$C_4$-alkoxy-$C_1$-$C_3$-alkyl, $C_1$-$C_4$-alkyl-S—$C_1$-$C_3$-alkyl, $C_1$-$C_4$-alkyl-S(O)—$C_1$-$C_3$-alkyl, $C_1$-$C_4$-alkyl-S(O)$_2$—$C_1$-$C_3$-alkyl, is $R^{18}$—CO—$C_1$-$C_2$-alkyl, is $NR^{18}R^{19}$—CO—$C_1$-$C_2$-alkyl, is optionally mono- or di-oxygen- (leads to C=O), —$C_1$-$C_4$-alkyl-, —$C_3$-$C_6$-cycloalkyl-, —$C_1$-$C_4$-alkoxy- and —$C_1$-$C_4$-haloalkyl-substituted $C_3$-$C_6$-cycloalkyl, is optionally mono- or di-oxygen- (leads to C=O), —$C_1$-$C_4$-alkyl-, —$C_3$-$C_6$-cycloalkyl-, —$C_1$-$C_4$-alkoxy- and —$C_1$-$C_4$-haloalkyl-substituted $C_3$-$C_8$-cycloalkenyl, is optionally mono- or di-oxygen- (leads to C=O), —$C_1$-$C_4$-alkyl-, —$C_3$-$C_6$-cycloalkyl-, —$C_1$-$C_4$-alkoxy- and —$C_1$-$C_4$-haloalkyl-substituted $C_3$-$C_6$-cycloalkyl-$C_1$-$C_4$-alkyl, is optionally mono- or di-oxygen- (leads to C=O), —$C_1$-$C_4$-alkyl-, —$C_3$-$C_6$-cycloalkyl-, —$C_1$-$C_4$-alkoxy- and —$C_1$-$C_4$-haloalkyl-substituted $C_3$-$C_6$-cycloalkenyl-$C_1$-$C_4$-alkyl, is optionally mono- or di-oxygen- (leads to C=O), —$C_1$-$C_4$-alkyl-, —$C_3$-$C_6$-cycloalkyl-, —$C_1$-$C_4$-alkoxy- and —$C_1$-$C_4$-haloalkyl-substituted heterocyclyl, is optionally mono- or di-oxygen- (leads to C=O), —$C_1$-$C_4$-alkyl-, —$C_3$-$C_6$-cycloalkyl-, —$C_1$-$C_4$-alkoxy- and —$C_1$-$C_4$-haloalkyl-substituted heterocyclyl-$C_1$-$C_4$-alkyl or is in each case optionally mono- to tri-halogen-, -cyano-, —$C_1$-$C_4$-alkyl-, —$C_1$-$C_4$-haloalkyl-, —$C_3$-$C_6$-cycloalkyl-, —$C_1$-$C_4$-alkoxy- or —$C_1$-$C_4$-haloalkoxy-substituted phenyl, phenyl-$C_1$-$C_4$-alkyl, hetaryl and hetaryl-$C_1$-$C_4$-alkyl, $R^3$ is $C_1$-$C_4$-alkyl, $R^4$ is a radical from the group of hydrogen, $C_1$-$C_4$-alkyl, halo-$C_1$-$C_4$-alkyl, cyano-$C_1$-$C_4$-alkyl, $C_2$-$C_4$-alkynyl, $C_3$-$C_6$-cycloalkyl, $C_3$-$C_6$-cycloalkyl-$C_1$-$C_4$-alkyl, $C_1$-$C_4$-alkoxy-$C_1$-$C_4$-alkyl, $C_1$-$C_4$-alkoxycarbonyl, $C_1$-$C_4$-alkoxycarbonyl-$C_1$-$C_4$-alkyl and $C_1$-$C_4$-alkylthio-$C_1$-$C_4$-alkyl, $R^5$ is a radical from the group of hydrogen, $C_1$-$C_4$-alkyl, halo-$C_1$-$C_4$-alkyl, cyano-$C_1$-$C_4$-alkyl, $C_2$-$C_4$-alkynyl, $C_3$-$C_6$-cycloalkyl, $C_3$-$C_6$-cycloalkyl-$C_1$-$C_4$-alkyl, $C_1$-$C_4$-alkoxy-$C_1$-$C_4$-alkyl, $C_1$-$C_4$-alkoxycarbonyl, $C_1$-$C_4$-alkoxycarbonyl-$C_1$-$C_4$-alkyl and $C_1$-$C_4$-alkylthio-$C_1$-$C_4$-alkyl, $R^6$ is hydrogen or $C_1$-$C_4$-alkyl, $R^7$ is a radical from the group of hydrogen, $C_1$-$C_4$-alkyl, halo-$C_1$-$C_4$-alkyl, cyano-$C_1$-$C_4$-alkyl, $C_2$-$C_4$-alkynyl, $C_1$-$C_4$-alkoxy, halo-$C_1$-$C_4$-alkoxy, $C_1$-$C_4$-alkoxy-$C_1$-$C_4$-alkyl, $C_1$-$C_4$-alkoxycarbonyl, $C_1$-$C_4$-alkoxycarbonyl-$C_1$-$C_4$-alkyl, $C_1$-$C_4$-alkylthio-$C_1$-$C_4$-alkyl, aryl-$C_1$-$C_4$-alkyl or hetaryl-$C_1$-$C_4$-alkyl, or R[6] and R[7] together with the nitrogen atom to which they are bonded form a 4- to 7-membered ring which may contain one or two further heteroatoms from the group of nitrogen, oxygen and sulphur (where oxygen and sulphur atoms must not be directly adjacent to one another), R[8] is a radical from the group of hydrogen, $C_1$-$C_6$-alkyl, $C_1$-$C_6$-haloalkyl, cyano-$C_1$-$C_6$-alkyl, $C_1$-$C_6$-alkoxy, $C_1$-$C_6$-haloalkoxy, $C_2$-$C_6$-alkenyl, $C_1$-$C_6$-alkoxy-$C_1$-$C_6$-alkyl, in each case optionally halogen-substituted $C_1$-$C_6$-alkylcarbonyl and $C_1$-$C_6$-alkylsulphonyl, optionally halogen-substituted $C_1$-$C_6$-alkoxycarbonyl and optionally halogen-, $C_1$-$C_6$-alkyl-, $C_1$-$C_6$-alkoxy-, $C_1$-$C_6$-haloalkyl- and cyano-substituted $C_3$-$C_6$-cycloalkylcarbonyl, or is a cation or an optionally $C_1$-$C_6$-alkyl- or aryl-$C_1$-$C_6$-alkyl-substituted ammonium ion, R[9] is a radical from the group of in each case optionally halogen-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-haloalkylsulphinyl-, $C_1$-$C_4$-alkylsulphonyl- and $C_1$-$C_4$-haloalkylsulphonyl-substituted $C_1$-$C_4$-alkyl, $C_2$-$C_4$-alkenyl and $C_2$-$C_4$-alkynyl, in each case optionally halogen-, $C_1$-$C_4$-alkyl-, $C_1$-$C_4$-haloalkyl-, $C_1$-$C_4$-alkoxy-, $C_1$-$C_4$-haloalkoxy-substituted $C_3$-$C_6$-cycloalkyl, $C_3$-$C_6$-cycloalkyl-$C_1$-$C_4$-alkyl and $C_3$-$C_4$-cycloalkenyl, in which one or two ring members may each be replaced by a heteroatom from the group of sulphur, oxygen (where oxygen atoms must not be directly adjacent to one another) and nitrogen (and in this case is especially

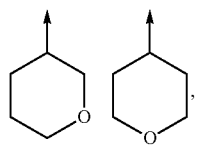

where the arrow in each case denotes the bond to the sulphur atom in the (C-1) radical), in each case optionally halogen-, cyano- (including in the alkyl moiety), nitro-, $C_1$-$C_4$-alkyl-, $C_1$-$C_4$-haloalkyl-, $C_3$-$C_6$-cycloalkyl-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-haloalkylsulphinyl-, $C_1$-$C_4$-alkylsulphonyl-, $C_1$-$C_4$-haloalkylsulphonyl-, amino-, $C_1$-$C_4$-alkyl amino-, di($C_1$-$C_4$-alkyl)amino-, $C_1$-$C_4$-alkylcarbonylamino-, $C_1$-$C_4$-alkoxycarbonylamino-, $C_1$-$C_4$-alkoxy-$C_1$-$C_4$-alkyl-, $C_1$-$C_4$-haloalkoxy-$C_1$-$C_4$-alkyl-, $C_2$-$C_4$-alkenyl-, $C_2$-$C_4$-alkynyl-, $C_3$-$C_6$-cycloalkyl-$C_1$-$C_4$-alkyl-, $C_1$-$C_4$-alkylcarbonyl-, $C_1$-$C_4$-alkoxycarbonyl- or aminocarbonyl-substituted aryl, heteroaryl, aryl-$C_1$-$C_4$-alkyl and heteroaryl-$C_1$-$C_4$-alkyl, or is NR'R" in which R' and R" are independently a radical from the group of hydrogen and $C_1$-$C_4$-alkyl, or R[8] and R[9] in the (C-1) radical, together with the N—S(O)n group to which they are bonded, may also form a saturated or unsaturated and optionally halogen-, $C_1$-$C_6$-alkyl-, $C_1$-$C_6$-haloalkyl-, $C_1$-$C_6$-alkoxy-, $C_1$-$C_6$-haloalkoxy-substituted 5- to 7-membered ring which may contain one or two heteroatoms from the group of sulphur, oxygen (where oxygen atoms must not be directly adjacent to one another) and nitrogen and/or at least one and preferably exactly one carbonyl group; R[8] and R[9] together with the N—S(O)n group to which they are bonded may especially be a radical from the group of

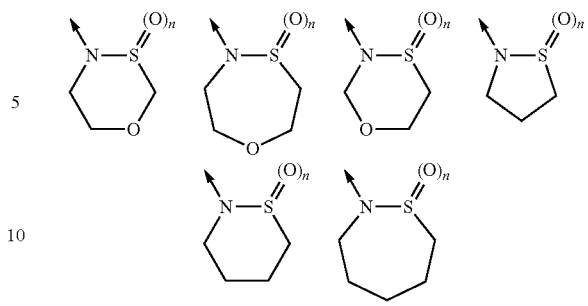

(in which the arrow in each case denotes the bond to the C(X) group),

R[15] is a radical from the group of in each case optionally methyl-substituted $C_1$-$C_6$-alkyl, $C_2$-$C_6$-alkenyl and $C_2$-$C_6$-alkynyl and in each case optionally methyl-, halogen-, cyano- or carbamoyl-substituted $C_3$-$C_6$-cycloalkyl, $C_3$-$C_6$-cycloalkyl-$C_1$-$C_2$-alkyl and $C_3$-$C_6$-cycloalkenyl, R[8] and R[15] in the (C-6) radical, together with the N—S(O)n group to which they are bonded, may also form a saturated or unsaturated and optionally substituted 4- to 8-membered ring which may contain one or two further heteroatoms from the group of sulphur, oxygen (where oxygen and sulphur atoms must not be directly adjacent to one another) and nitrogen and/or at least one carbonyl group, R[17] is a radical from the group of in each case optionally halogen-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-haloalkylsulphinyl-, $C_1$-$C_4$-alkylsulphonyl- and $C_1$-$C_4$-haloalkylsulphonyl-substituted $C_1$-$C_4$-alkyl, $C_2$-$C_4$-alkenyl and $C_2$-$C_4$-alkynyl, in each case optionally halogen-, $C_1$-$C_4$-alkyl-, $C_1$-$C_4$-haloalkyl-, $C_1$-$C_4$-alkoxy-, $C_1$-$C_4$-haloalkoxy-substituted $C_3$-$C_6$-cycloalkyl, $C_3$-$C_6$-cycloalkyl-$C_1$-$C_4$-alkyl, $C_3$-$C_4$-cycloalkenyl, N-pyrrolidinyl, N-piperidinyl, N-morpholinyl, N-thiomorpholinyl, N-thiomorpholinyl 1-oxide, N-thiomorpholinyl 1,1-dioxide, N-piperazinyl, N-1-methylpiperazinyl and N-2-oxo-1-methylpiperazinyl, in each case optionally halogen-, cyano- (including in the alkyl moiety), nitro-, $C_1$-$C_4$-alkyl-, $C_1$-$C_4$-haloalkyl-, $C_3$-$C_6$-cycloalkyl-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-haloalkylsulphinyl-, $C_1$-$C_4$-alkylsulphonyl-, $C_1$-$C_4$-haloalkylsulphonyl-, amino-, $C_1$-$C_4$-alkylamino-, di-($C_1$-$C_4$-alkyl)amino-, $C_1$-$C_4$-alkylcarbonylamino-, $C_1$-$C_4$-alkoxycarbonylamino-, $C_1$-$C_4$-alkoxy-$C_1$-$C_4$-alkyl-, $C_1$-$C_4$-haloalkoxy-$C_1$-$C_4$-alkyl-, $C_2$-$C_4$-alkenyl-, $C_2$-$C_4$-alkynyl-, $C_3$-$C_6$-cycloalkyl-$C_1$-$C_4$-alkyl-, $C_1$-$C_4$-alkylcarbonyl-, $C_1$-$C_4$-alkoxycarbonyl- or aminocarbonyl-substituted aryl, heteroaryl, aryl-$C_1$-$C_4$-alkyl and heteroaryl-$C_1$-$C_4$-alkyl, or is NR'R" in which R' and R" are independently a radical from the group of hydrogen and $C_1$-$C_4$-alkyl, R[18] is a radical from the group of hydrogen, hydroxyl, in each case optionally mono- or poly-halogen-substituted or mono- or di-cyano-substituted $C_1$-$C_4$-alkyl, $C_1$-$C_4$-alkoxy, $C_1$-$C_4$-alkoxy-$C_1$-$C_4$-alkyl, $C_1$-$C_4$-alkyl-S—$C_1$-$C_3$-alkyl, $C_1$-$C_4$-alkyl-S(O)—$C_1$-$C_3$-alkyl, $C_1$-$C_4$-alkyl-S(O)$_2$—$C_1$-$C_3$-alkyl, $C_1$-$C_4$-alkylcarbonyl, $C_1$-$C_4$-alkoxycarbonyl, $C_3$-$C_6$-cycloalkyl, $C_3$-$C_6$-cycloalkyl-$C_1$-$C_3$-alkyl, heterocyclyl, heterocyclyl-$C_1$-$C_3$-alkyl and in each case optionally mono- to tri-$C_1$-$C_4$-alkyl-, —$C_1$-$C_3$-haloalkyl-, —$C_1$-$C_3$-alkoxy-, —$C_1$-$C_3$-haloalkoxy-, -cyclopropyl-, -fluorine-, -chlorine-, -bromine- or -cyano-substituted phenyl, benzyl, pyridyl, pyrimidyl, thiazolyl, oxazolyl, pyrazolyl, thienyl, furanyl, pyridinylmethyl and thiazolylmethyl, $R^{19}$ is hydrogen, is an alkali metal or alkaline earth metal ion, or is an optionally mono- to tetra-$C_1$-$C_4$-alkyl-substituted ammonium ion or an in each case optionally mono- or poly-halogen-substituted or mono- or di-cyano-substituted radical from the group of $C_1$-$C_4$-alkyl, $C_1$-$C_4$-alkoxy, $C_1$-$C_4$-alkoxy-$C_1$-$C_2$-alkyl, $C_1$-$C_4$-alkyl-S—$C_1$-$C_2$-alkyl, $C_1$-$C_4$-alkyl-S(O)—$C_1$-$C_2$-alkyl and $C_1$-$C_4$-alkyl-S(O)$_2$—$C_1$-$C_2$-alkyl, $Y^3$ is a radical from the group of hydrogen, fluorine, chlorine, bromine, iodine, cyano, $C_1$-$C_4$-alkyl, $C_1$-$C_4$-haloalkyl, $C_3$-$C_6$-cycloalkyl, $C_1$-$C_4$-alkoxy and $C_1$-$C_4$-haloalkoxy, W is a radical from the group of S, SO and SO$_2$, and in the case that $R^2$ is f)

$R^{22}$ is a radical from the group of hydrogen, $C_1$-$C_4$-alkyl, $C_2$-$C_4$-haloalkyl, cyano-$C_1$-$C_4$-alkyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkoxy, $C_1$-$C_4$-haloalkoxy, optionally halogen-substituted $C_1$-$C_2$-alkoxy-$C_1$-$C_4$-alkyl, optionally halogen-substituted bis($C_1$-$C_2$-alkoxy)-$C_1$-$C_4$-alkyl, optionally halogen-substituted $C_1$-$C_4$-alkylsulphanyl-$C_1$-$C_4$-alkyl, optionally halogen-substituted $C_1$-$C_4$-alkylcarbonyl-$C_1$-$C_4$-alkyl, optionally halogen-substituted $C_1$-$C_4$-alkylsulphinyl-$C_1$-$C_4$-alkyl, optionally halogen-substituted $C_1$-$C_4$-alkylsulphonyl-$C_1$-$C_4$-alkyl, di-($C_1$-$C_4$-alkyl)aminosulphanyl-$C_1$-$C_4$-alkyl, di-($C_1$-$C_4$-alkyl)aminosulphinyl-$C_1$-$C_4$-alkyl, di-($C_1$-$C_4$-alkyl)aminosulphonyl-$C_1$-$C_4$-alkyl, optionally halogen-substituted $C_1$-$C_4$-alkoxycarbonyl-$C_1$-$C_4$-alkyl, optionally halogen-substituted $C_2$-$C_4$-alkynyloxy, di-($C_1$-$C_4$-alkyl)aminocarbonyl-$C_1$-$C_4$-alkyl, N—$C_1$-$C_4$-alkyl-N—$C_3$-$C_6$-cycloalkylaminocarbonyl-$C_1$-$C_4$-alkyl, heterocyclylcarbonyl-$C_1$-$C_4$-alkyl, $C_1$-$C_4$-alkylsulphanyl, $C_1$-$C_4$-haloalkylsulphanyl, $C_1$-$C_4$-alkylsulphinyl, $C_1$-$C_4$-haloalkylsulphinyl, $C_1$-$C_4$-alkylsulphonyl, $C_1$-$C_4$-haloalkylsulphonyl, $C_3$-$C_6$-cycloalkyl optionally substituted by halogen, cyano, nitro, $C_1$-$C_4$-alkyl, $C_1$-$C_4$-haloalkyl, $C_3$-$C_6$-cycloalkyl, $C_1$-$C_4$-alkoxy, $C_1$-$C_4$-haloalkoxy, $C_1$-$C_4$-alkoxycarbonyl, $C_1$-$C_4$-haloalkoxycarbonyl or pyridyl (which for its part is optionally substituted by $C_1$-$C_4$-alkyl or halogen), $C_3$-$C_6$-cycloalkyl-$C_1$-$C_4$-alkyl optionally substituted by halogen, cyano, nitro, $C_1$-$C_4$-alkyl, $C_1$-$C_4$-haloalkyl, $C_3$-$C_6$-cycloalkyl, $C_1$-$C_4$-alkoxy, $C_1$-$C_4$-haloalkoxy, $C_1$-$C_4$-alkoxycarbonyl, $C_1$-$C_4$-haloalkoxycarbonyl, pyridyl, pyrimidyl, pyrazanyl, pyridazinyl, thiazolyl, isothiazolyl, thiadiazolyl, oxazolyl, isoxazolyl, oxadiazolyl, pyrazolyl, triazinyl or triazolyl (where the hetaryls mentioned for their part are optionally substituted by $C_1$-$C_4$-alkyl or halogen), heterocyclyl-$C_1$-$C_4$-alkyl optionally substituted by halogen, cyano (including in the $C_1$-$C_4$-alkyl moiety of heterocyclyl-$C_1$-$C_4$-alkyl), nitro, hydroxyl, $C_1$-$C_4$-alkyl, $C_1$-$C_4$-haloalkyl, $C_3$-$C_6$-cycloalkyl (which is optionally substituted by halogen, cyano, $C_1$-$C_4$-alkyl and $C_3$-$C_6$-cycloalkyl), $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulphinyl, $C_1$-$C_4$-alkylsulphonyl, $C_1$-$C_4$-haloalkylsulphinyl, $C_1$-$C_4$-haloalkylsulphonyl, amino, $C_1$-$C_4$-alkylamino, di-($C_1$-$C_4$-alkyl)amino, $C_1$-$C_4$-alkylcarbonylamino, $C_1$-$C_4$-alkoxycarbonylamino, $C_1$-$C_4$-alkoxy-$C_1$-$C_4$-alkyl, $C_1$-$C_4$-haloalkoxy-$C_1$-$C_4$-alkyl, $C_2$-$C_4$-alkenyl, $C_2$-$C_4$-alkynyl, $C_3$-$C_6$-cycloalkyl-$C_1$-$C_4$-alkyl, $C_1$-$C_4$-alkylcarbonyl, $C_1$-$C_4$-alkoxycarbonyl or aminocarbonyl, aryl optionally substituted by halogen, cyano, nitro, hydroxyl, amino, $C_1$-$C_4$-alkyl, $C_1$-$C_4$-haloalkyl, $C_3$-$C_6$-cycloalkyl (which is optionally substituted by halogen, cyano, $C_1$-$C_4$-alkyl and $C_3$-$C_6$-cycloalkyl), $C_1$-$C_4$-alkoxy or $C_1$-$C_4$-haloalkoxy, aryl-$C_1$-$C_4$-alkyl optionally substituted by halogen, cyano (including in the $C_1$-$C_4$-alkyl moiety of aryl-$C_1$-$C_4$-alkyl), nitro, hydroxyl, amino, $C_1$-$C_4$-alkyl, $C_1$-$C_4$-haloalkyl, $C_3$-$C_6$-cycloalkyl (which is optionally substituted by halogen, cyano, $C_1$-$C_4$-alkyl and $C_3$-$C_6$-cycloalkyl), $C_1$-$C_4$-alkoxy or $C_1$-$C_4$-haloalkoxy, hetaryl-$C_1$-$C_4$-alkyl optionally substituted by halogen, cyano (including in the $C_1$-$C_4$-alkyl moiety of hetaryl-$C_1$-$C_4$-alkyl), nitro, hydroxyl, $C_1$-$C_4$-alkyl, $C_1$-$C_4$-haloalkyl, $C_3$-$C_6$-cycloalkyl (which is optionally substituted by halogen, cyano, $C_1$-$C_4$-alkyl and $C_3$-$C_6$-cycloalkyl), $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulphinyl, $C_1$-$C_4$-alkylsulphonyl, $C_1$-$C_4$-haloalkylsulphinyl, $C_1$-$C_4$-haloalkylsulphonyl, amino, $C_1$-$C_4$-alkylamino, di-($C_1$-$C_4$-alkyl)amino, $C_1$-$C_4$-alkylcarbonylamino, $C_1$-$C_4$-alkoxycarbonylamino, $C_1$-$C_4$-alkoxy-$C_1$-$C_4$-alkyl, $C_1$-$C_4$-haloalkoxy-$C_1$-$C_4$-alkyl, $C_2$-$C_4$-alkenyl, $C_2$-$C_4$-alkynyl, $C_3$-$C_6$-cycloalkyl-$C_1$-$C_4$-alkyl, $C_1$-$C_4$-alkylcarbonyl, $C_1$-$C_4$-alkoxycarbonyl or aminocarbonyl, and in the case that $R^2$ is c), d) or f)

$R^{22}$ is one of the following D radicals:

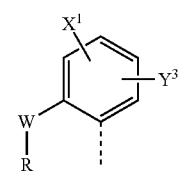

(D-1)

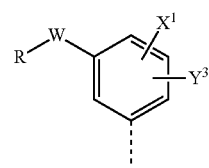

(D-2)

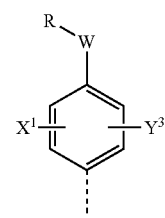

(D-3)

or one of the following E radicals:

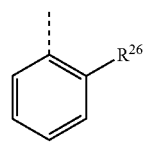

E-1

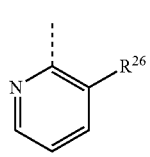

E-2

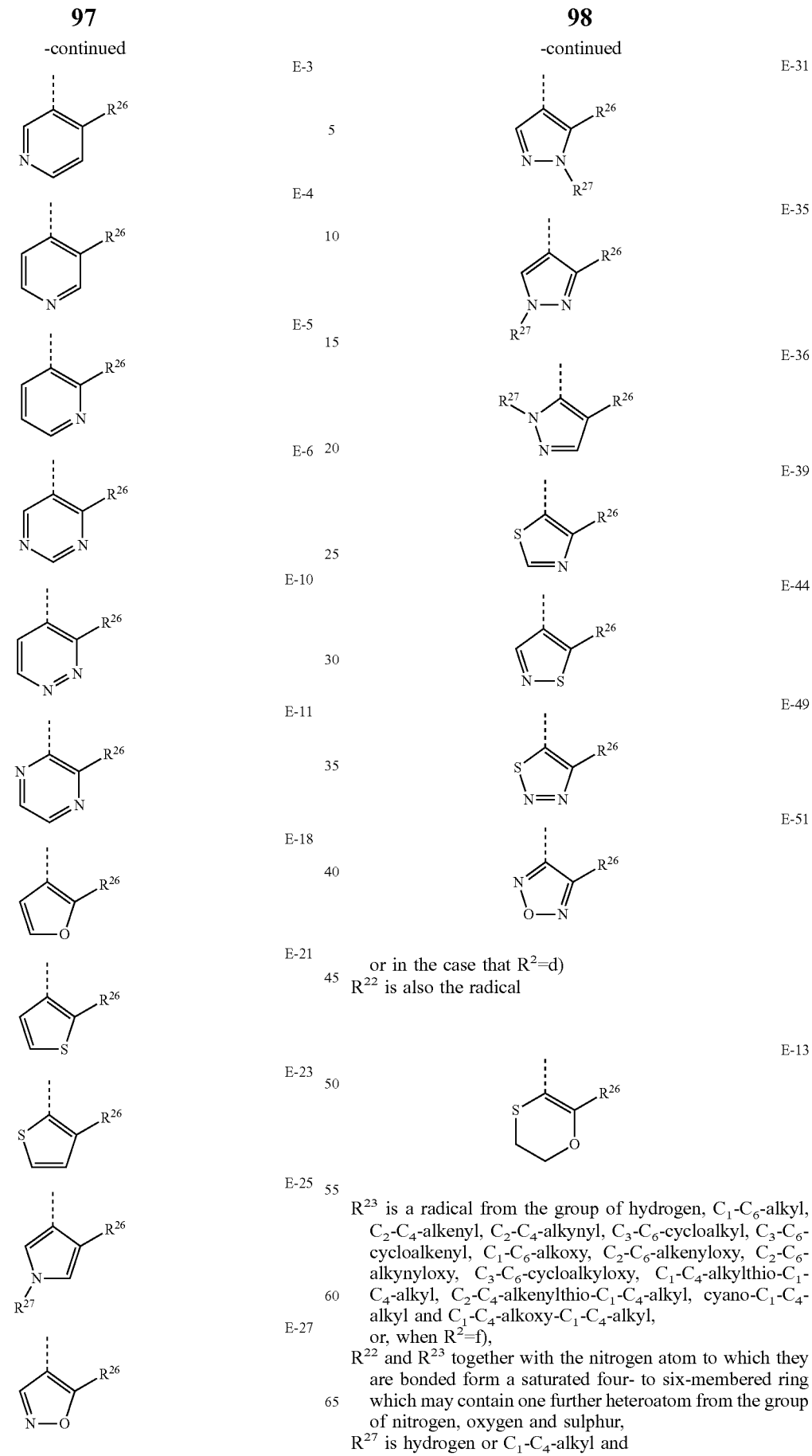

or in the case that $R^2$=d)
$R^{22}$ is also the radical $R^{23}$ is a radical from the group of hydrogen, $C_1$-$C_6$-alkyl, $C_2$-$C_4$-alkenyl, $C_2$-$C_4$-alkynyl, $C_3$-$C_6$-cycloalkyl, $C_3$-$C_6$-cycloalkenyl, $C_1$-$C_6$-alkoxy, $C_2$-$C_6$-alkenyloxy, $C_2$-$C_6$-alkynyloxy, $C_3$-$C_6$-cycloalkyloxy, $C_1$-$C_4$-alkylthio-$C_1$-$C_4$-alkyl, $C_2$-$C_4$-alkenylthio-$C_1$-$C_4$-alkyl, cyano-$C_1$-$C_4$-alkyl and $C_1$-$C_4$-alkoxy-$C_1$-$C_4$-alkyl, or, when $R^2$=f), $R^{22}$ and $R^{23}$ together with the nitrogen atom to which they are bonded form a saturated four- to six-membered ring which may contain one further heteroatom from the group of nitrogen, oxygen and sulphur, $R^{27}$ is hydrogen or $C_1$-$C_4$-alkyl and $R^{26}$ is a radical from the group of hydrogen, $C_1$-$C_4$-alkyl, $C_1$-$C_4$-haloalkyl, $C_2$-$C_4$-alkenyl, $C_2$-$C_4$-alkynyl, $C_3$-$C_6$-cycloalkyl, $C_3$-$C_6$-cycloalkyl-$C_1$-$C_4$-alkyl, $C_1$-$C_4$-alkoxy-$C_1$-$C_2$-alkyl, $C_1$-$C_4$-alkylsulphanyl, $C_1$-$C_4$-haloalkylsulphanyl, $C_1$-$C_4$-alkylsulphinyl, $C_1$-$C_4$-haloalkylsulphinyl, $C_1$-$C_4$-alkylsulphonyl, $C_1$-$C_4$-alkylthio-$C_1$-$C_2$-alkyl, $C_1$-$C_4$-alkylsulphinyl-$C_1$-$C_2$-alkyl, $C_1$-$C_4$-alkylsulphonyl-$C_1$-$C_2$-alkyl and cyano-$C_1$-$C_4$-alkyl.

Area of preference (3): Very particular preference is given to compounds of the formula (I) in which
A is an A radical from the group of (A-b) and (A-f)

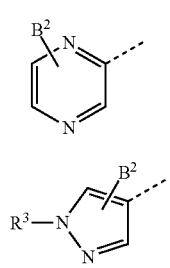
(A-b)

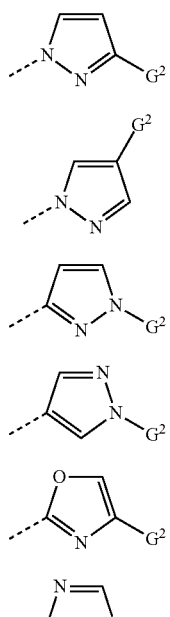
(A-f)

in which the broken line denotes the bond to the carbon atom of the bicyclic system of the formula (I),
$B^2$ is hydrogen,
Q is sulphur,
$R^1$ is hydrogen,
$R^2$ is a B radical from the group of (B-1)

(B-2)

(B-3)

(B-4)

(B-5)

(B-9)

(B-10)

(B-11)

-continued

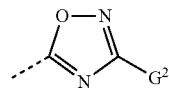
(B-12)

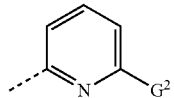
(B-21)

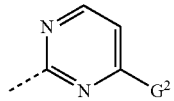
(B-23)

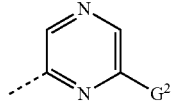
(B-25)

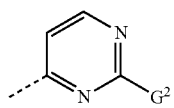
(B-27)

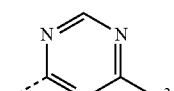
(B-28)

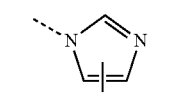
(B-37)

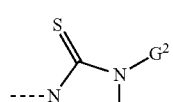
(B-41)

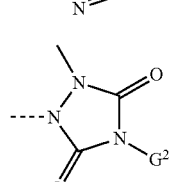
(B-42)

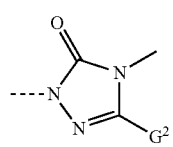
(B-43)

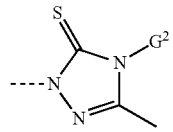
(B-46)

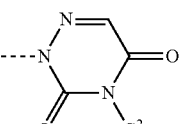
(B-47)

in which the broken line denotes the bond to the carbon atom of the bicyclic system of the formula (I), or $R^2$ b) is a D radical from the group of

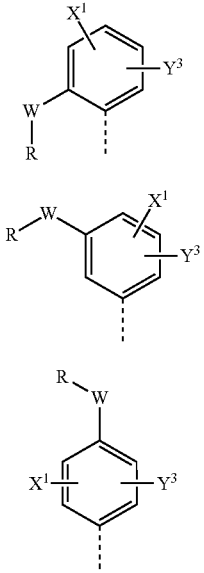

(D-1)

(D-2)

(D-3)

in which the broken line denotes the bond to the carbon atom of the bicyclic system of the formula (I), or
$R^2$ c) is a radical of the formula

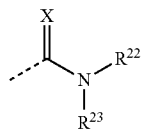

in which the broken line denotes the bond to the carbon atom of the bicyclic system of the formula (I), or
$R^2$ d) is a radical of the formula

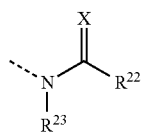

in which the broken line denotes the bond to the carbon atom of the bicyclic system of the formula (I), or
$R^2$ e) is an F radical from the group of (F-1), (F-8) and (F-10)

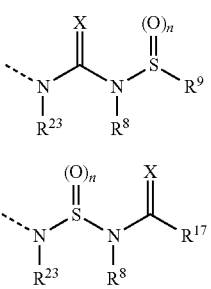

(F-1)

(F-8)

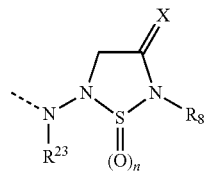

(F-10)

in which the broken line denotes the bond to the carbon atom of the bicyclic system of the formula (I), or
$R^2$ f) is a radical of the formula

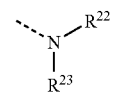

in which the broken line denotes the bond to the carbon atom of the bicyclic system of the formula (I), or
$R^2$ g) is a radical of the formula

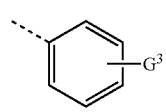

in which the broken line denotes the bond to the carbon atom of the bicyclic system of the formula (I),
$G^2$ is hydrogen or a radical from the group of halogen, nitro, amino, cyano, $C_1$-$C_4$-alkylamino, halo-$C_1$-$C_4$-alkylamino, di-($C_1$-$C_4$-alkyl)amino, $C_1$-$C_4$-alkyl, halo-$C_1$-$C_4$-alkyl, $C_1$-$C_4$-alkoxy, halo-$C_1$-$C_4$-alkoxy, $C_1$-$C_4$-alkoxy-$C_1$-$C_4$-alkyl, halogenated $C_1$-$C_4$-alkoxy-$C_1$-$C_4$-alkyl, bis($C_1$-$C_4$-alkoxy)-$C_1$-$C_4$-alkyl, bis(halo-$C_1$-$C_4$-alkoxy)-$C_1$-$C_4$-alkyl, $C_1$-$C_4$-alkoxy-($C_1$-$C_4$-alkylsulphanyl)-$C_1$-$C_4$-alkyl, $C_1$-$C_4$-alkoxy-($C_1$-$C_4$-alkylsulphinyl)-$C_1$-$C_4$-alkyl, $C_1$-$C_4$-alkoxy-($C_1$-$C_4$-alkylsulphonyl)-$C_1$-$C_4$-alkyl, bis($C_1$-$C_4$-alkylsulphanyl)-$C_1$-$C_4$-alkyl, bis(halo-$C_1$-$C_4$-alkylsulphanyl)-$C_1$-$C_4$-alkyl, bis(hydroxy-$C_1$-$C_4$-alkylsulphanyl)-$C_1$-$C_4$-alkyl, $C_1$-$C_4$-alkoxycarbonyl, $C_1$-$C_4$-alkoxycarbonyl-$C_1$-$C_4$-alkyl, $C(X^2)NR^3R^4$, $NR^6R^7$, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl and $C_1$-$C_4$-haloalkylsulphonyl, or
$G^2$ is a (C-1) or (C-9) radical

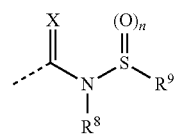

(C-1)

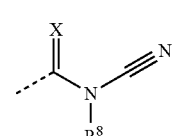

(C-9)

in which the broken line denotes the bond to the B radicals,
$G^3$ is a radical from the group of hydrogen, halogen, $C_1$-$C_6$-alkyl and $C_1$-$C_6$-haloalkyl, X is oxygen,
X¹ is a radical from the group of hydrogen, fluorine, chlorine, bromine, cyano, methyl, ethyl, trifluoromethyl, methoxy, ethoxy, difluoromethoxy and trifluoromethoxy,
X² is oxygen, sulphur, NR⁵ or NOH,
n is 2,
R is NR¹⁸R¹⁹ or is an in each case optionally mono-, di-, tri-, tetra- or penta-fluorine- or -chlorine-substituted or mono- or di-cyano-substituted radical from the group of $C_1$-$C_4$-alkyl, $C_3$-$C_4$-alkenyl, $C_3$-$C_4$-alkynyl, $C_1$-$C_2$-alkoxy-$C_1$-$C_2$-alkyl and $C_1$-$C_2$-alkyl-S—$C_1$-$C_2$-alkyl, $C_1$-$C_2$-alkyl-S(O)—$C_1$-$C_2$-alkyl, $C_1$-$C_2$-alkyl-S(O)$_2$—$C_1$-$C_2$-alkyl, is R¹⁸—CO—$C_1$-$C_2$-alkyl, is NR¹⁸R¹⁹—CO—$C_1$-$C_2$-alkyl, is optionally mono- or di-$C_1$-$C_2$-alkyl-, —$C_1$-$C_2$-alkoxy- or —$C_1$-$C_2$-haloalkyl-substituted or oxygen atom-substituted (leads to C=O) $C_3$-$C_6$-cycloalkyl, is optionally mono- or di-$C_1$-$C_2$-alkyl-, —$C_1$-$C_2$-alkoxy- or —$C_1$-$C_2$-haloalkyl or oxygen atom-substituted (leads to C=O) $C_3$-$C_6$-cycloalkenyl, is optionally mono- or di-$C_1$-$C_2$-alkyl-, —$C_1$-$C_2$-alkoxy- or —$C_1$-$C_2$-haloalkyl-substituted $C_3$-$C_6$-cycloalkyl-$C_1$-$C_2$-alkyl, is optionally mono- or di-$C_1$-$C_2$-alkyl-, —$C_1$-$C_2$-alkoxy- or —$C_1$-$C_2$-haloalkyl-substituted $C_3$-$C_6$-cycloalkenyl-$C_1$-$C_2$-alkyl, is optionally mono- or di-$C_1$-$C_2$-alkyl-, —$C_1$-$C_2$-alkoxy- or —$C_1$-$C_2$-haloalkyl-substituted heterocyclyl, is optionally mono- or di-$C_1$-$C_2$-alkyl-, —$C_1$-$C_2$-alkoxy- or —$C_1$-$C_2$-haloalkyl-substituted heterocyclyl-$C_1$-$C_2$-alkyl or is in each case optionally mono- or di-fluorine-, -chlorine-, -bromine-, -cyano-, -methyl-, -ethyl-, -difluoromethyl-, -trifluoromethyl-, -methoxy-, -ethoxy-, -difluoromethoxy- or -trifluoromethoxy-substituted phenyl, benzyl, pyridyl, pyrimidyl, thiazolyl, oxazolyl, pyrazolyl, thienyl, furanyl, pyridinylmethyl or thiazolylmethyl,
R³ is $C_1$-$C_4$-alkyl,
R⁴ is a radical from the group of hydrogen, $C_1$-$C_4$-alkyl, halo-$C_1$-$C_4$-alkyl, cyano-$C_1$-$C_4$-alkyl, $C_2$-$C_4$-alkynyl, $C_3$-$C_6$-cycloalkyl, $C_3$-$C_6$-cycloalkyl-$C_1$-$C_4$-alkyl, $C_1$-$C_4$-alkoxy-$C_1$-$C_4$-alkyl, $C_1$-$C_4$-alkoxycarbonyl, $C_1$-$C_4$-alkoxycarbonyl-$C_1$-$C_4$-alkyl and $C_1$-$C_4$-alkylthio-$C_1$-$C_4$-alkyl,
R⁵ is a radical from the group of hydrogen, $C_1$-$C_4$-alkyl, halo-$C_1$-$C_4$-alkyl, cyano-$C_1$-$C_4$-alkyl, $C_2$-$C_4$-alkynyl, $C_3$-$C_6$-cycloalkyl, $C_3$-$C_6$-cycloalkyl-$C_1$-$C_4$-alkyl, $C_1$-$C_4$-alkoxy-$C_1$-$C_4$-alkyl, $C_1$-$C_4$-alkoxycarbonyl, $C_1$-$C_4$-alkoxycarbonyl-$C_1$-$C_4$-alkyl and $C_1$-$C_4$-alkylthio-$C_1$-$C_4$-alkyl,
R⁶ is hydrogen or $C_1$-$C_4$-alkyl,
R⁷ is a radical from the group of hydrogen, $C_1$-$C_4$-alkyl, halo-$C_1$-$C_4$-alkyl, cyano-$C_1$-$C_4$-alkyl, $C_2$-$C_4$-alkynyl, $C_1$-$C_4$-alkoxy, halo-$C_1$-$C_4$-alkoxy, $C_1$-$C_4$-alkoxy-$C_1$-$C_4$-alkyl, $C_1$-$C_4$-alkoxycarbonyl, $C_1$-$C_4$-alkoxycarbonyl-$C_1$-$C_4$-alkyl, $C_1$-$C_4$-alkylthio-$C_1$-$C_4$-alkyl, aryl-$C_1$-$C_4$-alkyl or hetaryl-$C_1$-$C_4$-alkyl, or
R⁶ and R⁷ together with the nitrogen atom to which they are bonded form a 4- to 7-membered ring which may contain one or two further heteroatoms from the group of nitrogen, oxygen and sulphur (where oxygen and sulphur atoms must not be directly adjacent to one another),
R⁸ is a radical from the group of hydrogen, $C_1$-$C_6$-alkyl, $C_1$-$C_6$-haloalkyl, cyano-$C_1$-$C_6$-alkyl, $C_1$-$C_6$-alkoxy, $C_1$-$C_6$-haloalkoxy, $C_2$-$C_6$-alkenyl, $C_1$-$C_6$-alkoxy-$C_1$-$C_6$-alkyl, in each case optionally halogen-substituted $C_1$-$C_6$-alkylcarbonyl and $C_1$-$C_6$-alkylsulphonyl, optionally halogen-substituted $C_1$-$C_6$-alkoxycarbonyl and optionally halogen-, $C_1$-$C_6$-alkyl-, $C_1$-$C_6$-alkoxy-, $C_1$-$C_6$-haloalkyl- and cyano-substituted $C_3$-$C_6$-cycloalkylcarbonyl, or is a cation or an optionally $C_1$-$C_6$-alkyl- or aryl-$C_1$-$C_6$-alkyl-substituted ammonium ion,
R⁹ is a radical from the group of in each case optionally halogen-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-haloalkylsulphinyl-, $C_1$-$C_4$-alkylsulphonyl- and $C_1$-$C_4$-haloalkylsulphonyl-substituted $C_1$-$C_4$-alkyl, $C_2$-$C_4$-alkenyl and $C_2$-$C_4$-alkynyl, in each case optionally halogen-, $C_1$-$C_4$-alkyl-, $C_1$-$C_4$-haloalkyl-, $C_1$-$C_4$-alkoxy-, $C_1$-$C_4$-haloalkoxy-substituted $C_3$-$C_6$-cycloalkyl, $C_3$-$C_6$-cycloalkyl-$C_1$-$C_4$-alkyl and $C_3$-$C_4$-cycloalkenyl, in which one or two ring members may each be replaced by a heteroatom from the group of sulphur, oxygen (where oxygen atoms must not be directly adjacent to one another) and nitrogen (and in this case is especially

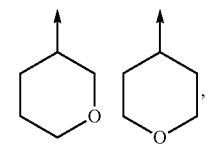

where the arrow in each case denotes the bond to the sulphur atom in the (C-1) radical and in the (F-1) radical), in each case optionally halogen-, cyano- (including in the alkyl moiety), nitro-, $C_1$-$C_4$-alkyl-, $C_1$-$C_4$-haloalkyl-, $C_3$-$C_6$-cycloalkyl-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-haloalkylsulphinyl-, $C_1$-$C_4$-alkyl sulphonyl-, $C_1$-$C_4$-haloalkylsulphonyl-, amino-, $C_1$-$C_4$-alkyl amino-, di($C_1$-$C_4$-alkyl)amino-, $C_1$-$C_4$-alkylcarbonylamino-, $C_1$-$C_4$-alkoxycarbonylamino-, $C_1$-$C_4$-alkoxy-$C_1$-$C_4$-alkyl-, $C_1$-$C_4$-haloalkoxy-$C_1$-$C_4$-alkyl-, $C_2$-$C_4$-alkenyl-, $C_2$-$C_4$-alkynyl-, $C_3$-$C_6$-cycloalkyl-$C_1$-$C_4$-alkyl-, $C_1$-$C_4$-alkylcarbonyl-, $C_1$-$C_4$-alkoxycarbonyl- or aminocarbonyl-substituted aryl, heteroaryl, aryl-$C_1$-$C_4$-alkyl and heteroaryl-$C_1$-$C_4$-alkyl, or is NR'R" in which R' and R" are independently a radical from the group of hydrogen and $C_1$-$C_4$-alkyl,
R⁸ and R⁹ in the radical (C-1) and in the radical (F-1), together with the N—S(O)n group to which they are bonded, may also form a saturated or unsaturated and optionally halogen-, $C_1$-$C_6$-alkyl-, $C_1$-$C_6$-haloalkyl-, $C_1$-$C_6$-alkoxy-, $C_1$-$C_6$-haloalkoxy-substituted 5- to 7-membered ring which may contain one or two heteroatoms from the group of sulphur, oxygen (where oxygen atoms must not be directly adjacent to one another) and nitrogen and/or at least one and preferably one carbonyl group; R⁸ and R⁹ together with the N—S(O)n group to which they are bonded may especially be a radical from the group of

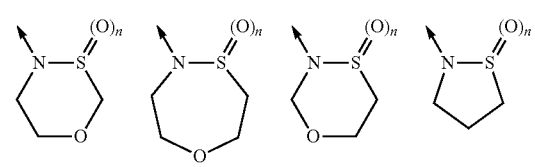

-continued

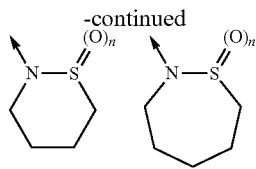

(in which the arrow in each case denotes the bond to the C(X) group), $R^{17}$ is a radical from the group of in each case optionally halogen-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-haloalkylsulphinyl-, $C_1$-$C_4$-alkylsulphonyl- and $C_1$-$C_4$-haloalkylsulphonyl-substituted $C_1$-$C_4$-alkyl, $C_2$-$C_4$-alkenyl and $C_2$-$C_4$-alkynyl, in each case optionally halogen-, $C_1$-$C_4$-alkyl-, $C_1$-$C_4$-haloalkyl-, $C_1$-$C_4$-alkoxy-, $C_1$-$C_4$-haloalkoxy-substituted $C_3$-$C_6$-cycloalkyl, $C_3$-$C_6$-cycloalkyl-$C_1$-$C_4$-alkyl, $C_3$-$C_4$-cycloalkenyl, N-pyrrolidinyl, N-piperidinyl, N-morpholinyl, N-thiomorpholinyl, N-thiomorpholinyl 1-oxide, N-thiomorpholinyl 1,1-dioxide, N-piperazinyl, N-1-methylpiperazinyl and N-2-oxo-1-methylpiperazinyl, in each case optionally halogen-, cyano- (including in the alkyl moiety), nitro-, $C_1$-$C_4$-alkyl-, $C_1$-$C_4$-haloalkyl-, $C_3$-$C_6$-cycloalkyl-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-haloalkylsulphinyl-, $C_1$-$C_4$-alkylsulphonyl-, $C_1$-$C_4$-haloalkylsulphonyl-, amino-, $C_1$-$C_4$-alkylamino-, di-($C_1$-$C_4$-alkyl)amino-, $C_1$-$C_4$-alkylcarbonylamino-, $C_1$-$C_4$-alkoxycarbonylamino-, $C_1$-$C_4$-alkoxy-$C_1$-$C_4$-alkyl-, $C_1$-$C_4$-haloalkoxy-$C_1$-$C_4$-alkyl-, $C_2$-$C_4$-alkenyl-, $C_2$-$C_4$-alkynyl-, $C_3$-$C_6$-cycloalkyl-$C_1$-$C_4$-alkyl-, $C_1$-$C_4$-alkylcarbonyl-, $C_1$-$C_4$-alkoxycarbonyl- or aminocarbonyl-substituted aryl, heteroaryl, aryl-$C_1$-$C_4$-alkyl and heteroaryl-$C_1$-$C_4$-alkyl, or is NR'R" in which R' and R" are independently a radical from the group of hydrogen and $C_1$-$C_4$-alkyl, $R^{18}$ is a radical from the group of hydrogen, hydroxyl, in each case optionally mono-, di-, tri-, tetra- or penta-fluorine- or -chlorine-substituted or mono- or di-cyano-substituted $C_1$-$C_4$-alkyl, $C_1$-$C_4$-alkoxy, $C_1$-$C_4$-alkoxy-$C_1$-$C_4$-alkyl, $C_1$-$C_4$-alkyl-S—$C_1$-$C_2$-alkyl, $C_1$-$C_4$-alkyl-S(O)—$C_1$-$C_2$-alkyl, $C_1$-$C_4$-alkyl-S(O)$_2$—$C_1$-$C_2$-alkyl, $C_1$-$C_4$-alkylcarbonyl, $C_1$-$C_4$-alkoxycarbonyl, $C_3$-$C_6$-cycloalkyl, $C_3$-$C_6$-cycloalkyl-$C_1$-$C_3$-alkyl, heterocyclyl and heterocyclyl-$C_1$-$C_3$-alkyl, and in each case optionally mono- to tri-$C_1$-$C_4$-alkyl-, —$C_1$-$C_3$-haloalkyl-, —$C_1$-$C_3$-alkoxy-, —$C_1$-$C_3$-haloalkoxy-, -cyclopropyl-, -fluorine-, -chlorine-, -bromine- or -cyano-substituted phenyl, benzyl, pyridyl, pyrimidyl, thiazolyl, oxazolyl, pyrazolyl, thienyl, furanyl, pyridinylmethyl and thiazolylmethyl, $R^{19}$ is hydrogen, an alkali metal or alkaline earth metal ion, an optionally mono- to tetra-$C_1$-$C_4$-alkyl-substituted ammonium ion or an in each case optionally mono-, di-, tri-, tetra- or penta-fluorine- or -chlorine-substituted or mono- or di-cyano-substituted radical from the group of $C_1$-$C_4$-alkyl, $C_1$-$C_4$-alkoxy, $C_1$-$C_4$-alkoxy-$C_1$-$C_2$-alkyl and $C_1$-$C_4$-alkyl-S—$C_1$-$C_2$-alkyl, $C_1$-$C_4$-alkyl-S(O)—$C_1$-$C_2$-alkyl and $C_1$-$C_4$-alkyl-S(O)$_2$—$C_1$-$C_2$-alkyl, W is a radical from the group of S, SO and $SO_2$, $Y^3$ is a radical from the group of hydrogen, fluorine, chlorine, bromine, cyano, methyl, ethyl, trifluoromethyl, methoxy, ethoxy, difluoromethoxy and trifluoromethoxy, $R^{22}$ is a radical from the group of methyl, ethyl, isopropyl, n-propyl, n-butyl, iso-butyl, sec-butyl, tert-butyl, 2,2,2-trifluoroethyl, 2,2-difluoroethyl, 2,2-difluoro-n-propyl, methylsulphanylmethyl, methylsulphanylethyl, methylsulphanyl-n-propyl, trifluoromethylsulphonylmethyl, ethylsulphonylmethyl, 2,2,2-trifluoroethylsulphonylmethyl, 2,2-difluoroethylsulphonylmethyl, isopropylsulphanylmethyl, methylsulphinylmethyl, trifluoromethylsulphinylmethyl, ethylsulphinylmethyl, 2,2,2-trifluoroethylsulphinylmethyl, 2,2-difluoroethylsulphinylmethyl, isopropylsulphinylmethyl, methylsulphonylmethyl, trifluoromethylsulphonylmethyl, ethylsulphonylmethyl, 2,2,2-trifluoroethylsulphonylmethyl, 2,2-difluoroethylsulphonylmethyl, isopropylsulphonylmethyl, methoxycarbonyl, ethoxycarbonyl, methoxycarbonylmethyl, ethoxycarbonylmethyl, methoxycarbonylethyl, ethoxycarbonylethyl, dimethylaminocarbonyl, diethylaminocarbonyl, N-ethyl-N-methylaminocarbonyl, N-isopropyl-N-methylaminocarbonyl, dimethylaminocarbonylmethyl, diethylaminocarbonylmethyl, N-ethyl-N-methylaminocarbonylmethyl, N-isopropyl-N-methylaminocarbonylmethyl, dimethylaminocarbonylethyl, diethylaminocarbonylethyl, N-ethyl-N-methylaminocarbonylethyl, N-isopropyl-N-methylaminocarbonylethyl, N-cyclopropyl-N-methylaminocarbonylmethyl, N-cyclopropyl-N-methylaminocarbonylethyl, methylsulphanyl, trifluoromethylsulphanyl, ethylsulphanyl, 2,2,2-trifluoroethylsulphanyl, 2,2-difluoroethylsulphanyl, isopropylsulphanyl, methylsulphinyl, trifluoromethylsulphinyl, ethylsulphinyl, 2,2,2-trifluoroethylsulphinyl, 2,2-difluoroethylsulphinyl, isopropylsulphinyl, methylsulphonyl, trifluoromethylsulphonyl, ethylsulphonyl, 2,2,2-trifluoroethylsulphonyl, 2,2-difluoroethylsulphonyl, isopropylsulphonyl, cyclopropyl, 1-cyanocyclopropyl, 1-chlorocyclopropyl, 1-fluorocyclopropyl, 2-cyanocyclopropyl, 2-chlorocyclopropyl, 2-fluorocyclopropyl, 2,2,3,3-tetrafluorocyclopropyl, 2-cyclopropylcyclopropyl, cyclobutyl, cyclopentyl, cyclohexyl, 4-trifluoromethylcyclohexyl, cyclopropylmethyl, cyclopropylethyl, cyclobutylmethyl, N-cyclopropyl-N-methylaminocarbonyl, morpholin-4-ylcarbonylmethyl, piperazin-1-ylcarbonylmethyl, 4-methylpiperazin-1-ylcarbonylmethyl, heterocyclylmethyl and heterocyclylethyl each optionally mono-, di- or trisubstituted identically or differently by fluorine, chlorine, bromine, cyano, nitro, hydroxyl, amino, methyl, ethyl, isopropyl, tert-butyl, trifluoromethyl, difluoromethyl, methoxy, trifluoromethoxy or difluoromethoxy, in each case cyclopropyl-substituted heterocyclylmethyl and heterocyclylethyl, where the cyclopropyl radical is optionally mono- or disubstituted by methyl, fluorine, chlorine or cyano or monosubstituted by cyclopropyl, aryl optionally mono-, di- or trisubstituted identically or differently by fluorine, chlorine, bromine, cyano, nitro, hydroxyl, amino, methyl, ethyl, isopropyl, tert-butyl, trifluoromethyl, difluoromethyl, methoxy, trifluoromethoxy or difluoromethoxy, cyclopropyl-substituted aryl, where the cyclopropyl radical is optionally mono- or disubstituted by methyl, fluorine, chlorine or cyano or monosubstituted by cyclopropyl, arylmethyl and arylethyl each optionally mono-, di- or trisubstituted identically or differently by fluorine, chlorine, bromine, cyano, nitro, hydroxyl, amino, methyl, ethyl, isopropyl, tert-butyl, trifluoromethyl, difluoromethyl, methoxy, trifluoromethoxy or difluoromethoxy, cyclopropyl-substituted arylmethyl and arylethyl, where the cyclopropyl radical is optionally mono- or disubstituted by methyl, fluorine, chlorine or cyano or monosubstituted by cyclopropyl, hetarylmethyl and hetarylethyl each optionally mono- or disubstituted identically or differently by fluorine, chlorine, bromine, cyano, nitro, hydroxyl, amino, methyl, ethyl, isopropyl, tert-butyl, trifluoromethyl, difluoromethyl, methoxy, trifluoromethoxy or difluoromethoxy, cyclopropyl-substituted hetarylmethyl and hetarylethyl, where the cyclopropyl radical is optionally mono- or disubstituted by methyl, fluorine, chlorine or cyano or monosubstituted by cyclopropyl, or $R^{22}$ is a D radical from the group of

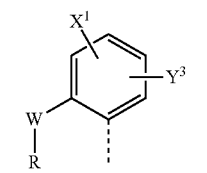

(D-1)

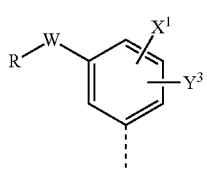

(D-2)

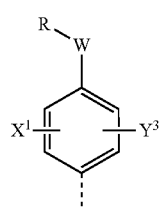

(D-3)

or is an E radical from the group of

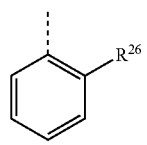

E-1

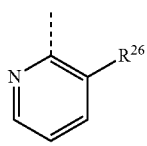

E-2

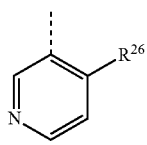

E-3

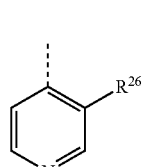

E-4

-continued

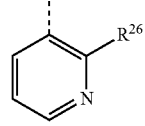

E-5

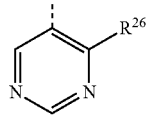

E-6

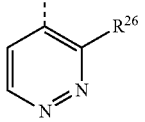

E-10

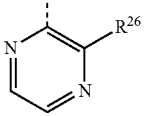

E-11

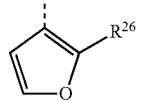

E-18

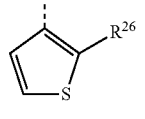

E-21

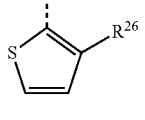

E-23

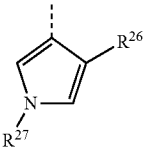

E-25

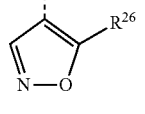

E-27

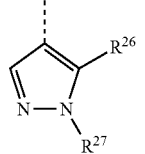

E-31

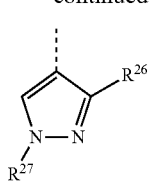 E-35

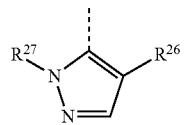 E-36

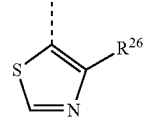 E-39

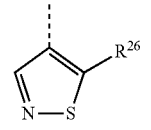 E-44

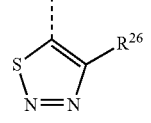 E-49

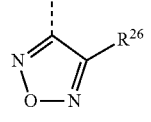 E-51 or in the case that $R^2$=d)
$R^{22}$ is also the radical

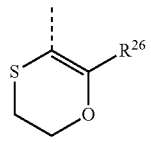 E-13

$R^{23}$ is a radical from the group of hydrogen, $C_1$-$C_6$-alkyl, $C_2$-$C_4$-alkenyl, $C_2$-$C_4$-alkynyl, $C_3$-$C_6$-cycloalkyl, $C_3$-$C_6$-cycloalkenyl, $C_1$-$C_6$-alkoxy, $C_2$-$C_6$-alkenyloxy, $C_2$-$C_6$-alkynyloxy, $C_3$-$C_6$-cycloalkyloxy, $C_1$-$C_4$-alkylthio-$C_1$-$C_4$-alkyl, $C_2$-$C_4$-alkenylthio-$C_1$-$C_4$-alkyl, cyano-$C_1$-$C_4$-alkyl, $C_1$-$C_4$-alkoxy-$C_1$-$C_4$-alkyl, and or, when $R^2$=c) or f), $R^{22}$ and $R^{23}$ together with the nitrogen atom to which they are bonded are pyrrolidinyl, piperidinyl, morpholinyl, thiomorpholinyl, thiomorpholinyl 1-oxide, thiomorpholinyl 1,1-dioxide, piperazinyl, 1-methylpiperazinyl or 2-oxo-1-methylpiperazinyl, $R^{27}$ is hydrogen or methyl and $R^{26}$ is a radical from the group of hydrogen, methyl, 2,2,2-trifluoroethyl, 2,2-difluoroethyl, propenyl, propargyl, cyclopropyl, cyclopropylmethyl, methoxymethyl, methylsulphanyl, trifluoromethylsulphanyl, ethylsulphanyl, trifluoroethylsulphanyl, methylsulphinyl, trifluoromethylsulphinyl, ethylsulphinyl, trifluoroethylsulphinyl, methylthioethyl, methylsulphinylethyl, methylsulphonylethyl and cyanomethyl and compounds of the formula (I) in which
A is the A radical

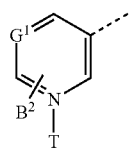 (A-a)

in which the broken line denotes the bond to the carbon atom of the bicyclic system of the formula (I), $G^1$ is N or C—$B^1$, $B^1$ is a radical from the group of hydrogen and fluorine, $B^2$ is hydrogen, T is oxygen or an electron pair, Q is sulphur, $R^1$ is hydrogen, $R^2$ is a B radical from the group of

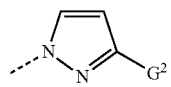 (B-1)

(B-2)

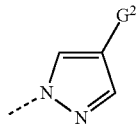 (B-3)

(B-4)

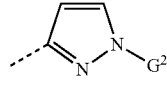 (B-5)

(B-9)

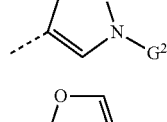 (B-10)

(B-11)

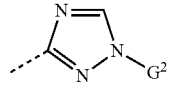 (B-12)

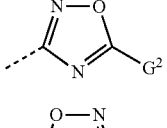

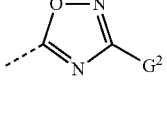

-continued (B-21) 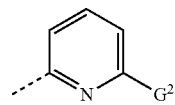

(B-23) 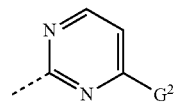

(B-25) 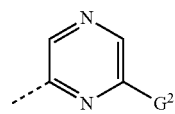

(B-27) 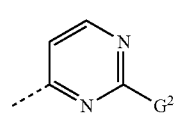

(B-28) 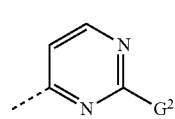

(B-31) 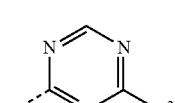

(B-37) 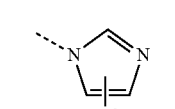

(B-41) 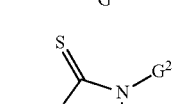

(B-42) 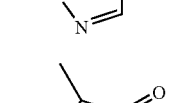

(B-43) 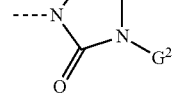

(B-46) 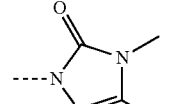

(B-47) 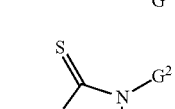

in which the broken line denotes the bond to the carbon atom of the bicyclic system of the formula (I), or $R^2$ c) is a radical of the formula

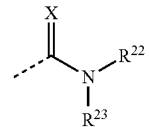

in which the broken line denotes the bond to the carbon atom of the bicyclic system of the formula (I), or $R^2$ d) is a radical of the formula

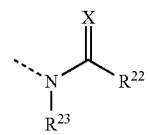

in which the broken line denotes the bond to the carbon atom of the bicyclic system of the formula (I), or $R^2$ e) is an F radical from the group of (F-8) and (F-10)

(F-8) 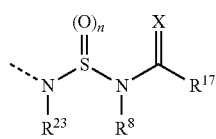

(F-10) 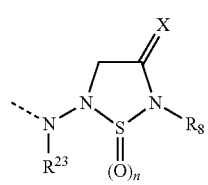

in which the broken line denotes the bond to the carbon atom of the bicyclic system of the formula (I), or $R^2$ f) is a radical of the formula

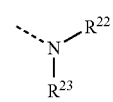

in which the broken line denotes the bond to the carbon atom of the bicyclic system of the formula (I), $G^2$ is hydrogen or a radical from the group of halogen, nitro, amino, cyano, $C_1$-$C_4$-alkylamino, halo-$C_1$-$C_4$-alkylamino, di-($C_1$-$C_4$-alkyl)amino, $C_1$-$C_4$-alkyl, halo-$C_1$-$C_4$-alkyl, $C_1$-$C_4$-alkoxy, halo-$C_1$-$C_4$-alkoxy, $C_1$-$C_4$-alkoxy-$C_1$-$C_4$-alkyl, halogenated $C_1$-$C_4$-alkoxy-$C_1$-$C_4$-alkyl, bis($C_1$-$C_4$-alkoxy)-$C_1$-$C_4$-alkyl, bis(halo-$C_1$-$C_4$-alkoxy)-$C_1$-$C_4$-alkyl, $C_1$-$C_4$-alkoxy-($C_1$-$C_4$-alkylsulphanyl)-$C_1$-$C_4$-alkyl, $C_1$-$C_4$-alkoxy-($C_1$-$C_4$-alkylsulphinyl)-$C_1$-$C_4$-alkyl, $C_1$-$C_4$-alkoxy-($C_1$-$C_4$-alkylsulphonyl)-$C_1$-$C_4$-alkyl, bis($C_1$-$C_4$-alkylsulphanyl)-$C_1$-$C_4$-alkyl, bis(halo-$C_1$-$C_4$-alkylsulphanyl)-$C_1$-$C_4$-alkyl, bis(hydroxy-$C_1$-$C_4$-alkylsulphanyl)-$C_1$-$C_4$-alkyl, $C_1$-$C_4$-alkoxycarbonyl, $C_1$-$C_4$-alkoxycarbonyl-$C_1$-$C_4$-alkyl, $C(X^2)NR^3R^4$, $NR^6R^7$, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl and $C_1$-$C_4$-haloalkylsulphonyl, or $G^2$ is a (C-1) or (C-9) radical

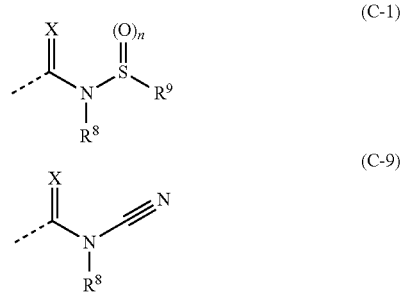

in which the broken line denotes the bond to the B radicals,

X is oxygen, $X^1$ is a radical from the group of hydrogen, fluorine, chlorine, bromine, cyano, methyl, ethyl, trifluoromethyl, methoxy, ethoxy, difluoromethoxy and trifluoromethoxy, $X^2$ is oxygen, sulphur, $NR^5$ or NOH, n is 2, R is $NR^{18}R^{19}$ or is an in each case optionally mono-, di-, tri-, tetra- or penta-fluorine- or -chlorine-substituted or mono- or di-cyano-substituted radical from the group of $C_1$-$C_4$-alkyl, $C_3$-$C_4$-alkenyl, $C_3$-$C_4$-alkynyl, $C_1$-$C_2$-alkoxy-$C_1$-$C_2$-alkyl and $C_1$-$C_2$-alkyl-S—$C_1$-$C_2$-alkyl, $C_1$-$C_2$-alkyl-S(O)—$C_1$-$C_2$-alkyl, $C_1$-$C_2$-alkyl-S(O)$_2$—$C_1$-$C_2$-alkyl, is $R^{18}$—CO—$C_1$-$C_2$-alkyl, is $NR^{18}R^{19}$—CO—$C_1$-$C_2$-alkyl, is optionally mono- or di-$C_1$-$C_2$-alkyl-, —$C_1$-$C_2$-alkoxy- or —$C_1$-$C_2$-haloalkyl-substituted or oxygen atom-substituted (leads to C=O) $C_3$-$C_6$-cycloalkyl, is optionally mono- or di-$C_1$-$C_2$-alkyl-, —$C_1$-$C_2$-alkoxy- or —$C_1$-$C_2$-haloalkyl or oxygen atom-substituted (leads to C=O) $C_3$-$C_6$-cycloalkenyl, is optionally mono- or di-$C_1$-$C_2$-alkyl-, —$C_1$-$C_2$-alkoxy- or —$C_1$-$C_2$-haloalkyl-substituted $C_3$-$C_6$-cycloalkyl-$C_1$-$C_2$-alkyl, is optionally mono- or di-$C_1$-$C_2$-alkyl-, —$C_1$-$C_2$-alkoxy- or —$C_1$-$C_2$-haloalkyl-substituted $C_3$-$C_6$-cycloalkenyl-$C_1$-$C_2$-alkyl, is optionally mono- or di-$C_1$-$C_2$-alkyl-, —$C_1$-$C_2$-alkoxy- or —$C_1$-$C_2$-haloalkyl-substituted heterocyclyl, is optionally mono- or di-$C_1$-$C_2$-alkyl-, —$C_1$-$C_2$-alkoxy- or —$C_1$-$C_2$-haloalkyl-substituted heterocyclyl-$C_1$-$C_2$-alkyl or is in each case optionally mono- or di-fluorine-, -chlorine-, -bromine-, -cyano-, -methyl-, -ethyl-, -difluoromethyl-, -trifluoromethyl-, -methoxy-, -ethoxy-, -difluoromethoxy- or -trifluoromethoxy-substituted phenyl, benzyl, pyridyl, pyrimidyl, thiazolyl, oxazolyl, pyrazolyl, thienyl, furanyl, pyridinylmethyl or thiazolylmethyl, $R^3$ is $C_1$-$C_4$-alkyl, $R^4$ is a radical from the group of hydrogen, $C_1$-$C_4$-alkyl, halo-$C_1$-$C_4$-alkyl, cyano-$C_1$-$C_4$-alkyl, $C_2$-$C_4$-alkynyl, $C_3$-$C_6$-cycloalkyl, $C_3$-$C_6$-cycloalkyl-$C_1$-$C_4$-alkyl, $C_1$-$C_4$-alkoxy-$C_1$-$C_4$-alkyl, $C_1$-$C_4$-alkoxycarbonyl, $C_1$-$C_4$-alkoxycarbonyl-$C_1$-$C_4$-alkyl and $C_1$-$C_4$-alkylthio-$C_1$-$C_4$-alkyl, $R^5$ is a radical from the group of hydrogen, $C_1$-$C_4$-alkyl, halo-$C_1$-$C_4$-alkyl, cyano-$C_1$-$C_4$-alkyl, $C_2$-$C_4$-alkynyl, $C_3$-$C_6$-cycloalkyl, $C_3$-$C_6$-cycloalkyl-$C_1$-$C_4$-alkyl, $C_1$-$C_4$-alkoxy-$C_1$-$C_4$-alkyl, $C_1$-$C_4$-alkoxycarbonyl, $C_1$-$C_4$-alkoxycarbonyl-$C_1$-$C_4$-alkyl and $C_1$-$C_4$-alkylthio-$C_1$-$C_4$-alkyl, $R^6$ is hydrogen or $C_1$-$C_4$-alkyl, $R^7$ is a radical from the group of hydrogen, $C_1$-$C_4$-alkyl, halo-$C_1$-$C_4$-alkyl, cyano-$C_1$-$C_4$-alkyl, $C_2$-$C_4$-alkynyl, $C_1$-$C_4$-alkoxy, halo-$C_1$-$C_4$-alkoxy, $C_1$-$C_4$-alkoxy-$C_1$-$C_4$-alkyl, $C_1$-$C_4$-alkoxycarbonyl, $C_1$-$C_4$-alkoxycarbonyl-$C_1$-$C_4$-alkyl, $C_1$-$C_4$-alkylthio-$C_1$-$C_4$-alkyl, aryl-$C_1$-$C_4$-alkyl or hetaryl-$C_1$-$C_4$-alkyl, or $R^6$ and $R^7$ together with the nitrogen atom to which they are bonded form a 4- to 7-membered ring which may contain one or two further heteroatoms from the group of nitrogen, oxygen and sulphur (where oxygen and sulphur atoms must not be directly adjacent to one another), $R^8$ is a radical from the group of hydrogen, $C_1$-$C_6$-alkyl, $C_1$-$C_6$-haloalkyl, cyano-$C_1$-$C_6$-alkyl, $C_1$-$C_6$-alkoxy, $C_1$-$C_6$-haloalkoxy, $C_2$-$C_6$-alkenyl, $C_1$-$C_6$-alkoxy-$C_1$-$C_6$-alkyl, in each case optionally halogen-substituted $C_1$-$C_6$-alkylcarbonyl and $C_1$-$C_6$-alkylsulphonyl, optionally halogen-substituted $C_1$-$C_6$-alkoxycarbonyl and optionally halogen-, $C_1$-$C_6$-alkyl-, $C_1$-$C_6$-alkoxy-, $C_1$-$C_6$-haloalkyl- and cyano-substituted $C_3$-$C_6$-cycloalkylcarbonyl, or is a cation or an optionally $C_1$-$C_6$-alkyl- or aryl-$C_1$-$C_6$-alkyl-substituted ammonium ion, $R^9$ is a radical from the group of in each case optionally halogen-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-haloalkylsulphinyl-, $C_1$-$C_4$-alkylsulphonyl- and $C_1$-$C_4$-haloalkylsulphonyl-substituted $C_1$-$C_4$-alkyl, $C_2$-$C_4$-alkenyl and $C_2$-$C_4$-alkynyl, in each case optionally halogen-, $C_1$-$C_4$-alkyl-, $C_1$-$C_4$-haloalkyl-, $C_1$-$C_4$-alkoxy-, $C_1$-$C_4$-haloalkoxy-substituted $C_3$-$C_6$-cycloalkyl, $C_3$-$C_6$-cycloalkyl-$C_1$-$C_4$-alkyl and $C_3$-$C_4$-cycloalkenyl, in which one or two ring members may each be replaced by a heteroatom from the group of sulphur, oxygen (where oxygen atoms must not be directly adjacent to one another) and nitrogen (and in this case is especially

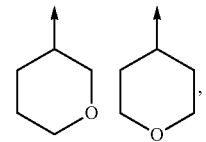

where the arrow in each case denotes the bond to the sulphur atom in the (C-1) radical), in each case optionally halogen-, cyano- (including in the alkyl moiety), nitro-, $C_1$-$C_4$-alkyl-, $C_1$-$C_4$-haloalkyl-, $C_3$-$C_6$-cycloalkyl-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-haloalkylsulphinyl-, $C_1$-$C_4$-alkylsulphonyl-, $C_1$-$C_4$-haloalkylsulphonyl-, amino-, $C_1$-$C_4$-alkyl amino-, di($C_1$-$C_4$-alkyl)amino-, $C_1$-$C_4$-alkylcarbonylamino-, $C_1$-$C_4$-alkoxycarbonylamino-, $C_1$-$C_4$-alkoxy-$C_1$-$C_4$-alkyl-, $C_1$-$C_4$-haloalkoxy-$C_1$-$C_4$-alkyl-, $C_2$-$C_4$-alkenyl-, $C_2$-$C_4$-alkynyl-, $C_3$-$C_6$-cycloalkyl-$C_1$-$C_4$-alkyl-, $C_1$-$C_4$-alkylcarbonyl-, $C_1$-$C_4$-alkoxycarbonyl- or aminocarbonyl-substituted aryl, heteroaryl, aryl-$C_1$-$C_4$-alkyl and heteroaryl-$C_1$-$C_4$-alkyl, or is NR'R" in which R' and R" are independently a radical from the group of hydrogen and $C_1$-$C_4$-alkyl, $R^8$ and $R^9$ in the (C-1) radical, together with the N—S(O)n group to which they are bonded, may also form a saturated or unsaturated and optionally halogen-, $C_1$-$C_6$-alkyl-, $C_1$-$C_6$-haloalkyl-, $C_1$-$C_6$-alkoxy-, $C_1$-$C_6$-haloalkoxy-substituted 5- to 7-membered ring which may contain one or two heteroatoms from the group of sulphur, oxygen (where oxygen atoms must not be directly adjacent to one another) and nitrogen and/or at least one and preferably one carbonyl group; $R^8$ and $R^9$ together with the N—S(O)n group to which they are bonded may especially be a radical from the group of

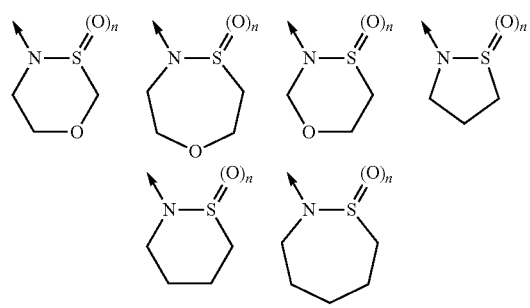

(in which the arrow in each case denotes the bond to the C(X) group), $R^{17}$ is a radical from the group of in each case optionally halogen-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-haloalkylsulphinyl-, $C_1$-$C_4$-alkylsulphonyl- and $C_1$-$C_4$-haloalkylsulphonyl-substituted $C_1$-$C_4$-alkyl, $C_2$-$C_4$-alkenyl and $C_2$-$C_4$-alkynyl, in each case optionally halogen-, $C_1$-$C_4$-alkyl-, $C_1$-$C_4$-haloalkyl-, $C_1$-$C_4$-alkoxy-, $C_1$-$C_4$-haloalkoxy-substituted $C_3$-$C_6$-cycloalkyl, $C_3$-$C_6$-cycloalkyl-$C_1$-$C_4$-alkyl, $C_3$-$C_4$-cycloalkenyl, N-pyrrolidinyl, N-piperidinyl, N-morpholinyl, N-thiomorpholinyl, N-thiomorpholinyl 1-oxide, N-thiomorpholinyl 1,1-dioxide, N-piperazinyl, N-1-methylpiperazinyl and N-2-oxo-1-methylpiperazinyl, in each case optionally halogen-, cyano- (including in the alkyl moiety), nitro-, $C_1$-$C_4$-alkyl-, $C_1$-$C_4$-haloalkyl-, $C_3$-$C_6$-cycloalkyl-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-haloalkylsulphinyl-, $C_1$-$C_4$-alkylsulphonyl-, $C_1$-$C_4$-haloalkylsulphonyl-, amino-, $C_1$-$C_4$-alkylamino-, di-($C_1$-$C_4$-alkyl)amino-, $C_1$-$C_4$-alkylcarbonylamino-, $C_1$-$C_4$-alkoxycarbonylamino-, $C_1$-$C_4$-alkoxy-$C_1$-$C_4$-alkyl-, $C_1$-$C_4$-haloalkoxy-$C_1$-$C_4$-alkyl-, $C_2$-$C_4$-alkenyl, $C_2$-$C_4$-alkynyl-, $C_3$-$C_6$-cycloalkyl-$C_1$-$C_4$-alkyl-, $C_1$-$C_4$-alkylcarbonyl-, $C_1$-$C_4$-alkoxycarbonyl- or aminocarbonyl-substituted aryl, heteroaryl, aryl-$C_1$-$C_4$-alkyl and heteroaryl-$C_1$-$C_4$-alkyl, or is NR'R" in which R' and R" are independently a radical from the group of hydrogen and $C_1$-$C_4$-alkyl, $R^{18}$ is a radical from the group of hydrogen, hydroxyl, in each case optionally mono-, di-, tri-, tetra- or penta-fluorine- or -chlorine-substituted or mono- or di-cyano-substituted $C_1$-$C_4$-alkyl, $C_1$-$C_4$-alkoxy, $C_1$-$C_4$-alkoxy-$C_1$-$C_4$-alkyl, $C_1$-$C_4$-alkyl-S—$C_1$-$C_2$-alkyl, $C_1$-$C_4$-alkyl-S(O)—$C_1$-$C_2$-alkyl, $C_1$-$C_4$-alkyl-S(O)$_2$—$C_1$-$C_2$-alkyl, $C_1$-$C_4$-alkylcarbonyl, $C_1$-$C_4$-alkoxycarbonyl, $C_3$-$C_6$-cycloalkyl, $C_3$-$C_6$-cycloalkyl-$C_1$-$C_3$-alkyl, heterocyclyl and heterocyclyl-$C_1$-$C_3$-alkyl, and in each case optionally mono- to tri-$C_1$-$C_4$-alkyl-, —$C_1$-$C_3$-haloalkyl-, —$C_1$-$C_3$-alkoxy-, —$C_1$-$C_3$-haloalkoxy-, -cyclopropyl-, -fluorine-, -chlorine-, -bromine- or -cyano-substituted phenyl, benzyl, pyridyl, pyrimidyl, thiazolyl, oxazolyl, pyrazolyl, thienyl, furanyl, pyridinylmethyl and thiazolylmethyl, $R^{19}$ is hydrogen, an alkali metal or alkaline earth metal ion, an optionally mono- to tetra-$C_1$-$C_4$-alkyl-substituted ammonium ion or an in each case optionally mono-, di-, tri-, tetra- or penta-fluorine- or -chlorine-substituted or mono- or di-cyano-substituted radical from the group of $C_1$-$C_4$-alkyl, $C_1$-$C_4$-alkoxy, $C_1$-$C_4$-alkoxy-$C_1$-$C_2$-alkyl and $C_1$-$C_4$-alkyl-S—$C_1$-$C_2$-alkyl, $C_1$-$C_4$-alkyl-S(O)—$C_1$-$C_2$-alkyl and $C_1$-$C_4$-alkyl-S(O)$_2$—$C_1$-$C_2$-alkyl, W is a radical from the group of S, SO and SO$_2$, $Y^3$ is a radical from the group of hydrogen, fluorine, chlorine, bromine, cyano, methyl, ethyl, trifluoromethyl, methoxy, ethoxy, difluoromethoxy and trifluoromethoxy, and in the case that $R^2$ is f)

$R^{22}$ is a radical from the group of methyl, ethyl, isopropyl, n-propyl, n-butyl, iso-butyl, sec-butyl, tert-butyl, 2,2,2-trifluoroethyl, 2,2-difluoroethyl, 2,2-difluoro-n-propyl, methylsulphanylmethyl, methylsulphanylethyl, methylsulphanyl-n-propyl, trifluoromethylsulphonylmethyl, ethylsulphonylmethyl, 2,2,2-trifluoroethylsulphonylmethyl, 2,2-difluoroethylsulphonylmethyl, isopropylsulphanylmethyl, methylsulphinylmethyl, trifluoromethylsulphinylmethyl, ethylsulphinylmethyl, 2,2,2-trifluoroethylsulphinylmethyl, 2,2-difluoroethylsulphinylmethyl, isopropylsulphinylmethyl, methylsulphonylmethyl, trifluoromethylsulphonylmethyl, ethylsulphonylmethyl, 2,2,2-trifluoroethylsulphonylmethyl, 2,2-difluoroethylsulphonylmethyl, isopropylsulphonylmethyl, methoxycarbonylmethyl, ethoxycarbonylmethyl, methoxycarbonylethyl, ethoxycarbonylethyl, dimethylaminocarbonylmethyl, diethylaminocarbonylmethyl, N-ethyl-N-methylaminocarbonylmethyl, N-isopropyl-N-methylaminocarbonylmethyl, dimethylaminocarbonylethyl, diethylaminocarbonylethyl, N-ethyl-N-methylaminocarbonylethyl, N-isopropyl-N-methylaminocarbonylethyl, N-cyclopropyl-N-methylaminocarbonylmethyl, N-cyclopropyl-N-methylaminocarbonylethyl, methylsulphanyl, trifluoromethylsulphanyl, ethylsulphanyl, 2,2,2-trifluoroethylsulphanyl, 2,2-difluoroethylsulphanyl, isopropylsulphanyl, methylsulphinyl, trifluoromethylsulphinyl, ethylsulphinyl, 2,2,2-trifluoroethylsulphinyl, 2,2-difluoroethylsulphinyl, isopropylsulphinyl, methylsulphonyl, trifluoromethylsulphonyl, ethylsulphonyl, 2,2,2-trifluoroethylsulphonyl, 2,2-difluoroethylsulphonyl, isopropylsulphonyl, cyclopropyl, 1-cyanocyclopropyl, 1-chlorocyclopropyl, 1-fluorocyclopropyl, 2-cyanocyclopropyl, 2-chlorocyclopropyl, 2-fluorocyclopropyl, 2,2,3,3-tetrafluorocyclopropyl, 2-cyclopropylcyclopropyl, cyclobutyl, cyclopentyl, cyclohexyl, 4-trifluoromethylcyclohexyl, cyclopropylmethyl, cyclopropylethyl, cyclobutylmethyl, morpholin-4-ylcarbonylmethyl, piperazin-1-ylcarbonylmethyl, 4-methylpiperazin-1-ylcarbonylmethyl, heterocyclylmethyl and heterocyclylethyl each optionally mono-, di- or trisubstituted identically or differently by fluorine, chlorine, bromine, cyano, nitro, hydroxyl, amino, methyl, ethyl, isopropyl, tert-butyl, trifluoromethyl, difluoromethyl, methoxy, trifluoromethoxy or difluoromethoxy, in each case cyclopropyl-substituted heterocyclylmethyl and heterocyclylethyl, where the cyclopropyl radical is optionally mono- or disubstituted by methyl, fluorine, chlorine or cyano or monosubstituted by cyclopropyl, aryl optionally mono-, di- or trisubstituted identically or differently by fluorine, chlorine, bromine, cyano, nitro, hydroxyl, amino, methyl, ethyl, isopropyl, tert-butyl, trifluoromethyl, difluoromethyl, methoxy, trifluoromethoxy or difluoromethoxy, cyclopropyl-substituted aryl, where the cyclopropyl radical is optionally mono- or disubstituted by methyl, fluorine, chlorine or cyano or monosubstituted by cyclopropyl, arylmethyl and arylethyl each optionally mono-, di- or trisubstituted identically or differently by fluorine, chlorine, bromine, cyano, nitro, hydroxyl, amino, methyl, ethyl, isopropyl, tert-butyl, trifluoromethyl, difluoromethyl, methoxy, trifluoromethoxy or difluoromethoxy, cyclopropyl-substituted arylmethyl and arylethyl, where the cyclopropyl radical is optionally mono- or disubstituted by methyl, fluorine, chlorine or cyano or monosubstituted by cyclopropyl, hetarylmethyl and hetarylethyl each optionally mono- or disubstituted identically or differently by fluorine, chlorine, bromine, cyano, nitro, hydroxyl, amino, methyl, ethyl, isopropyl, tert-butyl, trifluoromethyl, difluoromethyl, methoxy, trifluoromethoxy or difluoromethoxy, cyclopropyl-substituted hetarylmethyl and hetarylethyl, where the cyclopropyl radical is optionally mono- or disubstituted by methyl, fluorine, chlorine or cyano or monosubstituted by cyclopropyl, and in the case that $R^2$ is c), d) or f)

$R^{22}$ is a D radical from the group of

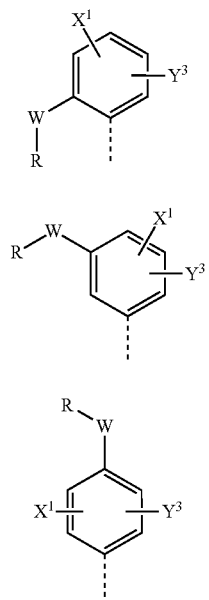

(D-1)

(D-2)

(D-3)

or is an E radical from the group of

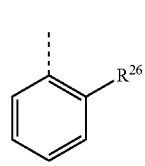

E-1

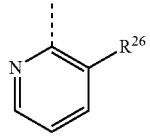

E-2

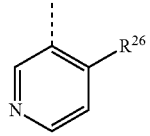

E-3

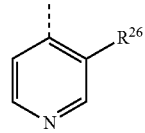

E-4

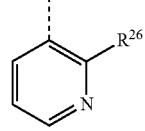

E-5

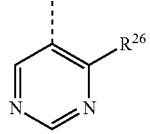

E-6

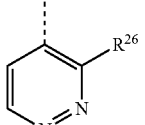

E-10

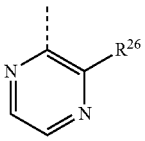

E-11

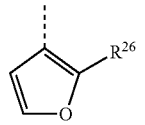

E-18

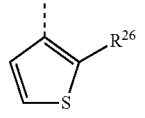

E-21

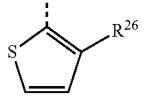

E-23

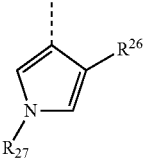

E-25

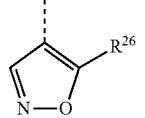

E-27

-continued

E-31 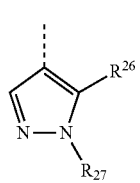

E-35 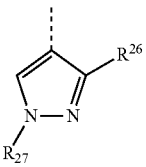

E-36 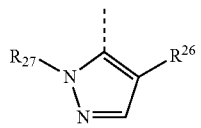

E-39 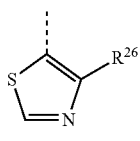

E-44 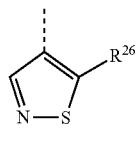

E-49 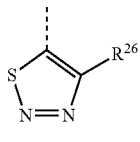

E-51 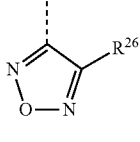

or in the case that R²=d)
R²² is also the radical

E-13 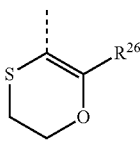

R²³ is a radical from the group of hydrogen, C₁-C₆-alkyl, C₂-C₄-alkenyl, C₂-C₄-alkynyl, C₃-C₆-cycloalkyl, C₃-C₆-cycloalkenyl, C₁-C₆-alkoxy, C₂-C₆-alkenyloxy, C₂-C₆-alkynyloxy, C₃-C₆-cycloalkyloxy, C₁-C₄-alkylthio-C₁-C₄-alkyl, C₂-C₄-alkenylthio-C₁-C₄-alkyl, cyano-C₁-C₄-alkyl, C₁-C₄-alkoxy-C₁-C₄-alkyl, and
or, when R²=f),
R²² and R²³ together with the nitrogen atom to which they are bonded are pyrrolidinyl, piperidinyl, morpholinyl, thiomorpholinyl, thiomorpholinyl 1-oxide, thiomorpholinyl 1,1-dioxide, piperazinyl, 1-methylpiperazinyl or 2-oxo-1-methylpiperazinyl, R²⁷ is hydrogen or methyl and
R²⁶ is a radical from the group of hydrogen, methyl, 2,2,2-trifluoroethyl, 2,2-difluoroethyl, propenyl, propargyl, cyclopropyl, cyclopropylmethyl, methoxymethyl, methylsulphanyl, trifluoromethylsulphanyl, ethylsulphanyl, trifluoroethylsulphanyl, methylsulphinyl, trifluoromethylsulphinyl, ethylsulphinyl, trifluoroethylsulphinyl, methylthioethyl, methylsulphinylethyl, methylsulphonylethyl and cyanomethyl.

Area of preference (4): A particular group of compounds of the formula (I) is that of those in which
A is the (A-a) radical (A-a) 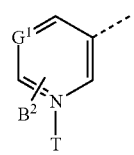

in which the broken line denotes the bond to the carbon atom of the bicyclic system of the formula (I),
G¹ is C—B¹,
B¹ is hydrogen or fluorine,
B² is hydrogen,
T is an electron pair or oxygen,
Q is sulphur,
R¹ is hydrogen,
R² a) is one of the following B radicals:

(B-1) 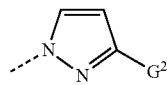

(B-2) 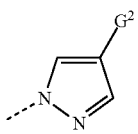

(B-41) 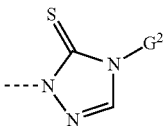

(B-42) 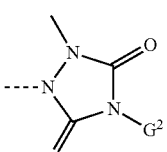

(B-43) 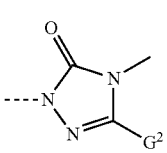

(B-46) 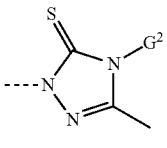

-continued

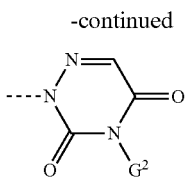
(B-47)

in which the broken line denotes the bond to the carbon atom of the bicyclic system of the formula (I), or R² c) is a radical of the formula

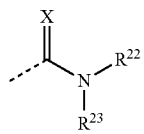

in which the broken line denotes the bond to the carbon atom of the bicyclic system of the formula (I), or R² f) is a radical of the formula

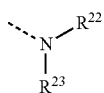

in which the broken line denotes the bond to the carbon atom of the bicyclic system of the formula (I), in which G² is a radical from the group of hydrogen, $C_1$-$C_4$-alkyl, halo-$C_1$-$C_4$-alkyl, $C_1$-$C_4$-alkoxy, halo-$C_1$-$C_4$-alkoxy, $C_1$-$C_4$-alkylthio and $C_1$-$C_4$-haloalkylthio, and in the case that R² is c)

R²² is the D radical

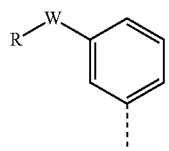
(D-2)

in which

R is optionally mono-, di-, tri-, tetra- or penta-fluorine- or -chlorine-substituted $C_1$-$C_4$-alkyl, W is a radical from the group of S, SO and $SO_2$, and in the case that R² is f)

R²² is optionally fluorine-, chlorine- or bromine-substituted phenyl and

R²³ is hydrogen or $C_1$-$C_6$-alkyl.

When sulphur and/or nitrogen occur in rings in the above definitions, for example in expressions such as "in which the rings may contain at least one heteroatom from the group of sulphur, oxygen (where oxygen and sulphur atoms must not be directly adjacent) and nitrogen" or "in which one or two ring members may each be replaced by a heteroatom from the group of sulphur, oxygen (where oxygen atoms must not be directly adjacent) and nitrogen", unless stated otherwise, the sulphur may also be in the form of SO or $SO_2$; the nitrogen, if it is not in the form of —N═, as well as NH, may also be in the form of N-alkyl (especially N—$C_1$-$C_6$-alkyl).

In the preferred definitions whose combination forms the range of preference (1), unless stated otherwise, cation is an alkali metal ion selected from the group of lithium, sodium, potassium, rubidium, caesium, preferably from the group of lithium, sodium, potassium, or an alkaline earth metal ion selected from the group of beryllium, magnesium, calcium, strontium, barium, preferably from the group of magnesium and calcium, halogen is selected from the group of fluorine, chlorine, bromine and iodine, preferably in turn from the group of fluorine, chlorine and bromine, aryl (including as part of a larger unit, for example arylalkyl) is selected from the group of phenyl, naphthyl, anthryl, phenanthrenyl, and preferably in turn is phenyl, hetaryl (synonymous with heteroaryl, including as part of a larger unit, for example hetarylalkyl) is selected from the group of furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzoisofuryl, benzothienyl, benzoisothienyl, indolyl, isoindolyl, indazolyl, benzothiazolyl, benzoisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl, heterocyclyl is a saturated 4-, 5- or 6-membered ring containing 1 or 2 nitrogen atoms and/or one oxygen atom and/or one sulphur atom, for example azetidinyl, azolidinyl, azinanyl, oxetanyl, oxolanyl, oxanyl, dioxanyl, thiethanyl, thiolanyl, thianyl, tetrahydrofuryl, piperazinyl, morpholinyl.

In the particularly preferred definitions whose combination forms the range of preference (2), unless stated otherwise, cation is an alkali metal ion selected from the group of lithium, sodium, potassium, rubidium, caesium, preferably from the group of lithium, sodium, potassium, or an alkaline earth metal ion selected from the group of beryllium, magnesium, calcium, strontium, barium, preferably from the group of magnesium and calcium, halogen is selected from the group of fluorine, chlorine, bromine and iodine, preferably in turn from the group of fluorine, chlorine and bromine, aryl (including as part of a larger unit, for example arylalkyl) is selected from the group of phenyl, naphthyl, anthryl, phenanthrenyl, and preferably in turn is phenyl, hetaryl (synonymous with heteroaryl, also as part of a larger unit, for example hetarylalkyl) is selected from the group of pyrazolyl, imidazolyl, 1,2,3-triazolyl, 1,2,4-triazolyl, oxazolyl, isoxazolyl, thiazolyl, isothiazolyl, pyridyl, pyrimidinyl, pyridazinyl, pyrazinyl, 1,2,3-triazinyl, 1,2,4-triazinyl, 1,3,5-triazinyl, heterocyclyl is selected from the group of azetidinyl, azolidinyl, azinanyl, oxetanyl, oxolanyl, oxanyl, dioxanyl, thiethanyl, thiolanyl, thianyl, tetrahydrofuryl, piperazinyl, morpholinyl.

In the very particularly preferred definitions and the especially preferred definitions, the combination of which forms the range of preference (3), unless stated otherwise, cation is an alkali metal ion from the group of lithium, sodium, potassium, rubidium, caesium, preferably from the group of lithium, sodium, potassium, or an alkaline earth metal ion from the group of beryllium, magnesium, calcium, strontium, barium, preferably from the group of magnesium and calcium, heterocyclyl is oxetanyl, thiethanyl, tetrahydrofuryl and morpholinyl, aryl is phenyl, hetaryl (synonymous with heteroaryl, including as part of a larger unit, for example hetarylalkyl) is a radical from the group of pyridyl, pyrimidyl, pyrazinyl, pyridazinyl, thiazolyl and pyrazolyl.

In the definitions which form the range of preference (4), halogen is fluorine, chlorine, bromine and iodine, preferably in turn fluorine, chlorine and bromine.

Halogen-substituted radicals, for example haloalkyl, are mono- or polyhalogenated, up to the maximum number of possible substituents. In the case of polyhalogenation, the halogen atoms may be identical or different. In this case, halogen is fluorine, chlorine, bromine or iodine, especially fluorine, chlorine or bromine.

Saturated or unsaturated hydrocarbon radicals, such as alkyl or alkenyl, may each be straight-chain or branched if possible, including in combination with heteroatoms, as, for example, in alkoxy.

Unless stated otherwise, optionally substituted radicals may be mono- or polysubstituted, where the substituents in the case of polysubstitutions may be the same or different.

When T in the A radical of the formula (A-a)

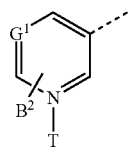

(A-a)

is an electron pair, the radical takes the form of the pyridine derivative of the formula

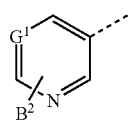

When T in the A radical of the formula (A-a)

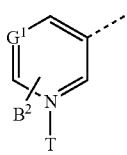

(A-a)

is oxygen, the radical takes the form of the pyridine N-oxide derivative of the formula

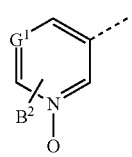

The representation of the formal charges (+ at nitrogen and − at oxygen) was dispensed with here.

The radical definitions or elucidations given in general terms or listed within areas of preference apply correspondingly to end products and to starting materials and intermediates. These radical definitions can be combined with one another as desired, i.e. including combinations between the respective ranges of preference.

According to the invention, preference is given to compounds of the formula (I) which contain a combination of the definitions listed above as being preferred (range of preference (1)).

According to the invention, particular preference is given to compounds of the formula (I) which contain a combination of the definitions listed above as being particularly preferred (range of preference (2)).

According to the invention, very particular preference is given to compounds of the formula (I) which contain a combination of the definitions listed above as being very particularly preferred (range of preference (3)).

According to the invention, special preference is given to compounds of the formula (I) which contain a combination of the definitions listed above as being special (range of preference (4)).

A preferred embodiment of the invention relates to compounds of the formula (I) in which A is the radical of the formula (A-a)

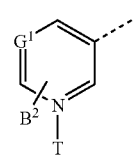

(A-a)

A further preferred embodiment of the invention relates to compounds of the formula (I) in which A is pyridin-3-yl.

A further preferred embodiment of the invention relates to compounds of the formula (I) in which A is 5-fluoropyridin-3-yl.

A further preferred embodiment of the invention relates to compounds of the formula (I) in which A is pyrimidin-5-yl.

A further preferred embodiment of the invention relates to compounds of the formula (I) in which A is pyridazin-4-yl.

A further preferred embodiment of the invention relates to compounds of the formula (I) in which $R^2$ has the definitions given under a).

A further preferred embodiment of the invention relates to compounds of the formula (I) in which $R^2$ has the definitions given under b).

A further preferred embodiment of the invention relates to compounds of the formula (I) in which $R^2$ has the definitions given under c).

A further preferred embodiment of the invention relates to compounds of the formula (I) in which $R^2$ has the definitions given under d).

A further preferred embodiment of the invention relates to compounds of the formula (I) in which $R^2$ has the definitions given under e).

A further preferred embodiment of the invention relates to compounds of the formula (I) in which $R^2$ has the definitions given under f).

A further preferred embodiment of the invention relates to compounds of the formula (I) in which $R^2$ has the definitions given under g).

A further preferred embodiment of the invention relates to compounds of the formula (I) in which R² is the radical (D-2)

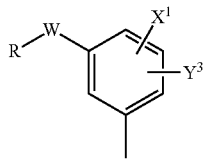
(D-2)

The radical definitions or elucidations given above in general terms or within areas of preference apply correspondingly to the end products (including the compounds of the formulae (I-A) to (I-P) shown later) and to the starting materials and intermediates. These radical definitions can be combined with one another as desired, i.e. including combinations between the respective ranges of preference.

In a preferred embodiment, the invention relates to compounds of the formula (I-A)

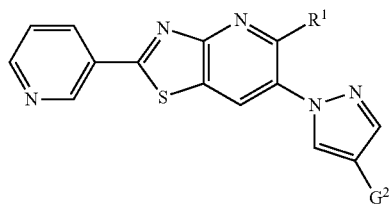

In a further preferred embodiment, the invention relates to compounds of the formula (I-B)

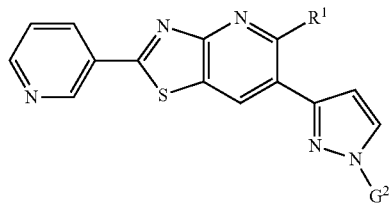

In a further preferred embodiment, the invention relates to compounds of the formula (I-C)

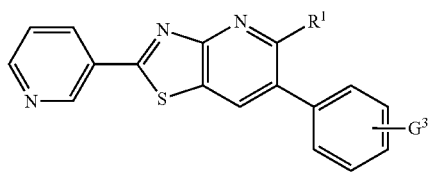

In a further preferred embodiment, the invention relates to compounds of the formula (I-D)

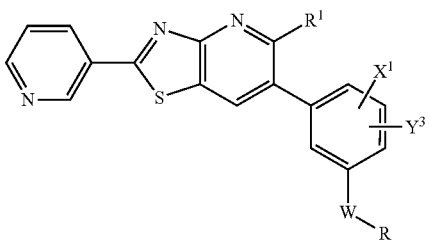

In a further preferred embodiment, the invention relates to compounds of the formula (I-E)

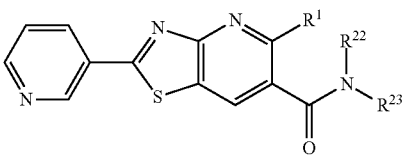

In a further preferred embodiment, the invention relates to compounds of the formula (I-F)

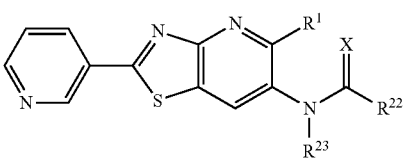

In a further preferred embodiment, the invention relates to compounds of the formula (I-G)

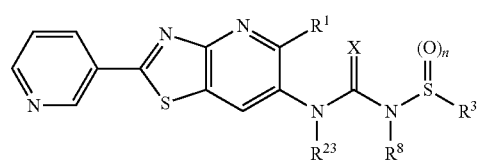

In a further preferred embodiment, the invention relates to compounds of the formula (I-H)

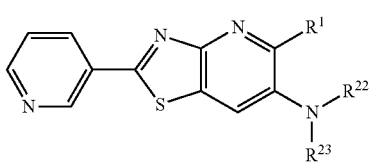

In a further preferred embodiment, the invention relates to compounds of the formula (I-I)

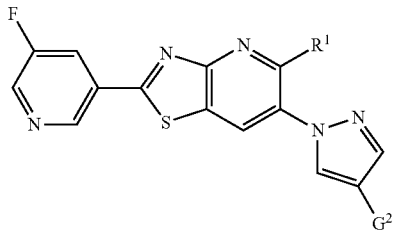

In a further preferred embodiment, the invention relates to compounds of the formula (I-J)

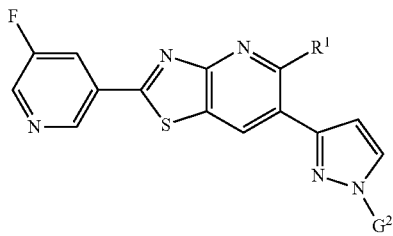

In a further preferred embodiment, the invention relates to compounds of the formula (I-K)

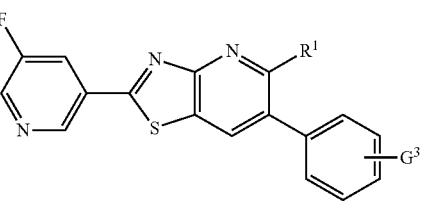

In a further preferred embodiment, the invention relates to compounds of the formula (I-L)

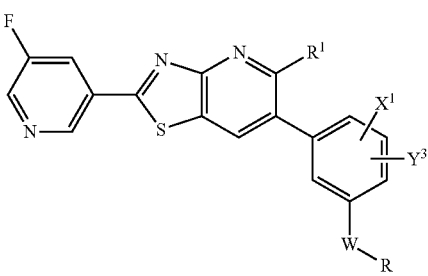

In a further preferred embodiment, the invention relates to compounds of the formula (I-M)

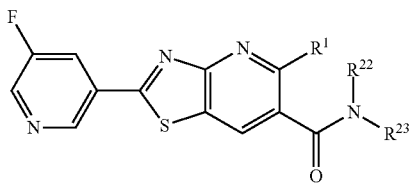

In a further preferred embodiment, the invention relates to compounds of the formula (I-N)

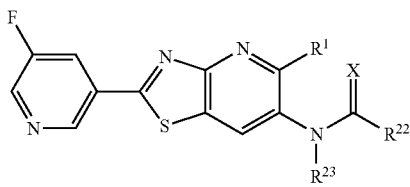

In a further preferred embodiment, the invention relates to compounds of the formula (I-O)

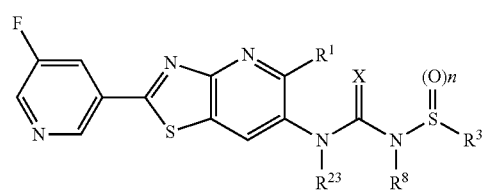

In a further preferred embodiment, the invention relates to compounds of the formula (I-P)

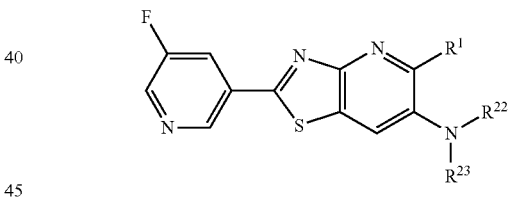

In the formulae (I-A) to (I-P), the variables have the definitions given further up.

The compounds of the formula (I) and their acid addition salts and metal salt complexes have good efficacy, especially for control of animal pests including arthropods and especially insects.

Suitable salts of the compounds of the general formula (I) include customary nontoxic salts, i.e. salts with appropriate bases and salts with added acids. Preference is given to salts with inorganic bases, such as alkali metal salts, for example sodium, potassium or caesium salts, alkaline earth metal salts, for example calcium or magnesium salts, ammonium salts, salts with organic bases and with inorganic amines, for example triethylammonium, dicyclohexylammonium, N,N'-dibenzylethylenediammonium, pyridinium, picolinium or ethanolammonium salts, salts with inorganic acids, for example hydrochlorides, hydrobromides, dihydrosulphates, trihydrosulphates, or phosphates, salts with organic carboxylic acids or organic sulphonic acids, for example formates, acetates, trifluoroacetates, maleates, tartrates, methanesulphonates, benzenesulphonates or para-toluenesulphonates, salts with basic amino acids, for example arginates, aspartates or glutamates, and the like.

The compounds of the formula (I) may possibly also, depending on the nature of the substituents, take the form of stereoisomers, i.e. the form of geometric and/or optical isomers or isomer mixtures in different compositions. This invention provides both the pure stereoisomers and any desired mixtures of these isomers, even though it is generally only compounds of the formula (I) that are discussed here.

The invention therefore relates both to the pure enantiomers and diastereomers and to mixtures thereof for controlling animal pests, including arthropods and particularly insects.

However, preference is given in accordance with the invention to using the optically active, stereoisomeric forms of the compounds of the formula (I) and salts thereof.

The terms "synthesis example" and "use example" are used synonymously here, unless stated otherwise.

It has additionally been found that the compounds of the formula (I) and also those compounds listed in Table 1 that are not covered by the formula (I) can be prepared by the processes described hereinafter.

Method A: Compounds of the formula (I) in which the heterocycle A is optionally $B^2$-substituted pyrimidin-5-yl (A-a; $G^1$=N), pyridin-3-yl (A-a; $G^1$=C—$B^1$), pyrazin-2-yl (A-b), pyridazin-3-yl (A-c), thiazol-5-yl (A-d), isothiazol-4-yl (A-e) and pyrazol-4-yl (A-f) can be prepared, for example, by Method A (cf. Reaction Scheme I) in three steps.

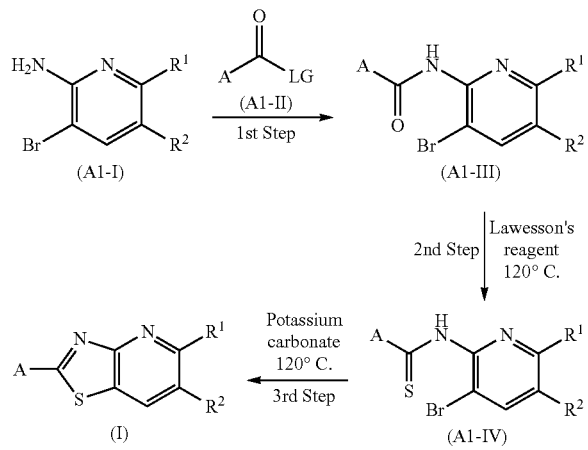

Reaction Scheme I - Method A

LG = Leaving group, e.g. halogen, CO—OR (R = aryl, alkyl)
N-imidazol-1-yl, OH etc.

In Reaction Scheme I, A, $R^1$ and $R^2$, unless indicated otherwise, have the meanings mentioned above.

For example, the substituted anilines of the formula (A1-I) can be reacted with the appropriate activated carboxylic acids (for example in the form of the carbonyl chloride or the hydrochloride thereof) of the formula (A1-II) in the presence of basic reaction auxiliaries in a first reaction step to give compounds of the formula (A1-III). These are then thionated by appropriate sulphur donors, for example Lawesson's reagent, to give compounds of the formula (A1-IV). In a third reaction step, these can then be cyclized in the presence of a suitable base, for example potassium carbonate, to form the compounds (I).

Method A—Step 1: Some of the compounds of the formula (A1-I) are known and commercially available or can be obtained by preparation processes known in principle (for example when $R^1$=H, $R^2$=Br; 3,5-dibromopyridin-2-amine (Tetrahedron Letters (2014), 55(36), 5058-5061).

Some of the compounds of the formula (A1-II) are known and commercially available or can be obtained by preparation processes known in principle (for example when A=pyridin-3-yl, LG=Cl; nicotinyl chloride (Journal of the American Chemical Society (1953), 75, 4364) or when A=5-fluoropyridin-3-yl, LG=Cl; 5-fluoronicotinyl chloride (U.S. Pat. No. 2,516,830).

For the amidation step, numerous reaction conditions have been described, for example G. Benz in Comprehensive Organic Synthesis, 1st ed., Pergamon Press, Oxford, 1991, vol. 6, p. 381-417; P. D. Bailey et al. in Comprehensive Organic Functional Group Transformation, 1st ed., Elsevier Science Ltd., Oxford, 1995, vol. 5, p. 257-308 and R. C. Larock in Comprehensive Organic Transformations, 2nd ed., Wiley-VCH, New York, Weinheim, 1999, p. 1929-1994. Some of these reactions proceed via intermediate carbonyl chlorides, which can be used in isolated form or having been generated in situ from A1-II (LG=OH).

The amidation reactions are optionally carried out in the presence of a condensing agent, optionally in the presence of an acid acceptor and optionally in the presence of a solvent.

Useful condensing agents are all the condensing agents typically usable for such amidation reactions. Examples include acid halide formers such as phosgene, phosphorus trichloride, oxalyl chloride or thionyl chloride; carbodiimides such as N,N'-dicyclohexylcarbodiimide (DCC) and 1-(3-dimethylaminopropyl)-3-ethylcarbodiimide (EDCI), or other customary condensing agents such as phosphorus pentoxide, polyphosphoric acid, N,N'-carbonyldiimidazole, 2-chloropyridine 1-methiodide (Mukaiyama's reagent), 2-ethoxy-N-ethoxycarbonyl-1,2-dihydroquinoline (EEDQ), triphenylphosphine/carbon tetrachloride, bromotripyrrolidinophosphonium hexafluorophosphate (BROP), O-(1H-benzotriazol-1-yloxy)tris(dimethylamino)phosphonium hexafluorophosphate (BOP), N,N,N',N'-bis(tetramethylene) chlorouronium tetrafluoroborate, O-(1H-benzotriazol-1-yl)-N,N,N',N'-tetramethyluronium hexafluorophosphate (HBTU), O-(1H-benzotriazol-1-yl)-N,N,N',N'-bis(tetramethylene)uronium hexafluorophosphate, O-(1H-benzotriazol-1-yl)-N,N,N',N'-tetramethyluronium tetrafluoroborate (TBTU), O-(1H-benzotriazol-1-yl)-N,N,N',N'-bis(tetramethylene)uronium tetrafluoroborate, O-(7-azabenzotriazol-1-yl)-N,N,N',N'-tetramethyluronium hexafluorophosphate (HATU), 1-hydroxybenzotriazole (HOBt) and 4-(4,6-dimethoxy-1,3,5-triazin-2-yl)-4-methylmorpholinium salt (DMT.MM), usually available as chloride. These reagents can be used separately or, if appropriate, in combination.

Useful acid acceptors are all customary inorganic or organic bases, for example triethylamine, diisopropylethylamine, N-methylmorpholine or N,N-dimethylaminopyridine. Process A according to the invention is optionally carried out in the presence of a suitable reaction auxiliary, for example N,N-dimethylformamide or N,N-dimethylaminopyridine.

Solvents or diluents include all inert organic solvents, for example aliphatic or aromatic hydrocarbons (such as petroleum ether, toluene), halogenated hydrocarbons (such as chlorotoluene, dichloromethane, chloroform, 1,2-dichloroethane), ethers (such as diethyl ether, dioxane, tetrahydrofuran, 1,2-dimethoxyethane), esters (such as ethyl or methyl acetate), nitrohydrocarbons (such as nitromethane, nitroethane, nitrobenzene), nitriles (such as acetonitrile, benzonitrile), amides (such as N,N-dimethylformamide, N,N-dimethylacetamides, N-methylformanilide, N-methylpyrrolidone, hexamethylphosphoramide), and also dimethyl sulphoxide or water or mixtures of the solvents mentioned.

For synthesis of the compounds of the formula (A1-III), it is alternatively possible to use mixed anhydrides (LG=COOR) (cf. G. W. Anderson et al. J. Am. Chem. Soc. 1967, 89, 5012-5017). In this process, which goes via compounds of the formula (A1-II, LG=CO—OR, R=alkyl, aryl), it is possible to use chloroformic esters, for example isobutyl chloroformate (LG=COOR with R=isobutyl) and isopropyl chloroformate (LG=COOR with R=isopropyl). It is likewise possible to use diethylacetyl chloride, trimethylacetyl chloride and similar compounds for this purpose.

Method A—Step 2: The amide function of the carboxamides of the (A1-III) type can be converted to a thioamide function by means of suitable thionating reagents, for example Lawesson's reagent or phosphorus(V) sulphide, while heating in a suitable solvent, for example toluene or anisole, which gives rise to compounds of the (A1-IV) type (cf., for example, WO 2013/33901 for 5-bromo-N-(2,6-difluorophenyl)pyridine-3-carbothioamide). In the case of this reaction type, cyclization to give compounds of the formula (I) may already proceed in some cases.

Method A—Step 3: Finally, the compounds of the formula (I) can be converted to the bicyclic thiazoles of the (I) type by literature methods (cf., for example, WO 2013/33901 for 2-(5-bromopyridin-3-yl)-4-fluoro-1,3-benzothiazole) by heating in suitable solvent, for example toluene or DMF, in the presence of a base, for example sodium hydride or potassium carbonate.

If, in the process according to the invention for preparing the compounds of the formula (I), the compound of the formula (A1-1) used is 3,5-dibromopyridin-2-amine ($R^1$=H, $R^2$=Br) and the compound of the formula (A1-II) used is 3-(chlorocarbonyl)pyridinium chloride (A=3-pyridin-3-yl), this at first forms N-(3,5-dibromopyridin-2-yl)nicotinamide (A=3-pyridin-3-yl, $R^1$=H, $R^2$=Br). Subsequent thionation and cyclization then leads to 6-bromo-2-(pyridin-3-yl)[1,3]thiazolo[4,5-b]pyridine (I-a-1)), A=pyridin-3-yl, $R^1$=H, $R^2$=Br) [cf. Synthesis Example I-a-1].

Compounds of the formula (I) in which $R^2$ is halogen, for example bromine or iodine, can be obtained according to Reaction Scheme I from halogenated 2-bromoaniline derivatives (A1-I). From these, it is possible to generate further compounds of the formula (I) by literature methods (B to F). By way of example, methods B to F and the resulting product types are shown in Reaction Scheme II.

Method B/F: According to WO 2010/71819 and Bioorganic and Medicinal Chemistry Letters (2009), 19(21), 6176-6180, it is possible to arylate brominated thiazolopyridines with substituted arylboronic acids or arylboronic acid pinacol esters optionally generated in situ, in the presence of suitable coupling catalysts, for example tetrakis(triphenylphosphine)palladium(0) or bis(triphenylphosphine)palladium(II) chloride, in the presence of a base, for example sodium carbonate, in an inert organic solvent or diluent, for example toluene in combination with ethanol (Method B), by means of which it is possible to obtain carbon-bonded compounds of the (I-b) type [cf. also Synthesis Example (19)]. It is also possible to react optionally substituted heteroaromatic boronic acids or the pinacol esters thereof analogously with brominated bicyclic heteroaromatic systems by Method B (cf., for example, EP 1 214 319 B1 for 3-[6-(3-furyl)-3H-imidazo[4,5-b]pyridin-3-yl]phenol).

Alternatively, the compounds of the formula (I-a) can first be converted by means of methods known from the literature to compounds of the (I-h) type, which then subsequently react further with halogen-activated, optionally further-substituted heterocycles according to Reaction Scheme II (Method F) [cf. T. Ishiyama et al., J. Org. Chem., 1995, 60, 7508-7510; WO 2010/151601] in an inert organic solvent or diluent to give carbon-bonded compounds of the (I-i) type.

Reaction Scheme II - Methods B to F

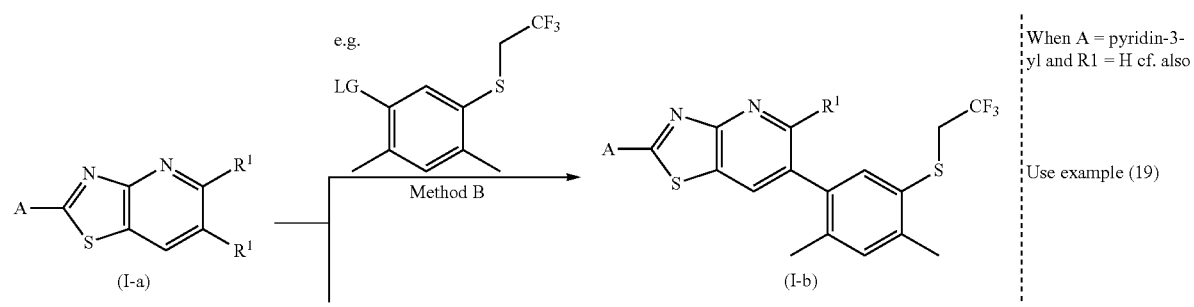

-continued

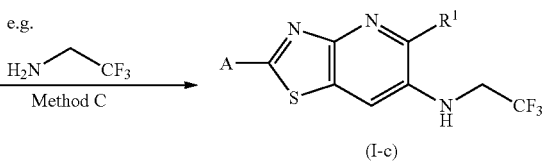
(I-c)

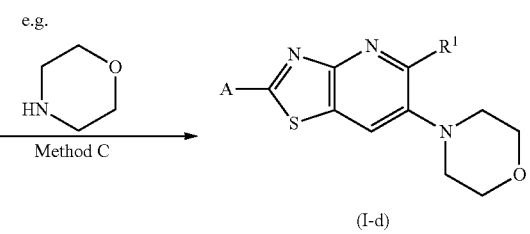
(I-d)

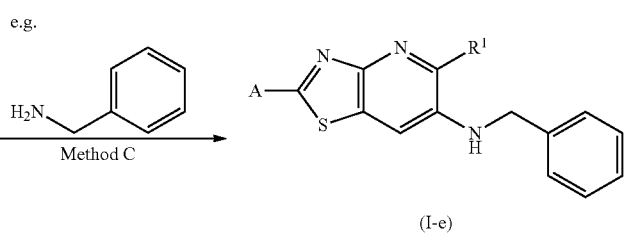
(I-e)

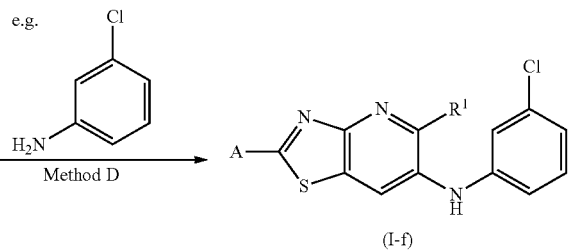
(I-f)

Use example (25)

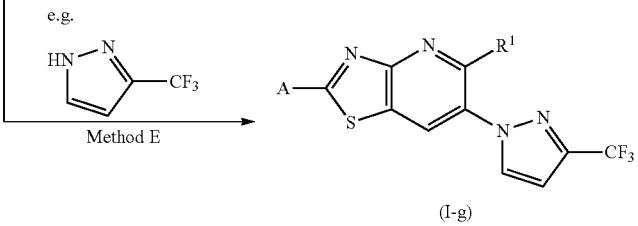
(I-g)

Use example (27)

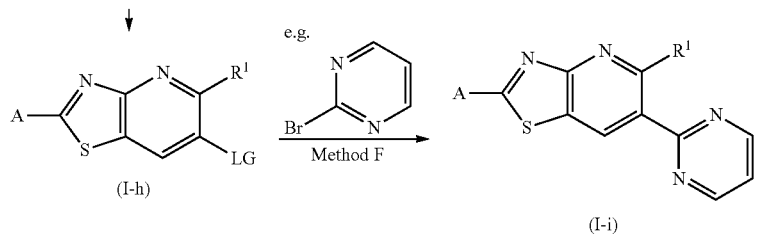
(I-h)    (I-i)

LG = nuclefugic leaving group LG optionally generated in situ

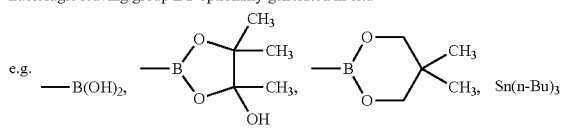

Useful coupling catalysts include palladium catalysts such as [1,1'-bis(diphenylphosphino)ferrocene]dichloropalladium(II) or tetrakis(triphenylphosphine)palladium(0).

Suitable basic reaction auxiliaries used to conduct the processes according to Reaction Scheme II are preferably carbonates of sodium or potassium.

Preferred solvents are nitriles such as acetonitrile, benzonitrile, especially acetonitrile, or ethers such as diethyl ether, dioxane, tetrahydrofuran, 1,2-dimethoxyethane, especially 1,2-dimethoxyethane in combination with water.

Method C: Preferably by means of catalysis by suitable coupling catalysts, for example tris(dibenzylideneacetone)dipalladium(0), using suitable ligands, for example 2,2'-bis-(diphenylphosphino)-1,1'-binaphthyl (BINAP), and a base, for example sodium tert-butoxide, it is also possible to react brominated heteroaromatic bicyclic systems with optionally substituted aliphatic primary or secondary amines or arylmethyl- or hetarylmethylamines in an inert organic solvent or diluent (example type (I-e)) [cf., for example, WO 2013/123215 A2 with regard to the synthesis of 3-(4-ethoxybenzyl)-N-(4-ethylbenzyl)-3H-imidazo[4,5-b]pyridin-6-amine].

Useful solvents or diluents include all inert organic solvents, for example aliphatic or aromatic hydrocarbons. Preference is given to using aromatic hydrocarbons, for example toluene.

Method D: Brominated heteroaromatic bicyclic systems react with optionally substituted anilines in an inert organic solvent or diluent to give the corresponding arylamino compounds (cf. example type (I-f) and Use Example (25)), preferably under catalysis by suitable coupling catalysts, for example tris(dibenzylideneacetone)dipalladium(0), in the presence of a suitable ligand, for example *Xantphos*, and of a base, e.g. caesium carbonate (cf., for example, EP 2 341 052 with regard to the preparation of 7-anilino-N-phenyl-4H-pyrido[3,2-b][1,4]oxazine-4-carboxamide). It is also possible to convert optionally substituted aminoheteroaromatics in an analogous manner in an inert organic solvent or diluent, for example with catalysis by suitable coupling catalysts such as tris(dibenzylideneacetone)dipalladium(0), with suitable ligands, e.g. 2,2'-bis(diphenylphosphino)-1,1'-binaphthyl (BINAP), and a base, for example sodium tert-butoxide.

Useful solvents or diluents include all inert organic solvents, for example aliphatic or aromatic hydrocarbons. Preference is given to using aromatic hydrocarbons (for example toluene).

Method E: Heterocyclic amines, for example imidazoles, pyrazoles or triazoles, optionally in substituted form, can be introduced into brominated bicyclic systems on the basis of Method E shown in Reaction Scheme II [cf. US 2012/122843 with regard to the preparation of 6-amino-3-(4-methyl-1H-imidazol-1-yl)pyridine-2-carbonitrile], preferably in the presence of suitable catalysts such as copper(I) iodide, in the presence of basic ligands, e.g. L-proline or trans-N,N'-dimethylcyclohexane-1,2-diamine, and of a base such as caesium carbonate or potassium carbonate, in an inert organic solvent or diluent (cf. example type (I-g) and Use Example (27)).

Useful solvents or diluents include all inert organic solvents, for example aliphatic or aromatic hydrocarbons. Preference is given to using aromatic hydrocarbons, for example toluene, but also more polar solvents such as DMF. Compounds of the formula (I) in which $R^2$ is halogen, for example bromine or iodine, can be obtained according to Reaction Scheme I from halogenated 2-bromoaniline derivatives. From these, it is possible by literature methods (G) to generate further compounds of the formula (I) as shown in Reaction Scheme III.

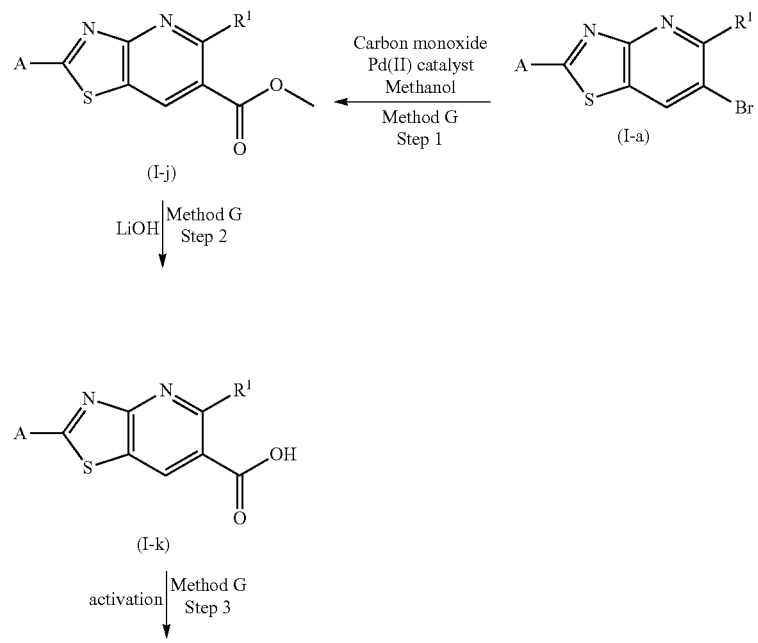

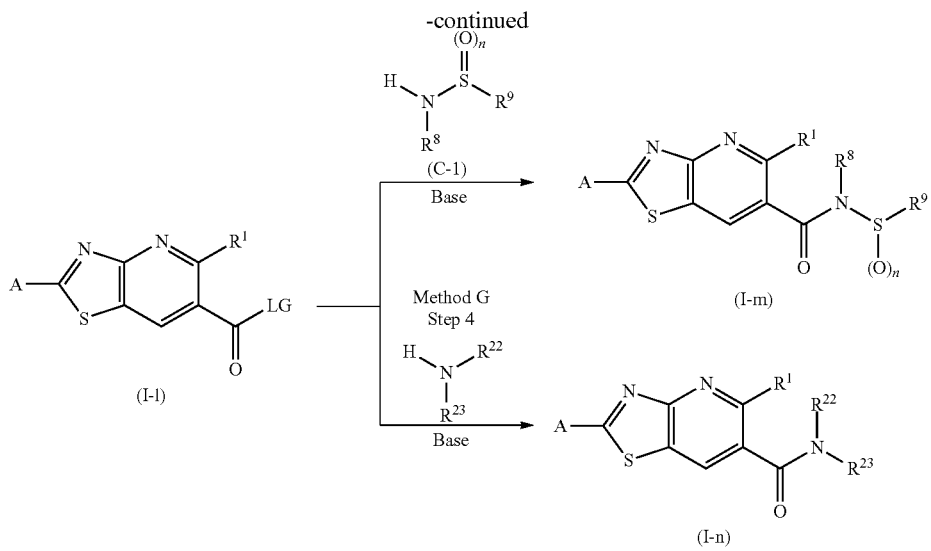

LG = Leaving group, e.g. halogen, O—CO—R (R = aryl, alkyl) N-imidazol-1-yl, etc.

Method G—Step 1: Compounds of the formula (I-a) in which $R^2$ is halogen, for example bromine or iodine, can be reacted by literature methods with carbon monoxide and an alcohol, for example methanol, with catalysis by suitable metal compounds, for example (1,1'-bis(diphenylphosphino)ferrocene)palladium(II) dichloride, and in the presence of bases such as triethylamine, in suitable solvents, for example the alcohol used itself, THF and/or DMF, to give the corresponding carboxylic esters (I-j) [cf., for example, WO 2009/152072 for methyl 2-{[(tert-butoxycarbonyl)amino]methyl}-3H-imidazo[4,5-b]pyridine-6-carboxylate].

Method G—Step 2: Esters of the (I-j) type can be converted to the compounds (I-k) having a free acid function by literature methods by means of suitable bases, for example aqueous lithium hydroxide or sodium hydroxide solution, in suitable solvents or diluents, for example dioxane or THF.

Method G—Steps 3 and 4: Compounds of the formula (I) in which $R^2$ is a radical from the group of (C-1) to (C-9) (I-m type) or is a group of the formula C(X)—$NR^{22}R^{23}$ (I-n type) can be prepared, for example, from compounds of the formula (I) in which $R^2$ is a carboxyl group (I-k type) after suitable activation (i.e. LG is a nucleofugic leaving group optionally generated in situ) by commonly known methods [cf. Method A, Step 1].

The subsequent reactions of the activated compounds of the formula (I-1) with the respective amine components according to Reaction Scheme III are optionally conducted in the presence of a suitable reaction auxiliary and in the presence of a suitable solvent or diluent.

Compounds of the formula (I) in which $R^2$ is —$NR^{23}$—C(X)—$R^{22}$ can be obtained, for example, from compounds of the formula (I) in which $R^2$ is —$NHR^{23}$ by means of N-acylation reaction using activated compounds of the formula LG-C(X)—$R^{22}$ in which LG is a nucleofugic leaving group which is optionally generated in situ.

These compounds of the formula (I) in which $R^2$ is a group of the formula —$NHR^{23}$ can be prepared by known methods from compounds of the formula (I) in which $R^2$ is a carboxyl group according to Reaction Scheme IV.

Reaction Scheme IV - Method H1

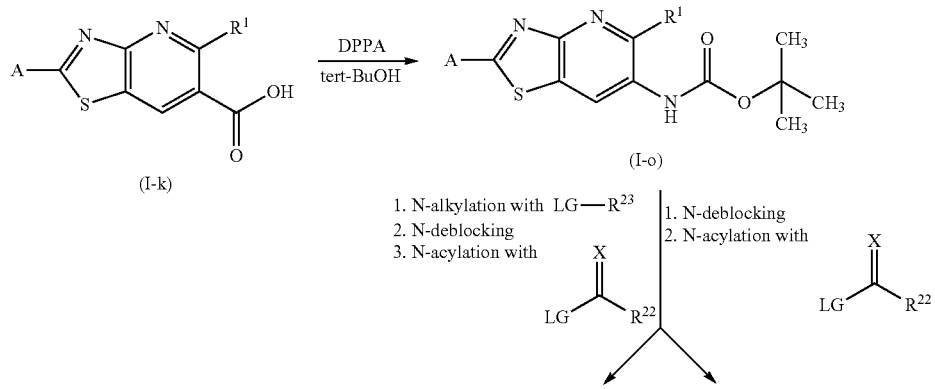

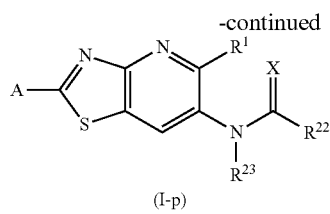

(I-p)

(I-q)

LG = Leaving group e.g. halogen
DPPA = diphenylphosphoryl azide

Method H1: For example, compounds of the formula (I-o) can be obtained by Curtius degradation as described, for example, in Houben-Weyl, *Methoden der Organischen Chemie* [Methods of Organic Chemistry], Volume XI/1 (Georg Thieme Verlag Stuttgart), p. 865.

In this case, the compounds of the formula (I-k) can, for example, react directly with diphenylphosphoryl azide (DPPA) in the presence of tert-butanol to give compounds of the formula (I-o).

water and/or an organic solvent such as tetrahydrofuran, dioxane, dichloromethane, chloroform, ethyl acetate, ethanol or methanol are used. Preference is given to mixtures of hydrochloric acid or acetic acid with water and/or an organic solvent such as ethyl acetate.

As an alternative to Method H1, the compounds of the I-p or I-q type can also be prepared by Method H2 described below from compounds synthesized by Method A:

Reaction Scheme V - Method H2:

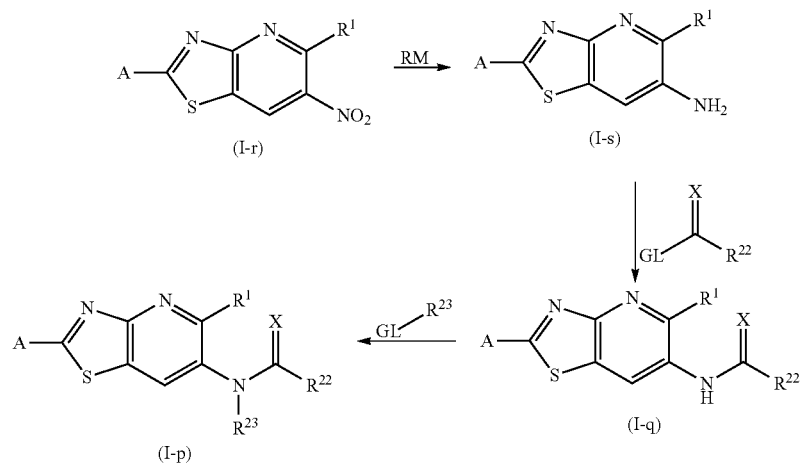

RM = reducing agent, e.g. Fe, Zn, Sn(II), sodium cyanoborohydride, hydrogen over Pd/c etc.
LG = Leaving group, e.g. halogen or OH From the compounds of the formula (I-o), it is possible to obtain the compounds of the formula (I-p) by N-alkylation in a first reaction step, N-deblocking (i.e. detachment of the Boc group) in a second reaction step, and subsequent N-acylation in a third reaction step.

The compounds of the formula (I-q) can be prepared by N-deblocking (i.e. cleavage of the Boc group) in a first reaction step and subsequent N-acylation in a second reaction step.

In general, for the removal of the protecting group, it is possible to use acidic or basic reaction auxiliaries according to the literature procedure. When protecting groups of the carbamate type are used, preference is given to using acidic reaction auxiliaries. When the tert-butyl carbamate protecting group (Boc group) is used, for example, mixtures of mineral acids such as hydrochloric acid, hydrobromic acid, nitric acid, sulphuric acid, phosphoric acid or of organic acids such as benzoic acid, formic acid, acetic acid, trifluoroacetic acid, methanesulphonic acid, benzenesulphonic acid or toluenesulphonic acid, in a suitable diluent such as Method H2: Compounds prepared by Method A in which $R^2$ is nitro (I-r) can be converted to the corresponding amino compounds (I-s) by reducing the nitro group by literature methods (cf., for example, WO2009/14674 A1, 2009 for reduction by Fe(0); US2005/197331 A1, 2005 for reduction by Sn(II)Cl2; WO2007/86800 A1, 2007 for reduction by sodium cyanoborohydride). The latter can be converted to the inventive compounds of the (I-q) or (I-p) type by acylation, if appropriate followed by alkylation, by literature methods.

Method I—General Processes for the Oxidation of Thioethers to Sulphoxides and Sulphones Compounds of the formula (I) in which W is SO (sulphoxides) or $SO_2$ (sulphones) can be prepared from compounds of the formula (I) in which W is S (thioethers) by oxidation by processes known from the literature, for example by means of an oxidizing agent in a suitable solvent or diluent. Suitable oxidizing agents are, for example, diluted nitric acid, hydrogen peroxide, Oxone® and peroxycarboxylic acids, for example meta-chloroperbenzoic acid.

Suitable solvents or diluents are inert organic solvents, typically acetonitrile and halogenated solvents such as dichloromethane, chloroform or dichloroethane, and water and alcohols such as methanol for the reaction with Oxone®.

It is also possible to introduce suitable anilines $R^1$—$NH_2$ or boronic acids $R^1$—$B(OH)_2$ in which W is SO or $SO_2$ by process B or D. These can be oxidized from the corresponding precursors in which W is S by processes known from the literature, as described, for example, in WO 2013/092350.

A variety of methods are suitable for producing enantiomerically enriched sulphoxides, as described by G. E. O'Mahony et al., in ARKIVOC (Gainesville, Fla., United States), 2011, 1, 1-110: metal-catalysed asymmetric oxidations of thioethers, for example with titanium or vanadium as the most frequently utilized catalyst sources, in the form of $Ti(O^iPr_4)$ or $VO(acac)_2$, together with a chiral ligand and an oxidizing agent such as tert-butyl hydroperoxide (TBHP), 2-phenylpropan-2-yl hydroperoxide (CHP) or hydrogen peroxide; non-metal-catalysed asymmetric oxidations through use of chiral oxidizing agents or chiral catalysts; electrochemical or biological asymmetric oxidations and also kinetic resolution of sulphoxides and nucleophilic displacement (by Andersen's method).

The enantiomers can also be obtained from the racemate, for example by preparative separation by means of a chiral HPLC.

When compounds of the formula (I) are mentioned hereinafter, this also includes those compounds in Table 1 which are not covered by the formula (I) (excluding intermediates).

Isomers

Depending on the nature of the substituents, the compounds of the formula (I) may be in the form of geometric and/or optically active isomers or corresponding isomer mixtures in different compositions. These stereoisomers are, for example, enantiomers, diastereomers, atropisomers or geometric isomers. The invention therefore encompasses pure stereoisomers and any desired mixtures of these isomers.

Methods and Uses

The invention also relates to methods for controlling animal pests, in which compounds of the formula (I) are allowed to act on animal pests and/or their habitat. The control of the animal pests is preferably conducted in agriculture and forestry, and in material protection. This preferably excludes methods for surgical or therapeutic treatment of the human or animal body and diagnostic methods carried out on the human or animal body.

The invention further relates to the use of the compounds of the formula (I) as pesticides, especially crop protection agents.

In the context of the present application, the term "pesticide" also always encompasses the term "crop protection agent".

The compounds of the formula (I), given good plant tolerance, favourable homeotherm toxicity and good environmental compatibility, are suitable for protecting plants and plant organs against biotic and abiotic stress factors, for increasing harvest yields, for improving the quality of the harvested material and for controlling animal pests, especially insects, arachnids, helminths, nematodes and molluscs, which are encountered in agriculture, in horticulture, in animal husbandry, in aquatic cultures, in forests, in gardens and leisure facilities, in the protection of stored products and of materials, and in the hygiene sector. They can preferably be used as pesticides. They are active against normally sensitive and resistant species and also against all or specific stages of development. The abovementioned pests include:

pests from the phylum of the Arthropoda, especially from the class of the Arachnida, for example Acarus spp., for example Acarus siro, Aceria kuko, Aceria sheldoni, Aculops spp., Aculus spp., for example Aculus fockeui, Aculus schlechtendali, Amblyomma spp., Amphitetranychus viennensis, Argas spp., Boophilus spp., Brevipalpus spp., for example Brevipalpus phoenicis, Bryobia graminum, Bryobia praetiosa, Centruroides spp., Chorioptes spp., Dermanyssus gallinae, Dermatophagoides pteronyssinus, Dermatophagoides farinae, Dermacentor spp., Eotetranychus spp., for example Eotetranychus hicoriae, Epitrimerus pyri, Eutetranychus spp., for example Eutetranychus banksi, Eriophyes spp., for example Eriophyes pyri, Glycyphagus domesticus, Halotydeus destructor, Hemitarsonemus spp., for example Hemitarsonemus latus (=Polyphagotarsonemus latus), Hyalomma spp., Ixodes spp., Latrodectus spp., Loxosceles spp., Neutrombicula autumnalis, Nuphersa spp., Oligonychus spp., for example Oligonychus coniferarum, Oligonychus ilicis, Oligonychus indicus, Oligonychus mangiferus, Oligonychus pratensis, Oligonychus punicae, Oligonychus yothersi, Ornithodorus spp., Ornithonyssus spp., Panonychus spp., for example Panonychus citri (=Metatetranychus citri), Panonychus ulmi (=Metatetranychus ulmi), Phyllocoptruta oleivora, Platytetranychus multidigituli, Polyphagotarsonemus latus, Psoroptes spp., Rhipicephalus spp., Rhizoglyphus spp., Sarcoptes spp., Scorpio maurus, Steneotarsonemus spp., Steneotarsonemus spinki, Tarsonemus spp., for example Tarsonemus confusus, Tarsonemus pallidus, Tetranychus spp., for example Tetranychus canadensis, Tetranychus cinnabarinus, Tetranychus turkestani, Tetranychus urticae, Trombicula alfreddugesi, Vaejovis spp., Vasates lycopersici;

from the class of the Chilopoda, for example Geophilus spp., Scutigera spp.;

from the order or the class of the Collembola, for example Onychiurus armatus; Sminthurus viridis;

from the class of the Diplopoda, for example Blaniulus guttulatus;

from the class of the Insecta, for example from the order of the Blattodea, for example Blatta orientalis, Blattella asahinai, Blattella germanica, Leucophaea maderae, Panchlora spp., Parcoblatta spp., Periplaneta spp., for example Periplaneta americana, Periplaneta australasiae, Supella longipalpa;

from the order of the Coleoptera, for example Acalymma vittatum, Acanthoscelides obtectus, Adoretus spp., Agelastica alni, Agriotes spp., for example Agriotes linneatus, Agriotes mancus, Alphitobius diaperinus, Amphimallon solstitialis, Anobium punctatum, Anoplophora spp., Anthonomus spp., for example Anthonomus grandis, Anthrenus spp., Apion spp., Apogonia spp., Atomaria spp., for example Atomaria linearis, Attagenus spp., Baris caerulescens, Bruchidius obtectus, Bruchus spp., for example Bruchus pisorum, Bruchus rufimanus, Cassida spp., Cerotoma trifurcata, Ceutorrhynchus spp., for example Ceutorrhynchus assimilis, Ceutorrhynchus quadridens, Ceutorrhynchus rapae, Chaetocnema spp., for example Chaetocnema confinis, Chaetocnema denticulata, Chaetocnema ectypa, Cleonus mendicus, Conoderus spp., Cosmopolites spp., for example Cosmopolites sordidus, Costelytra zealandica, Ctenicera spp., Curculio spp., for example Curculio caryae, Curculio caryatrypes, Curculio obtusus, Curculio sayi, Cryptolestes ferrugineus, Cryptolestes pusillus, Cryptorhynchus lapathi, Cryptorhynchus mangiferae, Cylindrocopturus spp., *Cylindrocopturus adspersus*, *Cylindrocopturus furnissi*, *Dermestes* spp., *Diabrotica* spp., for example *Diabrotica balteata*, *Diabrotica barberi*, *Diabrotica undecimpunctata*, *Diabrotica undecimpunctata howardi*, *Diabrotica undecimpunctata undecimpunctata*, *Diabrotica virgifera virgifera*, *Diabrotica virgifera zeae*, *Dichocrocis* spp., *Dicladispa armigera*, *Diloboderus* spp., *Epilachna* spp., for example *Epilachna borealis*, *Epilachna varivestis*, *Epitrix* spp., for example *Epitrix cucumeris*, *Epitrix fuscula*, *Epitrix hirtipennis*, *Epitrix subcrinita*, *Epitrix tuberis*, *Faustinus* spp., *Gibbium psylloides*, *Gnathocerus cornutus*, *Hellula undalis*, *Heteronychus arator*, *Heteronyx* spp., *Hylamorpha elegans*, *Hylotrupes bajulus*, *Hypera postica*, *Hypomeces squamosus*, *Hypothenemus* spp., for example *Hypothenemus hampei*, *Hypothenemus obscurus*, *Hypothenemus pubescens*, *Lachnosterna consanguinea*, *Lasioderma serricorne*, *Latheticus oryzae*, *Lathridius* spp., *Lema* spp., *Leptinotarsa decemlineata*, *Leucoptera* spp., for example *Leucoptera coffeella*, *Lissorhoptrus oryzophilus*, *Lixus* spp., *Luperomorpha xanthodera*, *Luperodes* spp., *Lyctus* spp., *Megascelis* spp., *Melanotus* spp., for example *Melanotus longulus oregonensis*, *Meligethes aeneus*, *Melolontha* spp., for example *Melolontha melolontha*, *Migdolus* spp., *Monochamus* spp., *Naupactus xanthographus*, *Necrobia* spp., *Niptus hololeucus*, *Oryctes rhinoceros*, *Oryzaephilus surinamensis*, *Oryzaphagus oryzae*, *Otiorhynchus* spp., for example *Otiorhynchus cribricollis*, *Otiorhynchus ligustici*, *Otiorhynchus ovatus*, *Otiorhynchus rugosostriarus*, *Otiorhynchus sulcatus*, *Oxycetonia jucunda*, *Phaedon cochleariae*, *Phyllophaga* spp., *Phyllophaga helleri*, *Phyllotreta* spp., for example *Phyllotreta armoraciae*, *Phyllotreta pusilla*, *Phyllotreta ramosa*, *Phyllotreta striolata*, *Popillia japonica*, *Premnotrypes* spp., *Prostephanus truncatus*, *Psylliodes* spp., for example *Psylliodes affinis*, *Psylliodes chrysocephala*, *Psylliodes punctulata*, *Ptinus* spp., *Rhizobius ventralis*, *Rhizopertha dominica*, *Sitophilus* spp., for example *Sitophilus granarius*, *Sitophilus linearis*, *Sitophilus oryzae*, *Sitophilus zeamais*, *Sphenophorus* spp., *Stegobium paniceum*, *Sternechus* spp., for example *Sternechus paludatus*, *Symphyletes* spp., *Tanymecus* spp., for example *Tanymecus dilaticollis*, *Tanymecus indicus*, *Tanymecus palliatus*, *Tenebrio molitor*, *Tenebrioides mauretanicus*, *Tribolium* spp., for example *Tribolium audax*, *Tribolium castaneum*, *Tribolium confusum*, *Trogoderma* spp., *Tychius* spp., *Xylotrechus* spp., *Zabrus* spp., for example *Zabrus tenebrioides*;

from the order of the Diptera, for example *Aedes* spp., for example *Aedes aegypti*, *Aedes albopictus*, *Aedes sticticus*, *Aedes vexans*, *Agromyza* spp., for example *Agromyza frontella*, *Agromyza parvicornis*, *Anastrepha* spp., *Anopheles* spp., for example *Anopheles quadrimaculatus*, *Anopheles gambiae*, *Asphondylia* spp., *Bactrocera* spp., for example *Bactrocera cucurbitae*, *Bactrocera dorsalis*, *Bactrocera oleae*, *Bibio hortulanus*, *Calliphora erythrocephala*, *Calliphora vicina*, *Ceratitis capitata*, *Chironomus* spp., *Chrysomya* spp., *Chrysops* spp., *Chrysozona pluvialis*, *Cochliomya* spp., *Contarinia* spp., for example *Contarinia johnsoni*, *Contarinia nasturtii*, *Contarinia pyrivora*, *Contarinia schulzi*, *Contarinia sorghicola*, *Contarinia tritici*, *Cordylobia anthropophaga*, *Cricotopus sylvestris*, *Culex* spp., for example *Culex pipiens*, *Culex quinquefasciatus*, *Culicoides* spp., *Culiseta* spp., *Cuterebra* spp., *Dacus oleae*, *Dasineura* spp., for example *Dasineura brassicae*, *Delia* spp., for example *Delia antiqua*, *Delia coarctata*, *Delia florilega*, *Delia platura*, *Delia radicum*, *Dermatobia hominis*, *Drosophila* spp., for example *Drosphila melanogaster*, *Drosophila suzukii*, *Echinocnemus* spp., *Fannia* spp., *Gasterophilus* spp., *Glossina* spp., *Haematopota* spp., *Hydrellia* spp., *Hydrellia griseola*, *Hylemya* spp., *Hippobosca* spp., *Hypoderma* spp., *Liriomyza* spp., for example *Liriomyza brassicae*, *Liriomyza huidobrensis*, *Liriomyza sativae*, *Lucilia* spp., for example *Lucilia cuprina*, *Lutzomyia* spp., *Mansonia* spp., *Musca* spp., for example *Musca domestica*, *Musca domestica vicina*, *Oestrus* spp., *Oscinella frit*, *Paratanytarsus* spp., *Paralauterborniella subcincta*, *Pegomya* spp., for example *Pegomya betae*, *Pegomya hyoscyami*, *Pegomya rubivora*, *Phlebotomus* spp., *Phorbia* spp., *Phormia* spp., *Piophila casei*, *Prodiplosis* spp., *Psila rosae*, *Rhagoletis* spp., for example *Rhagoletis cingulata*, *Rhagoletis completa*, *Rhagoletis fausta*, *Rhagoletis indifferens*, *Rhagoletis mendax*, *Rhagoletis pomonella*, *Sarcophaga* spp., *Simulium* spp., for example *Simulium meridionale*, *Stomoxys* spp., *Tabanus* spp., *Tetanops* spp., *Tipula* spp., for example *Tipula paludosa*, *Tipula simplex*;

from the order of the Hemiptera for example *Acizzia acaciaebaileyanae*, *Acizzia dodonaeae*, *Acizzia uncatoides*, *Acrida turrita*, *Acyrthosipon* spp., for example *Acyrthosiphon pisum*, *Acrogonia* spp., *Aeneolamia* spp., *Agonoscena* spp., *Aleyrodes proletella*, *Aleurolobus barodensis*, *Aleurothrixus floccosus*, *Allocaridara malayensis*, *Amrasca* spp., for example *Amrasca bigutulla*, *Amrasca devastans*, *Anuraphis cardui*, *Aonidiella* spp., for example *Aonidiella aurantii*, *Aonidiella citrina*, *Aonidiella inornata*, *Aphanostigma pini*, *Aphis* spp., for example *Aphis citricola*, *Aphis craccivora*, *Aphis fabae*, *Aphis forbesi*, *Aphis glycines*, *Aphis gossypii*, *Aphis hederae*, *Aphis illinoisensis*, *Aphis middletoni*, *Aphis nasturtii*, *Aphis nerii*, *Aphis pomi*, *Aphis spiraecola*, *Aphis viburniphila*, *Arboridia apicalis*, *Arytainilla* spp., *Aspidiella* spp., *Aspidiotus* spp., for example *Aspidiotus nerii*, *Atanus* spp., *Aulacorthum solani*, *Bemisia tabaci*, *Blastopsylla occidentalis*, *Boreioglycaspis melaleucae*, *Brachycaudus helichrysi*, *Brachycolus* spp., *Brevicoryne brassicae*, *Cacopsylla* spp., for example *Cacopsylla pyricola*, *Calligypona marginata*, *Carneocephala fulgida*, *Ceratovacuna lanigera*, *Cercopidae*, *Ceroplastes* spp., *Chaetosiphon fragaefolii*, *Chionaspis tegalensis*, *Chlorita onukii*, *Chondracris rosea*, *Chromaphis juglandicola*, *Chrysomphalus ficus*, *Cicadulina mbila*, *Coccomytilus halli*, *Coccus* spp., for example *Coccus hesperidum*, *Coccus longulus*, *Coccus pseudomagnoliarum*, *Coccus viridis*, *Cryptomyzus ribis*, *Cryptoneossa* spp., *Ctenarytaina* spp., *Dalbulus* spp., *Dialeurodes citri*, *Diaphorina citri*, *Diaspis* spp., *Drosicha* spp., *Dysaphis* spp., for example *Dysaphis apiifolia*, *Dysaphis plantaginea*, *Dysaphis tulipae*, *Dysmicoccus* spp., *Empoasca* spp., for example *Empoasca abrupta*, *Empoasca fabae*, *Empoasca maligna*, *Empoasca solana*, *Empoasca stevensi*, *Eriosoma* spp., for example *Eriosoma americanum*, *Eriosoma lanigerum*, *Eriosoma pyricola*, *Erythroneura* spp., *Eucalyptolyma* spp., *Euphyllura* spp., *Euscelis bilobatus*, *Ferrisia* spp., *Geococcus coffeae*, *Glycaspis* spp., *Heteropsylla cubana*, *Heteropsylla spinulosa*, *Homalodisca coagulata*, *Hyalopterus arundinis*, *Hyalopterus pruni*, *Icerya* spp., for example *Icerya purchasi*, *Idiocerus* spp., *Idioscopus* spp., *Laodelphax striatellus*, *Lecanium* spp., for example *Lecanium corni* (=*Parthenolecanium corni*), *Lepidosaphes* spp., for example *Lepidosaphes ulmi*, *Lipaphis erysimi*, *Lycorma delicatula*, *Macrosiphum* spp., for example *Macrosiphum euphorbiae*, *Macrosiphum lilii*, *Macrosiphum rosae*, *Macrosteles facifrons*, *Mahanarva* spp., *Melanaphis sacchari*, *Metcalfiella* spp., *Metcalfa pruinosa*, *Metopolophium dirhodum*, *Monellia costalis*, *Monelliopsis pecanis*, *Myzus* spp., for example *Myzus ascalonicus*, *Myzus cerasi*, *Myzus ligustri*, *Myzus ornatus*, *Myzus persicae*, *Myzus nicotianae*, *Nasonovia ribisnigri*, *Nephotettix* spp., for example *Nephotettix cincticeps*, *Nephotettix nigropictus*,

*Nilaparvata lugens, Oncometopia* spp., *Orthezia praelonga, Oxya chinensis, Pachypsylla* spp., *Parabemisia myricae, Paratrioza* spp., for example *Paratrioza cockerelli, Parlatoria* spp., *Pemphigus* spp., for example *Pemphigus bursarius, Pemphigus populivenae, Peregrinus maidis, Phenacoccus* spp., for example *Phenacoccus madeirensis, Phloeomyzus passerinii, Phorodon humuli, Phylloxera* spp., for example *Phylloxera devastatrix, Phylloxera notabilis, Pinnaspis aspidistrae, Planococcus* spp., for example *Planococcus citri, Prosopidopsylla flava, Protopulvinaria pyriformis, Pseudaulacaspis pentagona, Pseudococcus* spp., for example *Pseudococcus calceolariae, Pseudococcus comstocki, Pseudococcus longispinus, Pseudococcus maritimus, Pseudococcus viburni, Psyllopsis* spp., *Psylla* spp., for example *Psylla buxi, Psylla mali, Psylla* pyri, *Pteromalus* spp., *Pyrilla* spp., *Quadraspidiotus* spp., for example *Quadraspidiotus juglansregiae, Quadraspidiotus ostreaeformis, Quadraspidiotus perniciosus, Quesada gigas, Rastrococcus* spp., *Rhopalosiphum* spp., for example *Rhopalosiphum maidis, Rhopalosiphum oxyacanthae, Rhopalosiphum padi, Rhopalosiphum rufiabdominale, Saissetia* spp., for example *Saissetia coffeae, Saissetia miranda, Saissetia neglecta, Saissetia oleae, Scaphoideus titanus, Schizaphis graminum, Selenaspidus articulatus, Sitobion avenae, Sogata* spp., *Sogatella furcifera, Sogatodes* spp., *Stictocephala festina, Siphoninus phillyreae, Tenalaphara malayensis, Tetragonocephela* spp., *Tinocallis caryaefoliae, Tomaspis* spp., *Toxoptera* spp., for example *Toxoptera aurantii, Toxoptera citricidus, Trialeurodes vaporariorum, Trioza* spp., for example *Trioza diospyri, Typhlocyba* spp., *Unaspis* spp., *Viteus vitifolii, Zygina* spp.;

from the suborder of the Heteroptera, for example *Anasa tristis, Antestiopsis* spp., *Boisea* spp., *Blissus* spp., *Calocoris* spp., *Campylomma livida, Cavelerius* spp., *Cimex* spp., for example *Cimex adjunctus, Cimex hemipterus, Cimex lectularius, Cimex pilosellus, Collaria* spp., *Creontiades dilutus, Dasynus piperis, Dichelops furcatus, Diconocoris hewetti, Dysdercus* spp., *Euschistus* spp., for example *Euschistus heros, Euschistus servus, Euschistus tristigmus, Euschistus variolarius, Eurygaster* spp., *Halyomorpha halys, Heliopeltis* spp., *Horcias nobilellus, Leptocorisa* spp., *Leptocorisa varicornis, Leptoglossus occidentalis, Leptoglossus phyllopus, Lygocoris* spp., for example *Lygocoris pabulinus, Lygus* spp., for example *Lygus elisus, Lygus hesperus, Lygus lineolaris, Macropes excavatus, Monalonion atratum, Nezara* spp., for example *Nezara viridula, Oebalus* spp., *Piesma quadrata, Piezodorus* spp., for example *Piezodorus guildinii, Psallus* spp., *Pseudacysta persea, Rhodnius* spp., *Sahlbergella singularis, Scaptocoris castanea, Scotinophora* spp., *Stephanitis nashi, Tibraca* spp., *Triatoma* spp.;

from the order of the Hymenoptera, for example *Acromyrmex* spp., *Athalia* spp., for example *Athalia rosae, Atta* spp., *Diprion* spp., for example *Diprion similis, Hoplocampa* spp., for example *Hoplocampa cookei, Hoplocampa testudinea, Lasius* spp., *Linepithema humile, Monomorium pharaonis, Sirex* spp., *Solenopsis invicta, Tapinoma* spp., *Urocerus* spp., *Vespa* spp., for example *Vespa crabro, Xeris* spp.;

from the order of the Isopoda, for example *Armadillidium vulgare, Oniscus asellus, Porcellio scaber;* from the order of the Isoptera, for example *Coptotermes* spp., for example *Coptotermes formosanus, Cornitermes cumulans, Cryptotermes* spp., *Incisitermes* spp., *Microtermes obesi, Odontotermes* spp., *Reticulitermes* spp., for example *Reticulitermes flavipes, Reticulitermes hesperus;* from the order of the Lepidoptera, for example *Achroia grisella, Acronicta major, Adoxophyes* spp., for example *Adoxophyes orana, Aedia leucomelas, Agrotis* spp., for example *Agrotis segetum, Agrotis ipsilon, Alabama* spp., for example *Alabama argillacea, Amyelois transitella, Anarsia* spp., *Anticarsia* spp., for example *Anticarsia gemmatalis, Argyroploce* spp., *Barathra brassicae, Borbo cinnara, Bucculatrix thurberiella, Bupalus piniarius, Busseola* spp., *Cacoecia* spp., *Caloptilia theivora, Capua reticulana, Carpocapsa pomonella, Carposina niponensis, Cheimatobia brumata, Chilo* spp., for example *Chilo plejadellus, Chilo suppressalis, Choristoneura* spp., *Clysia ambiguella, Cnaphalocerus* spp., *Cnaphalocrocis medinalis, Cnephasia* spp., *Conopomorpha* spp., *Conotrachelus* spp., *Copitarsia* spp., *Cydia* spp., for example *Cydia nigricana, Cydia pomonella, Dalaca noctuides, Diaphania* spp., *Diatraea saccharalis, Earias* spp., *Ecdytolopha aurantium, Elasmopalpus lignosellus, Eldana saccharina, Ephestia* spp., for example *Ephestia elutella, Ephestia kuehniella, Epinotia* spp., *Epiphyas postvittana, Etiella* spp., *Eulia* spp., *Eupoecilia ambiguella, Euproctis* spp., for example *Euproctis chrysorrhoea, Euxoa* spp., *Feltia* spp., *Galleria mellonella, Gracilaria* spp., *Grapholitha* spp., for example *Grapholita molesta, Grapholita prunivora, Hedylepta* spp., *Helicoverpa* spp., for example *Helicoverpa armigera, Helicoverpa zea, Heliothis* spp., for example *Heliothis virescens, Hofmannophila pseudospretella, Homoeosoma* spp., *Homona* spp., *Hyponomeuta padella, Kakivoria flavofasciata, Laphygma* spp., *Leucinodes orbonalis, Leucoptera* spp., for example *Leucoptera coffeella, Lithocolletis* spp., for example *Lithocolletis blancardella, Lithophane antennata, Lobesia* spp., for example *Lobesia botrana, Loxagrotis albicosta, Lymantria* spp., for example *Lymantria dispar, Lyonetia* spp., for example *Lyonetia clerkella, Malacosoma neustria, Maruca testulalis, Mamestra brassicae, Melanitis leda, Mocis* spp., *Monopis obviella, Mythimna separata, Nemapogon cloacellus, Nymphula* spp., *Oiketicus* spp., *Oria* spp., *Orthaga* spp., *Ostrinia* spp., for example *Ostrinia nubilalis, Oulema melanopus, Oulema oryzae, Panolis flammea, Parnara* spp., *Pectinophora* spp., for example *Pectinophora gossypiella, Perileucoptera* spp., *Phthorimaea* spp., for example *Phthorimaea operculella, Phyllocnistis citrella, Phyllonorycter* spp., for example *Phyllonorycter blancardella, Phyllonorycter cratraegella, Pieris* spp., for example *Pieris rapae, Platynota stultana, Plodia interpunctella, Plusia* spp., *Plutella xylostella* (=*Plutella maculipennis*), *Prays* spp., *Prodenia* spp., *Protoparce* spp., *Pseudaletia* spp., for example *Pseudaletia unipuncta, Pseudoplusia includens, Pyrausta nubilalis, Rachiplusia nu, Schoenobius* spp., for example *Schoenobius bipunctifer, Scirpophaga* spp., for example *Scirpophaga innotata, Scotia segetum, Sesamia* spp., for example *Sesamia inferens, Sparganothis* spp., *Spodoptera* spp., for example *Spodoptera eradiana, Spodoptera exigua, Spodoptera frugiperda, Spodoptera praefica, Stathmopoda* spp., *Stomopteryx subsecivella, Synanthedon* spp., *Tecia solanivora, Thermesia gemmatalis, Tinea cloacella, Tinea pellionella, Tineola bisselliella, Tortrix* spp., *Trichophaga tapetzella, Trichoplusia* spp., for example *Trichoplusia ni, Tryporyza incertulas, Tuta absoluta, Virachola* spp.;

from the order of the Orthoptera or Saltatoria, for example *Acheta domesticus, Dichroplus* spp., *Gryllotalpa* spp., for example *Gryllotalpa gryllotalpa, Hieroglyphus* spp., *Locusta* spp., for example *Locusta migratoria, Melanoplus* spp., for example *Melanoplus devastator, Paratlanticus ussuriensis, Schistocerca gregaria;* from the order of the Phthiraptera, for example *Damalinia* spp., *Haematopinus* spp., *Linognathus* spp., *Pediculus* spp., *Phylloxera vastatrix, Phthirus pubis, Trichodectes* spp.;

from the order of the Psocoptera, for example *Lepinotus* spp., *Liposcelis* spp.;

from the order of the Siphonaptera, for example *Ceratophyllus* spp., *Ctenocephalides* spp., for example *Ctenocephalides canis, Ctenocephalides felis, Pulex irritans, Tunga penetrans, Xenopsylla cheopis*;

from the order of the Thysanoptera, for example *Anaphothrips obscurus, Baliothrips biformis, Drepanothrips reuteri, Enneothrips flavens, Frankliniella* spp., for example *Frankliniella fusca, Frankliniella occidentalis, Frankliniella schultzei, Frankliniella tritici, Frankliniella vaccinii, Frankliniella williamsi, Heliothrips* spp., *Hercinothrips femoralis, Rhipiphorothrips cruentatus, Scirtothrips* spp., *Taeniothrips cardamomi, Thrips* spp., for example *Thrips palmi, Thrips tabaci*;

from the order of the Zygentoma (=Thysanura), for example *Ctenolepisma* spp., *Lepisma saccharina, Lepismodes inquilinus, Thermobia domestica*;

from the class of the Symphyla, for example *Scutigerella* spp., for example *Scutigerella immaculata*;

pests from the phylum of the Mollusca, in particular from the class of the Bivalvia, for example *Dreissena* spp.;

and also from the class of the Gastropoda, for example *Anion* spp., for example *Anion ater rufus, Biomphalaria* spp., *Bulinus* spp., *Deroceras* spp., for example *Deroceras laeve, Galba* spp., *Lymnaea* spp., *Oncomelania* spp., *Pomacea* spp., *Succinea* spp.;

animal and human parasites from the phyla of the Platyhelminthes and Nematoda, for example *Aelurostrongylus* spp., *Amidostomum* spp., *Ancylostoma* spp., *Angiostrongylus* spp., *Anisakis* spp., *Anoplocephala* spp., *Ascaris* spp., *Ascaridia* spp., *Baylisascaris* spp., *Brugia* spp., *Bunostomum* spp., *Capillaria* spp., *Chabertia* spp., *Clonorchis* spp., *Cooperia* spp., *Crenosoma* spp., *Cyathostoma* spp., *Dicrocoelium* spp., *Dictyocaulus* spp., *Diphyllobothrium* spp., *Dipylidium* spp., *Dirofilaria* spp., *Dracunculus* spp., *Echinococcus* spp., *Echinostoma* spp., *Enterobius* spp., *Eucoleus* spp., *Fasciola* spp., *Fascioloides* spp., *Fasciolopsis* spp., *Filaroides* spp., *Gongylonema* spp., *Gyrodactylus* spp., *Habronema* spp., *Haemonchus* spp., *Heligmosomoides* spp., *Heterakis* spp., *Hymenolepis* spp., *Hyostrongylus* spp., *Litomosoides* spp., *Loa* spp., *Metastrongylus* spp., *Metorchis* spp., *Mesocestoides* spp., *Moniezia* spp., *Muellerius* spp., *Necator* spp., *Nematodirus* spp., *Nippostrongylus* spp., *Oesophagostomum* spp., *Ollulanus* spp., *Onchocerca* spp., *Opisthorchis* spp., *Oslerus* spp., *Ostertagia* spp., *Oxyuris* spp., *Paracapillaria* spp., *Parafilaria* spp., *Paragonimus* spp., *Paramphistomum* spp., *Paranoplocephala* spp., *Parascaris* spp., *Passalurus* spp., *Protostrongylus* spp., *Schistosoma* spp., *Setaria* spp., *Spirocerca* spp., *Stephanofilaria* spp., *Stephanurus* spp., *Strongyloides* spp., *Strongylus* spp., *Syngamus* spp., *Taenia* spp., *Teladorsagia* spp., *Thelazia* spp., *Toxascaris* spp., *Toxocara* spp., *Trichinella* spp., *Trichobilharzia* spp., *Trichostrongylus* spp., *Trichuris* spp., *Uncinaria* spp., *Wuchereria* spp.;

plant pests from the phylum of the Nematoda, i.e. phytoparasitic nematodes, especially *Aglenchus* spp., for example *Aglenchus agricola, Anguina* spp., for example *Anguina tritici, Aphelenchoides* spp., for example *Aphelenchoides arachidis, Aphelenchoides fragariae, Belonolaimus* spp., for example *Belonolaimus gracilis, Belonolaimus longicaudatus, Belonolaimus nortoni, Bursaphelenchus* spp., for example *Bursaphelenchus cocophilus, Bursaphelenchus eremus, Bursaphelenchus xylophilus, Cacopaurus* spp., for example *Cacopaurus pestis, Criconemella* spp., for example *Criconemella curvata, Criconemella onoensis, Criconemella ornata, Criconemella rusium, Criconemella xenoplax* (=*Mesocriconema xenoplax*), *Criconemoides* spp., for example *Criconemoides ferniae, Criconemoides onoense, Criconemoides ornatum, Ditylenchus* spp., for example *Ditylenchus dipsaci, Dolichodorus* spp., *Globodera* spp., for example *Globodera pallida, Globodera rostochiensis, Helicotylenchus* spp., for example *Helicotylenchus dihystera, Hemicriconemoides* spp., *Hemicycliophora* spp., *Heterodera* spp., for example *Heterodera avenae, Heterodera glycines, Heterodera schachtii, Hoplolaimus* spp., *Longidorus* spp., for example *Longidorus africanus, Meloidogyne* spp., for example *Meloidogyne chitwoodi, Meloidogyne fallax, Meloidogyne hapla, Meloidogyne incognita, Meloinema* spp., *Nacobbus* spp., *Neotylenchus* spp., *Paraphelenchus* spp., *Paratrichodorus* spp., for example *Paratrichodorus minor, Pratylenchus* spp., for example *Pratylenchus penetrans, Pseudohalenchus* spp., *Psilenchus* spp., *Punctodera* spp., *Quinisulcius* spp., *Radopholus* spp., for example *Radopholus citrophilus, Radopholus similis, Rotylenchulus* spp., *Rotylenchus* spp., *Scutellonema* spp., *Subanguina* spp., *Trichodorus* spp., for example *Trichodorus obtusus, Trichodorus primitivus, Tylenchorhynchus* spp., for example *Tylenchorhynchus annulatus, Tylenchulus* spp., for example *Tylenchulus semipenetrans, Xiphinema* spp., for example *Xiphinema index*.

In addition, it is possible to control, from the sub-kingdom of the Protozoa, the order of the Coccidia, for example *Eimeria* spp.

The compounds of the formula (I) can optionally, at certain concentrations or application rates, also be used as herbicides, safeners, growth regulators or agents to improve plant properties, as microbicides or gametocides, for example as fungicides, antimycotics, bactericides, virucides (including agents against viroids) or as agents against MLO (*mycoplasma*-like organisms) and RLO (*rickettsia*-like organisms). They can, as the case may be, also be used as intermediates or precursors for the synthesis of other active ingredients.

Formulations

The present invention further relates to formulations and use forms prepared therefrom as pesticides, for example drench, drip and spray liquors, comprising at least one compound of the formula (I). Optionally, the use forms comprise further pesticides and/or adjuvants which improve action, such as penetrants, e.g. vegetable oils, for example rapeseed oil, sunflower oil, mineral oils, for example paraffin oils, alkyl esters of vegetable fatty acids, for example rapeseed oil methyl ester or soya oil methyl ester, or alkanol alkoxylates and/or spreaders, for example alkylsiloxanes and/or salts, for example organic or inorganic ammonium or phosphonium salts, for example ammonium sulphate or diammonium hydrogenphosphate and/or retention promoters, for example dioctyl sulphosuccinate or hydroxypropylguar polymers and/or humectants, for example glycerol and/or fertilizers, for example ammonium-, potassium- or phosphorus-containing fertilizers.

Customary formulations are, for example, water-soluble liquids (SL), emulsion concentrates (EC), emulsions in water (EW), suspension concentrates (SC, SE, FS, OD), water-dispersible granules (WG), granules (GR) and capsule concentrates (CS); these and further possible formulation types are described, for example, by Crop Life International and in Pesticide Specifications, Manual on development and use of FAO and WHO specifications for pesticides, FAO Plant Production and Protection Papers—173, prepared by the FAO/WHO Joint Meeting on Pesticide Specifications, 2004, ISBN: 9251048576. The formulations, in addition to one or more compounds of the formula (I), optionally comprise further agrochemically active ingredients.

Preference is given to formulations or use forms comprising auxiliaries, for example extenders, solvents, spontaneity promoters, carriers, emulsifiers, dispersants, frost protection agents, biocides, thickeners and/or further auxiliaries, for example adjuvants. An adjuvant in this context is a component which enhances the biological effect of the formulation, without the component itself having any biological effect. Examples of adjuvants are agents which promote retention, spreading, attachment to the leaf surface or penetration.

These formulations are prepared in a known way, for example by mixing the compounds of the formula (I) with auxiliaries such as, for example, extenders, solvents and/or solid carriers and/or other auxiliaries such as, for example, surfactants. The formulations are produced either in suitable facilities or else before or during application.

The auxiliaries used may be substances suitable for imparting special properties, such as certain physical, technical and/or biological properties, to the formulation of the compounds of the formula (I), or to the use forms prepared from these formulations (for example ready-to-use pesticides such as spray liquors or seed dressing products).

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the simple and substituted amines, amides, lactams (such as N-alkylpyrrolidones) and lactones, the sulphones and sulphoxides (such as dimethyl sulphoxide).

If the extender utilized is water, it is also possible to use, for example, organic solvents as auxiliary solvents. Useful liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and water.

In principle, it is possible to use all suitable solvents. Examples of suitable solvents are aromatic hydrocarbons, such as xylene, toluene or alkylnaphthalenes, chlorinated aromatic or aliphatic hydrocarbons, such as chlorobenzene, chloroethylene or methylene chloride, aliphatic hydrocarbons, such as cyclohexane, paraffins, mineral oil fractions, mineral and vegetable oils, alcohols, such as methanol, ethanol, isopropanol, butanol or glycol and their ethers and esters, ketones such as acetone, methyl ethyl ketone, methyl isobutyl ketone or cyclohexanone, strongly polar solvents, such as dimethyl sulphoxide, and also water.

In principle, it is possible to use all suitable carriers. Useful carriers especially include: for example ammonium salts and ground natural minerals such as kaolins, clays, talc, chalk, quartz, attapulgite, montmorillonite or diatomaceous earth, and ground synthetic minerals such as finely divided silica, alumina and natural or synthetic silicates, resins, waxes and/or solid fertilizers. It is likewise possible to use mixtures of such carriers. Useful carriers for granules include: for example crushed and fractionated natural rocks such as calcite, marble, pumice, sepiolite, dolomite, and synthetic granules of inorganic and organic flours, and also granules of organic material such as sawdust, paper, coconut shells, maize cobs and tobacco stalks.

It is also possible to use liquefied gaseous extenders or solvents. Especially suitable are those extenders or carriers which are gaseous at standard temperature and under atmospheric pressure, for example aerosol propellants such as halogenated hydrocarbons, and also butane, propane, nitrogen and carbon dioxide.

Examples of emulsifiers and/or foam formers, dispersants or wetting agents having ionic or nonionic properties or mixtures of these surface-active substances are salts of polyacrylic acid, salts of lignosulphonic acid, salts of phenolsulphonic acid or naphthalenesulphonic acid, polycondensates of ethylene oxide with fatty alcohols or with fatty acids or with fatty amines, with substituted phenols (preferably alkylphenols or arylphenols), salts of sulphosuccinic esters, taurine derivatives (preferably alkyl taurates), phosphoric esters of polyethoxylated alcohols or phenols, fatty acid esters of polyols, and derivatives of the compounds containing sulphates, sulphonates and phosphates, for example alkylaryl polyglycol ethers, alkylsulphonates, alkyl sulphates, arylsulphonates, protein hydrolysates, lignosulphite waste liquors and methylcellulose. The presence of a surfactant is advantageous if one of the compounds of the formula (I) and/or one of the inert carriers is insoluble in water and if the application takes place in water.

Further auxiliaries which may be present in the formulations and the use forms derived therefrom are dyes such as inorganic pigments, for example iron oxide, titanium oxide and Prussian Blue, and organic dyes such as alizarin dyes, azo dyes and metal phthalocyanine dyes, and nutrients and trace nutrients such as salts of iron, manganese, boron, copper, cobalt, molybdenum and zinc.

Additional components which may be present are stabilizers, such as cold stabilizers, preservatives, antioxidants, light stabilizers, or other agents which improve chemical and/or physical stability. Foam generators or antifoams may also be present.

In addition, the formulations and the use forms derived therefrom may also comprise, as additional auxiliaries, stickers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids. Further auxiliaries may be mineral and vegetable oils.

It is possible if appropriate for still further auxiliaries to be present in the formulations and the use forms derived therefrom. Examples of such additives are fragrances, protective colloids, binders, adhesives, thickeners, thixotropic agents, penetrants, retention promoters, stabilizers, sequestrants, complexing agents, humectants, spreaders. In general, the compounds of the formula (I) can be combined with any solid or liquid additive commonly used for formulation purposes.

Useful retention promoters include all those substances which reduce dynamic surface tension, for example dioctyl sulphosuccinate, or increase viscoelasticity, for example hydroxypropylguar polymers.

Useful penetrants in the present context are all those substances which are typically used to improve the penetration of active agrochemical ingredients into plants. Penetrants are defined in this context by their ability to penetrate from the (generally aqueous) application liquor and/or from the spray coating into the cuticle of the plant and hence increase the mobility of the active ingredients in the cuticle. The method described in the literature (Baur et al., 1997, Pesticide Science 51, 131-152) can be used for determining this property. Examples include alcohol alkoxylates such as coconut fatty ethoxylate (10) or isotridecyl ethoxylate (12), fatty acid esters, for example rapeseed oil methyl ester or soya oil methyl ester, fatty amine alkoxylates, for example tallowamine ethoxylate (15), or ammonium and/or phosphonium salts, for example ammonium sulphate or diammonium hydrogenphosphate.

The formulations preferably comprise between 0.00000001% and 98% by weight of the compound of the formula (I), more preferably between 0.01% and 95% by weight of the compound of the formula (I), most preferably between 0.5% and 90% by weight of the compound of the formula (I), based on the weight of the formulation.

The content of the compound of the formula (I) in the use forms prepared from the formulations (in particular pesticides) may vary within wide ranges. The concentration of the compound of the formula (I) in the use forms may typically be between 0.00000001% and 95% by weight of the compound of the formula (I), preferably between 0.00001% and 1% by weight, based on the weight of the use form. Application is accomplished in a customary manner appropriate for the use forms.

Mixtures

The compounds of the formula (I) can also be used in a mixture with one or more suitable fungicides, bactericides, acaricides, molluscicides, nematicides, insecticides, microbiological agents, beneficial organisms, herbicides, fertilizers, bird repellents, phytotonics, sterilants, safeners, semiochemicals and/or plant growth regulators, in order thus, for example, to broaden the spectrum of action, prolong the period of action, enhance the rate of action, prevent repellency or prevent evolution of resistance. In addition, active ingredient combinations of this kind can improve plant growth and/or tolerance to abiotic factors, for example high or low temperatures, to drought or to elevated water content or soil salinity. It is also possible to improve flowering and fruiting performance, optimize germination capacity and root development, facilitate harvesting and improve yields, influence maturation, improve the quality and/or the nutritional value of the harvested products, prolong storage life and/or improve the processability of the harvested products.

In addition, the compounds of the formula (I) may be present in a mixture with other active ingredients or semiochemicals such as attractants and/or bird repellents and/or plant activators and/or growth regulators and/or fertilizers. Likewise, the compounds of the formula (I) can be used in mixtures with agents to improve plant properties, for example growth, yield and quality of the harvested material.

In a particular embodiment according to the invention, the compounds of the formula (I) are present in formulations or in the use forms prepared from these formulations in a mixture with further compounds, preferably those as described below.

If one of the compounds mentioned below can occur in different tautomeric forms, these forms are also included even if not explicitly mentioned in each case.

Insecticides/Acaricides/Nematicides

The active ingredients specified here with their common names are known and are described for example in "The Pesticide Manual", 16th ed., British Crop Protection Council 2012, or can be searched for on the Internet (e.g. http://www.alanwood.net/pesticides).

(1) Acetylcholinesterase (AChE) inhibitors, for example carbamates, e.g. alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, e.g. acephate, azamethiphos, azinphos-ethyl, azinphos-methyl, cadusafos, chlorethoxyfos, chlorfenvinphos, chlormephos, chloropyrifos, chloropyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel antagonists, for example cyclodiene-organochlorines, e.g. chlordane and endosulphan or phenylpyrazoles (fiproles), e.g. ethiprole and fipronil.

(3) Sodium channel modulators/voltage-gated sodium channel blockers such as, for example, pyrethroids, e.g. acrinathrin, allethrin, d-cis-trans allethrin, d-trans allethrin, bifenthrin, bioallethrin, bioallethrin S-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans-isomer], deltamethrin, empenthrin [(EZ)-(1R)-isomer], esfenvalerate, etofenprox, fenpropathrin, fenvalerate, flucythrinate, flumethrin, tau-fluvalinate, halfenprox, imiprothrin, kadethrin, permethrin, phenothrin [(1R)-trans-isomer], prallethrin, pyrethrins (pyrethrum), resmethrin, silafluofen, tefluthrin, tetramethrin, tetramethrin [(1R)-isomer)], tralomethrin and transfluthrin or DDT or methoxychlor.

(4) Nicotinergic acetylcholine receptor (nAChR) agonists, for example neonicotinoids, e.g. acetamiprid, clothianidin, dinotefuran, imidacloprid, nitenpyram, thiacloprid and thiamethoxam or nicotine or sulphoxaflor or flupyradifurone.

(5) Allosteric activators of the nicotinergic acetylcholine receptor (nAChR), for example spinosyns, e.g. spinetoram and spinosad.

(6) Chloride channel activators, for example avermectins/milbemycins, e.g. abamectin, emamectin benzoate, lepimectin and milbemectin.

(7) Juvenile hormone imitators, for example, juvenile hormone analogues, e.g. hydroprene, kinoprene and methoprene or fenoxycarb or pyriproxyfen.

(8) Active compounds having unknown or nonspecific mechanisms of action, for example alkyl halides, e.g. methyl bromide and other alkyl halides; or chloropicrine or sulphuryl fluoride or borax or tartar emetic.

(9) Selective antifeedants, e.g. pymetrozine or flonicamid.

(10) Mite growth inhibitors, e.g. clofentezine, hexythiazox and diflovidazin or etoxazole.

(11) Microbial disruptors of the insect gut membrane, e.g. *Bacillus thuringiensis* subspecies *israelensis*, *Bacillus sphaericus*, *Bacillus thuringiensis* subspecies *aizawai*, *Bacillus thuringiensis* subspecies *kurstaki*, *Bacillus thuringiensis* subspecies *tenebrionis*, and BT plant proteins: Cry1Ab, Cry1Ac, Cry1Fa, Cry2Ab, mCry3A, Cry3Ab, Cry3Bb, Cry34/35Ab1.

(12) Oxidative phosphorylation inhibitors, ATP disruptors, for example diafenthiuron or organotin compounds, e.g. azocyclotin, cyhexatin and fenbutatin oxide or propargite or tetradifon.

(13) Oxidative phosphorylation decouplers that interrupt the H proton gradient, for example chlorfenapyr, DNOC and sulphluramid.

(14) Nicotinergic acetylcholine receptor antagonists, for example bensultap, cartap hydrochloride, thiocyclam, and thiosultap-sodium.

(15) Inhibitors of chitin biosynthesis, type 0, for example bistrifluron, chlorfluazuron, diflubenzuron, flucycloxuron, flufenoxuron, hexaflumuron, lufenuron, novaluron, noviflumuron, teflubenzuron and triflumuron.

(16) Inhibitors of chitin biosynthesis, type 1, for example buprofezin.

(17) Moulting inhibitors (especially for Diptera, i.e. dipterans), for example cyromazine.

(18) Ecdysone receptor agonists, for example chromafenozide, halofenozide, methoxyfenozide and tebufenozide.

(19) Octopaminergic agonists, for example amitraz.

(20) Complex-III electron transport inhibitors, for example hydramethylnon or acequinocyl or fluacrypyrim.

(21) Complex-I electron transport inhibitors, for example METI acaricides, e.g. fenazaquin, fenpyroximate, pyrimidifen, pyridaben, tebufenpyrad and tolfenpyrad or rotenone (Derris).

(22) Voltage-gated sodium channel blockers, for example indoxacarb or metaflumizone.

(23) Inhibitors of acetyl-CoA carboxylase, for example tetronic and tetramic acid derivatives, e.g. spirodiclofen, spiromesifen and spirotetramat.

(24) Complex-IV electron transport inhibitors, for example phosphines, e.g. aluminium phosphide, calcium phosphide, phosphine and zinc phosphide or cyanide.

(25) Complex-II electron transport inhibitors, for example cyenopyrafen and cyflumetofen.

(28) Ryanodine receptor effectors, for example diamides, e.g. chlorantraniliprole, cyantraniliprole and flubendiamide.

Further active ingredients having an unknown or unclear mechanism of action, for example afidopyropen, afoxolaner, azadirachtin, benclothiaz, benzoximate, bifenazate, bromopropylate, chinomethionat, cryolite, cyclaniliprole, cycloxaprid, cyhalodiamide, dicloromezotiaz, dicofol, diflovidazin, flometoquin, fluensulfone, flufenerim, flufenoxystrobin, flufiprole, fluhexafon, fluopyram, fluralaner, fufenozide, guadipyr, heptafluthrin, imidaclothiz, iprodione, meperfluthrin, paichongding, pyflubumide, pyridalyl, pyrifluquinazon, pyriminostrobin, tetramethylfluthrin, tetraniliprole, tetrachlorantraniliprole, tioxazafen, triflumezopyrim and iodomethane; and additionally preparations based on *Bacillus firmus* (I-1582, BioNeem, Votivo), and the following known active compounds: 1-{2-fluoro-4-methyl-5-[(2,2,2-trifluoroethyl)sulphinyl]phenyl}-3-(trifluoromethyl)-1H-1,2,4-triazole-5-amine (known from WO2006/043635), {1'-[(2E)-3-(4-chlorophenyl)prop-2-en-1-yl]-5-fluorospiro[indole-3,4'-piperidin]-1(2H)-yl}(2-chloropyridin-4-yl)methanone (known from WO2003/106457), 2-chloro-N-[2-{1-[(2E)-3-(4-chlorophenyl)prop-2-en-1-yl]piperidin-4-yl}-4-(trifluoromethyl)phenyl]isonicotinamide (known from WO2006/003494), 3-(2,5-dimethylphenyl)-4-hydroxy-8-methoxy-1,8-diazaspiro[4.5]dec-3-en-2-one (known from WO2009/049851), 3-(2,5-dimethylphenyl)-8-methoxy-2-oxo-1,8-diazaspiro[4.5]dec-3-en-4-ylethyl carbonate (known from WO2009/049851), 4-(but-2-yn-1-yloxy)-6-(3,5-dimethylpiperidin-1-yl)-5-fluoropyrimidine (known from WO2004/099160), 4-(but-2-yn-1-yloxy)-6-(3-chlorophenyl)pyrimidine (known from WO2003/076415), PF1364 (CAS Reg. No. 1204776-60-2), methyl 2-[2-({[3-bromo-1-(3-chloropyridin-2-yl)-1H-pyrazol-5-yl]carbonyl}amino)-5-chloro-3-methylbenzoyl]-2-methylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-ethylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-methylhydrazinecarboxylate (known from WO2005/085216), methyl 2-[3,5-dibromo-2-({[3-bromo-1-(3-chloropyridin-2-yl)-1H-pyrazol-5-yl]carbonyl}amino)benzoyl]-2-ethylhydrazinecarboxylate (known from WO2005/085216), N-[2-(5-amino-1,3,4-thiadiazol-2-yl)-4-chloro-6-methylphenyl]-3-bromo-1-(3-chloropyridin-2-yl)-1H-pyrazole-5-carboxamide (known from CN102057925), 8-chloro-N-[(2-chloro-5-methoxyphenyl)sulphonyl]-6-(trifluoromethyl)imidazo[1,2-a]pyridine-2-carboxamide (known from WO2010/129500), 4-[5-(3,5-dichlorophenyl)-5-(trifluoromethyl)-4,5-dihydro-1,2-oxazol-3-yl]-2-methyl-N-(1-oxidothietan-3-yl)benzamide (known from WO2009/080250), N-[(2E)-1-[(6-chloropyridin-3-yl)methyl]pyridin-2(1H)-ylidene]-2,2,-2-trifluoroacetamide (known from WO2012/029672), 1-[(2-chloro-1,3-thiazol-5-yl)methyl]-4-oxo-3-phenyl-4H-pyrido[1,2-a]pyrimidin-1-ium-2-olate (known from WO2009/099929), 1-[(6-chloropyridin-3-yl)methyl]-4-oxo-3-phenyl-4H-pyrido[1,2-a]pyrimidin-1-ium-2-olate (known from WO2009/099929), 4-(3-{2,6-dichloro-4-[(3,3-dichloroprop-2-en-1-yl)oxy]phenoxy}propoxy)-2-methoxy-6-(trifluoromethyl)pyrimidine (known from CN101337940), N-[2-(tert-butylcarbamoyl)-4-chloro-6-methylphenyl]-1-(3-chloropyridin-2-yl)-3-(fluoromethoxy)-1H-pyrazole-5-carboxamide (known from WO2008/134969, 3-[benzoyl(methyl)amino]-N-[2-bromo-4-[1,2,2,2-tetrafluoro-1-(trifluoromethyl)ethyl]-6-(trifluoromethyl) phenyl]-2-fluorobenzamide (known from WO 2010018714), butyl [2-(2,4-dichlorophenyl)-3-oxo-4-oxaspiro[4.5]dec-1-en-1-yl]carbonate (known from CN 102060818), 4-[5-(3,5-dichlorophenyl)-5-(trifluoromethyl)-4H-isoxazol-3-yl]-N—[(Z)-methoxyiminomethyl]-2-methylbenzamide (known from WO2007/026965), 3E)-3-[1-[(6-chloro-3-pyridyl)methyl]-2-pyridylidene]-1,1,1-trifluoropropan-2-one (known from WO2013/144213, N-(methylsulphonyl)-6-[2-(pyridin-3-yl)-1,3-thiazol-5-yl]pyridine-2-carboxamide (known from WO2012/000896), N-[3-(benzylcarbamoyl)-4-chlorophenyl]-1-methyl-3-(pentafluoroethyl)-4-(trifluoromethyl)-1H-pyrazole-5-carboxamide (known from WO2010/051926).

Fungicides

The active ingredients specified herein by their common name are known and described, for example, in "Pesticide Manual" or on the Internet (for example: http://www.alanwood.net/pesticides).

All the fungicidal mixing components listed in classes (1) to (15) may optionally form salts with corresponding bases or acids if suitable functional groups are present. In addition, the fungicidal mixing components listed in classes (1) to (15) also include tautomeric forms if tautomerism is possible.

1) ergosterol biosynthesis inhibitors, for example (1.01) aldimorph, (1.02) azaconazole, (1.03) bitertanol, (1.04) bromuconazole, (1.05) cyproconazole, (1.06) diclobutrazole, (1.07) difenoconazole, (1.08) diniconazole, (1.09) diniconazole-M, (1.10) dodemorph, (1.11) dodemorph acetate, (1.12) epoxiconazole, (1.13) etaconazole, (1.14) fenarimol, (1.15) fenbuconazole, (1.16) fenhexamide, (1.17) fenpropidin, (1.18) fenpropimorph, (1.19) fluquinconazole, (1.20) flurprimidol, (1.21) flusilazole, (1.22) flutriafol, (1.23) furconazole, (1.24) furconazole-cis, (1.25) hexaconazole, (1.26) imazalil, (1.27) imazalil sulphate, (1.28) imibenconazole, (1.29) ipconazole, (1.30) metconazole, (1.31) myclobutanil, (1.32) naftifine, (1.33) nuarimol, (1.34) oxpoconazole, (1.35) paclobutrazole, (1.36) pefurazoate, (1.37) penconazole, (1.38) piperalin, (1.39) prochloraz, (1.40) propiconazole, (1.41) prothioconazole, (1.42) pyributicarb, (1.43) pyrifenox, (1.44) quinconazole, (1.45) simeconazole, (1.46) spiroxamine, (1.47) tebuconazole, (1.48) terbinafin, (1.49) tetraconazole, (1.50) triadimefon, (1.51) triadimenol, (1.52) tridemorph, (1.53) triflumizole, (1.54) triforin, (1.55) triticonazole, (1.56) uniconazole, (1.57) uniconazole-p, (1.58) viniconazole, (1.59) voriconazole, (1.60) 1-(4-chlorophenyl)-2-(1H-1,2,4-triazol-1-yl)cycloheptanol, (1.61) methyl 1-(2,2-dimethyl-2,3-dihydro-1H-inden-1-yl)-1H-imidazole-5-carboxylate, (1.62) N'-{5-(difluoromethyl)-2-methyl-4-[3-(trimethylsilyl)propoxy]phenyl}-N-ethyl-N-methylimidoformamide, (1.63) N-ethyl-N-methyl-N'-{2-methyl-5-(trifluoromethyl)-4-[3-(trimethylsilyl)propoxy]phenyl}imidoformamide, (1.64) O-[1-(4-methoxyphenoxy)-3,3-dimethylbutan-2-yl]-1H-imidazole-1-carbothioate, (1.65) pyrisoxazole, (1.66) 2-{[3-(2-chlorophenyl)-2-(2,4-difluorophenyl)oxiran-2-yl]methyl}-2,4-dihydro-3H-1,2,4-triazole-3-thione, (1.67) 1-{[3-(2-chlorophenyl)-2-(2,4-difluorophenyl)oxiran-2-yl]methyl}-1H-1,2,4-triazol-5-ylthiocyanate, (1.68) 5-(allylsulphanyl)-1-{[3-(2-chlorophenyl)-2-(2,4-difluorophenyl)oxiran-2-yl]methyl}-1H-1,2,4-triazole, (1.69) 2-[1-(2,4-dichlorophenyl)-5-hydroxy-2,6,6-trimethylheptan-4-yl]-2,4-dihydro-3H-1,2,4-triazole-3-thione, (1.70) 2-{[rel(2R,3S)-3-(2-chlorophenyl)-2-(2,4-difluorophenyl)oxiran-2-yl]methyl}-2,4-dihydro-3H-1,2,4-triazole-3-thione, (1.71) 2-{[rel(2R,3R)-3-(2-chlorophenyl)-2-(2,4-difluorophenyl)oxiran-2-yl]methyl}-2,4-dihydro-3H-1,2,4-triazole-3-thione, (1.72) 1-{[rel(2R,3S)-3-(2-chlorophenyl)-2-(2,4-difluorophenyl)oxiran-2-yl]methyl}-1H-1,2,4-triazol-5-ylthiocyanate, (1.73) 1-{[rel(2R,3R)-3-(2-chlorophenyl)-2-(2,4-difluorophenyl)oxiran-2-yl]methyl}-1H-1,2,4-triazol-5-ylthiocyanate, (1.74) 5-(allylsulphanyl)-1-{[rel(2R,3S)-3-(2-chlorophenyl)-2-(2,4-difluorophenyl)oxiran-2-yl]methyl}-1H-1,2,4-triazole, (1.75) 5-(allylsulphanyl)-1-{[rel(2R,3R)-3-(2-chlorophenyl)-2-(2,4-difluorophenyl)oxiran-2-yl]methyl}-1H-1,2,4-triazole, (1.76) 2-[(2S,4S,5S)-1-(2,4-dichlorophenyl)-5-hydroxy-2,6,6-trimethylheptan-4-yl]-2,4-dihydro-3H-1,2,4-triazole-3-thione, (1.77) 2-[(2R,4S,5S)-1-(2,4-dichlorophenyl)-5-hydroxy-2,6,6-trimethylheptan-4-yl]-2,4-dihydro-3H-1,2,4-triazole-3-thione, (1.78) 2-[(2R,4R,5R)-1-(2,4-dichlorophenyl)-5-hydroxy-2,6,6-trimethylheptan-4-yl]-2,4-dihydro-3H-1,2,4-triazole-3-thione, (1.79) 2-[(2S,4R,5R)-1-(2,4-dichlorophenyl)-5-hydroxy-2,6,6-trimethylheptan-4-yl]-2,4-dihydro-3H-1,2,4-triazole-3-thione, (1.80) 2-[(2S,4S,5R)-1-(2,4-dichlorophenyl)-5-hydroxy-2,6,6-trimethylheptan-4-yl]-2,4-dihydro-3H-1,2,4-triazole-3-thione, (1.81) 2-[(2R,4S,5R)-1-(2,4-dichlorophenyl)-5-hydroxy-2,6,6-trimethylheptan-4-yl]-2,4-dihydro-3H-1,2,4-triazole-3-thione, (1.82) 2-[(2R,4R,5S)-1-(2,4-dichlorophenyl)-5-hydroxy-2,6,6-trimethylheptan-4-yl]-2,4-dihydro-3H-1,2,4-triazole-3-thione, (1.83) 2-[(2S,4R,5S)-1-(2,4-dichlorophenyl)-5-hydroxy-2,6,6-trimethylheptan-4-yl]-2,4-dihydro-3H-1,2,4-triazole-3-thione, (1.84) 2-[4-(4-chlorophenoxy)-2-(trifluoromethyl)phenyl]-1-(1H-1,2,4-triazol-1-yl)propan-2-ol, (1.85) 2-[4-(4-chlorophenoxy)-2-(trifluoromethyl)phenyl]-1-(1H-1,2,4-triazol-1-yl)butan-2-ol, (1.86) 2-[4-(4-chlorophenoxy)-2-(trifluoromethyl)phenyl]-1-(1H-1,2,4-triazol-1-yl)pentan-2-ol, (1.87) 2-[2-chloro-4-(4-chlorophenoxy)phenyl]-1-(1H-1,2,4-triazol-1-yl)butan-2-ol, (1.88) 2-[2-chloro-4-(2,4-dichlorophenoxy)phenyl]-1-(1H-1,2,4-triazol-1-yl)propan-2-ol, (1.89) (2R)-2-(1-chlorocyclopropyl)-4-[(1R)-2,2-dichlorocyclopropyl]-1-(1H-1,2,4-triazol-1-yl)butan-2-ol, (1.90) (2R)-2-(1-chlorocyclopropyl)-4-[(1 S)-2,2-dichlorocyclopropyl]-1-(1H-1,2,4-triazol-1-yl)butan-2-ol, (1.91) (2S)-2-(1-chlorocyclopropyl)-4-[(1 S)-2,2-dichlorocyclopropyl]-1-(1H-1,2,4-triazol-1-yl)butan-2-ol, (1.92) (2S)-2-(1-chlorocyclopropyl)-4-[(1R)-2,2-dichlorocyclopropyl]-1-(1H-1,2,4-triazol-1-yl)butan-2-ol, (1.93) (1S,2R,5R)-5-(4-chlorobenzyl)-2-(chloromethyl)-2-methyl-1-(1H-1,2,4-triazol-1-ylmethyl)cyclopentanol, (1.94) (1R,2S,5S)-5-(4-chlorobenzyl)-2-(chloromethyl)-2-methyl-1-(1H-1,2,4-triazol-1-ylmethyl)cyclopentanol, (1.95) 5-(4-chlorobenzyl)-2-(chloromethyl)-2-methyl-1-(1H-1,2,4-triazol-1-ylmethyl)cyclopentanol.

2) Inhibitors of the respiratory chain on complex I or II, for example (2.01) bixafen, (2.02) boscalid, (2.03) carboxin, (2.04) diflumetorim, (2.05) fenfuram, (2.06) fluopyram, (2.07) flutolanil, (2.08) fluxapyroxad, (2.09) furametpyr, (2.10) furmecyclox, (2.11) isopyrazam (mixture of syn-epimeric racemate 1RS,4SR,9RS and anti-epimeric racemate 1RS,4SR,9SR), (2.12) isopyrazam (anti-epimeric racemate 1RS,4SR,9SR), (2.13) isopyrazam (anti-epimeric enantiomer 1R,4S,9S), (2.14) isopyrazam (anti-epimeric enantiomer 1S,4R,9R), (2.15) isopyrazam (syn-epimeric racemate 1RS,4SR,9RS), (2.16) isopyrazam (syn-epimeric enantiomer 1R,4S,9R), (2.17) isopyrazam (syn-epimeric enantiomer 1S,4R,9S), (2.18) mepronil, (2.19) oxycarboxin, (2.20) penflufen, (2.21) penthiopyrad, (2.22) sedaxane, (2.23) thifluzamide, (2.24) 1-methyl-N-[2-(1,1,2,2-tetrafluoroethoxy)phenyl]-3-(trifluoromethyl)-1H-pyrazole-4-carboxamide, (2.25) 3-(difluoromethyl)-1-methyl-N-[2-(1,1,2,2-tetrafluoroethoxy)phenyl]-1H-pyrazole-4-carboxamide, (2.26) 3-(difluoromethyl)-N-[4-fluoro-2-(1,1,2,3,3,3-hexafluoropropoxy)phenyl]-1-methyl-1H-pyrazole-4-carboxamide, (2.27) N-[1-(2,4-dichlorophenyl)-1-methoxypropan-2-yl]-3-(difluoromethyl)-1-methyl-1H-pyrazole-4-carboxamide, (2.28) 5,8-difluoro-N-[2-(2-fluoro-4-{[4-(trifluoromethyl)pyridin-2-yl]oxy}phenyl)ethyl]quinazolin-4-amine, (2.29) benzovindiflupyr, (2.30) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide, (2.31) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (2.32) 3-(difluoromethyl)-1-methyl-N-(1,1,3-trimethyl-2,3-dihydro-1H-inden-4-yl)-1H-pyrazole-4-carboxamide, (2.33) 1,3,5-trimethyl-N-(1,1,3-trimethyl-2,3-dihydro-1H-inden-4-yl)-1H-pyrazole-4-carboxamide, (2.34) 1-methyl-3-(trifluoromethyl)-N-(1,1,3-trimethyl-2,3-dihydro-1H-inden-4-yl)-1H-pyrazole-4-carboxamide, (2.35) 1-methyl-3-(trifluoromethyl)-N-[(3R)-1,1,3-trimethyl-2,3-dihydro-1H-inden-4-yl]-1H-pyrazole-4-carboxamide, (2.36) 1-methyl-3-(trifluoromethyl)-N-[(3S)-1,1,3-trimethyl-2,3-dihydro-1H-inden-4-yl]-1H-pyrazole-4-carboxamide, (2.37) 3-(difluoromethyl)-1-methyl-N-[(3S)-1,1,3-trimethyl-2,3-dihydro-1H-inden-4-yl]-1H-pyrazole-4-carboxamide, (2.38) 3-(difluoromethyl)-1-methyl-N-[(3R)-1,1,3-trimethyl-2,3-dihydro-1H-inden-4-yl]-1H-pyrazole-4-carboxamide, (2.39) 1,3,5-trimethyl-N-[(3R)-1,1,3-trimethyl-2,3-dihydro-1H-inden-4-yl]-1H-pyrazole-4- carboxamide, (2.40) 1,3,5-trimethyl-N-[(3S)-1,1,3-trimethyl-2,3-dihydro-1H-inden-4-yl]-1H-pyrazole-4-carboxamide, (2.41) benodanil, (2.42) 2-chloro-N-(1,1,3-trimethyl-2,3-dihydro-1H-inden-4-yl)pyridine-3-carboxamide, (2.43) isofetamid, (2.44) 1-methyl-3-(trifluoromethyl)-N-[2'-(trifluoromethyl)biphenyl-2-yl]-1H-pyrazole-4-carboxamide, (2.45) N-(4'-chlorobiphenyl-2-yl)-3-(difluoromethyl)-1-methyl-1H-pyrazole-4-carboxamide, (2.46) N-(2',4'-dichlorobiphenyl-2-yl)-3-(difluoromethyl)-1-methyl-1H-pyrazole-4-carboxamide, (2.47) 3-(difluoromethyl)-1-methyl-N-[4'-(trifluoromethyl)biphenyl-2-yl]-1H-pyrazole-4-carboxamide, (2.48) N-(2',5'-difluorobiphenyl-2-yl)-1-methyl-3-(trifluoromethyl)-1H-pyrazole-4-carboxamide, (2.49) 3-(difluoromethyl)-1-methyl-N-[4'-(prop-1-yn-1-yl)biphenyl-2-yl]-1H-pyrazole-4-carboxamide, (2.50) 5-fluoro-1,3-dimethyl-N-[4'-(prop-1-yn-1-yl)biphenyl-2-yl]-1H-pyrazole-4-carboxamide, (2.51) 2-chloro-N-[4'-(prop-1-yn-1-yl)biphenyl-2-yl]nicotinamide, (2.52) 3-(difluoromethyl)-N-[4'-(3,3-dimethylbut-1-yn-1-yl)biphenyl-2-yl]-1-methyl-1H-pyrazole-4-carboxamide, (2.53) N-[4'-(3,3-dimethylbut-1-yn-1-yl)biphenyl-2-yl]-5-fluoro-1,3-dimethyl-1H-pyrazole-4-carboxamide, (2.54) 3-(difluoromethyl)-N-(4'-ethynylbiphenyl-2-yl)-1-methyl-1H-pyrazole-4-carboxamide, (2.55) N-(4'-ethynylbiphenyl-2-yl)-5-fluoro-1,3-dimethyl-1H-pyrazole-4-carboxamide, (2.56) 2-chloro-N-(4'-ethynylbiphenyl-2-yl)nicotinamide, (2.57) 2-chloro-N-[4'-(3,3-dimethylbut-1-yn-1-yl)biphenyl-2-yl]nicotinamide, (2.58) 4-(difluoromethyl)-2-methyl-N-[4'-(trifluoromethyl)biphenyl-2-yl]-1,3-thiazole-5-carboxamide, (2.59) 5-fluoro-N-[4'-(3-hydroxy-3-methylbut-1-yn-1-yl)biphenyl-2-yl]-1,3-dimethyl-1H-pyrazole-4-carboxamide, (2.60) 2-chloro-N-[4'-(3-hydroxy-3-methylbut-1-yn-1-yl)biphenyl-2-yl]nicotinamide, (2.61) 3-(difluoromethyl)-N-[4'-(3-methoxy-3-methylbut-1-yn-1-yl)biphenyl-2-yl]-1-methyl-1H-pyrazole-4-carboxamide, (2.62) 5-fluoro-N-[4'-(3-methoxy-3-methylbut-1-yn-1-yl)biphenyl-2-yl]-1,3-dimethyl-1H-pyrazole-4-carboxamide, (2.63) 2-chloro-N-[4'-(3-methoxy-3-methylbut-1-yn-1-yl)biphenyl-2-yl]nicotinamide, (2.64) 1,3-dimethyl-N-(1,1,3-trimethyl-2,3-dihydro-1H-inden-4-yl)-1H-pyrazole-4-carboxamide, (2.65) 1,3-dimethyl-N-[(3R)-1,1,3-trimethyl-2,3-dihydro-1H-inden-4-yl]-1H-pyrazole-4-carboxamide, (2.66) 1,3-dimethyl-N-[(3S)-1,1,3-trimethyl-2,3-dihydro-1H-inden-4-yl]-1H-pyrazole-4-carboxamide, (2.67) 3-(difluoromethyl)-N-methoxy-1-methyl-N-[1-(2,4,6-trichlorophenyl)propan-2-yl]-1H-pyrazole-4-carboxamide, (2.68) 3-(difluoromethyl)-N-(7-fluoro-1,1,3-trimethyl-2,3-dihydro-1H-inden-4-yl)-1-methyl-1H-pyrazole-4-carboxamide, (2.69) 3-(difluoromethyl)-N-[(3R)-7-fluoro-1,1,3-trimethyl-2,3-dihydro-1H-inden-4-yl]-1-methyl-1H-pyrazole-4-carboxamide, (2.70) 3-(difluoromethyl)-N-[(3S)-7-fluoro-1,1,3-trimethyl-2,3-dihydro-1H-inden-4-yl]-1-methyl-1H-pyrazole-4-carboxamide.

3) Inhibitors of complex III of the respiratory chain, for example (3.01) ametoctradin, (3.02) amisulbrom, (3.03) azoxystrobin, (3.04) cyazofamid, (3.05) coumethoxystrobin, (3.06) coumoxystrobin, (3.07) dimoxystrobin, (3.08) enoxastrobin, (3.09) famoxadon, (3.10) fenamidon, (3.11) flufenoxystrobin, (3.12) fluoxastrobin, (3.13) kresoxim-methyl, (3.14) metominostrobin, (3.15) orysastrobin, (3.16) picoxystrobin, (3.17) pyraclostrobin, (3.18) pyrametostrobin, (3.19) pyraoxystrobin, (3.20) pyribencarb, (3.21) triclopyricarb, (3.22) trifloxystrobin, (3.23) (2E)-2-(2-{[6-(3-chloro-2-methylphenoxy)-5-fluoropyrimidin-4-yl]oxy}phenyl)-2-(methoxyimino)-N-methylacetamide, (3.24) (2E)-2-(methoxyimino)-N-methyl-2-(2-{[({(1E)-1-[3-(trifluoromethyl)phenyl]ethylidene}amino)oxy]methyl}phenyl) acetamide, (3.25) (2E)-2-(methoxyimino)-N-methyl-2-{2-[(E)-({1-[3-(trifluoromethyl)phenyl]ethoxy}imino)methyl]phenyl}acetamide, (3.26) (2E)-2-{2-[({[(1E)-1-(3-{[(E)-1-fluoro-2-phenylvinyl]oxy}phenyl)ethylidene]amino}oxy)methyl]phenyl}-2-(methoxyimino)-N-methylacetamide, (3.27) fenaminostrobin, (3.28) 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, (3.29) methyl (2E)-2-{2-[({cyclopropyl[(4-methoxyphenyl)imino]methyl}sulphanyl)methyl]phenyl}-3-methoxyacrylate, (3.30) N-(3-ethyl-3,5,5-trimethylcyclohexyl)-3-formamido-2-hydroxybenzamide, (3.31) 2-{2-[(2,5-dimethylphenoxy)methyl]phenyl}-2-methoxy-N-methylacetamide, (3.32) 2-{2-[(2,5-dimethylphenoxy)methyl]phenyl}-2-methoxy-N-methylacetamide, (3.33) (2E,3Z)-5-{[1-(4-chlorophenyl)-1H-pyrazol-3-yl]oxy}-2-(methoxyimino)-N,3-dimethylpent-3-enamide.

4) Mitosis and cell division inhibitors, for example (4.01) benomyl, (4.02) carbendazim, (4.03) chlorfenazole, (4.04) diethofencarb, (4.05) ethaboxam, (4.06) fluopicolide, (4.07) fuberidazole, (4.08) pencycuron, (4.09) thiabendazole, (4.10) thiophanate-methyl, (4.11) thiophanate, (4.12) zoxamide, (4.13) 5-chloro-7-(4-methylpiperidin-1-yl)-6-(2,4,6-trifluorophenyl) [1,2,4]triazolo[1,5-a]pyrimidine, (4.14) 3-chloro-5-(6-chloropyridin-3-yl)-6-methyl-4-(2,4,6-trifluorophenyl)pyridazine.

5) Compounds capable of having multisite action, for example (5.01) Bordeaux mixture, (5.02) captafol, (5.03) captan, (5.04) chlorothalonil, (5.05) copper hydroxide, (5.06) copper naphthenate, (5.07) copper oxide, (5.08) copper oxychloride, (5.09) copper(2+) sulphate, (5.10) dichlofluanid, (5.11) dithianon, (5.12) dodine, (5.13) dodine free base, (5.14) ferbam, (5.15) fluorofolpet, (5.16) folpet, (5.17) guazatine, (5.18) guazatine acetate, (5.19) iminoctadine, (5.20) iminoctadine albesilate, (5.21) iminoctadine triacetate, (5.22) mancopper, (5.23) mancozeb, (5.24) maneb, (5.25) metiram, (5.26) metiram zinc, (5.27) oxine-copper, (5.28) propamidine, (5.29) propineb, (5.30) sulphur and sulphur preparations including calcium polysulphide, (5.31) thiram, (5.32) tolylfluanid, (5.33) zineb, (5.34) ziram, (5.35) anilazine.

6) Compounds capable of inducing host defence, for example (6.01) acibenzolar-S-methyl, (6.02) isotianil, (6.03) probenazole, (6.04) tiadinil, (6.05) laminarin.

7) Amino acid and/or protein biosynthesis inhibitors, for example (7.01) andoprim, (7.02) blasticidin-S, (7.03) cyprodinil, (7.04) kasugamycin, (7.05) kasugamycin hydrochloride hydrate, (7.06) mepanipyrim, (7.07) pyrimethanil, (7.08) 3-(5-fluoro-3,3,4,4-tetramethyl-3,4-dihydroisoquinolin-1-yl)quinoline, (7.09) oxytetracycline, (7.10) streptomycin.

8) ATP production inhibitors, for example (8.01) fentin acetate, (8.02) fentin chloride, (8.03) fentin hydroxide, (8.04) silthiofam.

9) Cell wall synthesis inhibitors, for example (9.01) benthiavalicarb, (9.02) dimethomorph, (9.03) flumorph, (9.04) iprovalicarb, (9.05) mandipropamid, (9.06) polyoxins, (9.07) polyoxorim, (9.08) validamycin A, (9.09) valifenalate, (9.10) polyoxin B, (9.11) (2E)-3-(4-tert-butylphenyl)-3-(2-chloropyridin-4-yl)-1-(morpholin-4-yl)prop-2-en-1-one, (9.12) (2Z)-3-(4-tert-butylphenyl)-3-(2-chloropyridin-4-yl)-1-(morpholin-4-yl)prop-2-en-1-one.

10) Lipid and membrane synthesis inhibitors, for example (10.01) biphenyl, (10.02) chloroneb, (10.03) dicloran, (10.04) edifenphos, (10.05) etridiazole, (10.06) iodocarb, (10.07) iprobenfos, (10.08) isoprothiolane, (10.09) propamocarb, (10.10) propamocarb hydrochloride, (10.11) prothiocarb, (10.12) pyrazophos, (10.13) quintozene, (10.14) tecnazene, (10.15) tolclofos-methyl.

11) Melanin biosynthesis inhibitors, for example (11.01) carpropamid, (11.02) diclocymet, (11.03) fenoxanil, (11.04) phthalide, (11.05) pyroquilon, (11.06) tricyclazole, (11.07) 2,2,2-trifluoroethyl {3-methyl-1-[(4-methylbenzoyl)amino]butan-2-yl}carbamate.

12) Nucleic acid synthesis inhibitors, for example (12.01) benalaxyl, (12.02) benalaxyl-M (kiralaxyl), (12.03) bupirimate, (12.04) clozylacon, (12.05) dimethirimol, (12.06) ethirimol, (12.07) furalaxyl, (12.08) hymexazole, (12.09) metalaxyl, (12.10) metalaxyl-M (mefenoxam), (12.11) ofurace, (12.12) oxadixyl, (12.13) oxolinic acid, (12.14) octhilinone.

13) Signal transduction inhibitors, for example (13.01) chlozolinate, (13.02) fenpiclonil, (13.03) fludioxonil, (13.04) iprodione, (13.05) procymidone, (13.06) quinoxyfen, (13.07) vinclozolin, (13.08) proquinazid.

14) Compounds capable of acting as uncouplers, for example (14.01) binapacryl, (14.02) dinocap, (14.03) ferimzone, (14.04) fluazinam, (14.05) meptyldinocap.

15) Further compounds, for example (15.001) benthiazole, (15.002) bethoxazin, (15.003) capsimycin, (15.004) carvone, (15.005) quinomethionate, (15.006) pyriofenone (chlazafenone), (15.007) cufraneb, (15.008) cyflufenamid, (15.009) cymoxanil, (15.010) cyprosulfamide, (15.011) dazomet, (15.012) debacarb, (15.013) dichlorophen, (15.014) diclomezin, (15.015) difenzoquat, (15.016) difenzoquat metilsulfate, (15.017) diphenylamine, (15.018) ecomate, (15.019) fenpyrazamine, (15.020) flumetover, (15.021) fluoroimide, (15.022) flusulfamide, (15.023) flutianil, (15.024) fosetyl-aluminium, (15.025) fosetyl-calcium, (15.026) fosetyl-sodium, (15.027) hexachlorobenzene, (15.028) irumamycin, (15.029) methasulfocarb, (15.030) methyl isothiocyanate, (15.031) metrafenone, (15.032) mildiomycin, (15.033) natamycin, (15.034) nickel dimethyldithiocarbamate, (15.035) nitrothal-isopropyl, (15.036) oxamocarb, (15.037) oxyfenthiin, (15.038) pentachlorophenol and salts, (15.039) phenothrin, (15.040) phosphorous acid and salts thereof, (15.041) propamocarb-fosetylate, (15.042) propanosin-sodium, (15.043) pyrimorph, (15.044) pyrrolnitrin, (15.045) tebufloquin, (15.046) tecloftalam, (15.047) tolnifanid, (15.048) triazoxide, (15.049) trichlamid, (15.050) zarilamid, (15.051) (3S,6S,7R, 8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, (15.052) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.053) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.054) oxathiapiproline, (15.055) 1-(4-methoxyphenoxy)-3,3-dimethylbutan-2-yl 1H-imidazole-1-carboxylate, (15.056) 2,3,5,6-tetrachloro-4-(methylsulphonyl)pyridine, (15.057) 2,3-dibutyl-6-chlorothieno[2,3-d]pyrimidin-4(3H)-one, (15.058) 2,6-dimethyl-1H,5H-[1,4]dithiino[2,3-c: 5,6-c] dipyrrole-1,3,5,7(2H,6H)-tetrone, (15.059) 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, (15.060) 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, (15.061) 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, (15.062) 2-butoxy-6-iodo-3-propyl-4H-chromen-4-one, (15.063) 2-chloro-5-[2-chloro-1-(2,6-difluoro-4-methoxyphenyl)-4-methyl-1H-imidazol-5-yl]pyridine, (15.064) 2-phenylphenol and salts, (15.065) 3-(4,4,5-trifluoro-3,3-dimethyl-3,4-dihydroisoquinolin-1-yl)quinoline, (15.066) 3,4,5-trichloropyridine-2,6-dicarboxylic acid nitrile, (15.067) 3-chloro-5-(4-chlorophenyl)-4-(2,6-difluorophenyl)-6-methylpyridazine, (15.068) 4-(4-chlorophenyl)-5-(2,6-difluorophenyl)-3,6-dimethylpyridazine, (15.069) 5-amino-1,3,4-thiadiazole-2-thiol, (15.070) 5-chloro-N'-phenyl-N'-(prop-2-yn-1-yl)thiophene-2-sulphonohydrazide, (15.071) 5-fluoro-2-[(4-fluorobenzyl)oxy]pyrimidin-4-amine, (15.072) 5-fluoro-2-[(4-methylbenzyl)oxy]pyrimidin-4-amine, (15.073) 5-methyl-6-octyl[1,2,4]triazolo[1,5-a]pyrimidin-7-amine, (15.074) ethyl (2Z)-3-amino-2-cyano-3-phenylacrylate, (15.075) N'-(4-{[3-(4-chlorobenzyl)-1,2,4-thiadiazol-5-yl]oxy}-2,5-dimethylphenyl)-N-ethyl-N-methylimidoformamide, (15.076) N-(4-chlorobenzyl)-3-[3-methoxy-4-(prop-2-yn-1-yloxy)phenyl]propanamide, (15.077) N-[(4-chlorophenyl)(cyano)methyl]-3-[3-methoxy-4-(prop-2-yn-1-yloxy)phenyl]propanamide, (15.078) N-[(5-bromo-3-chloropyridin-2-yl)methyl]-2,4-dichloronicotinamide, (15.079) N-[1-(5-bromo-3-chloropyridin-2-yl)ethyl]-2,4-dichloronicotinamide, (15.080) N-[1-(5-bromo-3-chloropyridin-2-yl)ethyl]-2-fluoro-4-iodonicotinamide, (15.081) N—{(E)-[(cyclopropylmethoxy)imino][6-(difluoromethoxy)-2,3-difluorophenyl]methyl}-2-phenylacetamide, (15.082) N—{(Z)-[(cyclopropylmethoxy)imino][6-(difluoromethoxy)-2,3-difluorophenyl]methyl}-2-phenylacetamide, (15.083) N'-{4-[(3-tert-butyl-4-cyano-1,2-thiazol-5-yl)oxy]-2-chloro-5-methylphenyl}-N-ethyl-N-methylimidoformamide, (15.084) N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, (15.085) N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, (15.086) N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide, (15.087) pentyl {6-[({[(1-methyl-1H-tetrazol-5-yl)(phenyl)methylene]amino}oxy)methyl]pyridin-2-yl}carbamate, (15.088) phenazine-1-carboxylic acid, (15.089) quinolin-8-ol, (15.090) quinolin-8-ol sulphate (2:1), (15.091) tert-butyl {6-[({[(1-methyl-1H-tetrazol-5-yl)(phenyl)methylene]amino}oxy)methyl]pyridin-2-yl}carbamate, (15.092) (5-bromo-2-methoxy-4-methylpyridin-3-yl)(2,3,4-trimethoxy-6-methylphenyl)methanone, (15.093) N-[2-(4-{[3-(4-chlorophenyl)prop-2-yn-1-yl]oxy}-3-methoxyphenyl)ethyl]-N2-(methylsulphonyl)valinamide, (15.094) 4-oxo-4-[(2-phenylethyl)amino]butanoic acid, (15.095) but-3-yn-1-yl {6-[({[(Z)-(1-methyl-1H-tetrazol-5-yl)(phenyl)methylene]amino}oxy)methyl]pyridin-2-yl}carbamate, (15.096) 4-amino-5-fluoropyrimidin-2-ol (tautomeric form: 4-amino-5-fluoropyrimidin-2(1H)-one), (15.097) propyl 3,4,5-trihydroxybenzoate, (15.098) [3-(4-chloro-2-fluorophenyl)-5-(2,4-difluorophenyl)-1,2-oxazol-4-yl](pyridin-3-yl)methanol, (15.099) (S)-[3-(4-chloro-2-fluorophenyl)-5-(2,4-difluorophenyl)-1,2-oxazol-4-yl](pyridin-3-yl)methanol, (15.100) (R)-[3-(4-chloro-2-fluorophenyl)-5-(2,4-difluorophenyl)-1,2-oxazol-4-yl](pyridin-3-yl)methanol, (15.101) 2-fluoro-6-(trifluoromethyl)-N-(1,1,3-trimethyl-2,3-dihydro-1H-inden-4-yl)benzamide, (15.102) 2-(6-benzylpyridin-2-yl)quinazoline, (15.103) 2-[6-(3-fluoro-4-methoxyphenyl)-5-methylpyridin-2-yl]quinazoline, (15.104) 3-(4,4-difluoro-3,3-dimethyl-3,4-dihydroisoquinolin-1-yl)quinoline, (15.105) abscisic acid, (15.106) N'-[5-bromo-6-(2,3-dihydro-1H-inden-2-yloxy)-2-methylpyridin-3-yl]-N-ethyl-N-methylimidoformamide, (15.107) N'-{5-bromo-6-[1-(3,5-difluorophenyl)ethoxy]-2-methylpyridin-3-yl}-N-ethyl-N-methylimidoformamide, (15.108) N'-{5-bromo-6-[(1R)-1-(3,5-difluorophenyl)ethoxy]-2-methylpyridin-3-yl}-N-ethyl-N-methylimidoformamide, (15.109) N'-{5-bromo-6-[(1S)-1-(3,5-difluorophenyl)ethoxy]-2-methylpyridin-3-yl}-N-ethyl-N-methylimidoformamide, (15.110) N'-{5-bromo-6-[(cis-4-isopropylcyclohexyl)oxy]-2-methylpyridin-3-yl}-N-ethyl-N-methylimidoformamide, (15.111) N'-{5-bromo-6-[(trans-4-isopropylcyclohexyl)oxy]-2-methylpyridin-3-yl}-N-ethyl-N-methylimidoformamide, (15.112) N-cyclopropyl-3-(difluoromethyl)-5-fluoro-N-(2-isopropylbenzyl)-1-methyl-1H-pyrazole-4-carboxamide, (15.113) N-cyclopropyl-N-(2-cyclopropylbenzyl)-3-(difluoromethyl)-5-fluoro-1-methyl-1H-pyrazole-4-carboxamide, (15.114) N-(2-tert-butylbenzyl)-N-cyclopropyl-3-(difluoromethyl)-5-fluoro-1-methyl-1H-pyrazole-4-carboxamide, (15.115) N-(5-chloro-2-ethylbenzyl)-N-cyclopropyl-3-(difluoromethyl)-5-fluoro-1-methyl-1H-pyrazole-4-carboxamide, (15.116) N-(5-chloro-2-isopropylbenzyl)-N-cyclopropyl-3-(difluoromethyl)-5-fluoro-1-methyl-1H-pyrazole-4-carboxamide, (15.117) N-cyclopropyl-3-(difluoromethyl)-N-(2-ethyl-5-fluorobenzyl)-5-fluoro-1-methyl-1H-pyrazole-4-carboxamide, (15.118) N-cyclopropyl-3-(difluoromethyl)-5-fluoro-N-(5-fluoro-2-isopropylbenzyl)-1-methyl-1H-pyrazole-4-carboxamide, (15.119) N-cyclopropyl-N-(2-cyclopropyl-5-fluorobenzyl)-3-(difluoromethyl)-5-fluoro-1-methyl-1H-pyrazole-4-carboxamide, (15.120) N-(2-cyclopentyl-5-fluorobenzyl)-N-cyclopropyl-3-(difluoromethyl)-5-fluoro-1-methyl-1H-pyrazole-4-carboxamide, (15.121) N-cyclopropyl-3-(difluoromethyl)-5-fluoro-N-(2-fluoro-6-isopropylbenzyl)-1-methyl-1H-pyrazole-4-carboxamide, (15.122) N-cyclopropyl-3-(difluoromethyl)-N-(2-ethyl-5-methylbenzyl)-5-fluoro-1-methyl-1H-pyrazole-4-carboxamide, (15.123) N-cyclopropyl-3-(difluoromethyl)-5-fluoro-N-(2-isopropyl-5-methylbenzyl)-1-methyl-1H-pyrazole-4-carboxamide, (15.124) N-cyclopropyl-N-(2-cyclopropyl-5-methylbenzyl)-3-(difluoromethyl)-5-fluoro-1-methyl-1H-pyrazole-4-carboxamide, (15.125) N-(2-tert-butyl-5-methylbenzyl)-N-cyclopropyl-3-(difluoromethyl)-5-fluoro-1-methyl-1H-pyrazole-4-carboxamide, (15.126) N-[5-chloro-2-(trifluoromethyl)benzyl]-N-cyclopropyl-3-(difluoromethyl)-5-fluoro-1-methyl-1H-pyrazole-4-carboxamide, (15.127) N-cyclopropyl-3-(difluoromethyl)-5-fluoro-1-methyl-N-[5-methyl-2-(trifluoromethyl)benzyl]-1H-pyrazole-4-carboxamide, (15.128) N-[2-chloro-6-(trifluoromethyl)benzyl]-N-cyclopropyl-3-(difluoromethyl)-5-fluoro-1-methyl-1H-pyrazole-4-carboxamide, (15.129) N-[3-chloro-2-fluoro-6-(trifluoromethyl)benzyl]-N-cyclopropyl-3-(difluoromethyl)-5-fluoro-1-methyl-1H-pyrazole-4-carboxamide, (15.130) N-cyclopropyl-3-(difluoromethyl)-N-(2-ethyl-4,5-dimethylbenzyl)-5-fluoro-1-methyl-1H-pyrazole-4-carboxamide, (15.131) N-cyclopropyl-3-(difluoromethyl)-5-fluoro-N-(2-isopropylbenzyl)-1-methyl-1H-pyrazole-4-carbothioamide, (15.132) N'-(2,5-dimethyl-4-phenoxyphenyl)-N-ethyl-N-methylimidoformamide, (15.133) N'-{4-[(4,5-dichloro-1,3-thiazol-2-yl)oxy]-2,5-dimethylphenyl}-N-ethyl-N-methylimidoformamide, (15.134) N-(4-chloro-2,6-difluorophenyl)-4-(2-chloro-4-fluorophenyl)-1,3-dimethyl-1H-pyrazol-5-amine, (15.135) 9-fluoro-2,2-dimethyl-5-(quinolin-3-yl)-2,3-dihydro-1,4-benzoxazepine, (15.136) 2-{2-fluoro-6-[(8-fluoro-2-methylquinolin-3-yl)oxy]phenyl}propan-2-ol, (15.137) 2-{2-[(7,8-difluoro-2-methylquinolin-3-yl)oxy]-6-fluorophenyl}propan-2-ol, (15.138) 4-(2-chloro-4-fluorophenyl)-N-(2-fluorophenyl)-1,3-dimethyl-1H-pyrazol-5-amine, (15.139) 4-(2-chloro-4-fluorophenyl)-N-(2,6-difluorophenyl)-1,3-dimethyl-1H-pyrazol-5-amine, (15.140) 4-(2-chloro-4-fluorophenyl)-N-(2-chloro-6-fluorophenyl)-1,3-dimethyl-1H-pyrazol-5-amine, (15.141) 4-(2-bromo-4-fluorophenyl)-N-(2-chloro-6-fluorophenyl)-1,3-dimethyl-1H-pyrazol-5-amine, (15.142) N-(2-bromo-6-fluorophenyl)-4-(2-chloro-4-fluorophenyl)-1,3-dimethyl-1H-pyrazol-5-amine, (15.143) 4-(2-bromo-4-fluorophenyl)-N-(2-bromophenyl)-1,3-dimethyl-1H-pyrazol-5-amine, (15.144) 4-(2-bromo-4-fluorophenyl)-N-(2-bromo-6-fluorophenyl)-1,3-dimethyl-1H-pyrazol-5-amine, (15.145) 4-(2-bromo-4-fluorophenyl)-N-(2-chlorophenyl)-1,3-dimethyl-1H-pyrazol-5-amine, (15.146) N-(2-bromophenyl)-4-(2-chloro-4-fluorophenyl)-1,3-dimethyl-1H-pyrazol-5-amine, (15.147) 4-(2-chloro-4-fluorophenyl)-N-(2-chlorophenyl)-1,3-dimethyl-1H-pyrazol-5-amine, (15.148) 4-(2-bromo-4-fluorophenyl)-N-(2,6-difluorophenyl)-1,3-dimethyl-1H-pyrazol-5-amine, (15.149) 4-(2-bromo-4-fluorophenyl)-N-(2-fluorophenyl)-1,3-dimethyl-1H-pyrazol-5-amine, (15.150) N'-(4-{3-[(difluoromethyl)sulphanyl]phenoxy}-2,5-dimethylphenyl)-N-ethyl-N-methylimidoformamide, (15.151) N'-(2,5-dimethyl-4-{3-[(1,1,2,2-tetrafluoroethyl)sulphanyl]phenoxy}phenyl)-N-ethyl-N-methylimidoformamide, (15.152) N'-(2,5-dimethyl-4-{3-[(2,2,2-trifluoroethyl)sulphanyl]phenoxy}phenyl)-N-ethyl-N-methylimidoformamide, (15.153) N'-(2,5-dimethyl-4-{3-[(2,2,3,3-tetrafluoropropyl)sulphanyl]phenoxy}phenyl)-N-ethyl-N-methylimidoformamide, (15.154) N'-(2,5-dimethyl-4-{3-[(pentafluoroethyl)sulphanyl]phenoxy}phenyl)-N-ethyl-N-methylimidoformamide, (15.155) N'-(4-{[3-(difluoromethoxy)phenyl]sulphanyl}-2,5-dimethylphenyl)-N-ethyl-N-methylimidoformamide, (15.156) N'-(2,5-dimethyl-4-{[3-(1,1,2,2-tetrafluoroethoxy)phenyl]sulphanyl}phenyl)-N-ethyl-N-methylimidoformamide, (15.157) N'-(2,5-dimethyl-4-{[3-(2,2,2-trifluoroethoxy)phenyl]sulphanyl}phenyl)-N-ethyl-N-methylimidoformamide, (15.158) N'-(2,5-dimethyl-4-{[3-(2,2,3,3-tetrafluoropropoxy)phenyl]sulphanyl}phenyl)-N-ethyl-N-methylimidoformamide, (15.159) N'-(2,5-dimethyl-4-{[3-(pentafluoroethoxy)phenyl]sulphanyl}phenyl)-N-ethyl-N-methylimidoformamide, (15.160) 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone, (15.161) 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.162) 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone, (15.163) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenylmethanesulphonate, (15.164) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenylmethanesulphonate, (15.165) 2-[3,5-bis(difluoromethyl)-1H-pyrazol-1-yl]-1-[4-(4-{(5S)-5-[2-(prop-2-yn-1-yloxy)phenyl]-4,5-dihydro-1,2-oxazol-3-yl}-1,3-thiazol-2-yl)piperidin-1-yl]ethanone, (15.166) 2-[3,5-bis(difluoromethyl)-1H-pyrazol-1-yl]-1-[4-(4-{(5R)-5-[2-(prop-2-yn-1-yloxy)phenyl]-4,5-dihydro-1,2-oxazol-3-yl}-1,3-thiazol-2-yl)piperidin-1-yl]ethanone, (15.167) 2-[3,5-bis(difluoromethyl)-1H-pyrazol-1-yl]-1-[4-(4-{(5S)-5-[2- fluoro-6-(prop-2-yn-1-yloxy)phenyl]-4,5-dihydro-1,2-oxazol-3-yl}-1,3-thiazol-2-yl)piperidin-1-yl]ethanone, (15.168) 2-[3,5-bis(difluoromethyl)-1H-pyrazol-1-yl]-1-[4-(4-{(5R)-5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.169) 2-[3,5-bis(difluoromethyl)-1H-pyrazol-1-yl]-1-[4-(4-{(5S)-5-[2-chloro-6-(prop-2-yn-1-yloxy)phenyl]-4,5-dihydro-1,2-oxazol-3-yl}-1,3-thiazol-2-yl)piperidin-1-yl]ethanone, (15.170) 2-[3,5-bis(difluoromethyl)-1H-pyrazol-1-yl]-1-[4-(4-{(5R)-5-[2-chloro-6-(prop-2-yn-1-yloxy)phenyl]-4,5-dihydro-1,2-oxazol-3-yl}-1,3-thiazol-2-yl)piperidin-1-yl]ethanone, (15.171) 2-{(5S)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenylmethanesulphonate, (15.172) 2-{(5R)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenylmethanesulphonate, (15.173) 2-{(5S)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenylmethanesulphonate, (15.174) 2-{(5R)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenylmethanesulphonate.

Biological Pesticides as Mixing Components

The compounds of the formula (I) can be combined with biological pesticides.

Biological pesticides include especially bacteria, fungi, yeasts, plant extracts and products formed by microorganisms, including proteins and secondary metabolites.

Biological pesticides include bacteria such as spore-forming bacteria, root-colonizing bacteria and bacteria which act as biological insecticides, fungicides or nematicides.

Examples of such bacteria which are used or can be used as biological pesticides are:

*Bacillus amyloliquefaciens*, strain FZB42 (DSM 231179), or *Bacillus cereus*, especially *B. cereus* strain CNCM I-1562 or *Bacillus firmus*, strain I-1582 (Accession number CNCM I-1582) or *Bacillus pumilus*, especially strain GB34 (Accession No. ATCC 700814) and strain QST2808 (Accession No. NRRL B-30087), or *Bacillus subtilis*, especially strain GB03 (Accession No. ATCC SD-1397), or *Bacillus subtilis* strain QST713 (Accession No. NRRL B-21661) or *Bacillus subtilis* strain OST 30002 (Accession No. NRRL B-50421) *Bacillus thuringiensis*, especially *B. thuringiensis* subspecies *israelensis* (serotype H-14), strain AM65-52 (Accession No. ATCC 1276), or *B. thuringiensis* subsp. *aizawai*, especially strain ABTS-1857 (SD-1372), or *B. thuringiensis* subsp. *kurstaki* strain HD-1, or *B. thuringiensis* subsp. *tenebrionis* strain NB 176 (SD-5428), *Pasteuria penetrans*, *Pasteuria* spp. (*Rotylenchulus reniformis* nematode)-PR3 (Accession Number ATCC SD-5834), *Streptomyces microflavus* strain AQ6121 (=QRD 31.013, NRRL B-50550), *Streptomyces galbus* strain AQ 6047 (Accession Number NRRL 30232).

Examples of fungi and yeasts which are used or can be used as biological pesticides are:

*Beauveria bassiana*, in particular strain ATCC 74040, *Coniothyrium minitans*, in particular strain CON/M/91-8 (Accession No. DSM-9660), *Lecanicillium* spp., in particular strain HRO LEC 12, *Lecanicillium lecanii*, (formerly known as *Verticillium lecanii*), in particular strain KV01, *Metarhizium anisopliae*, in particular strain F52 (DSM3884/ATCC 90448), *Metschnikowia fructicola*, in particular strain NRRL Y-30752, *Paecilomyces fumosoroseus* (new: *Isaria fumosorosea*), in particular strain IFPC 200613, or strain Apopka 97 (Accession No. ATCC 20874), *Paecilomyces lilacinus*, in particular *P. lilacinus* strain 251 (AGAL 89/030550), *Talaromyces flavus*, in particular strain V117b, *Trichoderma atroviride*, in particular strain SC1 (Accession Number CBS 122089), *Trichoderma harzianum*, in particular *T. harzianum rifai* T39 (Accession Number CNCM I-952).

Examples of viruses which are used or can be used as biological pesticides are:

*Adoxophyes orana* (summer fruit *tortrix*) granulosis virus (GV), *Cydia pomonella* (codling moth) granulosis virus (GV), *Helicoverpa armigera* (cotton bollworm) nuclear polyhedrosis virus (NPV), *Spodoptera exigua* (beet armyworm) mNPV, *Spodoptera frugiperda* (fall armyworm) mNPV, *Spodoptera littoralis* (African cotton leafworm) NPV.

Also included are bacteria and fungi which are added as 'inoculant' to plants or plant parts or plant organs and which, by virtue of their particular properties, promote plant growth and plant health. Examples include:

*Agrobacterium* spp., *Azorhizobium caulinodans*, *Azospirillum* spp., *Azotobacter* spp., *Bradyrhizobium* spp., *Burkholderia* spp., especially *Burkholderia cepacia* (formerly known as *Pseudomonas cepacia*), *Gigaspora* spp., or *Gigaspora monosporum*, *Glomus* spp., *Laccaria* spp., *Lactobacillus buchneri*, *Paraglomus* spp., *Pisolithus tinctorus*, *Pseudomonas* spp., *Rhizobium* spp., especially *Rhizobium trifolii*, *Rhizopogon* spp., *Scleroderma* spp., *Suillus* spp., *Streptomyces* spp.

Examples of plant extracts and products formed by microorganisms, including proteins and secondary metabolites, which are used or can be used as biological pesticides are:

*Allium sativum*, *Artemisia absinthium*, azadirachtin, Biokeeper WP, *Cassia nigricans*, *Celastrus angulatus*, *Chenopodium anthelminticum*, chitin, Armour-Zen, *Dryopteris filix-mas*, *Equisetum arvense*, Fortune Aza, Fungastop, Heads Up (*Chenopodium quinoa* saponin extract), pyrethrum/pyrethrins, *Quassia amara*, *Quercus*, *Quillaja*, Regalia, "Requiem™ Insecticide", rotenone, ryania/ryanodine, *Symphytum officinale*, *Tanacetum vulgare*, thymol, Triact 70, TriCon, *Tropaeulum majus*, *Urtica dioica*, Veratrin, *Viscum album*, *Brassicaceae* extract, especially oilseed rape powder or mustard powder.

Safeners as Mixing Components

The compounds of the formula (I) can be combined with safeners, for example benoxacor, cloquintocet (-mexyl), cyometrinil, cyprosulphamide, dichlormid, fenchlorazole (-ethyl), fenclorim, flurazole, fluxofenim, furilazole, isoxadifen (-ethyl), mefenpyr (-diethyl), naphthalic anhydride, oxabetrinil, 2-methoxy-N-({4-[methylcarbamoyl)amino]phenyl}sulphonyl)benzamide (CAS 129531-12-0), 4-(dichloroacetyl)-1-oxa-4-azaspiro[4.5]decane (CAS 71526-07-3), 2,2,5-trimethyl-3-(dichloroacetyl)-1,3-oxazolidine (CAS 52836-31-4).

Plants and Plant Parts

All plants and plant parts can be treated in accordance with the invention. Plants are understood here to mean all plants and populations of plants, such as desirable and undesirable wild plants or crop plants (including naturally occurring crop plants), for example cereals (wheat, rice, triticale, barley, rye, oats), maize, soya bean, potato, sugar beet, sugar cane, tomatoes, peas and other vegetable species, cotton, tobacco, oilseed rape, and also fruit plants (with the fruits apples, pears, citrus fruits and grapes). Crop plants may be plants which can be obtained by conventional breeding and optimization methods or by biotechnological and genetic engineering methods or combinations of these methods, including the transgenic plants and including the plant cultivars which are protectable or non-protectable by plant breeders' rights. Plant parts shall be understood to mean all parts and organs of the plants above and below ground, such as shoot, leaf, flower and root, examples given being leaves, needles, stalks, stems, flowers, fruit bodies, fruits and seeds, and also roots, tubers and rhizomes. Plant parts also include harvested material and vegetative and generative propagation material, for example cuttings, tubers, rhizomes, slips and seeds.

The treatment according to the invention of the plants and parts of plants with the compounds of the formula (I) is carried out directly or by allowing them to act on the surroundings, habitat or storage space thereof by the customary treatment methods, for example by dipping, spraying, evaporating, fogging, scattering, painting on, injecting, and, in the case of propagation material, especially in the case of seeds, also by applying one or more coats.

As already mentioned above, it is possible to treat all plants and parts thereof in accordance with the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (genetically modified organisms), and parts thereof are treated. The term "parts" or "parts of plants" or "plant parts" has been explained above. Particular preference is given in accordance with the invention to treating plants of the respective commercially customary plant cultivars or those that are in use. Plant cultivars are understood to mean plants having new properties ("traits") and which have been grown by conventional breeding, by mutagenesis or by recombinant DNA techniques. They may be cultivars, varieties, biotypes or genotypes.

Transgenic Plants, Seed Treatment and Integration Events

The preferred transgenic plants or plant cultivars (those obtained by genetic engineering) which are to be treated in accordance with the invention include all plants which, through the genetic modification, received genetic material which imparts particular advantageous useful properties ("traits") to these plants. Examples of such properties are better plant growth, increased tolerance to high or low temperatures, increased tolerance to drought or to levels of water or soil salinity, enhanced flowering performance, easier harvesting, accelerated ripening, higher yields, higher quality and/or higher nutritional value of the harvested products, better storage life and/or processibility of the harvested products. Further and particularly emphasized examples of such properties are increased resistance of the plants against animal and microbial pests, such as insects, arachnids, nematodes, mites, slugs and snails, owing, for example, to toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof), and also increased resistance of the plants against phytopathogenic fungi, bacteria and/or viruses caused, for example, by systemic acquired resistance (SAR), systemin, phytoalexins, elicitors and resistance genes and correspondingly expressed proteins and toxins, and also increased tolerance of the plants to certain herbicidally active ingredients, for example imidazolinones, sulphonylureas, glyphosates or phosphinothricin (for example the "PAT" gene). The genes which impart the desired properties ("traits") in question may also be present in combinations with one another in the transgenic plants. Examples of transgenic plants include the important crop plants, such as cereals (wheat, rice, triticale, barley, rye, oats), maize, soya beans, potatoes, sugar beet, sugar cane, tomatoes, peas and other types of vegetable, cotton, tobacco, oilseed rape and also fruit plants (with the fruits apples, pears, citrus fruits and grapes), particular emphasis being given to maize, soya beans, wheat, rice, potatoes, cotton, sugar cane, tobacco and oilseed rape. Properties ("traits") which are particularly emphasized are the increased resistance of the plants to insects, arachnids, nematodes and slugs and snails.

Crop Protection—Types of Treatment

The plants and plant parts are treated with the compounds of the formula (I) directly or by action on their surroundings, habitat or storage space using customary treatment methods, for example by dipping, spraying, atomizing, irrigating, evaporating, dusting, fogging, broadcasting, foaming, painting, spreading-on, injecting, watering (drenching), drip irrigating and, in the case of propagation material, in particular in the case of seed, additionally by dry seed treatment, liquid seed treatment, slurry treatment, by incrusting, by coating with one or more coats, etc. It is furthermore possible to apply the compounds of the formula (I) by the ultra-low volume method or to inject the application form or the compound of the formula (I) itself into the soil.

A preferred direct treatment of the plants is foliar application, i.e. compounds of the formula (I) are applied to the foliage, where treatment frequency and the application rate should be adjusted according to the level of infestation with the pest in question.

In the case of systemically active ingredients, the compounds of the formula (I) also access the plants via the root system. The plants are then treated by the action of the compounds of the formula (I) on the habitat of the plant. This can be accomplished, for example, by drenching, or by mixing into the soil or the nutrient solution, meaning that the locus of the plant (e.g. soil or hydroponic systems) is impregnated with a liquid form of the compounds of the formula (I), or by soil application, meaning that the compounds of the formula (I) are introduced in solid form (e.g. in the form of granules) into the locus of the plants. In the case of paddy rice crops, this can also be accomplished by metering the compound of the formula (I) in a solid application form (for example as granules) into a flooded paddy field.

Seed Treatment

The control of animal pests by the treatment of the seed of plants has long been known and is the subject of constant improvements. Nevertheless, the treatment of seed entails a series of problems which cannot always be solved in a satisfactory manner. Thus, it is desirable to develop methods for protecting the seed and the germinating plant which dispense with, or at least reduce considerably, the additional application of pesticides during storage, after sowing or after emergence of the plants. It is additionally desirable to optimize the amount of active ingredient used so as to provide optimum protection for the seed and the germinating plant from attack by animal pests, but without damage to the plant itself by the active ingredient used. In particular, methods for the treatment of seed should also take account of the intrinsic insecticidal or nematicidal properties of pest-resistant or -tolerant transgenic plants in order to achieve optimal protection of the seed and the germinating plant with a minimum expenditure on pesticides.

The present invention therefore in particular also relates to a method for the protection of seed and germinating plants from attack by pests, by treating the seed with one of the compounds of the formula (I). The method according to the invention for protecting seed and germinating plants against attack by pests further comprises a method in which the seed is treated simultaneously in one operation or sequentially with a compound of the formula (I) and a mixing component. It further also comprises a method where the seed is treated at different times with a compound of the formula (I) and a mixing component.

The invention likewise relates to the use of the compounds of the formula (I) for the treatment of seed for protecting the seed and the resulting plant from animal pests.

The invention further relates to seed which has been treated with a compound of the formula (I) for protection from animal pests. The invention also relates to seed which has been treated simultaneously with a compound of the formula (I) and a mixing component. The invention further relates to seed which has been treated at different times with a compound of the formula (I) and a mixing component. In the case of seed which has been treated at different times with a compound of the formula (I) and a mixing component, the individual substances may be present on the seed in different layers. In this case, the layers comprising a compound of the formula (I) and a mixing component may optionally be separated by an intermediate layer. The invention also relates to seed in which a compound of the formula (I) and a mixing component have been applied as part of a coating or as a further layer or further layers in addition to a coating.

The invention further relates to seed which, after the treatment with a compound of the formula (I), is subjected to a film-coating process to prevent dust abrasion on the seed.

One of the advantages encountered with a systemically acting compound of the formula (I) is the fact that, by treating the seed, not only the seed itself but also the plants resulting therefrom are, after emergence, protected against animal pests. In this way, the immediate treatment of the crop at the time of sowing or shortly thereafter can be dispensed with.

A further advantage is that the treatment of the seed with a compound of the formula (I) can enhance germination and emergence of the treated seed.

It is likewise considered to be advantageous that compounds of the formula (I) can especially also be used for transgenic seed.

Furthermore, compounds of the formula (I) can be employed in combination with compositions of signalling technology, leading to better colonization by symbionts such as, for example, rhizobia, mycorrhizae and/or endophytic bacteria or fungi, and/or to optimized nitrogen fixation.

The compounds of the formula (I) are suitable for protection of seed of any plant variety which is used in agriculture, in the greenhouse, in forests or in horticulture. More particularly, this includes seed of cereals (for example wheat, barley, rye, millet and oats), maize, cotton, soya beans, rice, potatoes, sunflowers, coffee, tobacco, canola, oilseed rape, beet (for example sugar beet and fodder beet), peanuts, vegetables (for example tomatoes, cucumbers, beans, cruciferous vegetables, onions and lettuce), fruit plants, lawns and ornamental plants. Of particular significance is the treatment of the seed of cereals (such as wheat, barley, rye and oats), maize, soya beans, cotton, canola, oilseed rape and rice.

As already mentioned above, the treatment of transgenic seed with a compound of the formula (I) is also of particular importance. This involves the seed of plants which generally contain at least one heterologous gene which controls the expression of a polypeptide having insecticidal and/or nematicidal properties in particular. The heterologous genes in transgenic seed may originate in this case from microorganisms such as *Bacillus, Rhizobium, Pseudomonas, Serratia, Trichoderma, Clavibacter, Glomus* or *Gliocladium*. The present invention is particularly suitable for the treatment of transgenic seed containing at least one heterologous gene originating from *Bacillus* sp. The heterologous gene is more preferably derived from *Bacillus thuringiensis*.

In the context of the present invention, the compound of the formula (I) is applied to the seed. The seed is preferably treated in a state in which it is sufficiently stable for no damage to occur in the course of treatment. In general, the seed can be treated at any time between harvest and sowing. It is customary to use seed which has been separated from the plant and freed from cobs, shells, stalks, coats, hairs or the flesh of the fruits. For example, it is possible to use seed which has been harvested, cleaned and dried down to a moisture content which allows storage. Alternatively, it is also possible to use seed which, after drying, has been treated with, for example, water and then dried again, for example priming. In the case of rice seed, it is also possible to use seed which has been pre-swollen in water up to a certain stage (pigeon breast stage) for example, which leads to improved germination and more uniform emergence.

When treating the seed, care must generally be taken that the amount of the compound of the formula (I) applied to the seed and/or the amount of further additives is chosen in such a way that the germination of the seed is not adversely affected, or that the resulting plant is not damaged. This has to be ensured particularly in the case of active ingredients which can exhibit phytotoxic effects at certain application rates.

In general, the compounds of the formula (I) are applied to the seed in the form of a suitable formulation. Suitable formulations and processes for seed treatment are known to the person skilled in the art.

The compounds of the formula (I) can be converted to the customary seed-dressing formulations, such as solutions, emulsions, suspensions, powders, foams, slurries or other coating compositions for seed, and also ULV formulations.

These formulations are prepared in a known manner, by mixing compounds of the formula (I) with customary additives such as, for example, customary extenders and also solvents or diluents, dyes, wetting agents, dispersants, emulsifiers, antifoams, preservatives, secondary thickeners, adhesives, gibberellins and also water.

Dyes which may be present in the seed-dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed-dressing formulations usable in accordance with the invention are all substances which promote wetting and which are customary for the formulation of active agrochemical ingredients. Alkyl naphthalenesulphonates, such as diisopropyl or diisobutyl naphthalenesulphonates, can be used with preference.

Suitable dispersants and/or emulsifiers which may be present in the seed-dressing formulations usable in accordance with the invention are all nonionic, anionic and cationic dispersants customary for the formulation of active agrochemical ingredients. Nonionic or anionic dispersants or mixtures of nonionic or anionic dispersants can be used with preference. Suitable nonionic dispersants include in particular ethylene oxide/propylene oxide block polymers, alkylphenol polyglycol ethers and tristyrylphenol polyglycol ethers, and the phosphated or sulphated derivatives thereof. Suitable anionic dispersants are especially lignosulphonates, polyacrylic acid salts and arylsulphonate-formaldehyde condensates.

Antifoams which may be present in the seed-dressing formulations usable in accordance with the invention are all foam-inhibiting substances customary for the formulation of active agrochemical ingredients. Silicone antifoams and magnesium stearate can be used with preference.

Preservatives which may be present in the seed-dressing formulations usable in accordance with the invention are all substances usable for such purposes in agrochemical compositions. Examples include dichlorophene and benzyl alcohol hemiformal.

Secondary thickeners which may be present in the seed-dressing formulations usable in accordance with the invention are all substances which can be used for such purposes in agrochemical compositions.

Preferred examples include cellulose derivatives, acrylic acid derivatives, xanthan, modified clays and finely divided silica.

Useful stickers which may be present in the seed-dressing formulations usable in accordance with the invention are all customary binders usable in seed-dressing products. Preferred examples include polyvinylpyrrolidone, polyvinyl acetate, polyvinyl alcohol and tylose.

Gibberellins which may be present in the seed-dressing formulations usable in accordance with the invention are preferably the gibberellins A1, A3 (=gibberellic acid), A4 and A7; particular preference is given to using gibberellic acid. The gibberellins are known (cf. R. Wegler "Chemie der Pflanzenschutz-und Schädlingsbekämpfungsmittel", vol. 2, Springer Verlag, 1970, pp. 401-412).

The seed-dressing formulations usable in accordance with the invention can be used to treat a wide variety of different kinds of seed, either directly or after prior dilution with water. For instance, the concentrates or the preparations obtainable therefrom by dilution with water can be used to dress the seed of cereals, such as wheat, barley, rye, oats and triticale, and also the seed of maize, rice, oilseed rape, peas, beans, cotton, sunflowers, soya beans and beets, or else a wide variety of different vegetable seed. The seed-dressing formulations usable in accordance with the invention, or the dilute use forms thereof, can also be used to dress seed of transgenic plants.

For the treatment of seed with the seed-dressing formulations usable in accordance with the invention, or use forms prepared therefrom, all mixing units usable customarily for the seed dressing are useful. Specifically, the procedure in seed dressing is to place the seed into a mixer in batchwise or continuous operation, to add the particular desired amount of seed-dressing formulations, either as such or after prior dilution with water, and to mix until the formulation is distributed homogeneously on the seed. If appropriate, this is followed by a drying operation.

The application rate of the seed-dressing formulations usable in accordance with the invention can be varied within a relatively wide range. It is guided by the particular content of the compounds of the formula (I) in the formulations and by the seed. The application rates of the compound of the formula (I) are generally between 0.001 and 50 g per kilogram of seed, preferably between 0.01 and 15 g per kilogram of seed.

Animal Health

In the animal health field, i.e. the field of veterinary medicine, the compounds of the formula (I) are active against animal parasites, in particular ectoparasites or endoparasites. The term "endoparasites" includes especially helminths and protozoa, such as coccidia. Ectoparasites are typically and preferably arthropods, especially insects and acarids.

In the field of veterinary medicine, the compounds of the formula (I) having favourable endotherm toxicity are suitable for controlling parasites which occur in animal breeding and animal husbandry in livestock, breeding animals, zoo animals, laboratory animals, experimental animals and domestic animals. They are active against all or specific stages of development of the parasites.

Agricultural livestock include, for example, mammals such as sheep, goats, horses, donkeys, camels, buffalo, rabbits, reindeer, fallow deer, and particularly cattle and pigs; poultry such as turkeys, ducks, geese, and particularly chickens; fish and crustaceans, for example in aquaculture, and also insects such as bees.

Domestic animals include, for example, mammals, such as hamsters, guinea pigs, rats, mice, chinchillas, ferrets, and particularly dogs, cats, caged birds, reptiles, amphibians and aquarium fish.

In a preferred embodiment, the compounds of the formula (I) are administered to mammals.

In another preferred embodiment, the compounds of the formula (I) are administered to birds, namely caged birds and particularly poultry.

Use of the compounds of the formula (I) for the control of animal parasites is intended to reduce or prevent illness, cases of death and reductions in performance (in the case of meat, milk, wool, hides, eggs, honey and the like), such that more economical and simpler animal husbandry is enabled and better animal well-being is achievable.

In relation to the field of animal health, the term "control" or "controlling" means that the compounds of the formula (I) are effective in reducing the incidence of the particular parasite in an animal infected with such parasites to an innocuous degree. More specifically, "controlling" in the present context means that the compound of the formula (I) can kill the respective parasite, inhibit its growth, or inhibit its proliferation.

Arthropods include:

from the order Anoplurida, for example *Haematopinus* spp., *Linognathus* spp., *Pediculus* spp., *Phtirus* spp., *Solenopotes* spp.; from the order Mallophagida and the suborders Amblycerina and Ischnocerina, for example *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.; from the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; from the order Siphonapterida, for example *Pulex* spp., *Ctenocephalides* spp., *Tunga* spp., *Xenopsylla* spp., *Ceratophyllus* spp.;

from the order Heteropterida, for example *Cimex* spp., *Triatoma* spp., *Rhodnius* spp., *Panstrongylus* spp.; and also nuisance and hygiene pests from the order Blattarida.

Arthropods further include:

from the subclass Acari (Acarina) and the order Metastigmata, for example from the family Argasidae like *Argas* spp., *Ornithodorus* spp., *Otobius* spp., from the family Ixodidae like *Ixodes* spp., *Amblyomma* spp., *Rhipicephalus* (*Boophilus*) spp., *Dermacentor* spp., *Haemophysalis* spp., *Hyalomma* spp., *Rhipicephalus* spp. (the original genus of multi-host ticks); from the order Mesostigmata like *Dermanyssus* spp., *Ornithonyssus* spp., *Pneumonyssus* spp., *Raillietia* spp., *Pneumonyssus* spp., *Sternostoma* spp., *Varroa* spp., *Acarapis* spp.; from the order Actinedida (Prostigmata), for example *Acarapis* spp., *Cheyletiella* spp., *Ornithocheyletia* spp., *Myobia* spp., *Psorergates* spp., *Demodex* spp., *Trombicula* spp., *Neotrombiculla* spp., *Listrophorus* spp.; and from the order Acaridida (Astigmata), for example *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

Parasitic protozoa include:

Mastigophora (*Flagellata*), for example Trypanosomatidae, for example *Trypanosoma b. brucei, T.b. gambiense, T.b. rhodesiense, T. congolense, T. cruzi, T. evansi, T. equinum, T. lewisi, T. percae, T. simiae, T. vivax, Leishmania brasiliensis, L. donovani, L. tropica*, for example Trichomonadidae, for example *Giardia lamblia, G. canis*;

Sarcomastigophora (Rhizopoda) such as Entamoebidae, for example *Entamoeba histolytica*, Hartmanellidae, for example *Acanthamoeba* sp., *Harmanella* sp.;

Apicomplexa (Sporozoa) such as Eimeridae, for example *Eimeria acervulina, E. adenoides, E. alabamensis, E. anatis, E. anserina, E. arloingi, E. ashata, E. auburnensis, E. bovis, E. brunetti, E. canis, E. chinchillae, E. clupearum, E. columbae, E. contorta, E. crandalis, E. debliecki, E. dispersa, E. ellipsoidales, E. falciformis, E. faurei, E. flavescens, E. gallopavonis, E. hagani, E. intestinalis, E. iroquoina, E. irresidua, E. labbeana, E. leucarti, E. magna, E. maxima, E. media, E. meleagridis, E. meleagrimitis, E. mitis, E. necatrix, E. ninakohlyakimovae, E. ovis, E. parva, E. pavonis, E. perforans, E. phasani, E. piriformis, E. praecox, E. residua, E. scabra, E. spec., E. stiedai, E. suis, E. tenella, E. truncata, E. truttae, E. zuernii, Globidium* spec., *Isospora belli, I. canis, I. felis, I. ohioensis, I. rivolta, I.* spec., *I. suis, Cystisospora* spec., *Cryptosporidium* spec., in particular *C. parvum*; such as Toxoplasmadidae, for example *Toxoplasma gondii, Hammondia heydornii, Neospora caninum, Besnoitia besnoitii*; such as Sarcocystidae, for example *Sarcocystis bovicanis, S. bovihominis, S. ovicanis, S. ovifelis, S. neurona, S.* spec., *S. suihominis*, such as Leucozoidae, for example *Leucozytozoon simondi*, such as Plasmodiidae, for example *Plasmodium berghei, P. falciparum, P. malariae, P. ovale, P. vivax, P.* spec., such as Piroplasmea, for example *Babesia argentina, B. bovis, B. canis, B.* spec., *Theileria parva, Theileria* spec., such as Adeleina, for example *Hepatozoon canis, H.* spec.

Pathogenic endoparasites which are helminths include Platyhelmintha (e.g. Monogenea, cestodes and trematodes), nematodes, Acanthocephala, and Pentastoma. These include:

Monogenea: for example: *Gyrodactylus* spp., *Dactylogyrus* spp., *Polystoma* spp.;

Cestodes: from the order of Pseudophyllidea, for example: *Diphyllobothrium* spp., *Spirometra* spp., *Schistocephalus* spp., *Ligula* spp., *Bothridium* spp., *Diphlogonoporus* spp.;

from the order Cyclophyllida, for example: *Mesocestoides* spp., *Anoplocephala* spp., *Paranoplocephala* spp., *Moniezia* spp., *Thysanosoma* spp., *Thysaniezia* spp., *Avitellina* spp., *Stilesia* spp., *Cittotaenia* spp., *Andyra* spp., *Bertiella* spp., *Taenia* spp., *Echinococcus* spp., *Hydatigera* spp., *Davainea* spp., *Raillietina* spp., *Hymenolepis* spp., *Echinolepis* spp., *Echinocotyle* spp., *Diorchis* spp., *Dipylidium* spp., *Joyeuxiella* spp., *Diplopylidium* spp.;

Trematodes: from the class of Digenea, for example: *Diplostomum* spp., *Posthodiplostomum* spp., *Schistosoma* spp., *Trichobilharzia* spp., *Ornithobilharzia* spp., *Austrobilharzia* spp., *Gigantobilharzia* spp., *Leucochloridium* spp., *Brachylaima* spp., *Echinostoma* spp., *Echinoparyphium* spp., *Echinochasmus* spp., *Hypoderaeum* spp., *Fasciola* spp., *Fascioloides* spp., *Fasciolopsis* spp., *Cyclocoelum* spp., *Typhlocoelum* spp., *Paramphistomum* spp., *Calicophoron* spp., *Cotylophoron* spp., *Gigantocotyle* spp., *Fischoederius* spp., *Gastrothylacus* spp., *Notocotylus* spp., *Catatropis* spp., *Plagiorchis* spp., *Prosthogonimus* spp., *Dicrocoelium* spp., *Eurytrema* spp., *Troglotrema* spp., *Paragonimus* spp., *Collyriclum* spp., *Nanophyetus* spp., *Opisthorchis* spp., *Clonorchis* spp., *Metorchis* spp., *Heterophyes* spp., *Metagonimus* spp.;

Nematodes: Trichinellida, for example: *Trichuris* spp., *Capillaria* spp., *Paracapillaria* spp., *Eucoleus* spp., *Trichomosoides* spp., *Trichinella* spp., from the order Tylenchida, for example: *Micronema* spp., *Strongyloides* spp.;

from the order Rhabditida, for example: *Strongylus* spp., *Triodontophorus* spp., *Oesophagodontus* spp., *Cylicostephanus* spp., *Oesophagostomum* spp., *Chabertia* spp., *Stephanurus* spp., *Ancylostoma* spp., *Uncinaria* spp., *Necator* spp., *Bunostomum* spp., *Globocephalus* spp., *Syngamus* spp., *Cyathostoma* spp., *Metastrongylus* spp., *Dictyocaulus* spp., *Muellerius* spp., *Protostrongylus* spp., *Neostrongylus* spp., spp., *Crenosoma* spp., *Paracrenosoma* spp., *Oslerus* spp., *Angiostrongylus* spp., *Aelurostrongylus* spp., *Filaroides* spp., *Parafilaroides* spp., *Trichostrongylus* spp., *Haemonchus* spp., *Ostertagia* spp., *Teladorsagia* spp., *Marshallagia* spp., *Cooperia* spp., *Nippostrongylus* spp., *Heligmosomoides* spp., *Nematodirus* spp., *Hyostrongylus* spp., *Obeliscoides* spp., *Amidostomum* spp., *Ollulanus* spp.;

from the order Spirurida, for example: *Oxyuris* spp., *Enterobius* spp., *Passalurus* spp., *Syphacia* spp., *Aspiculuris* spp., *Heterakis* spp.; *Ascaris* spp., *Toxascaris* spp., *Toxocara* spp., *Baylisascaris* spp., *Parascaris* spp., *Anisakis* spp., *Ascaridia* spp.; *Gnathostoma* spp., *Physaloptera* spp., *Thelazia* spp., *Gongylonema* spp., *Habronema* spp., *Parabronema* spp., *Draschia* spp., *Dracunculus* spp.; *Stephanofilaria* spp., *Parafilaria* spp., *Setaria* spp., *Loa* spp., *Dirofilaria* spp., *Litomosoides* spp., *Brugia* spp., *Wuchereria* spp., *Onchocerca* spp., *Spirocerca* spp.;

Acanthocephala: from the order of Oligacanthorhynchida, for example: *Macracanthorhynchus* spp., *Prosthenorchis* spp.; from the order Polymorphida for example: *Filicollis* spp.; from the order Moniliformida for example: *Moniliformis* spp.;

from the order Echinorhynchida, for example *Acanthocephalus* spp., *Echinorhynchus* spp., *Leptorhynchoides* spp.;

Pentastoma: from the order Porocephalida, for example *Linguatula* spp.

In the veterinary field and in animal husbandry, the compounds of the formula (I) are administered by methods generally known in the art, such as via the enteral, parenteral, dermal or nasal route in the form of suitable preparations. Administration may be prophylactic or therapeutic.

Thus, one embodiment of the present invention refers to the use of a compound of the formula (I) as a medicament.

A further aspect refers to the use of a compound of the formula (I) as an antiendoparasitic agent, in particular a helminthicidal agent or antiprotozoic agent. Compounds of the formula (I) are suitable for use as an antiendoparasitic agent, especially as a helminthicidal agent or antiprotozoic agent, for example in animal breeding, in animal husbandry, in animal houses and in the hygiene sector.

A further aspect in turn relates to the use of a compound of the formula (I) as an antiectoparasitic agent, in particular an arthropodicide such as an insecticide or an acaricide. A further aspect relates to the use of a compound of the formula (I) as an antiectoparasitic agent, in particular an arthropodicide such as an insecticide or an acaricide, for example in animal husbandry, in animal breeding, in animal houses or in the hygiene sector.

Vector Control

The compounds of the formula (I) can also be used in vector control. In the context of the present invention, a vector is an arthropod, especially an insect or arachnid, capable of transmitting pathogens, for example viruses, worms, single-cell organisms and bacteria, from a reservoir (plant, animal, human, etc.) to a host. The pathogens can be transmitted either mechanically (for example trachoma by non-stinging flies) to a host or after injection (for example malaria parasites by mosquitoes) into a host.

Examples of vectors and the diseases or pathogens they transmit are:

1) mosquitoes

*Anopheles*: malaria, filariasis;

*Culex*: Japanese encephalitis, filariasis, other viral diseases, transmission of worms;

*Aedes*: yellow fever, dengue fever, filariasis, other viral diseases;

Simuliidae: transmission of worms, in particular *Onchocerca volvulus*;

2) Lice: skin infections, epidemic typhus;

3) Fleas: plague, endemic typhus;

4) Flies: sleeping sickness (trypanosomiasis); cholera, other bacterial diseases;

5) Mites: acariosis, epidemic typhus, rickettsialpox, tularaemia, Saint Louis encephalitis, tick-borne encephalitis (TBE), Crimean-Congo haemorrhagic fever, borreliosis;

6) Ticks: borellioses such as *Borrelia duttoni*, tick-borne encephalitis, Q fever (*Coxiella burnetii*), babesioses (*Babesia canis canis*).

Examples of vectors in the context of the present invention are insects, such as aphids, flies, leafhoppers or *thrips*, which can transmit plant viruses to plants. Other vectors capable of transmitting plant viruses are spider mites, lice, beetles and nematodes.

Further examples of vectors in the context of the present invention are insects and arachnids such as mosquitoes, especially of the genera *Aedes, Anopheles*, for example *A. gambiae, A. arabiensis, A. funestus, A. dirus* (malaria) and *Culex*, lice, fleas, flies, mites and ticks, which can transmit pathogens to animals and/or humans.

Vector control is also possible if the compounds of the formula (I) are resistance-breaking.

Compounds of the formula (I) are suitable for use in the prevention of diseases and/or pathogens transmitted by vectors. Thus, a further aspect of the present invention is the use of compounds of the formula (I) for vector control, for example in agriculture, in horticulture, in forests, in gardens and in leisure facilities, and also in the protection of materials and stored products.

Protection of Industrial Materials

The compounds of the formula (I) are suitable for protecting industrial materials against attack or destruction by insects, for example from the orders Coleoptera, Hymenoptera, Isoptera, Lepidoptera, Psocoptera and Zygentoma.

Industrial materials in the present context are understood to mean inanimate materials, such as preferably plastics, adhesives, sizes, papers and cards, leather, wood, processed wood products and coating compositions. The use of the invention for protection of wood is particularly preferred.

In a further embodiment, the compounds of the formula (I) are used together with at least one further insecticide and/or at least one fungicide.

In a further embodiment, the compounds of the formula (I) are present as a ready-to-use pesticide, i.e. it can be applied to the material in question without further modifications. Suitable further insecticides or fungicides are in particular those mentioned above.

Surprisingly, it has also been found that the compounds of the formula (I) can be employed for protecting objects which come into contact with saltwater or brackish water, in particular hulls, screens, nets, buildings, moorings and signalling systems, against fouling. It is equally possible to use the compounds of the formula (I), alone or in combinations with other active ingredients, as antifouling agents.

Control of Animal Pests in the Hygiene Sector

The compounds of the formula (I) are suitable for controlling animal pests in the hygiene sector. More particularly, the invention can be used in the domestic protection sector, in the hygiene protection sector and in the protection of stored products, particularly for control of insects, arachnids and mites encountered in enclosed spaces, for example dwellings, factory halls, offices, vehicle cabins. For controlling animal pests, the compounds of the formula (I) are used alone or in combination with other active ingredients and/or auxiliaries. They are preferably used in domestic insecticide products. The compounds of the formula (I) are effective against sensitive and resistant species, and against all developmental stages.

These pests include, for example, pests from the class Arachnida, from the orders Scorpiones, Araneae and Opiliones, from the classes Chilopoda and Diplopoda, from the class Insecta the order Blattodea, from the orders Coleoptera, Dermaptera, Diptera, Heteroptera, Hymenoptera, Isoptera, Lepidoptera, Phthiraptera, Psocoptera, Saltatoria or Orthoptera, Siphonaptera and Zygentoma and from the class Malacostraca the order Isopoda.

Application is effected, for example, in aerosols, unpressurized spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or bait stations.

DESCRIPTION OF THE PROCESSES AND INTERMEDIATES

The preparation and use examples which follow illustrate the invention without limiting it. The products were characterized by ¹H NMR spectroscopy and/or LC-MS (Liquid Chromatography Mass Spectrometry).

The log P values were determined in accordance with OECD Guideline 117 (EC Directive 92/69/EEC) by HPLC (high-performance liquid chromatography) using reversed-phase (RP) columns (C18), by the following methods:

[a] The LC-MS determination in the acidic range is carried out at pH 2.7 with 0.1% aqueous formic acid and acetonitrile (contains 0.1% formic acid) as eluents; linear gradient from 10% acetonitrile to 95% acetonitrile.

[b] LC-MS determination in the neutral range is effected at pH 7.8 with 0.001 molar aqueous ammonium hydrogencarbonate solution and acetonitrile as eluents; linear gradient from 10% acetonitrile to 95% acetonitrile.

Calibration is carried out using unbranched alkan-2-ones (having 3 to 16 carbon atoms) with known log P values (log P values determined on the basis of the retention times by linear interpolation between two successive alkanones).

The NMR spectra were determined using a Bruker Avance 400 fitted with a flow probe head (60 µl volume). In individual cases, the NMR spectra were measured with a Bruker Avance II 600.

The 1H-NMR data of selected examples are noted in the form of 1H-NMR peak lists. For each signal peak, first the δ value in ppm and then the signal intensity in round brackets are listed. The pairs of δ value-signal intensity numbers for different signal peaks are listed with separation from one another by semicolons.

The peak list for one example therefore has the form: $\delta_1$ (intensity$_1$); $\delta_2$ (intensity$_2$); . . . ; $\delta_i$ (intensity$_i$); . . . ; $\delta_n$ (intensity$_n$)

The intensity of sharp signals correlates with the height of the signals in a printed example of an NMR spectrum in cm and shows the true ratios of the signal intensities. In the case of broad signals, several peaks or the middle of the signal and the relative intensity thereof may be shown in comparison to the most intense signal in the spectrum.

Calibration of the chemical shift of 1H NMR spectra is accomplished using tetramethylsilane and/or the chemical shift of the solvent, particularly in the case of spectra which are measured in DMSO. Therefore, the tetramethylsilane peak may but need not occur in NMR peak lists.

The lists of the 1H-NMR peaks are similar to the classic 1H-NMR prints and thus usually comprise all peaks listed in a classic NMR interpretation.

In addition, like classic 1H-NMR prints, they may show solvent signals, signals of stereoisomers of the target compounds, which are likewise the subject matter of the invention, and/or peaks of impurities.

When stating compound signals in the delta range of solvents and/or water, in our lists of 1H NMR peaks, the usual solvent peaks, for example peaks of DMSO in DMSO-$D_6$ and the peak of water are shown, which usually have on average a high intensity.

The peaks of stereoisomers of the target compounds and/or peaks of impurities usually have a lower intensity on average than the peaks of the target compounds (for example with a purity of >90%).

Such stereoisomers and/or impurities may be typical of the particular preparation process. Their peaks can thus help in this case to identify the reproduction of our preparation process with reference to "by-product fingerprints".

An expert calculating the peaks of the target compounds by known methods (MestreC, ACD simulation, but also with empirically evaluated expected values) can, if required, isolate the peaks of the target compounds, optionally using additional intensity filters. This isolation would be similar to the relevant peak picking in classic 1H-NMR interpretation.

Further details of 1H NMR peak lists can be found in the Research Disclosure Database Number 564025.

Synthesis of Benzothiazoles of the Formula (I) by Method A

6-Bromo-2-(pyridin-3-yl)-1,3-benzothiazole (I-a-1)

Step 1: N-(3,5-Dibromopyridin-2-yl)nicotinamide (A-III-1)

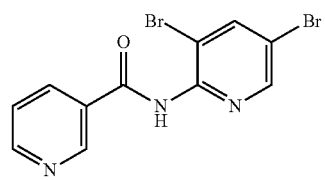 [SMILES: O=C(Nc1ncc(Br)cc1Br)c1cccnc1]

25.0 g (99.2 mmol) of 3,5-dibromopyridin-2-amine were dissolved in 200 ml of pyridine and cooled in an ice bath, and 19.0 g (106.7 mmol) of 3-(chlorocarbonyl)pyridinium chloride were added in portions. The mixture was warmed to room temperature, rotated on a rotary evaporator in a lukewarm water bath for 20 minutes and then concentrated under reduced pressure. The residue obtained was admixed with water and aqueous ammonia solution, and the precipitated solids were filtered off with suction. The solids were recrystallized from fluorobenzene/methyl-THF/ethanol, by briefly boiling with activated carbon and filtering while hot. The solids formed were washed with aqueous ammonia solution, water and petroleum ether and dried. In this way, 11.4 g (100% purity, 29.9% of theory) of the title compound (A-III-1) were obtained.

1H-NMR (400.0 MHz, $d_6$-DMSO): δ=11.050 (9.9); 9.136 (8.3); 9.134 (9.2); 9.130 (8.9); 9.128 (8.6); 8.809 (6.9); 8.805 (7.4); 8.797 (7.3); 8.793 (7.2); 8.674 (13.9); 8.669 (15.7); 8.593 (16.0); 8.588 (14.1); 8.333 (3.9); 8.327 (5.3); 8.323 (3.9); 8.313 (4.3); 8.307 (5.7); 8.303 (4.0); 7.610 (4.7); 7.609 (4.9); 7.598 (4.6); 7.597 (4.8); 7.591 (4.6); 7.589 (4.7); 7.578 (4.4); 7.577 (4.5); 3.327 (53.4); 2.676 (0.3); 2.672 (0.5); 2.667 (0.3); 2.525 (1.4); 2.512 (26.9); 2.507 (54.1); 2.503 (71.3); 2.498 (51.3); 2.494 (24.4); 2.334 (0.3); 2.330 (0.5); 2.325 (0.3); 0.146 (0.5); 0.008 (4.4); 0.000 (110.7); −0.009 (3.9); −0.150 (0.5)

Steps 2&3: 6-Bromo-2-(pyridin-3-yl)[1,3]thiazolo[4,5-b]pyridine (I-a-1)

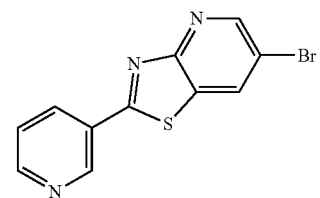 [SMILES: Brc1cnc2nc(-c3cccnc3)sc2c1]

14.7 g (41.2 mmol) of N-(3,5-dibromopyridin-2-yl)nicotinamide (A-III-1) and 10.0 g (61.8 mmol) of 2,4-bis(4-methoxyphenyl)-1,3,2,4-dithiadiphosphetane 2,4-disulphide (Lawesson's reagent) were dissolved in a minimum amount of anisole and stirred at 120° C. for 2 hours. Subsequently, the mixture was concentrated and cooled. The residue was taken up in ethyl acetate and aqueous potassium carbonate solution. The aqueous phase was extracted repeatedly with ethyl acetate. The combined organic phases were dried over magnesium sulfate, filtered and concentrated.

The residue was taken up directly in 400 ml of DMF, admixed with 24.0 g (173.7 mmol) of potassium carbonate and stirred at 120° C. for 2 hours. Subsequently, the mixture was concentrated, and water and petroleum ether were added. The solids which precipitate were filtered off, washed with aqueous ammonia solution and dried. In this way, 9.6 g (100% purity, 79.8% of theory) of the title compound (I-a-1) were obtained.

1H-NMR (400.0 MHz, $d_6$-DMSO): δ=9.339 (8.2); 9.337 (8.7); 9.333 (8.6); 9.332 (8.2); 9.046 (15.3); 9.040 (16.0); 8.842 (15.8); 8.836 (15.1); 8.830 (7.6); 8.827 (7.8); 8.818 (7.7); 8.814 (7.5); 8.548 (4.4); 8.544 (5.4); 8.543 (5.3); 8.538 (4.3); 8.528 (4.7); 8.524 (5.4); 8.523 (5.8); 8.518 (4.4); 8.318 (0.4); 7.679 (5.3); 7.677 (5.4); 7.667 (5.2); 7.665 (5.3); 7.659 (5.2); 7.657 (5.1); 7.647 (5.0); 7.645 (5.0); 3.757 (1.1); 3.329 (112.8); 2.678 (0.5); 2.674 (0.7); 2.669 (0.5); 2.527 (1.9); 2.514 (39.9); 2.509 (80.5); 2.505 (105.7); 2.500 (75.9); 2.496 (35.9); 2.336 (0.5); 2.331 (0.7); 2.327 (0.5); 0.146 (0.7); 0.008 (5.9); 0.000 (157.7); −0.009 (5.5); −0.150 (0.7)

Synthesis of Compounds of the Formula (I) by Method B and I 6-(2-Methylphenyl)-2-(pyridin-3-yl)[1,3]thiazolo[4,5-b]pyridine (2)

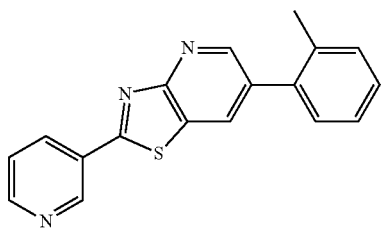 [SMILES: Cc1ccccc1-c1cnc2nc(-c3cccnc3)sc2c1]

Under argon, 150.0 mg (0.51 mmol) of 6-bromo-2-(pyridin-3-yl)[1,3]thiazolo[4,5-b]pyridine (I-a-1), 76.8 mg (0.56 mmol) of (2-methylphenyl)boric acid, 17.8 mg (0.01 mmol) of tetrakis(triphenylphosphine)palladium(0) and 108.8 mg (1.03 mmol) of sodium carbonate were weighed together into a microwave reaction vessel, and 3.8 ml of a 4:1 mixture of degassed dioxane and water were added. The vessel was flooded again with argon, sealed and heated in a Biotage Initiator microwave at 130° C. for 30 minutes. The cooled mixture was diluted with water and extracted repeatedly with dichloromethane. The combined organic phases were filtered through a silica gel cartridge and washed through with dichloromethane, and the filtrate was concentrated under reduced pressure. The residue was stirred with acetonitrile, filtered and dried. This gave 53.0 mg (97.5% purity, 33.2% of theory) of the title compound (2).

1H-NMR (400.0 MHz, $d_6$-DMSO): δ=9.366 (2.3); 9.361 (2.3); 8.833 (1.7); 8.829 (1.9); 8.821 (1.8); 8.817 (1.9); 8.748 (2.7); 8.748 (4.7); 8.735 (4.4); 8.730 (2.6); 8.573 (1.0); 8.569 (1.5); 8.564 (1.0); 8.553 (1.1); 8.549 (1.5); 8.544 (1.0); 7.693 (1.4); 7.681 (1.4); 7.673 (1.3); 7.661 (1.3); 7.404 (0.5); 7.393 (2.4); 7.390 (2.7); 7.383 (3.6); 7.376 (3.2); 7.369 (3.3); 7.362 (4.8); 7.355 (1.5); 7.349 (1.1); 7.340 (0.4); 3.329 (15.8); 2.526 (0.8); 2.508 (33.3); 2.504 (44.1); 2.500 (33.0); 2.383 (0.4); 2.331 (0.4); 2.315 (16.0); 0.008 (1.8); 0.000 (50.9); −0.009 (2.0)

6-(3-Chlorophenyl)-2-(pyridin-3-yl)[1,3]thiazolo[4,5-b]pyridine (7)

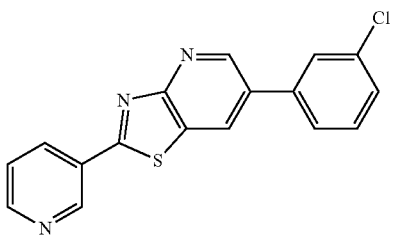 [SMILES: Clc1cccc(-c2cnc3nc(-c4cccnc4)sc3c2)c1]

Under argon, 150 mg (0.51 mmol) of 6-bromo-2-(pyridin-3-yl)[1,3]thiazolo[4,5-b]pyridine (I-a-1), 88.3 mg (0.57 mmol) of (3-chlorophenyl)boric acid, 17.8 mg (0.01 mmol) of tetrakis(triphenylphosphine)palladium(0) and 108.8 mg (1.03 mmol) of sodium carbonate were weighed together into a microwave reaction vessel, and 3.8 ml of a 4:1 mixture of degassed dioxane and water were added. The vessel was flooded again with argon, sealed and heated in a Biotage Initiator microwave at 130° C. for 30 minutes. The cooled mixture was diluted with water and extracted repeatedly with dichloromethane. The combined organic phases were filtered through a silica gel cartridge and washed through with dichloromethane, and the filtrate was concentrated under reduced pressure. The residue was stirred with acetonitrile, filtered and dried. Purification was by chromatography by MPLC (eluent: water/acetonitrile). This gave 14.0 mg (100.0% purity, 8.4% of theory) of the title compound (7).

1H-NMR (400.0 MHz, $d_6$-DMSO): δ=9.374 (8.4); 9.368 (8.3); 9.117 (11.3); 9.111 (15.3); 9.084 (16.0); 9.078 (11.2); 8.834 (6.6); 8.830 (6.7); 8.822 (6.8); 8.818 (6.5); 8.582 (3.8); 8.577 (5.3); 8.572 (3.6); 8.562 (4.1); 8.557 (5.5); 8.552 (3.5); 8.317 (1.9); 7.969 (6.9); 7.964 (12.0); 7.960 (6.7); 7.857 (5.8); 7.838 (6.5); 7.811 (0.4); 7.693 (5.3); 7.681 (5.2); 7.673 (5.1); 7.661 (4.9); 7.611 (4.5); 7.591 (10.7); 7.572 (7.8); 7.547 (7.4); 7.530 (2.8); 7.527 (3.2); 7.289 (0.4); 6.937 (0.5); 6.925 (0.4); 6.914 (0.4); 5.757 (0.7); 3.744 (3.2); 3.327 (467.3); 2.676 (4.1); 2.671 (5.6); 2.667 (4.1); 2.602 (0.5); 2.524 (15.1); 2.507 (606.6); 2.502 (788.2); 2.498 (575.0); 2.333 (3.8); 2.329 (5.2); 2.325 (3.7); 2.170 (0.5); 1.355 (0.5); 1.277 (0.4); 1.259 (0.5); 1.232 (5.8); 1.154 (0.4); 1.136 (0.6); 1.118 (0.4); 0.853 (0.7); 0.836 (0.4); 0.146 (2.7); 0.082 (0.4); 0.073 (6.2); 0.008 (20.0); 0.000 (579.1); −0.009 (21.1); −0.150 (2.8)

6-[2-(Ethylsulphanyl)phenyl]-2-(pyridin-3-yl)[1,3]thiazolo[4,5-b]pyridine (14)

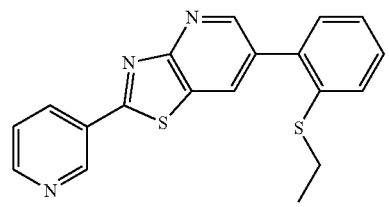 [SMILES: CCSc1ccccc1-c1cnc2nc(-c3cccnc3)sc2c1]

Under argon, 200.0 mg (0.68 mmol) of 6-bromo-2-(pyridin-3-yl)[1,3]thiazolo[4,5-b]pyridine (I-a-1), 137.1 mg (0.75 mmol) of [4-(ethylsulphanyl)phenyl]boric acid, 23.7 mg (0.02 mmol) of tetrakis(triphenylphosphine)palladium (0) and 145.1 mg (1.4 mmol) of sodium carbonate were weighed together into a reaction vessel, and 2 ml of a 1:1 mixture of degassed dioxane and water were added. The vessel was flooded again with argon, sealed and heated in a Biotage Initiator microwave at 130° C. for 30 minutes. The cooled mixture was diluted with water and extracted repeatedly with dichloromethane. The combined organic phases were filtered through a silica gel cartridge and washed through with dichloromethane, and the filtrate was concentrated under reduced pressure. Purification was by chromatography by MPLC (eluent: cyclohexane/ethyl acetate). This gave 240.0 mg (81.3% purity, 81.6% of theory) of the title compound (14).

1H-NMR (400.0 MHz, $d_6$-DMSO): δ=9.364 (3.7); 9.359 (3.7); 8.834 (2.8); 8.831 (3.0); 8.823 (3.0); 8.819 (2.9); 8.742 (4.8); 8.736 (6.6); 8.713 (6.5); 8.707 (4.7); 8.572 (1.6); 8.568 (2.3); 8.563 (1.6); 8.553 (1.8); 8.548 (2.4); 8.543 (1.6); 8.317 (0.4); 8.070 (6.5); 7.695 (2.2); 7.683 (2.2); 7.675 (2.1); 7.663 (2.0); 7.540 (2.1); 7.522 (3.9); 7.520 (3.9); 7.493 (1.8); 7.488 (1.9); 7.475 (2.3); 7.471 (2.7); 7.455 (1.1); 7.451 (1.4); 7.414 (1.8); 7.410 (2.1); 7.395 (4.0); 7.391 (3.4); 7.365 (3.2); 7.362 (3.2); 7.345 (4.2); 7.328 (2.3); 7.325 (2.4); 7.315 (0.8); 7.311 (0.7); 7.297 (0.9); 7.294 (0.9); 7.278 (0.4); 7.274 (0.4); 7.177 (0.6); 7.174 (0.7); 7.159 (1.0); 7.156 (1.0); 7.141 (0.4); 7.138 (0.4); 4.038 (0.5); 4.020 (0.6); 3.568 (0.4); 3.328 (165.3); 2.936 (2.2); 2.918 (7.2); 2.904 (3.7); 2.900 (7.5); 2.886 (3.1); 2.882 (2.7); 2.868 (0.9); 2.676 (1.1); 2.671 (1.5); 2.667 (1.1); 2.524 (4.1); 2.507 (166.9); 2.502 (217.8); 2.498 (164.7); 2.334 (1.1); 2.329 (1.5); 2.325 (1.1); 1.989 (2.2); 1.242 (0.4); 1.234 (0.3); 1.212 (2.8); 1.194 (6.2); 1.186 (7.9); 1.175 (4.5); 1.167 (16.0); 1.157 (1.3); 1.149 (7.4); 0.000 (0.5)

6-[2-(Ethylsulphinyl)phenyl]-2-(pyridin-3-yl)[1,3]thiazolo[4,5-b]pyridine (15)

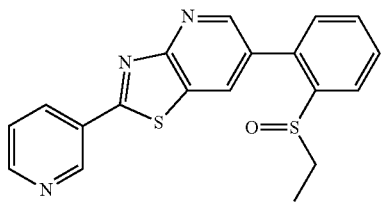 [SMILES: CCS(=O)c1ccccc1-c1cnc2nc(-c3cccnc3)sc2c1]

To an initial charge of 100.0 mg (0.28 mmol) of 6-[2-(ethylsulphanyl)phenyl]-2-(pyridin-3-yl)[1,3]thiazolo[4,5-b]pyridine (14) in 10 ml of dichloromethane were added 118.8 mg (0.68 mmol) of m-chloroperbenzoic acid. The mixture was stirred at room temperature overnight. Subsequently, the mixture was admixed with one drop of aqueous sodium hydrogensulphite, washed with aqueous sodium carbonate solution, dried and concentrated. Purification was by chromatography by MPLC (eluent: water/acetonitrile). This gave 26.0 mg (100.0% purity, 24.9% of theory) of the title compound (15).

1H-NMR (400.0 MHz, $d_6$-DMSO): δ=9.374 (4.2); 9.370 (4.3); 8.866 (6.3); 8.860 (7.5); 8.843 (3.2); 8.839 (3.5); 8.831 (3.4); 8.827 (3.5); 8.805 (7.3); 8.800 (6.2); 8.585 (1.8); 8.580 (2.5); 8.575 (1.9); 8.565 (2.0); 8.559 (2.7); 8.555 (1.9); 8.318 (0.3); 8.006 (2.9); 8.003 (3.1); 7.987 (3.4); 7.984 (3.5); 7.799 (1.4); 7.795 (1.5); 7.780 (3.2); 7.777 (3.2); 7.761 (2.2); 7.757 (2.2); 7.740 (2.0); 7.736 (2.1); 7.721 (3.3); 7.718 (3.4); 7.701 (3.5); 7.699 (3.7); 7.688 (2.4); 7.681 (2.3); 7.669 (2.2); 7.667 (2.2); 7.571 (3.6); 7.569 (3.6); 7.553 (3.0); 7.550 (2.9); 5.758 (1.5); 3.332 (197.0); 2.783 (0.5); 2.764 (1.8); 2.746 (2.1); 2.731 (2.4); 2.712 (2.2); 2.694 (0.7); 2.677 (0.8); 2.672 (1.0); 2.668 (0.8); 2.542 (0.6); 2.525 (2.5); 2.508 (116.7); 2.503 (153.0); 2.499 (113.2); 2.444 (0.7); 2.426 (2.1); 2.408 (2.4); 2.392 (2.1); 2.374 (1.8); 2.355 (0.6); 2.334 (0.7); 2.330 (1.0); 2.325 (0.8); 0.905 (7.4); 0.887 (16.0); 0.869 (7.1); 0.000 (6.3)

6-[2-(Ethylsulphinyl)phenyl]-2-(1-oxidopyridin-3-yl)[1,3]thiazolo[4,5-b]pyridine (16)

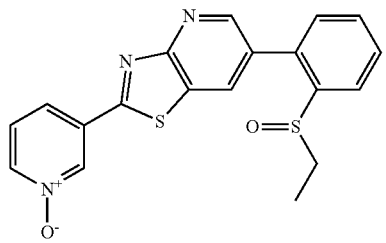 [SMILES: CCS(=O)c1ccccc1-c1cnc2nc(-c3ccc[n+]([O-])c3)sc2c1]

In the course of the preparation of compound (15), compound (16) was isolated as a by-product. This gave 16.7 mg (92.8% purity, 14.2% of theory) of the title compound (16).

1H-NMR (400.0 MHz, $d_6$-DMSO): δ=9.371 (4.2); 9.365 (4.1); 8.840 (3.2); 8.836 (3.3); 8.828 (3.3); 8.824 (3.3); 8.764 (5.8); 8.759 (7.2); 8.719 (7.0); 8.713 (5.7); 8.580 (1.8); 8.575 (2.5); 8.571 (1.9); 8.561 (1.9); 8.555 (2.6); 8.551 (1.8); 8.318 (1.8); 8.132 (3.1); 8.115 (3.4); 8.112 (3.4); 7.889 (1.6); 7.873 (3.3); 7.870 (3.3); 7.854 (2.3); 7.851 (2.2); 7.815 (2.1); 7.812 (2.5); 7.795 (3.0); 7.792 (3.1); 7.776 (1.3); 7.773 (1.3); 7.699 (2.5); 7.686 (2.5); 7.679 (2.5); 7.666 (2.4); 7.627 (0.5); 7.601 (3.6); 7.598 (3.7); 7.583 (3.2); 7.580 (3.1); 5.757 (1.7); 4.040 (0.5); 4.022 (0.5); 3.376 (0.5); 3.327 (653.5); 3.012 (2.1); 2.993 (7.0); 2.975 (7.2); 2.957 (2.2); 2.675 (4.7); 2.671 (6.3); 2.667 (4.8); 2.623 (0.3); 2.524 (17.2); 2.510 (380.2); 2.506 (748.3); 2.502 (973.4); 2.497 (719.5); 2.372 (0.3); 2.333 (4.7); 2.328 (6.4); 2.324 (4.8); 2.299 (0.4); 2.206 (0.3); 1.355 (0.3); 1.234 (1.4); 1.165 (1.7); 1.026 (7.4); 1.008 (16.0); 0.989 (7.2); 0.146 (17.1); 0.096 (0.3); 0.086 (0.7); 0.070 (0.7); 0.058 (1.2); 0.047 (1.5); 0.007 (153.7); 0.000 (3211.2); −0.009 (157.6); −0.068 (0.9); −0.075 (0.9); −0.095 (0.6); −0.121 (0.4); −0.150 (16.9)

6-{2,4-Dimethyl-5-[(2,2,2-trifluoroethyl)sulphanyl]phenyl}-2-(pyridin-3-yl)[1,3]thiazolo[4,5-b]pyridine (19)

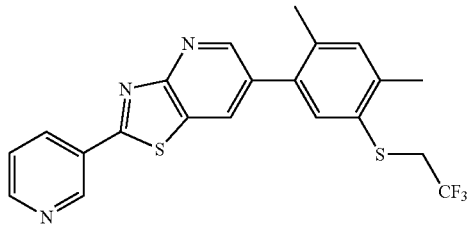 [SMILES: Cc1cc(C)c(-c2cnc3nc(-c4cccnc4)sc3c2)cc1SCC(F)(F)F]

200.0 mg (0.68 mmol) of 6-bromo-2-(pyridin-3-yl)[1,3]thiazolo[4,5-b]pyridine (I-a-1), 198.9 mg (0.75 mmol) of {2,4-dimethyl-5-[(2,2,2-trifluoroethyl)sulphanyl]phenyl}boric acid and 23.7 mg (0.02 mmol) of tetrakis(triphenylphosphine)palladium(0) were initially charged under argon, and then 9.4 ml of degassed acetonitrile and 1.4 ml of two molar sodium carbonate solution were added. The mixture was stirred under argon at 80° C. overnight. Subsequently, the cooled mixture was concentrated, admixed with dichloromethane and washed with a little water. The organic phase was dried, filtered and concentrated. Purification was by chromatography by MPLC (eluent: water/acetonitrile). This gave 92.0 mg (97.8% purity, 30.5% of theory) of the title compound (19).

1H-NMR (400.0 MHz, $d_6$-DMSO): δ=9.370 (2.7); 9.366 (2.7); 9.365 (2.7); 8.834 (2.3); 8.830 (2.5); 8.822 (2.4); 8.818 (2.5); 8.759 (2.5); 8.753 (8.0); 8.749 (7.8); 8.744 (2.3); 8.578 (1.3); 8.574 (1.7); 8.568 (1.3); 8.558 (1.4); 8.553 (1.8); 8.548 (1.3); 8.318 (0.3); 7.694 (1.6); 7.693 (1.6); 7.682 (1.6); 7.681 (1.6); 7.674 (1.6); 7.673 (1.6); 7.662 (1.5); 7.661 (1.5); 7.536 (5.9); 7.297 (4.6); 4.035 (1.2); 4.009 (3.8); 3.982 (4.0); 3.956 (1.4); 3.328 (100.9); 2.676 (0.7); 2.672 (0.9); 2.667 (0.7); 2.525 (2.7); 2.520 (3.9); 2.512 (49.4); 2.507 (100.6); 2.503 (133.6); 2.498 (97.4); 2.494 (47.0); 2.418 (14.4); 2.334 (0.6); 2.329 (0.9); 2.325 (0.6); 2.275 (16.0); 1.233 (0.4); 0.146 (0.8); 0.019 (0.4); 0.008 (6.1); 0.000 (176.8); −0.009 (6.0); −0.150 (0.8)

6-{2,4-Dimethyl-5-[(2,2,2-trifluoroethyl)sulphinyl]phenyl}-2-(pyridin-3-yl)[1,3]thiazolo[4,5-b]pyridine (20)

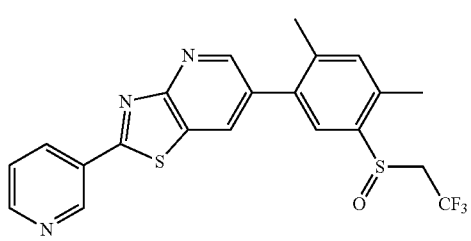 [SMILES: Cc1cc(C)c(S(=O)CC(F)(F)F)cc1-c1cnc2nc(-c3cccnc3)sc2c1]

To an initial charge of 60.0 mg (0.14 mmol) of 6-{2,4-dimethyl-5-[(2,2,2-trifluoroethyl)sulphanyl]phenyl}-2-(pyridin-3-yl)[1,3]thiazolo[4,5-b]pyridine (19) in 10 ml of dichloromethane were added 34.3 mg (0.15 mmol) of m-chloroperbenzoic acid. The mixture was stirred at room temperature overnight. Subsequently, the mixture was admixed with one drop of aqueous sodium hydrogensulphite, washed with aqueous sodium carbonate solution, dried and concentrated. Purification was by chromatography by MPLC (eluent: water/acetonitrile). This gave 28 mg (90.0% purity, 40.5% of theory) of the title compound (20).

1H-NMR (400.0 MHz, $d_6$-DMSO): δ=9.379 (3.2); 9.374 (3.0); 8.830 (7.8); 8.825 (9.1); 8.586 (1.4); 8.581 (1.9); 8.577 (1.3); 8.566 (1.5); 8.561 (2.0); 8.557 (1.3); 8.317 (0.5); 8.145 (0.6); 7.820 (6.5); 7.697 (1.8); 7.685 (1.8); 7.676 (1.8); 7.664 (1.7); 7.400 (4.8); 5.758 (2.3); 4.197 (1.1); 4.170 (3.3); 4.142 (3.5); 4.115 (1.2); 3.366 (0.8); 3.329 (136.7); 2.891 (0.7); 2.731 (0.6); 2.695 (0.4); 2.676 (1.3); 2.671 (1.7); 2.667 (1.3); 2.539 (1.9); 2.507 (193.1); 2.502 (244.6); 2.498 (184.8); 2.431 (15.1); 2.398 (0.8); 2.378 (16.0); 2.334 (1.3); 2.329 (1.7); 2.325 (1.3); 1.234 (1.0); 1.165 (1.0); 1.150 (0.6); 0.000 (6.2)

6-{2,4-Dimethyl-5-[(2,2,2-trifluoroethyl)sulphinyl]phenyl}-2-(pyridin-3-yl)[1,3]thiazolo[4,5-b]pyridine (21)

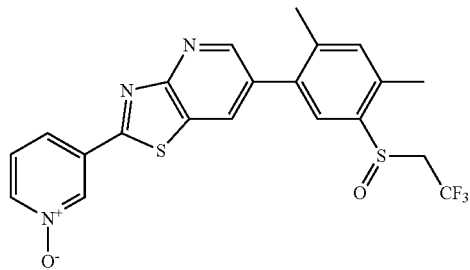 [SMILES: Cc1cc(C)c(S(=O)CC(F)(F)F)cc1-c1cnc2nc(-c3ccc[n+]([O-])c3)sc2c1]

In the course of the preparation of compound (20), compound (21) was isolated as a by-product. This gave 21 mg (90.0% purity, 29.3% of theory) of the title compound (21).

1H-NMR (400.0 MHz, $d_6$-DMSO): δ=8.927 (4.0); 8.861 (2.0); 8.854 (9.9); 8.848 (2.3); 8.841 (0.8); 8.830 (0.4); 8.814 (0.3); 8.690 (0.3); 8.466 (2.0); 8.448 (2.1); 8.317 (1.3); 8.148 (0.5); 8.104 (2.1); 8.084 (2.3); 7.846 (0.5); 7.818 (7.0); 7.680 (2.2); 7.663 (2.3); 7.660 (2.3); 7.643 (1.9); 7.555 (0.4); 7.401 (4.8); 7.383 (0.3); 5.757 (2.2); 4.194 (1.1); 4.167 (3.4); 4.140 (3.6); 4.113 (1.2); 4.037 (0.4); 4.020 (0.4); 3.428 (0.3); 3.416 (0.4); 3.402 (0.5); 3.368 (1.5); 3.330 (615.1); 3.294 (2.0); 2.891 (1.5); 2.731 (1.3); 2.695 (1.2); 2.676 (2.8); 2.671 (3.9); 2.667 (3.0); 2.545 (2.0); 2.540 (2.2); 2.524 (10.1); 2.507 (425.8); 2.502 (566.6); 2.498 (425.9); 2.430 (14.9); 2.392 (2.1); 2.372 (16.0); 2.333 (2.6); 2.329 (3.6); 2.324 (2.8); 1.234 (2.2); 1.165 (1.4); 1.149 (0.8); 0.853 (0.4); 0.008 (0.5); 0.000 (15.0); −0.008 (0.7)

6-{2-Fluoro-4-methyl-5-[(2,2,2-trifluoroethyl)sulphanyl]phenyl}-2-(pyridin-3-yl)[1,3]thiazolo[4,5-b]pyridine (22)

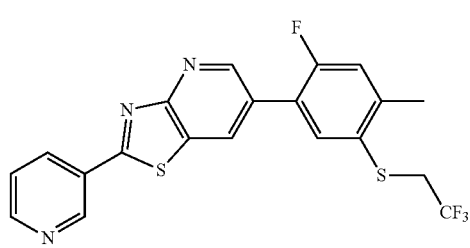 [SMILES: Cc1cc(F)c(-c2cnc3nc(-c4cccnc4)sc3c2)cc1SCC(F)(F)F]

150.0 mg (0.51 mmol) of 6-bromo-2-(pyridin-3-yl)[1,3]thiazolo[4,5-b]pyridine (I-a-1), 151.4 mg (0.56 mmol) of {2-fluoro-4-methyl-5-[(2,2,2-trifluoroethyl)sulphanyl]phenyl}boric acid, 17.8 mg (0.01 mmol) of tetrakis(triphenylphosphine)palladium(0) and 108.8 mg (1.0 mmol) of sodium carbonate were weighed into a reaction vessel under argon, and 4.8 ml of a 5:1 mixture of degassed dioxane and water were added.

The vessel was flooded again with argon, sealed and heated in a Biotage Initiator microwave at 130° C. for 30 minutes. The cooled mixture was diluted with water and extracted repeatedly with dichloromethane. The combined organic phases were filtered through a silica gel cartridge and washed with dichloromethane, then the filtrate was concentrated under reduced pressure. The residue was stirred with acetonitrile, filtered and dried. This gave 75.0 mg (96.2% purity, 32.3% of theory) of the title compound (22).

1H-NMR (400.0 MHz, d$_6$-DMSO): δ=9.375 (3.0); 9.370 (3.0); 8.953 (9.2); 8.950 (9.1); 8.836 (2.4); 8.833 (2.6); 8.824 (2.6); 8.821 (2.7); 8.583 (1.3); 8.578 (1.8); 8.573 (1.4); 8.563 (1.5); 8.558 (2.0); 8.553 (1.4); 7.902 (3.1); 7.882 (3.1); 7.693 (1.8); 7.681 (1.8); 7.673 (1.8); 7.663 (1.7); 7.661 (1.8); 7.422 (2.7); 7.393 (2.7); 5.758 (0.6); 4.114 (1.3); 4.088 (4.0); 4.062 (4.2); 4.036 (1.5); 3.328 (42.3); 2.677 (0.5); 2.673 (0.6); 2.668 (0.5); 2.526 (1.6); 2.521 (2.5); 2.512 (35.8); 2.508 (72.9); 2.503 (97.3); 2.499 (72.8); 2.495 (36.8); 2.468 (16.0); 2.403 (0.5); 2.335 (0.5); 2.330 (0.7); 2.326 (0.5); 2.076 (1.5); 0.146 (0.5); 0.008 (3.9); 0.000 (116.1); −0.009 (4.6); −0.150 (0.5)

6-{2-Fluoro-4-methyl-5-[(2,2,2-trifluoroethyl)sulphinyl]phenyl}-2-(pyridin-3-yl)[1,3]thiazolo[4,5-b]pyridine (23)

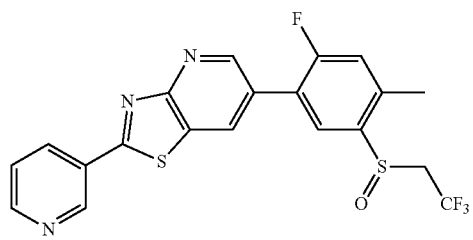 [SMILES: Cc1cc(F)c(-c2cnc3nc(-c4cccnc4)sc3c2)cc1S(=O)CC(F)(F)F]

To an initial charge of 155.0 mg (0.35 mmol) of 6-{2-fluoro-4-methyl-5-[(2,2,2-trifluoroethyl)sulphanyl]phenyl}-2-(pyridin-3-yl)[1,3]thiazolo[4,5-b]pyridine (22) in 25 ml of dichloromethane were added 87.7 mg (0.39 mmol) of m-chloroperbenzoic acid. The mixture was stirred at room temperature overnight. Subsequently, the mixture was admixed with one drop of aqueous sodium hydrogensulphite, washed with aqueous sodium carbonate solution, dried and concentrated. Purification was by chromatography by MPLC. This gave 43.2 mg (98.3% purity, 26.4% of theory) of the title compound (23).

1H-NMR (400.0 MHz, d$_6$-DMSO): δ=9.383 (12.6); 9.378 (12.3); 9.036 (15.7); 9.033 (14.8); 9.022 (12.3); 9.018 (16.0); 9.013 (7.6); 8.841 (9.7); 8.837 (10.6); 8.829 (10.1); 8.825 (10.6); 8.590 (5.6); 8.586 (7.4); 8.581 (5.7); 8.570 (6.1); 8.565 (8.1); 8.560 (5.8); 8.317 (1.4); 8.159 (13.2); 8.139 (13.3); 7.697 (7.3); 7.685 (7.1); 7.679 (6.9); 7.677 (7.0); 7.667 (6.7); 7.665 (6.9); 7.644 (0.6); 7.627 (0.8); 7.624 (0.8); 7.615 (0.7); 7.597 (0.8); 7.575 (0.6); 7.567 (0.7); 7.538 (10.5); 7.509 (10.2); 5.758 (3.5); 4.329 (0.4); 4.302 (1.4); 4.293 (2.2); 4.276 (2.8); 4.266 (7.1); 4.253 (6.9); 4.239 (7.4); 4.225 (7.4); 4.212 (2.8); 4.198 (2.7); 4.189 (1.6); 4.161 (0.5); 4.056 (1.0); 4.038 (2.9); 4.020 (3.0); 4.002 (1.0); 3.827 (0.4); 3.812 (0.5); 3.640 (0.6); 3.407 (0.3); 3.392 (0.7); 3.334 (1093.5); 3.268 (0.5); 3.175 (0.4); 3.162 (0.4); 2.677 (2.9); 2.672 (4.1); 2.668 (2.9); 2.645 (0.3); 2.525 (11.2); 2.512 (231.5); 2.508 (469.6); 2.503 (621.0); 2.499 (458.4); 2.494 (229.3); 2.485 (73.3); 2.434 (0.9); 2.410 (0.6); 2.388 (0.5); 2.372 (0.6); 2.334 (3.1); 2.330 (4.2); 2.325 (3.3); 1.990 (12.4); 1.909 (1.8); 1.298 (1.4); 1.259 (2.1); 1.233 (5.3); 1.193 (3.5); 1.175 (6.8); 1.157 (3.4); 0.853 (0.8); 0.836 (0.4); 0.146 (0.7); 0.008 (6.1); 0.000 (167.9); −0.008 (6.2); −0.150 (0.8)

Synthesis of Compounds of the Formula (I) by Method D

N-(3-Chlorophenyl)-2-(pyridin-3-yl)[1,3]thiazolo[4,5-b]pyridin-6-amine (25)

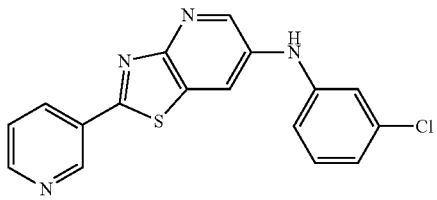 [SMILES: Clc1cccc(Nc2cnc3nc(-c4cccnc4)sc3c2)c1]

150 mg (0.51 mmol) of 6-bromo-2-(pyridin-3-yl)[1,3]thiazolo[4,5-b]pyridine (I-a-1), 78.6 mg (0.61 mmol) of 3-chloroaniline, 18.4 mg (0.08 mmol) of palladium(II) acetate, 57.5 mg (0.09 mmol) of rac-BINAP and 301.1 mg (0.92 mmol) of caesium carbonate were initially charged under argon, and then 5 ml of degassed toluene were added. The vessel was flooded again with argon, sealed and heated in a Biotage Initiator microwave at 140° C. for 60 minutes. The cooled mixture was diluted with water and extracted repeatedly with dichloromethane and ethyl acetate. The combined organic phases were filtered and concentrated under reduced pressure. Purification was by chromatography by MPLC (eluent: water/acetonitrile). This gave 44.0 mg (96.9% purity, 24.5% of theory) of the title compound (25).

1H-NMR (400.0 MHz, d$_6$-DMSO): δ=9.269 (6.7); 9.264 (6.8); 8.962 (11.3); 8.772 (5.4); 8.768 (5.9); 8.760 (5.8); 8.756 (5.9); 8.483 (9.8); 8.476 (13.1); 8.465 (3.5); 8.461 (4.5); 8.456 (3.4); 8.445 (3.7); 8.440 (5.6); 8.436 (16.0); 8.429 (10.0); 8.317 (1.2); 7.647 (4.3); 7.646 (4.3); 7.635 (4.1); 7.627 (4.1); 7.626 (4.1); 7.615 (4.0); 7.614 (3.9); 7.356 (0.3); 7.339 (4.5); 7.319 (9.7); 7.299 (6.0); 7.189 (4.3); 7.184 (10.1); 7.179 (7.2); 7.170 (5.9); 7.150 (4.0); 7.146 (3.3); 6.967 (4.5); 6.964 (4.4); 6.947 (3.9); 6.944 (4.1); 5.757 (0.5); 3.326 (236.5); 2.891 (1.4); 2.732 (1.2); 2.680 (1.3); 2.676 (2.6); 2.671 (3.6); 2.667 (2.7); 2.662 (1.3); 2.525 (8.9); 2.520 (13.4); 2.511 (186.4); 2.507 (384.3); 2.502 (519.2); 2.498 (389.2); 2.493 (195.6); 2.338 (1.2); 2.333 (2.5); 2.329 (3.5); 2.325 (2.6); 2.086 (4.0); 2.075 (1.1); 0.146 (2.0); 0.008 (14.5); 0.000 (450.0); −0.009 (17.3); −0.150 (2.0)

Synthesis of Compounds of the Formula (I) by Method E 6-(1H-Pyrazol-1-yl)-2-(pyridin-3-yl)[1,3]thiazolo[4,5-b]pyridine (26)

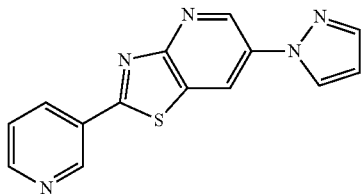 [SMILES: c1cncc(-c2nc3ncc(-n4cccn4)cc3s2)c1]

Under argon, 400.0 mg (1.4 mmol) of 6-bromo-2-(pyridin-3-yl)[1,3]thiazolo[4,5-b]pyridine (I-a-1), 1.0 g (14.7 mmol) of 1H-pyrazole, 21 mg (0.1 mmol) of copper(I) iodide, 568.0 mg (4.1 mmol) of potassium carbonate and 40 mg (0.14 mmol) of trans-1,2-bis(2'-pyridylidenamino)cyclohexane (racemic) [preparable according to Chem. Eur. J. 2005, 2483] were weighed into a reaction vessel, and 19.0 g of DMF were added. The mixture was heated under argon at 120° C. overnight. The cooled mixture was concentrated under reduced pressure, and the residue was admixed with water and extracted repeatedly with ethyl acetate. The combined organic phases were dried, filtered and concentrated. Purification was by chromatography by MPLC. This gave 20.0 mg (100% purity, 5.2% of theory) of the title compound (26).

1H-NMR (400.0 MHz, $d_6$-DMSO): δ=11.160 (0.7); 10.721 (0.7); 9.345 (14.2); 9.294 (15.7); 9.162 (14.9); 8.822 (10.6); 8.814 (10.8); 8.761 (0.5); 8.697 (15.8); 8.551 (8.4); 8.531 (8.8); 8.475 (0.5); 8.429 (0.4); 7.894 (16.0); 7.799 (0.4); 7.684 (7.1); 7.667 (8.7); 7.654 (6.8); 7.235 (0.5); 7.220 (0.4); 7.216 (0.4); 6.673 (14.6); 5.935 (0.7); 4.134 (0.5); 3.391 (0.6); 3.326 (63.2); 2.671 (2.1); 2.503 (265.8); 2.329 (2.3); 2.283 (0.7); 2.265 (0.6); 2.244 (0.5); 2.234 (0.5); 2.209 (0.4); 2.205 (0.4); 2.178 (0.4); 2.160 (0.4); 2.155 (0.4); 2.141 (0.4); 2.087 (4.1); 2.058 (0.6); 2.044 (0.4); 1.983 (0.7); 1.926 (0.4); 1.907 (0.5); 1.886 (0.4); 1.870 (0.4); 1.852 (0.4); 1.821 (0.4); 1.743 (1.2); 1.678 (0.5); 1.671 (0.5); 1.625 (1.4); 1.532 (0.7); 1.511 (0.7); 1.463 (0.6); 1.453 (0.6); 1.433 (0.6); 1.416 (0.6); 1.367 (0.9); 1.349 (1.1); 1.297 (3.4); 1.257 (4.8); 1.230 (8.0); 1.171 (2.8); 1.146 (4.1); 1.136 (4.0); 1.088 (1.2); 1.065 (1.0); 1.042 (0.9); 1.036 (0.9); 0.981 (0.6); 0.943 (0.6); 0.928 (0.7); 0.863 (3.1); 0.755 (0.5); 0.724 (0.4); 0.701 (0.4); 0.145 (0.9); 0.123 (0.4); 0.105 (0.5); 0.095 (0.6); −0.001 (131.7); −0.150 (1.2); −0.190 (0.4); −0.201 (0.4)

6-(1H-Pyrazol-1-yl)-2-(pyridin-3-yl)[1,3]thiazolo[4,5-b]pyridine (27)

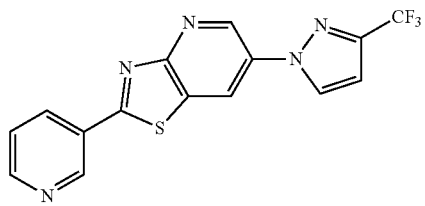 [SMILES: FC(F)(F)c1ccn(-c2cnc3nc(-c4cccnc4)sc3c2)n1]

Under argon, 300.0 mg (1.0 mmol) of 6-bromo-2-(pyridin-3-yl)[1,3]thiazolo[4,5-b]pyridine (I-a-1), 1.4 g (10.3 mmol) of 3-(trifluoromethyl)-1H-pyrazole and 147 mg (1.0 mmol) of copper(I) oxide were weighed into a reaction vessel, and 15.0 g of pyridine were added. The mixture was heated under argon at 90° C. overnight. Subsequently, a further 300 mg (1.0 mmol) of 6-bromo-2-(pyridin-3-yl)[1,3]thiazolo[4,5-b]pyridine (II-1) and 440 mg (3.0 mmol) of copper(I) oxide were added and the mixture was heated at 115° C. for a further 7 hours. The cooled mixture was then concentrated under reduced pressure. Purification was by chromatography by MPLC (at first water/acetonitrile eluent gradient; then for enriched fraction separation by petroleum ether/acetone eluent gradient). This gave 20.0 mg (82% purity, 4.6% of theory) of the title compound (27).

1H-NMR (601.6 MHz, CD3CN): δ=9.373 (4.7); 9.355 (0.8); 9.156 (8.3); 9.151 (8.5); 8.877 (8.9); 8.873 (8.7); 8.789 (3.3); 8.782 (3.4); 8.734 (0.6); 8.729 (0.6); 8.511 (2.6); 8.508 (3.8); 8.505 (2.6); 8.498 (3.3); 8.495 (3.9); 8.492 (3.0); 8.488 (1.3); 8.485 (1.1); 8.476 (0.6); 8.385 (5.8); 8.383 (5.8); 7.585 (3.2); 7.577 (3.3); 7.572 (3.3); 7.564 (3.3); 7.545 (0.5); 7.466 (0.6); 7.452 (1.5); 7.446 (0.9); 7.441 (0.7); 7.433 (0.7); 7.238 (0.5); 7.234 (0.4); 7.224 (0.4); 7.220 (0.4); 6.953 (6.6); 6.949 (6.5); 5.448 (0.7); 2.828 (1.2); 2.748 (0.6); 2.575 (2.2); 2.563 (2.3); 2.501 (0.5); 2.172 (9.1); 2.107 (5.6); 2.087 (3.1); 2.076 (2.7); 2.059 (3.2); 2.055 (4.1); 2.051 (5.1); 2.047 (3.9); 2.043 (2.7); 1.965 (67.2); 1.957 (37.4); 1.952 (51.3); 1.949 (253.4); 1.945 (433.6); 1.940 (624.6); 1.936 (441.3); 1.932 (228.3); 1.916 (4.5); 1.883 (1.7); 1.850 (1.1); 1.842 (1.1); 1.834 (2.0); 1.830 (3.1); 1.826 (4.2); 1.822 (3.0); 1.818 (1.8); 1.567 (0.5); 1.434 (0.5); 1.340 (13.1); 1.319 (2.0); 1.308 (2.5); 1.298 (2.3); 1.285 (16.0); 1.269 (9.4); 1.248 (1.2); 1.227 (1.0); 1.217 (1.0); 1.206 (1.0); 1.184 (1.3); 1.173 (1.2); 1.153 (0.8); 1.134 (0.8); 1.112 (0.7); 1.083 (0.8); 1.071 (0.7); 1.048 (0.6); 1.038 (0.6); 1.022 (4.4); 1.010 (8.3); 0.999 (4.3); 0.914 (0.7); 0.893 (1.2); 0.882 (2.1); 0.870 (1.5); 0.844 (1.3); 0.000 (2.8)

4,5-Dimethyl-2-[2-(pyridin-3-yl)[1,3]thiazolo[4,5-b]pyridin-6-yl]-2,4-dihydro-3H-1,2,4-triazol-3-one (30)

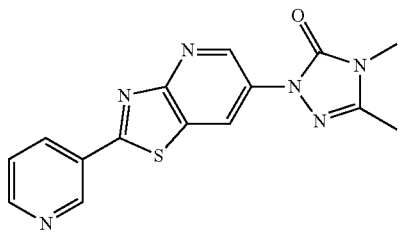 [SMILES: Cc1nn(-c2cnc3nc(-c4cccnc4)sc3c2)c(=O)n1C]

Under argon, 250 mg (0.86 mmol) of 6-bromo-2-(pyridin-3-yl)[1,3]thiazolo[4,5-b]pyridine (I-a-1), 136 mg (1.20 mmol) of 4,5-dimethyl-2,4-dihydro-3H-1,2,4-triazol-3-one, 16 mg (0.09 mmol) of copper(I) iodide, 355 mg (2.57 mmol) of potassium carbonate and 43 mg (0.26 mmol) of potassium iodide were initially charged in 5 ml of dioxane and the vessel was flooded with argon. Subsequently, 24 mg (0.17 mmol) of trans-N,N'-dimethylcyclohexane-1,2-diamine (racemic) were added, and the reaction vessel was sealed and stirred at 130° C. overnight. The cooled mixture was then diluted with 5 ml of ethyl acetate and filtered through Celite, and the filtrate was concentrated under reduced pressure. Purification was by chromatography by means of MPLC (eluent: water/acetonitrile). This gave 6.0 mg (90.0% purity, 1.95% of theory) of the title compound (30).

1H-NMR (400.0 MHz, d$_6$-DMSO): δ=9.336 (0.6); 9.317 (2.7); 9.310 (3.0); 9.307 (3.9); 9.300 (3.8); 9.119 (3.3); 9.113 (3.3); 8.808 (2.1); 8.800 (2.2); 8.796 (2.0); 8.712 (0.4); 8.543 (0.4); 8.522 (1.4); 8.518 (1.8); 8.512 (1.4); 8.502 (1.4); 8.497 (1.6); 8.493 (1.2); 7.673 (1.3); 7.661 (1.6); 7.655 (1.5); 7.643 (1.3); 3.556 (0.4); 3.322 (46.2); 3.255 (17.4); 3.177 (1.4); 3.141 (0.4); 3.127 (0.6); 3.122 (0.5); 3.076 (0.3); 3.060 (2.0); 2.755 (0.3); 2.736 (0.4); 2.728 (0.5); 2.670 (2.4); 2.666 (2.1); 2.505 (269.8); 2.501 (349.1); 2.497 (274.9); 2.356 (0.9); 2.338 (16.0); 2.250 (1.0); 2.227 (0.7); 2.119 (1.8); 1.234 (0.5); 0.883 (0.4); 0.000 (50.2)

4,5-Dimethyl-2-[2-(pyridin-3-yl)[1,3]thiazolo[4,5-b]pyridin-6-yl]-2,4-dihydro-3H-1,2,4-triazole-3-thione (31)

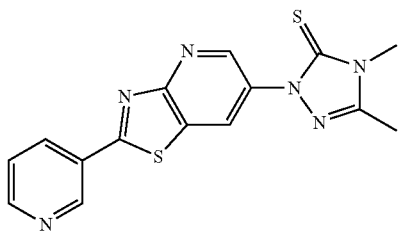 [SMILES: Cc1nn(-c2cnc3nc(-c4cccnc4)sc3c2)c(=S)n1C]

Under argon, 250 mg (0.86 mmol) of 6-bromo-2-(pyridin-3-yl)[1,3]thiazolo[4,5-b]pyridine (I-a-1), 155 mg (1.20 mmol) of 4,5-dimethyl-2,4-dihydro-3H-1,2,4-triazole-3-thione, 16 mg (0.09 mmol) of copper(I) iodide, 355 mg (2.57 mmol) of potassium carbonate and 43 mg (0.26 mmol) of potassium iodide were initially charged in 5 ml of dioxane and the vessel was flooded with argon. Subsequently, 24 mg (0.17 mmol) of trans-N,N'-dimethylcyclohexane-1,2-diamine (racemic) were added, and the reaction vessel was sealed and stirred at 130° C. overnight. The cooled mixture was then diluted with 5 ml of ethyl acetate and filtered through Celite, and the filtrate was concentrated under reduced pressure. Purification was by chromatography by means of MPLC (eluent: water/acetonitrile). This gave 4.0 mg (90.0% purity, 1.24% of theory) of the title compound (31).

1H-NMR (400.0 MHz, d$_6$-DMSO): δ=9.318 (0.6); 8.816 (0.4); 8.806 (0.4); 8.701 (0.7); 8.695 (1.0); 8.668 (0.9); 8.662 (0.8); 8.524 (0.4); 8.504 (0.4); 7.669 (0.4); 7.657 (0.4); 7.649 (0.4); 3.557 (4.4); 3.387 (0.7); 3.319 (4.7); 2.506 (37.0); 2.501 (51.1); 2.497 (42.5); 2.406 (4.4); 2.328 (0.3); 2.291 (0.5); 1.158 (2.3); 1.069 (16.0); 0.000 (7.1); −0.002 (4.9)

4-Methyl-2-[2-(pyridin-3-yl)[1,3]thiazolo[4,5-b]pyridin-6-yl]-1,2,4-triazine-3,5(2H,4H)-dione (39)

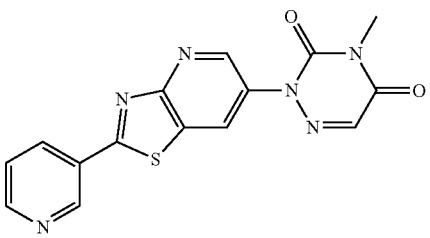 [SMILES: Cn1c(=O)cnn(-c2cnc3nc(-c4cccnc4)sc3c2)c1=O]

Under argon, 200 mg (0.69 mmol) of 6-bromo-2-(pyridin-3-yl)[1,3]thiazolo[4,5-b]pyridine (I-a-1), 122 mg (0.96 mmol) of 4-methyl-1,2,4-triazine-3,5(2H,4H)-dione, 13 mg (0.07 mmol) of copper(I) iodide, 284 mg (2.05 mmol) of potassium carbonate and 34 mg (0.21 mmol) of potassium iodide were initially charged in 5 ml of dioxane and the vessel was flooded with argon. Subsequently, 19 mg (0.14 mmol) of trans-N,N'-dimethylcyclohexane-1,2-diamine (racemic) were added, and the reaction vessel was sealed and stirred at 130° C. overnight. The cooled mixture was diluted with 5 ml of ethyl acetate and filtered through Celite, and the filtrate was concentrated under reduced pressure. Purification was by chromatography by means of MPLC (eluent: water/acetonitrile). This gave 8.0 mg (88.0% purity, 3.04% of theory) of the title compound (39).

1H-NMR (400.0 MHz, d$_6$-DMSO): δ=9.356 (8.6); 8.902 (8.8); 8.897 (11.6); 8.877 (11.6); 8.871 (8.2); 8.834 (6.1); 8.823 (6.3); 8.763 (1.1); 8.755 (1.0); 8.731 (0.9); 8.711 (0.9); 8.561 (5.1); 8.542 (5.7); 8.313 (0.5); 8.177 (0.4); 7.953 (1.0); 7.879 (16.0); 7.692 (4.3); 7.681 (5.2); 7.673 (4.7); 7.661 (4.5); 7.647 (0.9); 7.550 (0.8); 7.539 (0.7); 7.529 (0.7); 7.517 (0.6); 5.308 (0.4); 3.432 (0.6); 3.320 (260.1); 3.256 (48.0); 3.190 (0.5); 3.153 (0.4); 3.076 (0.3); 2.995 (3.2); 2.891 (4.8); 2.732 (4.6); 2.711 (1.2); 2.671 (2.4); 2.645 (0.4); 2.630 (0.5); 2.541 (215.4); 2.502 (389.5); 2.368 (2.0); 2.329 (3.0); 2.295 (0.8); 2.277 (0.7); 2.243 (0.6); 2.220 (0.7); 2.200 (0.6); 2.189 (1.2); 2.173 (0.6); 2.131 (0.6); 2.117 (0.9); 2.105 (0.7); 2.086 (0.6); 2.073 (0.6); 2.036 (0.6); 2.005 (0.5); 1.997 (0.5); 1.990 (0.5); 1.980 (0.5); 1.942 (0.5); 1.909 (5.1); 1.840 (0.9); 1.816 (0.4); 1.809 (0.4); 1.762 (0.4); 1.754 (0.4); 1.722 (0.3); 1.704 (0.4); 1.673 (0.3); 1.621 (0.3); 1.610 (0.4); 1.605 (0.4); 1.603 (0.4); 1.585 (0.4); 1.574 (0.4); 1.536 (0.5); 1.514 (0.6); 1.507 (0.6); 1.500 (0.6); 1.490 (0.6); 1.466 (0.7); 1.458 (0.6); 1.386 (1.4); 1.380 (1.4); 1.347 (1.8); 1.335 (1.8); 1.298 (1.7); 1.259 (1.7); 1.234 (2.6); 1.201 (1.3); 1.141 (1.4); 1.085 (0.5); 1.070 (0.6); 1.054 (0.5); 1.045 (0.5); 1.035 (0.5); 0.988 (0.5); 0.968 (0.4); 0.922 (0.3); 0.892 (0.4); 0.864 (0.6); 0.852 (0.9); 0.830 (1.3); 0.756 (0.5); 0.726 (0.3); 0.000 (43.1)

Synthesis of Compounds of the Formula (I) by Method G

Methyl 2-(pyridin-3-yl)[1,3]thiazolo[4,5-b]pyridine-6-carboxylate (I-j-1)

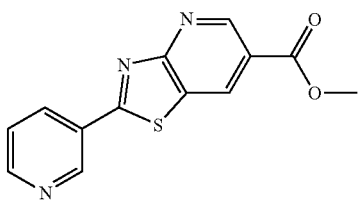 [SMILES: COC(=O)c1cnc2nc(-c3cccnc3)sc2c1]

To a mixture of 10.8 g (36.97 mmol) of 6-bromo-2-(pyridin-3-yl)[1,3]thiazolo[4,5-b]pyridine (I-a-1) in 200 ml of THF, 100 ml of DMF and 100 ml of methanol were added 11.22 g (110.91 mmol) of triethylamine and 5.41 g (7.39 mmol) of [1,1′-bis(diphenylphosphino)ferrocene]dichloropalladium(II). Carbon monoxide was introduced into the solution and the mixture was stirred at 70° C. and 45 psi CO pressure for 16 hours. Subsequently, the mixture was filtered and concentrated under reduced pressure. Purification was by chromatography by means of MPLC (eluent gradient: petroleum ether/ethyl acetate). This gave 7.50 g of the target compound (I-j-1), which was converted further to amides without further purification. For this purpose, a purity of 100% was assumed.

LC-MS: m/z 272 [M+H$^+$]

Methyl 2-(5-fluoropyridin-3-yl)[1,3]thiazolo[4,5-b]pyridine-6-carboxylate (I-j-2)

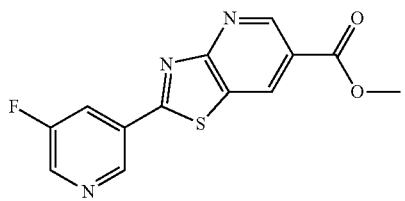 [SMILES: COC(=O)c1cnc2nc(-c3cncc(F)c3)sc2c1]

The preparation was effected in analogy to the synthesis of (I-j-1), except proceeding from 3-(chlorocarbonyl)-5-fluoropyridinium chloride in Method A, Step 1.

LC-MS: m/z 290 [M+H$^+$]

N-[2-(Methylsulphanyl)ethyl]-2-(pyridin-3-yl)[1,3]thiazolo[4,5-b]pyridine-6-carboxamide (52)

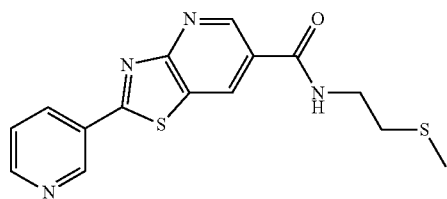 [SMILES: CSCCNC(=O)c1cnc2nc(-c3cccnc3)sc2c1]

To a solution of 300 mg (1.11 mmol, assumed purity 100%) of methyl 2-(pyridin-3-yl)[1,3]thiazolo[4,5-b]pyridine-6-carboxylate (I-j-1) in 8 ml of THF were added 1.2 molar equivalents (eq.) of potassium trimethylsilanolate. The mixture was stirred at 30° C. for another 16 hours and then concentrated under reduced pressure. The residue was taken up in 5 ml of DMF, and 1.2 molar equivalents (eq.) of 2-(7-aza-1H-benzotriazol-1-yl)-1,1,3,3-tetramethyluronium hexafluorophosphate (HATU) and 3 molar equivalents (eq.) of diisopropylethylamine were added. The mixture was stirred at 30° C. for 30 minutes. Subsequently, 121.4 mg (1.33 mmol, 1.2 eq.) of 2-(methylsulphanyl)ethanamine were added and the mixture was stirred at 30° C. for another 16 hours. Thereafter, the reaction mixture was concentrated under reduced pressure. Purification was by chromatography by means of MPLC. This gave 49.2 mg (95.4% purity, 12.8% of theory) of the title compound (52).

1H-NMR (400.0 MHz, d$_6$-DMSO): δ=9.365 (1.2); 9.153 (2.3); 9.148 (2.8); 9.101 (2.7); 9.096 (2.4); 8.981 (0.5); 8.967 (1.0); 8.953 (0.5); 8.843 (0.9); 8.831 (0.8); 8.574 (0.7); 8.568 (1.0); 8.564 (0.7); 8.554 (0.7); 8.548 (1.0); 8.544 (0.8); 7.695 (0.8); 7.683 (0.8); 7.676 (0.8); 7.664 (0.8); 3.902 (4.0); 3.556 (0.8); 3.540 (1.6); 3.522 (1.6); 3.507 (0.9); 3.356 (130.8); 3.349 (200.4); 2.724 (1.7); 2.706 (2.5); 2.689 (1.6); 2.678 (0.4); 2.673 (0.5); 2.669 (0.3); 2.526 (1.2); 2.513 (24.8); 2.509 (53.4); 2.504 (76.2); 2.500 (58.4); 2.495 (28.7); 2.331 (0.4); 2.326 (0.3); 2.128 (16.0); 0.000 (2.5)

N-[2-(Methylsulphonyl)ethyl]-2-(pyridin-3-yl)[1,3]thiazolo[4,5-b]pyridine-6-carboxamide (54)

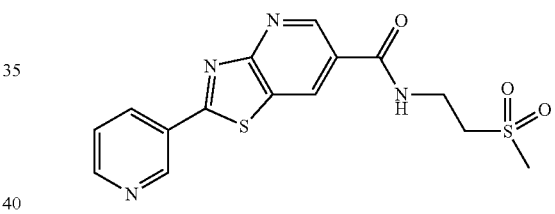

To a solution of 300 mg (1.11 mmol, assumed purity 100%) of methyl 2-(pyridin-3-yl)[1,3]thiazolo[4,5-b]pyridine-6-carboxylate (I-j-1) in 8 ml of THF were added 1.2 molar equivalents (eq.) of potassium trimethylsilanolate. The mixture was stirred at 30° C. for another 16 hours and then concentrated under reduced pressure. The residue was taken up in 5 ml of DMF, and 1.2 molar equivalents (eq.) of 2-(7-aza-1H-benzotriazol-1-yl)-1,1,3,3-tetramethyluronium hexafluorophosphate (HATU) and 3 molar equivalents (eq.) of diisopropylethylamine were added. The mixture was stirred at 30° C. for 30 minutes. Subsequently, 163.8 mg (1.33 mmol, 1.2 eq.) of 2-(methylsulphonyl)ethanamine were added and the mixture was stirred at 30° C. for another 16 hours. Thereafter, the reaction mixture was concentrated under reduced pressure. Purification was by chromatography by means of MPLC. This gave 74.3 mg (97.6% purity, 18.0% of theory) of the title compound (54).

1H-NMR (400.0 MHz, d$_6$-DMSO): δ=9.372 (1.9); 9.152 (3.4); 9.147 (4.5); 9.125 (1.7); 9.115 (4.8); 9.109 (4.2); 8.849 (1.3); 8.838 (1.3); 8.576 (1.0); 8.571 (1.4); 8.567 (1.1); 8.556 (1.1); 8.551 (1.5); 8.547 (1.1); 7.698 (1.2); 7.686 (1.2); 7.678 (1.2); 7.666 (1.1); 3.955 (0.6); 3.902 (8.0); 3.777 (0.9); 3.760 (2.4); 3.745 (2.5); 3.729 (1.2); 3.455 (2.2); 3.438 (4.0); 3.421 (1.9); 3.344 (186.2); 3.336 (242.0); 3.176 (0.6); 3.162 (0.6); 3.075 (16.0); 2.677 (0.6); 2.672 (0.8); 2.668 (0.6); 2.543 (0.6); 2.526 (2.1); 2.512 (47.9);

2.508 (101.9); 2.503 (144.1); 2.499 (111.8); 2.334 (0.6); 2.330 (0.8); 2.325 (0.6); 0.000 (3.8)

2-(5-Fluoropyridin-3-yl)-N-{3-[(trifluoromethyl)sulphanyl]phenyl}[1,3]thiazolo[4,5-b]pyridine-6-carboxamide (57)

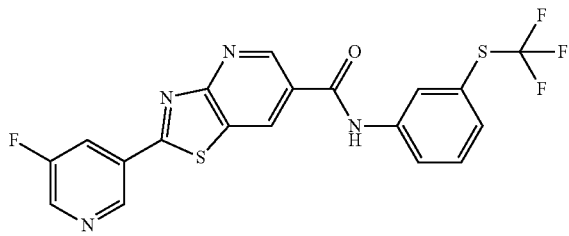 [SMILES: O=C(Nc1cccc(SC(F)(F)F)c1)c1cnc2nc(-c3cncc(F)c3)sc2c1]

To a solution of 300 mg (1.11 mmol, assumed purity 100%) of methyl 2-(5-fluoropyridin-3-yl)[1,3]thiazolo[4,5-b]pyridine-6-carboxylate (I-j-2) in 8 ml of THF were added 1.2 molar equivalents (eq.) of potassium trimethylsilanolate. The mixture was stirred at 30° C. for another 16 hours and then concentrated under reduced pressure. The residue was taken up in 5 ml of DMF, and 1.2 molar equivalents (eq.) of 2-(7-aza-1H-benzotriazol-1-yl)-1,1,3,3-tetramethyluronium hexafluorophosphate (HATU) and 3 molar equivalents (eq.) of diisopropylethylamine were added. The mixture was stirred at 30° C. for 30 minutes. Subsequently, 256.9 mg (1.33 mmol, 1.2 eq.) of 3-[(trifluoromethyl)sulphanyl]aniline were added and the mixture was stirred at 30° C. for another 16 hours. Thereafter, the reaction mixture was concentrated under reduced pressure. Purification was by chromatography by means of MPLC. This gave 41.3 mg (99.5% purity, 8.2% of theory) of the title compound (57).

1H-NMR (400.0 MHz, d$_6$-DMSO): δ=10.872 (8.7); 9.298 (6.5); 9.293 (10.8); 9.277 (16.0); 8.887 (6.9); 8.880 (7.1); 8.555 (2.2); 8.549 (3.3); 8.544 (2.4); 8.532 (2.3); 8.525 (3.3); 8.521 (2.3); 8.308 (0.3); 8.273 (7.1); 8.025 (3.4); 8.004 (3.7); 7.605 (3.2); 7.585 (7.0); 7.565 (4.6); 7.509 (5.1); 7.490 (3.2); 3.902 (15.3); 3.705 (0.4); 3.657 (0.4); 3.603 (0.6); 3.508 (1.4); 3.361 (1440.1); 3.174 (0.6); 2.678 (1.6); 2.674 (2.2); 2.670 (1.6); 2.582 (0.4); 2.544 (1.6); 2.509 (266.9); 2.505 (367.0); 2.500 (281.7); 2.336 (1.5); 2.331 (2.0); 1.233 (0.6); 0.000 (7.6)

2-(5-Fluoropyridin-3-yl)-N-{3-[(trifluoromethyl)sulphinyl]phenyl}[1,3]thiazolo[4,5-b]pyridine-6-carboxamide (58)

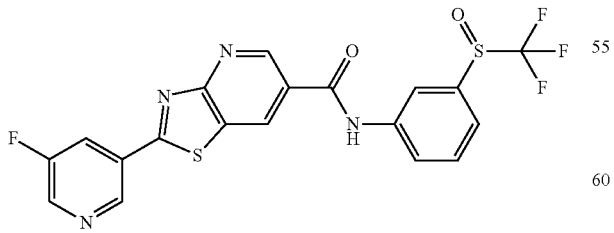

To a solution of 300 mg (0.67 mmol) of 2-(5-fluoropyridin-3-yl)-N-{3-[(trifluoromethyl)sulphanyl]phenyl}[1,3]thiazolo[4,5-b]pyridine-6-carboxamide (57) in 10 ml of dichloromethane were added 2 molar equivalents (222.5 mg, 1.3 mmol) of meta-chloroperbenzoic acid at 0° C. The reaction mixture was stirred at 20° C. for another 16 hours and then concentrated under reduced pressure. Purification was by chromatography by means of MPLC. This gave 17.4 mg (95.5% purity, 5.3% of theory) of the title compound (58).

1H-NMR (601.6 MHz, d$_6$-DMSO): δ=11.037 (1.3); 9.317 (7.8); 9.313 (14.4); 9.306 (16.0); 9.302 (8.6); 9.278 (8.6); 8.887 (8.8); 8.883 (10.4); 8.833 (0.9); 8.829 (0.8); 8.825 (0.9); 8.554 (2.8); 8.551 (3.7); 8.547 (2.8); 8.539 (3.0); 8.536 (3.8); 8.532 (2.6); 8.452 (8.0); 8.270 (1.6); 8.189 (0.8); 8.176 (0.9); 8.160 (4.1); 8.147 (4.3); 8.145 (4.3); 8.022 (0.8); 8.007 (0.8); 7.760 (4.0); 7.746 (8.2); 7.733 (4.8); 7.646 (5.2); 7.634 (4.1); 7.596 (0.7); 7.583 (1.5); 7.569 (0.9); 7.505 (1.0); 7.493 (0.8); 3.322 (411.9); 2.614 (2.3); 2.611 (1.7); 2.541 (1.0); 2.523 (4.5); 2.520 (5.8); 2.517 (6.8); 2.505 (256.7); 2.502 (334.0); 2.499 (250.5); 2.386 (2.0); 1.231 (0.6); 0.000 (7.3)

Synthesis of Compounds of the Formula (I) by Method H 2-(Pyridin-3-yl)[1,3]thiazolo[4,5-b]pyridin-6-amine (I-s-1)

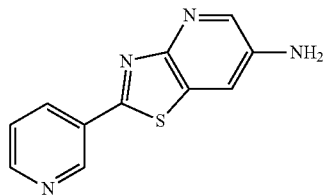 [SMILES: Nc1cnc2nc(-c3cccnc3)sc2c1]

To a stirred solution of 8.0 g (31 mmol) of 6-nitro-2-(pyridin-3-yl)[1,3]thiazolo[4,5-b]pyridine (I-r-1) (prepared analogously to the synthesis for compound (I-a-1), proceeding from 3-bromo-5-nitropyridin-2-amine in Method A, Step 1) in 300 ml of THF were added 1.6 g of Pd/C (10 wt %) under nitrogen at 30° C. The mixture was stirred at 50° C. under hydrogen (50 psi) for 48 hours. Subsequently, the reaction mixture was filtered and the filtrate was concentrated under reduced pressure. This gave 5.0 g of 2-(pyridin-3-yl)[1,3]thiazolo[4,5-b]pyridin-6-amine (I-s-1) as a crude product, which was converted further to amides without further purification. For this purpose, a purity of 100% was assumed.

LC-MS: m/z 229 [M+H$^+$]

2-(5-Fluoropyridin-3-yl)[1,3]thiazolo[4,5-b]pyridin-6-amine (I-s-2)

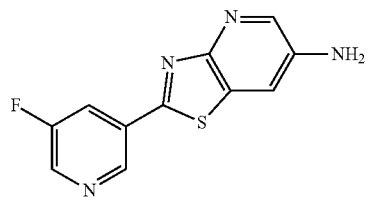 [SMILES: Nc1cnc2nc(-c3cncc(F)c3)sc2c1]

The preparation was effected in analogy to the synthesis of (I-s-1), except proceeding from 3-(chlorocarbonyl)-5-fluoropyridinium chloride in Method A, Step 1.

LC-MS: m/z 247 [M+H$^+$]

N-Methyl-N-[2-(pyridin-3-yl)[1,3]thiazolo[4,5-b]pyridin-6-yl]propanamide (59)

Step 1: N-[2-(Pyridin-3-yl)[1,3]thiazolo[4,5-b]pyridin-6-yl]propanamide

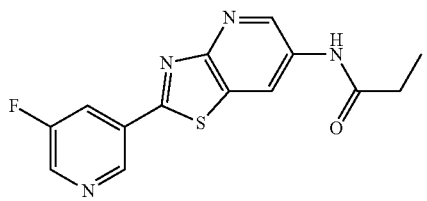 [SMILES: CCC(=O)Nc1cnc2nc(-c3cncc(F)c3)sc2c1]

To a mixture of 300 mg (1.31 mmol) of 2-(pyridin-3-yl)[1,3]thiazolo[4,5-b]pyridin-6-amine (I-s-2) and 398 mg (3.93 mmol) of triethylamine in 5 ml of dichloromethane were added 121.6 mg (1.31 mmol) of propanoyl chloride. The mixture was stirred at 30° C. for 16 hours and then concentrated under reduced pressure. Purification was by chromatography by means of MPLC (eluent gradient: petroleum ether/ethyl acetate). This gave 300 mg (80.5% of theory, assumed purity 100%) of the title compound N-[2-(pyridin-3-yl)[1,3]thiazolo[4,5-b]pyridin-6-yl]propanamide, which was converted further directly.

Step 2: N-Methyl-N-[2-(pyridin-3-yl)[1,3]thiazolo[4,5-b]pyridin-6-yl]propanamide (59)

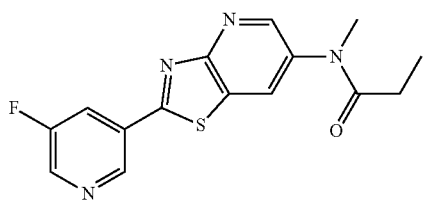 [SMILES: CCC(=O)N(C)c1cnc2nc(-c3cncc(F)c3)sc2c1]

172 mg (0.605 mmol) of N-[2-(pyridin-3-yl)-1,3-benzothiazol-6-yl]propanamide (Example 59, Step 1) were dissolved in 5 ml of THF and cooled to 0° C. Subsequently, 24.2 mg (0.605 mmol) of sodium hydride (60% suspension in paraffin) were added at 0° C. The mixture was stirred at this temperature for another 30 minutes and then 85.9 mg (0.605 mmol) of methyl iodide were added. The mixture was stirred at 30° C. for another 16 hours and then 1 ml of aqueous ammonium chloride solution was added at 0° C. After the mixture had been concentrated under reduced pressure, the residue was purified by chromatography by means of preparative HPLC. This gave 34.8 mg (99.9% purity, 19.3% of theory) of the title compound (59).

1H-NMR (400.0 MHz, $d_6$-DMSO): δ=9.231 (6.6); 8.861 (5.8); 8.854 (6.1); 8.761 (8.3); 8.508 (1.9); 8.503 (2.6); 8.485 (1.9); 8.480 (2.6); 8.475 (1.8); 3.902 (16.0); 3.508 (0.4); 3.342 (396.2); 3.338 (410.6); 3.176 (0.7); 3.164 (0.7); 2.677 (1.1); 2.672 (1.5); 2.668 (1.2); 2.548 (0.6); 2.525 (4.3); 2.512 (90.4); 2.508 (185.6); 2.503 (257.8); 2.499 (197.1); 2.335 (1.2); 2.330 (1.5); 2.325 (1.2); 2.199 (0.5); 2.143 (0.6); 2.130 (0.6); 2.112 (0.6); 2.074 (0.4); 1.249 (0.3); 1.235 (0.3); 0.969 (4.6); 0.008 (0.4); 0.000 (10.5)

Compounds of the formula (I) and also those not embraced by formula (I) are listed in the table below. The compounds not covered by the formula (I) also form part of the subject-matter of the invention.

The compounds I-a-1, I-j-1, I-j-2, I-s-1 and I-s-2 listed in the table also form part of the subject-matter of the invention.

TABLE 1

Compounds of the formula

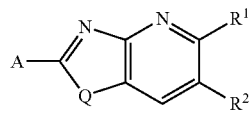

| Preparation method | Example No. | A | Q | R¹ | R² |
|---|---|---|---|---|---|
| B | 1 | 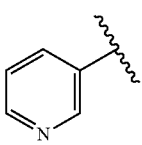 [SMILES: *c1cccnc1] | S | H | 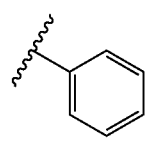 [SMILES: *c1ccccc1] |
| B | 2 | 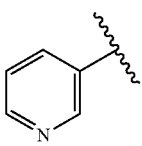 [SMILES: *c1cccnc1] | S | H | 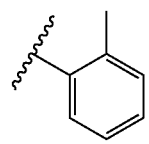 [SMILES: *c1ccccc1C] |

TABLE 1-continued
Compounds of the formula
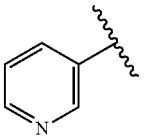
| Preparation method | Example No. | A | Q | R¹ | R² |
|---|---|---|---|---|---|
| B | 3 | 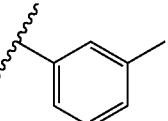 | S | H | 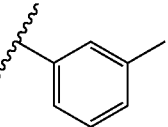 |
| B | 4 | 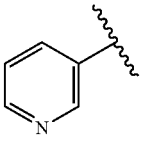 [SMILES: *c1cccnc1] | S | H | 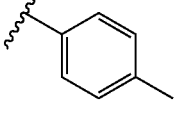 |
| B | 5 | 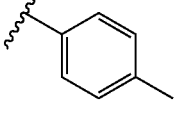 | S | H | 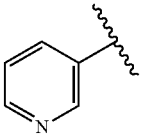 [SMILES: *c1cccnc1] |
| B | 6 | 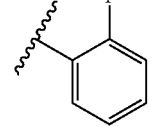 | S | H | 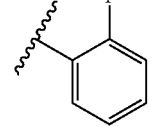 |
| B | 7 | 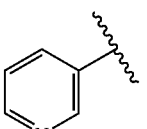 | S | H | 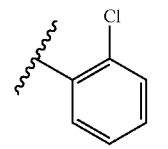 [SMILES: *c1ccccc1Cl] |
| B | 8 | 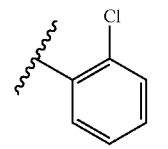 [SMILES: *c1ccccc1Cl] | S | H | 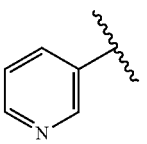 |
| B | 9 | 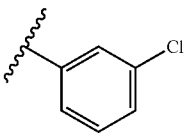 [SMILES: *c1cccc(Cl)c1] | S | H | 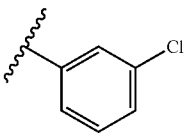 [SMILES: *c1cccc(Cl)c1] |
| B | 10 | 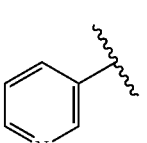 | S | H | 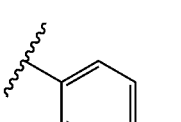 |
| B | 11 | 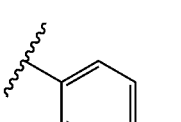 | S | H | 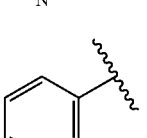 |

TABLE 1-continued
Compounds of the formula
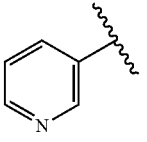 [SMILES: *c1cccnc1]
| Preparation method | Example No. | A | Q | R¹ | R² |
|---|---|---|---|---|---|
| I | 12 | 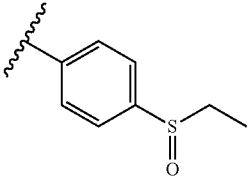 [SMILES: *c1ccc(S(=O)CC)cc1] | S | H | 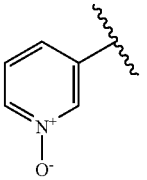 [SMILES: *c1ccc[n+]([O-])c1] |
| I | 13 | 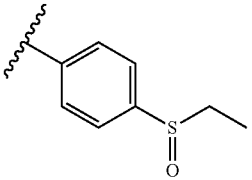 [SMILES: *c1ccc(S(=O)CC)cc1] | S | H | 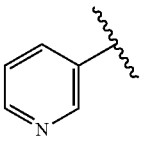 |
| B | 14 | 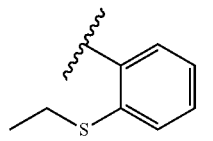 [SMILES: *c1ccccc1SCC] | S | H | 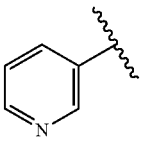 [SMILES: *c1cccnc1] |
| I | 15 | 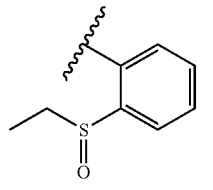 [SMILES: *c1ccccc1S(=O)CC] | S | H | 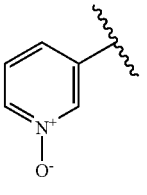 [SMILES: *c1ccc[n+]([O-])c1] |
| I | 16 | 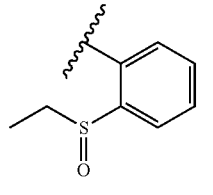 [SMILES: *c1ccccc1S(=O)CC] | S | H | 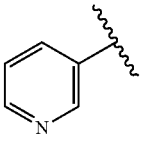 [SMILES: *c1cccnc1] |
| B | 17 | 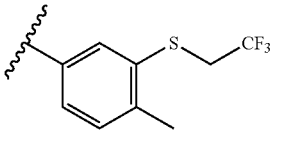 [SMILES: *c1ccc(C)c(SCC(F)(F)F)c1] | S | H | 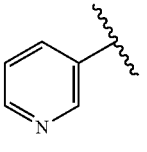 [SMILES: *c1cccnc1] |
| I | 18 | 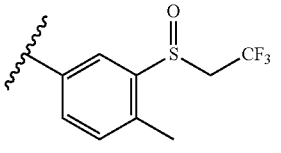 [SMILES: *c1ccc(C)c(S(=O)CC(F)(F)F)c1] | S | H | 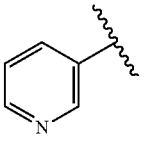 [SMILES: *c1cccnc1] |
| B | 19 | 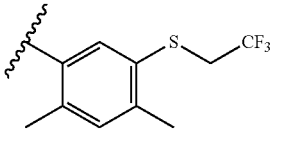 [SMILES: *c1cc(SCC(F)(F)F)c(C)cc1C] | S | H | |

TABLE 1-continued

Compounds of the formula

[Structure: A-oxazolo[5,4-b]pyridine with Q, R¹ at 5-position, R² at 6-position]

| Preparation method | Example No. | A | Q | R¹ | R² |
|---|---|---|---|---|---|
| I | 20 | 3-pyridyl | S | H | 2,5-dimethyl-4-(trifluoroethylsulfinyl)phenyl |
| I | 21 | 3-pyridyl N-oxide | S | H | 2,5-dimethyl-4-(trifluoroethylsulfinyl)phenyl |
| B | 22 | 3-pyridyl | S | H | 4-fluoro-2,5-dimethyl-...-(trifluoroethylthio)phenyl |
| I | 23 | 3-pyridyl | S | H | 4-fluoro-2-methyl-5-(trifluoroethylsulfinyl)phenyl |
| D | 24 | 3-pyridyl | S | H | NH-phenyl |
| D | 25 | 3-pyridyl | S | H | NH-(3-chlorophenyl) |
| E | 26 | 3-pyridyl | S | H | 1-pyrazolyl |
| E | 27 | 3-pyridyl | S | H | 3-(trifluoromethyl)-1-pyrazolyl |

TABLE 1-continued
Compounds of the formula
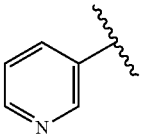
| Preparation method | Example No. | A | Q | R¹ | R² |
|---|---|---|---|---|---|
| E | 28 | 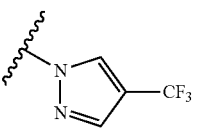 [SMILES: *n1cc(C(F)(F)F)cn1] | S | H | 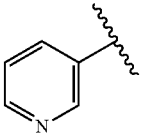 |
| E | 29 | 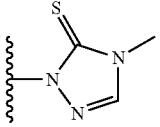 [SMILES: *n1ncn(C)c1=S] | S | H | 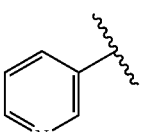 |
| E | 30 | 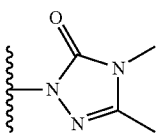 [SMILES: *n1nc(C)n(C)c1=O] | S | H | 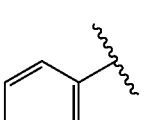 |
| E | 31 | 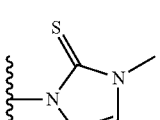 | S | H | 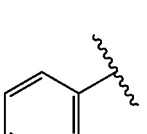 |
| E | 32 | 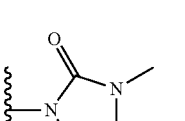 | S | H | 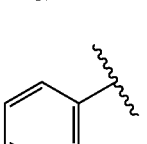 |
| E | 33 | 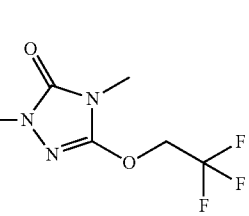 | S | H | 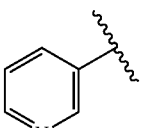 |
| E | 34 | 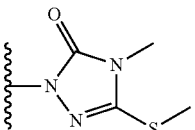 | S | H | 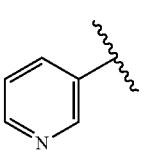 |
| E | 35 | 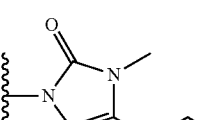 | S | H | |

TABLE 1-continued

Compounds of the formula

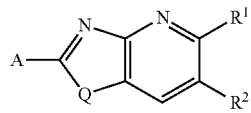

| Preparation method | Example No. | A | Q | R¹ | R² |
|---|---|---|---|---|---|
| E | 36 | 3-pyridyl | S | H | 4-methyl-5-oxo-3-((2,2,2-trifluoroethyl)thio)-4,5-dihydro-1H-1,2,4-triazol-1-yl |
| E | 37 | 3-pyridyl | S | H | 4-methyl-3-((methylthio)methyl)-5-oxo-4,5-dihydro-1H-1,2,4-triazol-1-yl |
| E | 38 | 3-pyridyl | S | H | 3,4-dimethyl-3,5-dioxo-1,2,4-triazolidin-1-yl |
| E | 39 | 3-pyridyl | S | H | 4-methyl-3,5-dioxo-4,5-dihydro-1,2,4-triazin-2(3H)-yl |
| G | 40 | 3-pyridyl | S | H | methylcarbamoyl |
| G | 41 | 5-fluoro-3-pyridyl | S | H | methylcarbamoyl |
| G | 42 | 5-fluoro-3-pyridyl | S | H | dimethylcarbamoyl |
| G | 43 | 3-pyridyl | S | H | dimethylcarbamoyl |

TABLE 1-continued

Compounds of the formula

[Structure: A-oxazolo[5,4-b]pyridine with Q, R¹, R²]

| Preparation method | Example No. | A | Q | R¹ | R² |
|---|---|---|---|---|---|
| G | 44 | 3-pyridyl | S | H | -C(O)N(CH₃)(CH₂CH₃) |
| G | 45 | 5-fluoro-3-pyridyl | S | H | -C(O)N(CH₃)(CH₂CH₃) |
| G | 46 | 3-pyridyl | S | H | -C(O)NH-CH₂-CF₃ |
| G | 47 | 5-fluoro-3-pyridyl | S | H | -C(O)NH-CH₂-CF₃ |
| G | 48 | 3-pyridyl | S | H | -C(O)N(CH₃)(OCH₃) |
| G | 49 | 5-fluoro-3-pyridyl | S | H | -C(O)N(CH₃)(OCH₃) |
| G | 50 | 3-pyridyl | S | H | -C(O)NH-CH₂-CF₂CH₃ |
| G | 51 | 5-fluoro-3-pyridyl | S | H | -C(O)NH-CH₂-CF₂CH₃ |

TABLE 1-continued

Compounds of the formula

[Structure: 2-A-oxazolo[5,4-b]pyridine with R¹ at 5-position, R² at 6-position, Q at position shown]

| Preparation method | Example No. | A | Q | R¹ | R² |
|---|---|---|---|---|---|
| G | 52 | pyridin-3-yl | S | H | -C(O)NH-CH₂CH₂-S-CH₃ |
| G | 53 | 5-fluoropyridin-3-yl | S | H | -C(O)NH-CH₂CH₂-S-CH₃ |
| G | 54 | pyridin-3-yl | S | H | -C(O)NH-CH₂CH₂-S(O)₂-CH₃ |
| G | 55 | 5-fluoropyridin-3-yl | S | H | -C(O)NH-CH₂CH₂-S(O)₂-CH₃ |
| G | 56 | pyridin-3-yl | S | H | -C(O)NH-(3-(SCF₃)phenyl) |
| G | 57 | 5-fluoropyridin-3-yl | S | H | -C(O)NH-(3-(SCF₃)phenyl) |
| I | 58 | 5-fluoropyridin-3-yl | S | H | -C(O)NH-(3-(S(O)CF₃)phenyl) |
| H2 | 59 | 5-fluoropyridin-3-yl | S | H | -C(O)-N(CH₃)-CH₂CH₃ |

TABLE 1-continued
Compounds of the formula
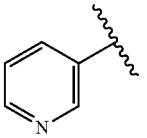
| Preparation method | Example No. | A | Q | R¹ | R² |
|---|---|---|---|---|---|
| A | I-a-1 | 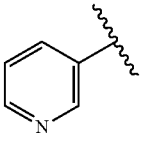 [SMILES: *c1cccnc1] | S | H | Br |
| G | I-j-1 | 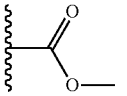 | S | H | 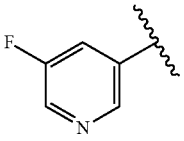 |
| G | I-j-2 | 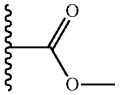 | S | H | 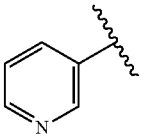 [SMILES: *c1cccnc1] |
| H2 | I-s-1 |  | S | H | —NH₂ |
| H2 | I-s-2 | 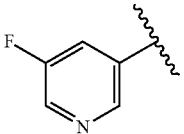 | S | H | —NH₂ |
TABLE 2
Analytical data for the compounds reported
| Ex. No. | LogP[a] | logP[b] | 1H-NMR [σ (ppm)] or LC-MS [m/z] |
|---|---|---|---|
| 1 | 2.47 | 2.56 | $^1$H-NMR (400.0 MHz, d$_6$-DMSO): δ = 9.366 (4.5); 9.361 (4.6); 9.084 (7.0); 9.079 (8.7); 9.029 (7.7); 9.023 (6.6); 8.830 (3.7); 8.826 (4.1); 8.818 (4.0); 8.814 (4.1); 8.574 (2.2); 8.570 (2.9); 8.564 (2.3); 8.554 (2.4); 8.549 (3.1); 8.544 (2.4); 8.316 (0.3); 7.875 (5.1); 7.871 (7.3); 7.853 (7.7); 7.692 (2.8); 7.690 (2.9); 7.678 (2.9); 7.672 (2.8); 7.670 (2.8); 7.660 (2.7); 7.658 (2.8); 7.585 (3.8); 7.567 (8.4); 7.547 (5.3); 7.495 (3.1); 7.492 (2.0); 7.481 (1.2); 7.476 (4.3); 7.471 (1.1); 7.458 (1.4); 3.762 (0.6); 3.569 (0.6); 3.351 (267.6); 3.349 (243.9); 3.340 (242.3); 3.335 (116.9); 2.682 (0.4); 2.677 (0.9); 2.673 (1.2); 2.668 (0.9); 2.526 (2.6); 2.521 (3.9); 2.513 (61.0); 2.508 (126.9); 2.504 (172.8); 2.499 (131.6); 2.495 (67.2); 2.335 (0.8); 2.331 (1.2); 2.326 (0.8); 2.075 (16.0); 0.146 (0.5); 0.008 (3.7); 0.000 (122.8); −0.008 (5.0); −0.150 (0.5) |
| 2 | 2.76 | 2.8 | $^1$H-NMR (400.0 MHz, d$_6$-DMSO): δ = 9.366 (2.3); 9.361 (2.3); 8.833 (1.7); 8.829 (1.9); 8.821 (1.8); 8.817 (1.9); 8.753 (2.7); 8.748 (4.7); 8.735 (4.4); 8.730 (2.6); 8.573 (1.0); 8.569 (1.5); 8.564 (1.0); 8.553 (1.1); 8.549 (1.5); 8.544 (1.0); 7.693 (1.4); 7.681 (1.4); 7.673 (1.3); 7.661 (1.3); 7.404 (0.5); 7.393 (2.4); 7.390 (2.7); 7.383 (3.6); 7.376 (3.2); 7.369 (3.3); 7.362 |

TABLE 2-continued

Analytical data for the compounds reported

| Ex. No. | LogP[a] | logP[b] | 1H-NMR [σ (ppm)] or LC-MS [m/z] |
|---|---|---|---|
| | | | (4.8); 7.355 (1.5); 7.349 (1.1); 7.340 (0.4); 3.329 (15.8); 2.526 (0.8); 2.508 (33.3); 2.504 (44.1); 2.500 (33.0); 2.383 (0.4); 2.331 (0.4); 2.315 (16.0); 0.008 (1.8); 0.000 (50.9); −0.009 (2.0) |
| 3 | 2.91 | 2.95 | $^1$H-NMR (400.0 MHz, $d_6$-DMSO): δ = 9.362 (2.9); 9.357 (2.9); 9.066 (3.5); 9.060 (4.2); 9.008 (4.0); 9.003 (3.7); 8.824 (2.3); 8.815 (2.1); 8.812 (2.2); 8.563 (1.8); 8.559 (1.3); 8.548 (1.3); 8.543 (1.9); 8.539 (1.3); 7.688 (5.2); 7.676 (2.1); 7.668 (1.9); 7.656 (3.4); 7.636 (2.1); 7.463 (1.6); 7.444 (3.2); 7.425 (1.7); 7.297 (2.2); 7.279 (1.7); 3.346 (101.5); 3.339 (98.5); 2.673 (0.5); 2.508 (59.8); 2.504 (75.9); 2.500 (59.5); 2.424 (16.0); 2.330 (0.5); 2.076 (0.4); 0.000 (41.3) |
| 4 | 2.91 | 2.96 | $^1$H-NMR (400.0 MHz, $d_6$-DMSO): δ = 9.358 (3.1); 9.353 (3.2); 9.060 (4.6); 9.054 (5.4); 8.992 (5.5); 8.987 (4.9); 8.824 (2.4); 8.820 (2.7); 8.812 (2.5); 8.808 (2.7); 8.564 (1.4); 8.559 (2.0); 8.554 (1.5); 8.544 (1.5); 8.539 (2.1); 8.534 (1.5); 7.914 (1.2); 7.766 (5.5); 7.746 (6.3); 7.685 (2.1); 7.672 (2.0); 7.665 (2.1); 7.652 (1.8); 7.378 (5.1); 7.358 (4.6); 3.328 (39.8); 2.677 (0.4); 2.672 (0.6); 2.668 (0.5); 2.544 (0.3); 2.525 (1.8); 2.512 (34.6); 2.508 (69.0); 2.503 (91.4); 2.499 (69.9); 2.388 (16.0); 2.330 (0.7); 2.326 (0.5); 2.298 (1.2); 0.146 (0.5); 0.008 (3.8); 0.000 (98.0); −0.008 (4.7); −0.150 (0.5) |
| 5 | 2.51 | 2.54 | $^1$H-NMR (400.0 MHz, $d_6$-DMSO): δ = 9.373 (11.3); 9.369 (11.2); 9.367 (10.9); 8.952 (7.9); 8.947 (14.9); 8.943 (13.7); 8.933 (12.1); 8.928 (15.9); 8.923 (7.2); 8.837 (9.0); 8.833 (10.0); 8.825 (9.6); 8.821 (9.8); 8.582 (5.5); 8.578 (7.1); 8.577 (6.9); 8.573 (5.6); 8.562 (5.9); 8.558 (7.1); 8.557 (7.6); 8.553 (5.7); 8.318 (2.6); 8.189 (1.8); 8.091 (0.4); 8.071 (0.5); 7.998 (1.3); 7.758 (3.8); 7.754 (4.3); 7.738 (7.0); 7.734 (8.3); 7.718 (4.2); 7.714 (4.9); 7.697 (7.1); 7.695 (7.1); 7.684 (6.6); 7.683 (6.8); 7.677 (6.6); 7.675 (6.8); 7.664 (6.4); 7.663 (6.6); 7.570 (1.7); 7.566 (2.0); 7.557 (2.0); 7.552 (4.2); 7.548 (4.0); 7.540 (2.9); 7.535 (4.5); 7.532 (5.5); 7.527 (3.4); 7.518 (3.1); 7.514 (2.9); 7.454 (6.4); 7.436 (4.4); 7.433 (4.7); 7.426 (14.0); 7.407 (16.0); 7.389 (4.9); 7.386 (4.5); 7.321 (0.8); 7.318 (0.7); 7.308 (2.2); 7.249 (0.7); 7.229 (0.7); 7.152 (0.4); 7.075 (0.4); 6.600 (0.3); 5.162 (0.6); 4.497 (0.9); 4.482 (0.8); 4.038 (0.6); 4.020 (0.7); 3.397 (0.4); 3.328 (888.9); 3.295 (0.5); 3.005 (0.7); 2.987 (0.7); 2.676 (4.7); 2.671 (6.6); 2.667 (4.9); 2.663 (2.4); 2.525 (16.1); 2.520 (24.4); 2.511 (350.0); 2.507 (724.8); 2.502 (967.1); 2.498 (711.5); 2.493 (349.4); 2.403 (0.6); 2.374 (0.7); 2.338 (2.1); 2.334 (4.6); 2.329 (6.4); 2.325 (4.8); 2.320 (2.3); 1.989 (2.6); 1.355 (0.7); 1.260 (0.9); 1.249 (0.4); 1.242 (1.8); 1.234 (1.4); 1.224 (0.9); 1.212 (0.3); 1.193 (1.0); 1.175 (1.6); 1.157 (0.7); 0.000 (2.4) |
| 6 | 2.77 | 2.78 | $^1$H-NMR (400.0 MHz, $d_6$-DMSO): δ = 9.373 (8.3); 9.368 (8.3); 8.854 (12.7); 8.848 (16.0); 8.839 (6.8); 8.835 (7.3); 8.827 (7.2); 8.823 (7.4); 8.806 (15.3); 8.800 (12.6); 8.582 (3.8); 8.577 (5.2); 8.572 (4.0); 8.562 (4.2); 8.556 (5.6); 8.552 (4.1); 8.318 (0.5); 7.696 (5.5); 7.687 (8.6); 7.681 (5.0); 7.676 (10.0); 7.672 (4.5); 7.664 (11.9); 7.655 (1.3); 7.651 (0.7); 7.634 (0.7); 7.626 (5.0); 7.618 (3.6); 7.614 (6.6); 7.608 (4.5); 7.602 (8.0); 7.594 (1.3); 7.589 (0.6); 7.567 (0.5); 7.555 (0.6); 7.548 (2.3); 7.543 (1.4); 7.535 (12.8); 7.530 (7.4); 7.524 (10.0); 7.518 (6.5); 7.512 (9.2); 7.500 (1.3); 7.493 (0.5); 6.535 (1.3); 5.758 (0.8); 3.569 (0.4); 3.328 (120.3); 2.681 (0.6); 2.677 (1.2); 2.672 (1.6); 2.668 (1.2); 2.526 (4.2); 2.521 (6.4); 2.512 (87.3); 2.508 (178.1); 2.503 (238.6); 2.499 (179.7); 2.495 (92.4); 2.335 (1.2); 2.330 (1.6); 2.326 (1.2); 2.076 (0.4); 0.146 (1.3); 0.008 (9.3); 0.000 (278.6); −0.008 (12.8); −0.020 (0.7); −0.0256 (0.3); −0.0263 (0.3); −0.150 (1.3) |
| 7 | 2.98 | 3.01 | $^1$H-NMR (400.0 MHz, $d_6$-DMSO): δ = 9.374 (8.4); 9.368 (8.3); 9.117 (11.3); 9.111 (15.3); 9.084 (16.0); 9.078 (11.2); 8.834 (6.6); 8.830 (6.7); 8.822 (6.8); 8.818 (6.5); 8.582 (3.8); 8.577 (5.3); 8.572 (3.6); 8.562 (4.1); 8.557 (5.5); 8.552 (3.5); 8.317 (1.9); 7.969 (6.9); 7.964 (12.0); 7.960 (6.7); 7.857 (5.8); 7.838 (6.5); 7.811 (0.4); 7.693 (5.3); 7.681 (5.2); 7.673 (5.1); 7.661 (4.9); 7.611 (4.5); 7.591 (10.7); 7.572 (7.8); 7.547 (7.4); 7.530 (2.8); 7.527 (3.2); 7.289 (0.4); 6.937 (0.5); 6.925 |

TABLE 2-continued

Analytical data for the compounds reported

| Ex. No. | LogP[a] | logP[b] | 1H-NMR [σ (ppm)] or LC-MS [m/z] |
|---|---|---|---|
| | | | (0.4); 6.914 (0.4); 5.757 (0.7); 3.744 (3.2); 3.327 (467.3); 2.676 (4.1); 2.671 (5.6); 2.667 (4.1); 2.602 (0.5); 2.524 (15.1); 2.507 (606.6); 2.502 (788.2); 2.498 (575.0); 2.333 (3.8); 2.329 (5.2); 2.325 (3.7); 2.170 (0.5); 1.355 (0.5); 1.277 (0.4); 1.259 (0.5); 1.232 (5.8); 1.154 (0.4); 1.136 (0.6); 1.118 (0.4); 0.853 (0.7); 0.836 (0.4); 0.146 (2.7); 0.082 (0.4); 0.073 (6.2); 0.008 (20.0); 0.000 (579.1); −0.009 (21.1); −0.150 (2.8) |
| 8 | 2.98 | 3.03 | $^1$H-NMR (400.0 MHz, d$_6$-DMSO): δ = 9.366 (4.0); 9.362 (3.8); 9.087 (5.4); 9.082 (6.9); 9.044 (7.1); 9.039 (5.5); 8.830 (3.1); 8.826 (3.3); 8.818 (3.2); 8.814 (3.2); 8.574 (1.8); 8.569 (2.5); 8.564 (1.8); 8.554 (1.9); 8.549 (2.6); 8.544 (1.8); 8.321 (3.9); 7.920 (1.0); 7.915 (1.3); 7.909 (7.7); 7.904 (3.1); 7.892 (3.1); 7.887 (9.1); 7.688 (2.5); 7.676 (2.4); 7.668 (2.4); 7.656 (2.3); 7.635 (8.9); 7.613 (7.6); 7.194 (0.5); 7.175 (0.6); 5.758 (0.3); 3.339 (24.8); 2.677 (0.7); 2.673 (1.0); 2.668 (0.7); 2.543 (0.8); 2.508 (100.8); 2.503 (131.2); 2.499 (99.0); 2.335 (0.6); 2.330 (0.9); 2.326 (0.6); 2.183 (0.4); 1.571 (16.0); 1.355 (3.1); 1.231 (0.4); 0.146 (0.6); 0.008 (5.1); 0.000 (130.0); −0.008 (6.4); −0.150 (0.6) |
| 9 | | 2.96 | $^1$H-NMR (400.0 MHz, d$_6$-DMSO): δ = 9.364 (1.9); 9.360 (1.9); 9.094 (2.7); 9.089 (3.3); 9.046 (3.4); 9.040 (2.7); 8.827 (1.5); 8.823 (1.6); 8.815 (1.6); 8.811 (1.5); 8.570 (0.9); 8.565 (1.1); 8.560 (0.9); 8.550 (1.0); 8.545 (1.2); 8.544 (1.2); 8.540 (0.9); 7.696 (1.5); 7.692 (2.6); 7.687 (2.3); 7.674 (1.2); 7.673 (1.2); 7.666 (1.2); 7.665 (1.1); 7.654 (1.1); 7.653 (1.0); 7.626 (1.1); 7.609 (1.2); 7.606 (1.4); 7.505 (1.2); 7.485 (2.3); 7.466 (1.2); 7.364 (1.3); 7.362 (1.3); 7.344 (1.0); 7.342 (1.0); 3.331 (13.1); 2.586 (16.0); 2.573 (0.8); 2.514 (7.5); 2.510 (14.4); 2.506 (18.7); 2.501 (13.5); 2.497 (6.7) |
| 10 | | 3.36 | $^1$H-NMR (400.0 MHz, d$_6$-DMSO): δ = 9.369 (4.3); 9.364 (4.5); 9.150 (0.3); 9.087 (5.0); 9.082 (6.4); 9.050 (6.4); 9.044 (5.1); 9.029 (0.4); 8.830 (3.4); 8.826 (3.3); 8.818 (3.6); 8.815 (3.2); 8.575 (1.9); 8.571 (2.7); 8.566 (1.9); 8.555 (2.1); 8.551 (2.8); 8.546 (1.9); 7.871 (0.4); 7.852 (0.5); 7.747 (5.6); 7.690 (2.6); 7.678 (2.7); 7.670 (3.2); 7.668 (3.3); 7.659 (3.8); 7.644 (3.2); 7.566 (0.4); 7.515 (2.3); 7.496 (4.8); 7.476 (2.8); 7.409 (3.3); 7.389 (2.2); 3.331 (74.9); 3.140 (2.4); 3.121 (7.6); 3.103 (7.9); 3.085 (2.7); 2.673 (0.7); 2.508 (86.2); 2.504 (107.9); 2.500 (82.1); 2.335 (0.5); 2.331 (0.7); 2.087 (0.8); 1.312 (7.8); 1.294 (16.0); 1.275 (7.6); 1.259 (1.0); 1.230 (2.9); 1.088 (0.5); 0.867 (0.3); 0.852 (0.6); 0.834 (0.4); 0.147 (0.5); 0.008 (4.7); 0.000 (101.5); −0.149 (0.5) |
| 11 | 3.34 | 3.37 | $^1$H-NMR (400.0 MHz, d$_6$-DMSO): δ = 9.362 (3.2); 9.357 (3.1); 9.090 (0.4); 9.080 (5.0); 9.075 (5.8); 9.048 (0.4); 9.017 (6.1); 9.011 (5.1); 8.826 (2.5); 8.822 (2.6); 8.814 (2.6); 8.810 (2.5); 8.569 (1.5); 8.565 (2.0); 8.559 (1.5); 8.549 (1.7); 8.544 (2.1); 8.539 (1.5); 8.317 (0.6); 7.911 (0.4); 7.889 (0.4); 7.829 (6.2); 7.812 (2.2); 7.808 (7.2); 7.688 (1.9); 7.686 (1.9); 7.674 (1.9); 7.666 (1.9); 7.656 (1.8); 7.654 (1.8); 7.637 (0.4); 7.616 (0.3); 7.484 (7.1); 7.463 (6.3); 3.327 (229.5); 3.099 (2.3); 3.081 (7.2); 3.063 (7.4); 3.044 (2.4); 2.676 (1.5); 2.671 (2.1); 2.667 (1.5); 2.663 (0.8); 2.525 (5.5); 2.520 (8.3); 2.511 (107.6); 2.507 (217.5); 2.502 (288.2); 2.498 (211.9); 2.493 (104.2); 2.334 (1.3); 2.329 (1.9); 2.325 (1.3); 1.308 (7.7); 1.290 (16.0); 1.272 (7.5); 1.234 (0.6); 0.146 (1.8); 0.008 (13.1); 0.000 (372.2); −0.009 (13.9); −0.150 (1.7) |
| 12 | 1.58 | 1.86 | $^1$H-NMR (400.0 MHz, d$_6$-DMSO): δ = 9.375 (4.2); 9.370 (4.2); 9.145 (5.6); 9.140 (7.4); 9.107 (7.5); 9.102 (5.8); 8.835 (3.1); 8.831 (3.4); 8.823 (3.3); 8.819 (3.4); 8.583 (1.8); 8.577 (2.5); 8.573 (1.9); 8.563 (2.0); 8.557 (2.7); 8.553 (1.9); 8.084 (7.3); 8.063 (8.9); 7.824 (8.7); 7.803 (7.7); 7.693 (2.4); 7.681 (2.4); 7.673 (2.4); 7.661 (2.3); 5.759 (0.4); 4.039 (0.3); 4.021 (0.3); 3.331 (69.7); 3.154 (0.5); 3.135 (1.8); 3.117 (2.1); 3.101 (2.4); 3.083 (2.2); 3.065 (0.7); 2.887 (0.6); 2.868 (2.2); 2.850 (2.5); 2.834 (2.0); 2.816 (1.8); 2.798 (0.5); 2.677 (0.6); 2.673 (0.8); 2.668 (0.6); 2.545 (0.5); 2.540 (0.6); 2.526 (2.3); 2.508 (95.9); 2.503 (127.4); 2.499 (95.8); 2.335 (0.6); 2.330 (0.8); 2.326 (0.6); 1.230 (0.4); |

TABLE 2-continued

Analytical data for the compounds reported

| Ex. No. | LogP[a] | logP[b] | 1H-NMR [σ (ppm)] or LC-MS [m/z] |
|---|---|---|---|
| | | | 1.182 (0.7); 1.166 (1.1); 1.151 (0.6); 1.096 (7.4); 1.078 (16.0); 1.059 (7.2); 0.000 (3.6) |
| 13 | 1.85 | 1.85 | $^1$H-NMR (400.0 MHz, $d_6$-DMSO): δ = 9.385 (4.0); 9.379 (4.3); 9.174 (3.9); 9.168 (7.7); 9.158 (8.0); 9.152 (4.2); 9.142 (0.9); 9.111 (0.8); 9.105 (0.6); 8.853 (0.6); 8.841 (2.9); 8.837 (3.3); 8.829 (3.1); 8.825 (3.3); 8.594 (1.6); 8.589 (2.4); 8.584 (1.9); 8.574 (1.8); 8.568 (2.6); 8.564 (1.9); 8.317 (1.3); 8.167 (5.9); 8.146 (9.0); 8.085 (1.0); 8.060 (9.1); 8.039 (6.1); 7.824 (1.0); 7.804 (0.8); 7.698 (2.4); 7.686 (2.3); 7.678 (2.4); 7.666 (2.3); 5.757 (0.7); 4.037 (0.8); 4.021 (0.8); 3.413 (2.2); 3.395 (6.9); 3.377 (7.2); 3.358 (3.3); 3.329 (568.0); 3.293 (2.4); 2.675 (2.8); 2.671 (3.9); 2.667 (3.0); 2.545 (0.9); 2.540 (1.0); 2.524 (11.0); 2.506 (445.4); 2.502 (589.5); 2.498 (444.2); 2.467 (4.1); 2.430 (1.1); 2.422 (0.5); 2.371 (0.9); 2.333 (2.9); 2.329 (3.9); 2.324 (3.0); 1.232 (1.3); 1.173 (8.4); 1.154 (16.0); 1.136 (7.0); 1.095 (0.9); 1.077 (1.8); 1.059 (0.8); 0.007 (0.5); 0.000 (14.8) |
| 14 | 3.12 | 3.13 | $^1$H-NMR (400.0 MHz, $d_6$-DMSO): δ = 9.364 (3.7); 9.359 (3.7); 8.834 (2.8); 8.831 (3.0); 8.823 (3.0); 8.819 (2.9); 8.742 (4.8); 8.736 (6.6); 8.713 (6.5); 8.707 (4.7); 8.572 (1.6); 8.568 (2.3); 8.563 (1.6); 8.553 (1.8); 8.548 (2.4); 8.543 (1.6); 8.317 (0.4); 8.070 (6.5); 7.695 (2.2); 7.683 (2.2); 7.675 (2.1); 7.663 (2.0); 7.540 (2.1); 7.522 (3.9); 7.520 (3.9); 7.493 (1.8); 7.488 (1.9); 7.475 (2.3); 7.471 (2.7); 7.455 (1.1); 7.451 (1.4); 7.414 (1.8); 7.410 (2.1); 7.395 (4.0); 7.391 (3.4); 7.365 (3.2); 7.362 (3.2); 7.345 (4.2); 7.328 (2.3); 7.325 (2.4); 7.315 (0.8); 7.311 (0.7); 7.297 (0.9); 7.294 (0.9); 7.278 (0.4); 7.274 (0.4); 7.177 (0.6); 7.174 (0.7); 7.159 (1.0); 7.156 (1.0); 7.141 (0.4); 7.138 (0.4); 4.038 (0.5); 4.020 (0.6); 3.568 (0.4); 3.328 (165.3); 2.936 (2.2); 2.918 (7.2); 2.904 (3.7); 2.900 (7.5); 2.886 (3.1); 2.882 (2.7); 2.868 (0.9); 2.676 (1.1); 2.671 (1.5); 2.667 (1.1); 2.524 (4.1); 2.507 (166.9); 2.502 (217.8); 2.498 (164.7); 2.334 (1.1); 2.329 (1.5); 2.325 (1.1); 1.989 (2.2); 1.242 (0.4); 1.234 (0.3); 1.212 (2.8); 1.194 (6.2); 1.186 (7.9); 1.175 (4.5); 1.167 (16.0); 1.157 (1.3); 1.149 (7.4); 0.000 (0.5) |
| 15 | 1.58 | 1.59 | $^1$H-NMR (400.0 MHz, $d_6$-DMSO): δ = 9.374 (4.2); 9.370 (4.3); 8.866 (6.3); 8.860 (7.5); 8.843 (3.2); 8.839 (3.5); 8.831 (3.4); 8.827 (3.5); 8.805 (7.3); 8.800 (6.2); 8.585 (1.8); 8.580 (2.5); 8.575 (1.9); 8.565 (2.0); 8.559 (2.7); 8.555 (1.9); 8.318 (0.3); 8.006 (2.9); 8.003 (3.1); 7.987 (3.4); 7.984 (3.5); 7.799 (1.4); 7.795 (1.5); 7.780 (3.2); 7.777 (3.2); 7.761 (2.2); 7.757 (2.2); 7.740 (2.0); 7.736 (2.1); 7.721 (3.3); 7.718 (3.4); 7.701 (3.5); 7.699 (3.7); 7.688 (2.4); 7.681 (2.3); 7.669 (2.2); 7.667 (2.2); 7.571 (3.6); 7.569 (3.6); 7.553 (3.0); 7.550 (2.9); 5.758 (1.5); 3.332 (197.0); 2.783 (0.5); 2.764 (1.8); 2.746 (2.1); 2.731 (2.4); 2.712 (2.2); 2.694 (0.7); 2.677 (0.8); 2.672 (1.0); 2.668 (0.8); 2.542 (0.6); 2.525 (2.5); 2.508 (116.7); 2.503 (153.0); 2.499 (113.2); 2.444 (0.7); 2.426 (2.1); 2.408 (2.4); 2.392 (2.1); 2.374 (1.8); 2.355 (0.6); 2.334 (0.7); 2.330 (1.0); 2.325 (0.8); 0.905 (7.4); 0.887 (16.0); 0.869 (7.1); 0.000 (6.3) |
| 16 | 1.86 | 1.87 | $^1$H-NMR (400.0 MHz, $d_6$-DMSO): δ = 9.371 (4.2); 9.365 (4.1); 8.840 (3.2); 8.836 (3.3); 8.828 (3.3); 8.824 (3.3); 8.764 (5.8); 8.759 (7.2); 8.719 (7.0); 8.713 (5.7); 8.580 (1.8); 8.575 (2.5); 8.571 (1.9); 8.561 (1.9); 8.555 (2.6); 8.551 (1.8); 8.318 (1.8); 8.132 (3.1); 8.115 (3.4); 8.112 (3.4); 7.889 (1.6); 7.873 (3.3); 7.870 (3.3); 7.854 (2.3); 7.851 (2.2); 7.815 (2.1); 7.812 (2.5); 7.795 (3.0); 7.792 (3.1); 7.776 (1.3); 7.773 (1.3); 7.699 (2.5); 7.686 (2.5); 7.679 (2.5); 7.666 (2.4); 7.627 (0.5); 7.601 (3.6); 7.598 (3.7); 7.583 (3.2); 7.580 (3.1); 5.757 (1.7); 4.040 (0.5); 4.022 (0.5); 3.376 (0.5); 3.327 (653.5); 3.012 (2.1); 2.993 (7.0); 2.975 (7.2); 2.957 (2.2); 2.675 (4.7); 2.671 (6.3); 2.667 (4.8); 2.623 (0.3); 2.524 (17.2); 2.510 (380.2); 2.506 (748.3); 2.502 (973.4); 2.497 (719.5); 2.372 (0.3); 2.333 (4.7); 2.328 (6.4); 2.324 (4.8); 2.299 (0.4); 2.206 (0.3); 1.355 (0.3); 1.234 (1.4); 1.165 (1.7); 1.026 (7.4); 1.008 (16.0); 0.989 (7.2); 0.146 (17.1); 0.096 (0.3); 0.086 (0.7); 0.070 (0.7); 0.058 (1.2); 0.047 (1.5); 0.007 (153.7); 0.000 (3211.2); −0.009 (157.6); −0.068 (0.9); −0.075 (0.9); −0.095 (0.6); −0.121 (0.4); −0.150 (16.9) |

TABLE 2-continued

Analytical data for the compounds reported

| Ex. No. | LogP[a] | logP[b] | 1H-NMR [σ (ppm)] or LC-MS [m/z] |
|---|---|---|---|
| 17 | 3.74 | 3.68 | $^1$H-NMR (400.0 MHz, $d_6$-DMSO): δ = 9.366 (3.2); 9.361 (3.2); 9.360 (3.1); 9.125 (4.6); 9.120 (5.3); 9.042 (5.4); 9.036 (4.8); 8.827 (2.5); 8.823 (2.8); 8.815 (2.7); 8.811 (2.8); 8.570 (1.4); 8.566 (1.9); 8.561 (1.5); 8.550 (1.6); 8.545 (2.1); 8.541 (1.5); 7.975 (3.8); 7.971 (4.0); 7.693 (2.0); 7.687 (3.0); 7.673 (4.1); 7.668 (3.2); 7.654 (1.8); 7.653 (1.8); 7.443 (3.2); 7.423 (2.8); 4.223 (1.3); 4.197 (4.1); 4.171 (4.3); 4.145 (1.5); 3.333 (12.5); 2.528 (0.7); 2.515 (13.7); 2.510 (27.0); 2.506 (35.7); 2.502 (27.0); 2.428 (16.0); 0.008 (1.8); 0.000 (45.7); −0.008 (2.1) |
| 18 | 2.4 | 2.34 | $^1$H-NMR (400.0 MHz, $d_6$-DMSO): δ = 9.378 (2.7); 9.373 (2.8); 9.196 (0.3); 9.191 (0.4); 9.168 (3.5); 9.162 (4.8); 9.153 (0.5); 9.133 (4.7); 9.127 (3.6); 8.921 (0.3); 8.834 (2.1); 8.830 (2.3); 8.822 (2.2); 8.818 (2.3); 8.753 (0.3); 8.749 (0.4); 8.584 (1.2); 8.579 (1.7); 8.574 (1.3); 8.564 (1.3); 8.558 (1.8); 8.554 (1.4); 8.317 (0.6); 8.295 (3.7); 8.290 (3.9); 8.150 (1.8); 8.024 (1.8); 8.020 (1.8); 8.004 (2.0); 8.000 (2.0); 7.693 (1.7); 7.681 (1.7); 7.674 (1.8); 7.660 (1.7); 7.562 (2.8); 7.542 (2.5); 4.256 (1.0); 4.229 (3.2); 4.202 (3.3); 4.174 (1.1); 3.328 (135.7); 2.738 (0.4); 2.676 (1.4); 2.671 (2.0); 2.667 (1.5); 2.525 (5.7); 2.507 (215.8); 2.502 (284.3); 2.498 (216.6); 2.470 (16.0); 2.429 (0.3); 2.417 (0.9); 2.333 (1.4); 2.329 (1.9); 2.325 (1.5); 2.275 (0.8); 1.754 (2.0); 1.351 (0.7); 1.230 (1.0); 0.146 (1.1); 0.008 (9.5); 0.000 (247.0); −0.008 (11.8); −0.150 (1.2) |
| 19 | 3.97 | 3.95 | $^1$H-NMR (400.0 MHz, $d_6$-DMSO): δ = 9.370 (2.7); 9.366 (2.7); 9.365 (2.7); 8.834 (2.3); 8.830 (2.5); 8.822 (2.4); 8.818 (2.5); 8.759 (2.5); 8.753 (8.0); 8.749 (7.8); 8.744 (2.3); 8.578 (1.3); 8.574 (1.7); 8.568 (1.3); 8.558 (1.4); 8.553 (1.8); 8.548 (1.3); 8.318 (0.3); 7.694 (1.6); 7.693 (1.6); 7.682 (1.6); 7.681 (1.6); 7.674 (1.6); 7.673 (1.6); 7.662 (1.5); 7.661 (1.5); 7.536 (5.9); 7.297 (4.6); 4.035 (1.2); 4.009 (3.8); 3.982 (4.0); 3.956 (1.4); 3.328 (100.9); 2.676 (0.7); 2.672 (0.9); 2.667 (0.7); 2.525 (2.7); 2.520 (3.9); 2.512 (49.4); 2.507 (100.6); 2.503 (133.6); 2.498 (97.4); 2.494 (47.0); 2.418 (14.4); 2.334 (0.6); 2.329 (0.9); 2.325 (0.6); 2.275 (16.0); 1.233 (0.4); 0.146 (0.8); 0.019 (0.4); 0.008 (6.1); 0.000 (176.8); −0.009 (6.0); −0.150 (0.8) |
| 20 | 2.54 | 2.52 | $^1$H-NMR (400.0 MHz, $d_6$-DMSO): δ = 9.379 (3.2); 9.374 (3.0); 8.830 (7.8); 8.825 (9.1); 8.586 (1.4); 8.581 (1.9); 8.577 (1.3); 8.566 (1.5); 8.561 (2.0); 8.557 (1.3); 8.317 (0.5); 8.145 (0.6); 7.820 (6.5); 7.697 (1.8); 7.685 (1.8); 7.676 (1.8); 7.664 (1.7); 7.400 (4.8); 5.758 (2.3); 4.197 (1.1); 4.170 (3.3); 4.142 (3.5); 4.115 (1.2); 3.366 (0.8); 3.329 (136.7); 2.891 (0.7); 2.731 (0.6); 2.695 (0.4); 2.676 (1.3); 2.671 (1.7); 2.667 (1.3); 2.539 (1.9); 2.507 (193.1); 2.502 (244.6); 2.498 (184.8); 2.431 (15.1); 2.398 (0.8); 2.378 (16.0); 2.334 (1.3); 2.329 (1.7); 2.325 (1.3); 1.234 (1.0); 1.165 (1.0); 1.150 (0.6); 0.000 (6.2) |
| 21 | 1.91 | 1.86 | $^1$H-NMR (400.0 MHz, $d_6$-DMSO): δ = 8.927 (4.0); 8.861 (2.0); 8.854 (9.9); 8.848 (2.3); 8.841 (0.8); 8.830 (0.4); 8.814 (0.3); 8.690 (0.3); 8.466 (2.0); 8.448 (2.1); 8.317 (1.3); 8.148 (0.5); 8.104 (2.1); 8.084 (2.3); 7.846 (0.5); 7.818 (7.0); 7.680 (2.2); 7.663 (2.3); 7.660 (2.3); 7.643 (1.9); 7.555 (0.4); 7.401 (4.8); 7.383 (0.3); 5.757 (2.2); 4.194 (1.1); 4.167 (3.4); 4.140 (3.6); 4.113 (1.2); 4.037 (0.4); 4.020 (0.4); 3.428 (0.3); 3.416 (0.4); 3.402 (0.5); 3.368 (1.5); 3.330 (615.1); 3.294 (2.0); 2.891 (1.5); 2.731 (1.3); 2.695 (1.2); 2.676 (2.8); 2.671 (3.9); 2.667 (3.0); 2.545 (2.0); 2.540 (2.2); 2.524 (10.1); 2.507 (425.8); 2.502 (566.6); 2.498 (425.9); 2.430 (14.9); 2.392 (2.1); 2.372 (16.0); 2.333 (2.6); 2.329 (3.6); 2.324 (2.8); 1.234 (2.2); 1.165 (1.4); 1.149 (0.8); 0.853 (0.4); 0.008 (0.5); 0.000 (15.0); −0.008 (0.7) |
| 22 | 3.83 | 3.78 | $^1$H-NMR (400.0 MHz, $d_6$-DMSO): δ = 9.375 (3.0); 9.370 (3.0); 8.953 (9.2); 8.950 (9.1); 8.836 (2.4); 8.833 (2.6); 8.824 (2.6); 8.821 (2.7); 8.583 (1.3); 8.578 (1.8); 8.573 (1.4); 8.563 (1.5); 8.558 (2.0); 8.553 (1.4); 7.902 (3.1); 7.882 (3.1); 7.693 (1.8); 7.681 (1.8); 7.673 (1.8); 7.663 (1.7); 7.661 (1.8); 7.422 (2.7); 7.393 (2.7); 5.758 (0.6); 4.114 (1.3); 4.088 (4.0); 4.062 (4.2); 4.036 (1.5); 3.328 (42.3); 2.677 (0.5); 2.673 (0.6); |

TABLE 2-continued

Analytical data for the compounds reported

| Ex. No. | LogP[a] | logP[b] | 1H-NMR [σ (ppm)] or LC-MS [m/z] |
|---|---|---|---|
| | | | 2.668 (0.5); 2.526 (1.6); 2.521 (2.5); 2.512 (35.8); 2.508 (72.9); 2.503 (97.3); 2.499 (72.8); 2.495 (36.8); 2.468 (16.0); 2.403 (0.5); 2.335 (0.5); 2.330 (0.7); 2.326 (0.5); 2.076 (1.5); 0.146 (0.5); 0.008 (3.9); 0.000 (116.1); −0.009 (4.6); −0.150 (0.5) |
| 23 | 2.5 | 2.46 | $^1$H-NMR (400.0 MHz, $d_6$-DMSO): δ = 9.383 (12.6); 9.378 (12.3); 9.036 (15.7); 9.033 (14.8); 9.022 (12.3); 9.018 (16.0); 9.013 (7.6); 8.841 (9.7); 8.837 (10.6); 8.829 (10.1); 8.825 (10.6); 8.590 (5.6); 8.586 (7.4); 8.581 (5.7); 8.570 (6.1); 8.565 (8.1); 8.560 (5.8); 8.317 (1.4); 8.159 (13.2); 8.139 (13.3); 7.697 (7.3); 7.685 (7.1); 7.679 (6.9); 7.677 (7.0); 7.667 (6.7); 7.665 (6.9); 7.644 (0.6); 7.627 (0.8); 7.624 (0.8); 7.615 (0.7); 7.597 (0.8); 7.575 (0.6); 7.567 (0.7); 7.538 (10.5); 7.509 (10.2); 5.758 (3.5); 4.329 (0.4); 4.302 (1.4); 4.293 (2.2); 4.276 (2.8); 4.266 (7.1); 4.253 (6.9); 4.239 (7.4); 4.225 (7.4); 4.212 (2.8); 4.198 (2.7); 4.189 (1.6); 4.161 (0.5); 4.056 (1.0); 4.038 (2.9); 4.020 (3.0); 4.002 (1.0); 3.827 (0.4); 3.812 (0.5); 3.640 (0.6); 3.407 (0.3); 3.392 (0.7); 3.334 (1093.5); 3.268 (0.5); 3.175 (0.4); 3.162 (0.4); 2.677 (2.9); 2.672 (4.1); 2.668 (2.9); 2.645 (0.3); 2.525 (11.2); 2.512 (231.5); 2.508 (469.6); 2.503 (621.0); 2.499 (458.4); 2.494 (229.3); 2.485 (73.3); 2.434 (0.9); 2.410 (0.6); 2.388 (0.5); 2.372 (0.6); 2.334 (3.1); 2.330 (4.2); 2.325 (3.3); 1.990 (12.4); 1.909 (1.8); 1.298 (1.4); 1.259 (2.1); 1.233 (5.3); 1.193 (3.5); 1.175 (6.8); 1.157 (3.4); 0.853 (0.8); 0.836 (0.4); 0.146 (0.7); 0.008 (6.1); 0.000 (167.9); −0.008 (6.2); −0.150 (0.8) |
| 24 | 2.25 | 2.27 | $^1$H-NMR (400.0 MHz, $d_6$-DMSO): δ = 9.251 (8.5); 9.247 (8.3); 9.245 (8.3); 8.790 (13.0); 8.758 (6.7); 8.754 (7.6); 8.746 (7.2); 8.742 (7.6); 8.465 (13.4); 8.458 (14.8); 8.445 (4.0); 8.441 (5.3); 8.439 (5.2); 8.435 (4.1); 8.425 (4.3); 8.419 (5.7); 8.415 (4.2); 8.326 (14.2); 8.319 (13.4); 7.637 (4.9); 7.635 (5.3); 7.623 (5.2); 7.617 (4.8); 7.615 (5.1); 7.605 (4.7); 7.603 (5.0); 7.350 (6.7); 7.329 (13.8); 7.310 (11.1); 7.231 (16.0); 7.212 (10.7); 6.980 (4.4); 6.962 (7.8); 6.943 (3.7); 3.326 (508.1); 2.731 (0.3); 2.676 (4.4); 2.671 (6.2); 2.667 (4.7); 2.524 (15.3); 2.520 (23.1); 2.511 (313.8); 2.507 (651.6); 2.502 (883.9); 2.498 (671.9); 2.494 (345.0); 2.447 (0.7); 2.431 (0.5); 2.338 (2.0); 2.333 (4.3); 2.329 (6.0); 2.324 (4.5); 1.055 (0.4); 0.146 (3.4); 0.032 (0.4); 0.008 (25.2); 0.000 (779.5); −0.009 (30.2); −0.150 (3.4) |
| 25 | 2.66 | 2.69 | $^1$H-NMR (400.0 MHz, $d_6$-DMSO): δ = 9.269 (6.7); 9.264 (6.8); 8.962 (11.3); 8.772 (5.4); 8.768 (5.9); 8.760 (5.8); 8.756 (5.9); 8.483 (9.8); 8.476 (13.1); 8.465 (3.5); 8.461 (4.5); 8.456 (3.4); 8.445 (3.7); 8.440 (5.6); 8.436 (16.0); 8.429 (10.0); 8.317 (1.2); 7.647 (4.3); 7.646 (4.3); 7.635 (4.1); 7.627 (4.1); 7.626 (4.1); 7.615 (4.0); 7.614 (3.9); 7.356 (0.3); 7.339 (4.5); 7.319 (9.7); 7.299 (6.0); 7.189 (4.3); 7.184 (10.1); 7.179 (7.2); 7.170 (5.9); 7.150 (4.0); 7.146 (3.3); 6.967 (4.5); 6.964 (4.4); 6.947 (3.9); 6.944 (4.1); 5.757 (0.5); 3.326 (236.5); 2.891 (1.4); 2.732 (1.2); 2.680 (1.3); 2.676 (2.6); 2.671 (3.6); 2.667 (2.7); 2.662 (1.3); 2.525 (8.9); 2.520 (13.4); 2.511 (186.4); 2.507 (384.3); 2.502 (519.2); 2.498 (389.2); 2.493 (195.6); 2.338 (1.2); 2.333 (2.5); 2.329 (3.5); 2.325 (2.6); 2.086 (4.0); 2.075 (1.1); 0.146 (2.0); 0.008 (14.5); 0.000 (450.0); −0.009 (17.3); −0.150 (2.0) |
| 26 | | 1.62 | $^1$H-NMR (400.0 MHz, $d_6$-DMSO): δ = 11.160 (0.7); 10.721 (0.7); 9.345 (14.2); 9.294 (15.7); 9.162 (14.9); 8.822 (10.6); 8.814 (10.8); 8.761 (0.5); 8.697 (15.8); 8.551 (8.4); 8.531 (8.8); 8.475 (0.5); 8.429 (0.4); 7.894 (16.0); 7.799 (0.4); 7.684 (7.1); 7.667 (8.7); 7.654 (6.8); 7.235 (0.5); 7.220 (0.4); 7.216 (0.4); 6.673 (14.6); 5.935 (0.7); 4.134 (0.5); 3.391 (0.6); 3.326 (63.2); 2.671 (2.1); 2.503 (265.8); 2.329 (2.3); 2.283 (0.7); 2.265 (0.6); 2.244 (0.5); 2.234 (0.5); 2.209 (0.4); 2.205 (0.4); 2.178 (0.4); 2.160 (0.4); 2.155 (0.4); 2.141 (0.4); 2.087 (4.1); 2.058 (0.6); 2.044 (0.4); 1.983 (0.7); 1.926 (0.4); 1.907 (0.5); 1.886 (0.4); 1.870 (0.4); 1.852 (0.4); 1.821 (0.4); 1.743 (1.2); 1.678 (0.5); 1.671 (0.5); 1.625 (1.4); 1.532 (0.7); 1.511 (0.7); 1.463 (0.6); 1.453 (0.6); 1.433 (0.6); 1.416 (0.6); 1.367 (0.9); 1.349 (1.1); 1.297 (3.4); 1.257 (4.8); 1.230 (8.0); 1.171 (2.8); 1.146 (4.1); 1.136 (4.0); 1.088 (1.2); 1.065 (1.0); 1.042 (0.9); 1.036 (0.9); |

TABLE 2-continued

Analytical data for the compounds reported

| Ex. No. | LogP[a] | logP[b] | 1H-NMR [σ (ppm)] or LC-MS [m/z] |
|---|---|---|---|
| | | | 0.981 (0.6); 0.943 (0.6); 0.928 (0.7); 0.863 (3.1); 0.755 (0.5); 0.724 (0.4); 0.701 (0.4); 0.145 (0.9); 0.123 (0.4); 0.105 (0.5); 0.095 (0.6); −0.001 (131.7); −0.150 (1.2); −0.190 (0.4); −0.201 (0.4) |
| 27 | | 2.57 | $^1$H-NMR (601.6 MHz, CD3CN): δ = 9.373 (4.7); 9.355 (0.8); 9.156 (8.3); 9.151 (8.5); 8.877 (8.9); 8.873 (8.7); 8.789 (3.3); 8.782 (3.4); 8.734 (0.6); 8.729 (0.6); 8.511 (2.6); 8.508 (3.8); 8.505 (2.6); 8.498 (3.3); 8.495 (3.9); 8.492 (3.0); 8.488 (1.3); 8.485 (1.1); 8.476 (0.6); 8.385 (5.8); 8.383 (5.8); 7.585 (3.2); 7.577 (3.3); 7.572 (3.3); 7.564 (3.3); 7.545 (0.5); 7.466 (0.6); 7.452 (1.5); 7.446 (0.9); 7.441 (0.7); 7.433 (0.7); 7.238 (0.5); 7.234 (0.4); 7.224 (0.4); 7.220 (0.4); 6.953 (6.6); 6.949 (6.5); 5.448 (0.7); 2.828 (1.2); 2.748 (0.6); 2.575 (2.2); 2.563 (2.3); 2.501 (0.5); 2.172 (9.1); 2.107 (5.6); 2.087 (3.1); 2.076 (2.7); 2.059 (3.2); 2.055 (4.1); 2.051 (5.1); 2.047 (3.9); 2.043 (2.7); 1.965 (67.2); 1.957 (37.4); 1.952 (51.3); 1.949 (253.4); 1.945 (433.6); 1.940 (624.6); 1.936 (441.3); 1.932 (228.3); 1.916 (4.5); 1.883 (1.7); 1.850 (1.1); 1.842 (1.1); 1.834 (2.0); 1.830 (3.1); 1.826 (4.2); 1.822 (3.0); 1.818 (1.8); 1.567 (0.5); 1.434 (0.5); 1.340 (13.1); 1.319 (2.0); 1.308 (2.5); 1.298 (2.3); 1.285 (16.0); 1.269 (9.4); 1.248 (1.2); 1.227 (1.0); 1.217 (1.0); 1.206 (1.0); 1.184 (1.3); 1.173 (1.2); 1.153 (0.8); 1.134 (0.8); 1.112 (0.7); 1.083 (0.8); 1.071 (0.7); 1.048 (0.6); 1.038 (0.6); 1.022 (4.4); 1.010 (8.3); 0.999 (4.3); 0.914 (0.7); 0.893 (1.2); 0.882 (2.1); 0.870 (1.5); 0.844 (1.3); 0.000 (2.8) |
| 28 | 2.48 | 2.53 | $^1$H-NMR (400.0 MHz, d$_6$-DMSO): δ = 9.366 (16.0); 9.362 (16.0); 9.356 (13.8); 9.312 (12.2); 9.306 (15.8); 9.302 (7.3); 9.288 (2.1); 9.238 (13.8); 9.232 (14.5); 9.214 (1.9); 8.836 (6.5); 8.832 (8.2); 8.824 (8.0); 8.820 (8.7); 8.569 (4.3); 8.564 (6.1); 8.560 (6.2); 8.550 (5.7); 8.544 (7.2); 8.540 (6.6); 8.370 (14.4); 8.352 (2.5); 8.238 (1.2); 8.166 (1.1); 7.690 (4.8); 7.678 (5.4); 7.673 (6.7); 7.660 (5.3); 7.659 (5.1); 7.642 (1.0); 3.320 (121.7); 3.303 (20.7); 2.676 (1.3); 2.671 (1.7); 2.667 (1.6); 2.507 (200.6); 2.502 (274.7); 2.498 (253.0); 2.494 (174.9); 2.329 (1.6); 2.325 (1.5); 2.075 (1.5); 2.071 (0.7); −0.001 (54.0); −0.005 (24.7); −0.019 (6.3) |
| 29 | 1.00 | 1.07 | $^1$H-NMR (400.0 MHz, d$_6$-DMSO): δ = 9.331 (1.1); 8.822 (1.1); 8.762 (4.6); 8.727 (6.8); 8.533 (1.6); 8.513 (1.6); 7.678 (1.1); 7.665 (1.2); 7.658 (1.2); 7.646 (1.1); 3.683 (16.0); 3.330 (24.3); 2.678 (0.4); 2.509 (58.9); 2.337 (0.4); 2.081 (0.8) |
| 30 | 1.23 | 1.42 | $^1$H-NMR (400.0 MHz, d$_6$-DMSO): δ = 9.336 (0.6); 9.317 (2.7); 9.310 (3.0); 9.307 (3.9); 9.300 (3.8); 9.119 (3.3); 9.113 (3.3); 8.808 (2.1); 8.800 (2.2); 8.796 (2.0); 8.712 (0.4); 8.543 (0.4); 8.522 (1.4); 8.518 (1.8); 8.512 (1.4); 8.502 (1.4); 8.497 (1.6); 8.493 (1.2); 7.673 (1.3); 7.661 (1.6); 7.655 (1.5); 7.643 (1.3); 3.556 (0.4); 3.322 (46.2); 3.255 (17.4); 3.177 (1.4); 3.141 (0.4); 3.127 (0.6); 3.122 (0.5); 3.076 (0.3); 3.060 (2.0); 2.755 (0.3); 2.736 (0.4); 2.728 (0.5); 2.670 (2.4); 2.666 (2.1); 2.505 (269.8); 2.501 (349.1); 2.497 (274.9); 2.356 (0.9); 2.338 (16.0); 2.250 (1.0); 2.227 (0.7); 2.119 (1.8); 1.234 (0.5); 0.883 (0.4); 0.000 (50.2) |
| 31 | 0.97 | 1.21 | $^1$H-NMR (400.0 MHz, d$_6$-DMSO): δ = 9.318 (0.6); 8.816 (0.4); 8.806 (0.4); 8.701 (0.7); 8.695 (1.0); 8.668 (0.9); 8.662 (0.8); 8.524 (0.4); 8.504 (0.4); 7.669 (0.4); 7.657 (0.4); 7.649 (0.4); 3.557 (4.4); 3.387 (0.7); 3.319 (4.7); 2.506 (37.0); 2.501 (51.1); 2.497 (42.5); 2.406 (4.4); 2.328 (0.3); 2.291 (0.5); 1.158 (2.3); 1.069 (16.0); 0.000 (7.1); −0.002 (4.9) |
| 32 | 1.15 | 1.25 | $^1$H-NMR (400.0 MHz, d$_6$-DMSO): δ = 9.347 (1.8); 9.341 (1.9); 8.830 (1.2); .826 (1.4); 8.815 (4.1); 8.809 (3.9); 8.757 (3.5); 8.750 (2.9); 8.559 (0.8); 8.554 (1.1); 8.549 (0.9); 8.539 (0.9); 8.533 (1.2); 8.529 (0.9); 7.690 (1.0); 7.678 (1.0); 7.671 (1.0); 7.658 (1.0); 5.747 (0.8); 3.882 (0.5); 3.601 (0.5); 3.415 (879.7); 3.409 (917.4); 3.297 (0.8); 3.274 (0.7); 3.238 (0.4); 3.221 (0.3); 3.213 (0.4); 3.123 (16.0); 3.099 (0.4); 3.038 (15.3); 3.018 (0.3); |

TABLE 2-continued

Analytical data for the compounds reported

| Ex. No. | LogP[a] | logP[b] | 1H-NMR [σ (ppm)] or LC-MS [m/z] |
|---|---|---|---|
| | | | 3.007 (0.4); 2.977 (0.3); 2.969 (0.5); 2.683 (0.8); 2.679 (1.0); 2.674 (0.7); 2.532 (2.0); 2.527 (3.1); 2.519 (55.9); 2.514 (120.3); 2.510 (163.2); 2.505 (117.1); 2.501 (55.4); 2.345 (0.4); 2.341 (0.7); 2.336 (1.0); 2.332 (0.7) |
| 33 | 2.21 | 2.21 | $^1$H-NMR (400.0 MHz, d$_6$-DMSO): δ = 9.318 (2.6); 9.313 (2.6); 9.253 (3.4); 9.247 (3.7); 9.067 (3.8); 9.061 (3.5); 8.811 (1.7); 8.807 (1.9); 8.799 (1.8); 8.795 (1.9); 8.520 (1.0); 8.515 (1.4); 8.511 (1.0); 8.501 (1.0); 8.495 (1.5); 8.491 (1.0); 7.672 (1.4); 7.660 (1.3); 7.652 (1.3); 7.640 (1.3); 5.240 (1.2); 5.218 (3.7); 5.197 (3.9); 5.175 (1.3); 3.316 (54.1); 3.189 (16.0); 2.891 (0.8); 2.732 (0.7); 2.675 (0.4); 2.671 (0.6); 2.667 (0.5); 2.506 (74.0); 2.502 (103.4); 2.497 (79.9); 2.333 (0.5); 2.328 (0.6); 2.324 (0.5); 0.146 (0.3); 0.008 (3.0); 0.000 (70.0); −0.008 (3.0); −0.150 (0.3) |
| 34 | 1.84 | 1.87 | $^1$H-NMR (400.0 MHz, d$_6$-DMSO): δ = 9.317 (1.4); 9.313 (1.4); 9.306 (3.1); 9.300 (3.1); 9.110 (3.2); 9.103 (3.0); 8.807 (1.0); 8.798 (1.0); 8.521 (0.8); 8.516 (1.0); 8.511 (0.8); 8.501 (0.8); 8.495 (1.1); 8.491 (0.8); 7.670 (0.9); 7.658 (1.0); 7.650 (0.9); 7.638 (0.9); 3.319 (6.7); 3.264 (0.5); 3.225 (13.6); 3.000 (0.4); 2.689 (16.0); 2.676 (0.4); 2.671 (0.5); 2.667 (0.3); 2.525 (1.0); 2.511 (22.4); 2.507 (47.2); 2.502 (66.0); 2.498 (49.3); 2.493 (23.7); 2.455 (0.5); 2.329 (0.4); 0.008 (1.0); 0.000 (31.8); −0.008 (1.1) |
| 35 | 2.17 | 2.25 | $^1$H-NMR (400.0 MHz, d$_6$-DMSO): δ = 9.322 (2.0); 9.318 (1.9); 9.301 (3.2); 9.294 (3.3); 9.113 (3.3); 9.106 (3.1); 8.822 (0.4); 8.810 (1.4); 8.801 (1.4); 8.798 (1.3); 8.526 (0.9); 8.522 (1.3); 8.517 (0.9); 8.506 (1.0); 8.501 (1.3); 8.497 (0.9); 7.674 (1.2); 7.662 (1.2); 7.654 (1.2); 7.642 (1.1); 5.756 (3.9); 3.318 (65.6); 3.275 (1.4); 3.257 (4.1); 3.239 (4.4); 3.225 (16.0); 2.675 (0.5); 2.671 (0.6); 2.666 (0.5); 2.510 (41.1); 2.506 (81.7); 2.502 (107.0); 2.497 (77.1); 2.493 (37.4); 2.333 (0.5); 2.329 (0.6); 2.324 (0.5); 1.445 (4.6); 1.426 (9.6); 1.408 (4.5); 0.008 (2.9); 0.000 (67.0); −0.008 (2.7) |
| 36 | | | $^1$H-NMR (400.0 MHz, d$_6$-DMSO): δ = 9.328 (4.1); 9.324 (3.8); 9.322 (4.0); 9.305 (6.7); 9.299 (7.1); 9.146 (7.1); 9.140 (6.6); 8.817 (3.0); 8.813 (3.3); 8.805 (3.2); 8.801 (3.3); 8.533 (1.7); 8.528 (2.2); 8.523 (1.7); 8.513 (1.9); 8.508 (2.4); 8.503 (1.7); 8.314 (0.3); 7.676 (2.2); 7.664 (2.1); 7.657 (1.9); 7.656 (2.1); 7.645 (1.9); 7.644 (2.1); 4.309 (1.5); 4.283 (4.7); 4.258 (4.9); 4.232 (1.7); 3.923 (2.2); 3.318 (93.5); 3.297 (28.7); 2.676 (0.6); 2.671 (0.8); 2.667 (0.6); 2.525 (2.0); 2.520 (3.0); 2.511 (45.6); 2.507 (96.4); 2.502 (135.1); 2.498 (100.4); 2.493 (47.8); 2.334 (0.6); 2.329 (0.8); 2.325 (0.6); 1.481 (0.4); 1.159 (0.4); 1.069 (16.0); 0.783 (0.4); 0.008 (0.8); 0.000 (27.0); −0.009 (0.8) |
| 37 | 1.69 | 1.79 | $^1$H-NMR (400.0 MHz, d$_6$-DMSO): δ = 9.325 (0.9); 9.296 (3.0); 9.290 (3.1); 9.113 (3.7); 9.107 (3.5); 8.815 (0.8); 8.523 (1.3); 8.502 (1.3); 7.677 (0.9); 7.664 (1.0); 7.657 (1.0); 7.645 (0.9); 3.840 (8.3); 3.328 (15.5); 3.318 (69.4); 2.671 (0.6); 2.506 (74.1); 2.502 (100.0); 2.497 (77.7); 2.333 (0.5); 2.329 (0.6); 2.135 (16.0); 2.075 (0.7); 0.000 (29.6) |
| 38 | 1.1 | 1.15 | $^1$H-NMR (400.0 MHz, d$_6$-DMSO): δ = 9.346 (2.1); 9.342 (2.2); 8.828 (1.5); 8.824 (1.8); 8.815 (2.0); 8.812 (4.5); 8.806 (4.1); 8.765 (4.1); 8.759 (3.2); 8.556 (0.9); 8.551 (1.1); 8.547 (1.0); 8.536 (1.1); 8.531 (1.3); 8.527 (1.0); 7.683 (1.1); 7.671 (1.2); 7.663 (1.1); 7.652 (1.1); 7.651 (1.1); 5.757 (1.5); 3.320 (12.5); 3.122 (16.0); 3.035 (15.1); 2.672 (0.3); 2.525 (1.0); 2.511 (18.4); 2.507 (38.7); 2.502 (54.2); 2.498 (40.4); 2.494 (19.4); 1.234 (0.6); 0.008 (0.9); 0.000 (24.3); −0.008 (0.9) |
| 39 | 1.29 | 1.36 | $^1$H-NMR (400.0 MHz, d$_6$-DMSO): δ = 9.356 (8.6); 8.902 (8.8); 8.897 (11.6); 8.877 (11.6); 8.871 (8.2); 8.834 (6.1); 8.823 (6.3); 8.763 (1.1); 8.755 (1.0); 8.731 (0.9); 8.711 (0.9); 8.561 (5.1); 8.542 (5.7); 8.313 (0.5); 8.177 (0.4); 7.953 (1.0); |

TABLE 2-continued

| | | Analytical data for the compounds reported |
|---|---|---|
| Ex. No. | LogP[a] logP[b] | 1H-NMR [σ (ppm)] or LC-MS [m/z] |
| | | 7.879 (16.0); 7.692 (4.3); 7.681 (5.2); 7.673 (4.7); 7.661 (4.5); 7.647 (0.9); 7.550 (0.8); 7.539 (0.7); 7.529 (0.7); 7.517 (0.6); 5.308 (0.4); 3.432 (0.6); 3.320 (260.1); 3.256 (48.0); 3.190 (0.5); 3.153 (0.4); 3.076 (0.3); 2.995 (3.2); 2.891 (4.8); 2.732 (4.6); 2.711 (1.2); 2.671 (2.4); 2.645 (0.4); 2.630 (0.5); 2.541 (215.4); 2.502 (389.5); 2.368 (2.0); 2.329 (3.0); 2.295 (0.8); 2.277 (0.7); 2.243 (0.6); 2.220 (0.7); 2.200 (0.6); 2.189 (1.2); 2.173 (0.6); 2.131 (0.6); 2.117 (0.9); 2.105 (0.7); 2.086 (0.6); 2.073 (0.6); 2.036 (0.6); 2.005 (0.5); 1.997 (0.5); 1.990 (0.5); 1.980 (0.5); 1.942 (0.5); 1.909 (5.1); 1.840 (0.9); 1.816 (0.4); 1.809 (0.4); 1.762 (0.4); 1.754 (0.4); 1.722 (0.3); 1.704 (0.4); 1.673 (0.3); 1.621 (0.3); 1.610 (0.4); 1.605 (0.4); 1.603 (0.4); 1.585 (0.4); 1.574 (0.4); 1.536 (0.5); 1.514 (0.6); 1.507 (0.6); 1.500 (0.6); 1.490 (0.6); 1.466 (0.7); 1.458 (0.6); 1.386 (1.4); 1.380 (1.4); 1.347 (1.8); 1.335 (1.8); 1.298 (1.7); 1.259 (1.7); 1.234 (2.6); 1.201 (1.3); 1.141 (1.4); 1.085 (0.5); 1.070 (0.6); 1.054 (0.5); 1.045 (0.5); 1.035 (0.5); 0.988 (0.5); 0.968 (0.4); 0.922 (0.3); 0.892 (0.4); 0.864 (0.6); 0.852 (0.9); 0.830 (1.3); 0.756 (0.5); 0.726 (0.3); 0.000 (43.1) |
| 40 | 0.83 | $^1$H-NMR (400.0 MHz, $d_6$-DMSO): δ = 9.369 (2.9); 9.323 (0.4); 9.317 (0.4); 9.230 (0.4); 9.225 (0.4); 9.152 (5.1); 9.147 (6.5); 9.110 (5.6); 9.104 (4.8); 8.847 (3.7); 8.837 (3.5); 8.571 (1.7); 8.567 (2.4); 8.562 (1.8); 8.551 (1.8); 8.546 (2.4); 8.542 (1.6); 7.696 (2.1); 7.684 (2.1); 7.677 (2.0); 7.664 (1.9); 3.955 (1.5); 3.903 (16.0); 3.511 (0.4); 3.339 (354.7); 3.337 (355.7); 3.175 (1.4); 3.162 (1.4); 2.866 (13.6); 2.854 (13.6); 2.678 (1.1); 2.673 (1.5); 2.669 (1.1); 2.526 (3.9); 2.513 (87.9); 2.508 (186.6); 2.504 (262.5); 2.499 (195.4); 2.495 (93.0); 2.340 (0.5); 2.335 (1.1); 2.331 (1.4); 2.326 (1.1); 1.234 (0.4); 0.008 (0.4); 0.000 (11.9); −0.008 (0.4) |
| 41 | 1.19 | $^1$H-NMR (400.0 MHz, $d_6$-DMSO): δ = 9.244 (6.1); 9.157 (6.1); 9.151 (8.2); 9.116 (7.1); 9.110 (6.5); 8.873 (5.3); 8.866 (5.6); 8.806 (2.3); 8.795 (2.3); 8.519 (1.8); 8.513 (2.7); 8.508 (2.0); 8.496 (1.8); 8.490 (2.7); 8.485 (1.9); 3.992 (0.4); 3.902 (10.4); 3.509 (0.5); 3.345 (426.7); 3.170 (1.1); 2.869 (15.8); 2.857 (16.0); 2.802 (0.3); 2.677 (1.0); 2.672 (1.4); 2.668 (1.1); 2.512 (81.1); 2.508 (169.0); 2.503 (238.2); 2.499 (183.7); 2.335 (0.9); 2.330 (1.3); 2.326 (1.0); 1.351 (0.4); 1.258 (0.4); 1.232 (1.4); 0.000 (7.1) |
| 42 | 1.29 | $^1$H-NMR (400.0 MHz, $d_6$-DMSO): δ = 9.245 (7.9); 8.870 (6.8); 8.863 (7.3); 8.850 (9.3); 8.845 (12.2); 8.810 (12.7); 8.805 (10.3); 8.521 (2.6); 8.514 (3.5); 8.509 (2.7); 8.497 (2.7); 8.493 (3.3); 8.491 (3.5); 8.486 (2.7); 8.309 (0.3); 3.902 (16.0); 3.509 (0.8); 3.360 (944.6); 3.176 (0.7); 3.165 (0.6); 3.062 (12.0); 3.013 (12.6); 2.868 (0.9); 2.679 (1.2); 2.674 (1.7); 2.670 (1.3); 2.528 (4.3); 2.514 (95.1); 2.510 (201.4); 2.505 (282.5); 2.501 (211.4); 2.496 (101.5); 2.337 (1.1); 2.332 (1.6); 2.327 (1.1); 1.275 (0.4); 1.259 (0.8); 1.245 (0.7); 1.234 (0.4); 0.000 (7.8) |
| 43 | 0.96 | $^1$H-NMR (400.0 MHz, $d_6$-DMSO): δ = 9.363 (3.6); 9.267 (0.7); 9.262 (0.9); 9.212 (0.8); 9.207 (0.8); 8.841 (2.6); 8.830 (2.6); 8.823 (7.2); 8.818 (9.1); 8.790 (9.2); 8.784 (7.3); 8.576 (1.9); 8.571 (3.1); 8.566 (2.4); 8.556 (2.2); 8.551 (3.2); 8.546 (2.2); 7.699 (2.4); 7.687 (2.6); 7.679 (2.5); 7.667 (2.3); 3.902 (16.0); 3.509 (0.7); 3.364 (596.5); 3.171 (1.6); 3.060 (9.1); 3.014 (9.4); 2.678 (1.0); 2.674 (1.3); 2.669 (1.0); 2.513 (72.9); 2.509 (152.8); 2.505 (214.9); 2.500 (163.4); 2.496 (80.5); 2.336 (0.8); 2.331 (1.2); 2.327 (0.9); 1.233 (0.8); 0.000 (5.6) |
| 44 | 1.23 | $^1$H-NMR (400.0 MHz, $d_6$-DMSO): δ = 9.361 (5.8); 8.840 (4.3); 8.829 (4.9); 8.791 (2.9); 8.746 (2.1); 8.571 (3.4); 8.566 (4.8); 8.561 (3.4); 8.551 (3.7); 8.546 (5.0); 8.541 (3.5); 8.313 (0.4); 7.696 (4.0); 7.684 (4.1); 7.676 (4.0); 7.664 (3.7); 3.902 (16.0); 3.539 (1.9); 3.523 (2.0); 3.509 (1.8); 3.346 (693.4); 3.170 (1.1); 3.020 (6.3); 2.989 (6.0); |

TABLE 2-continued

Analytical data for the compounds reported

| Ex. No. | LogP[a] | logP[b] | 1H-NMR [σ (ppm)] or LC-MS [m/z] |
|---|---|---|---|
| | | | 2.677 (1.8); 2.673 (2.4); 2.668 (1.8); 2.579 (0.4); 2.526 (6.4); 2.512 (144.2); 2.508 (304.1); 2.503 (426.5); 2.499 (317.6); 2.495 (151.3); 2.339 (0.9); 2.335 (1.7); 2.330 (2.4); 2.326 (1.7); 1.352 (0.4); 1.259 (0.5); 1.233 (1.7); 1.188 (3.4); 1.122 (3.5); 0.853 (0.4); 0.000 (7.2) |
| 45 | | 1.55 | $^1$H-NMR (400.0 MHz, d$_6$-DMSO): δ = 9.242 (6.8); 8.869 (6.0); 8.862 (6.5); 8.843 (1.6); 8.817 (1.8); 8.798 (1.6); 8.766 (1.5); 8.518 (2.1); 8.512 (3.0); 8.507 (2.2); 8.495 (2.2); 8.488 (3.0); 8.483 (2.2); 3.902 (16.0); 3.525 (1.8); 3.510 (1.6); 3.365 (833.6); 3.171 (2.1); 3.023 (4.5); 2.986 (4.4); 2.804 (0.4); 2.679 (1.2); 2.674 (1.6); 2.670 (1.2); 2.544 (1.0); 2.527 (4.2); 2.514 (90.1); 2.510 (189.9); 2.505 (266.6); 2.501 (199.8); 2.496 (95.7); 2.336 (1.1); 2.332 (1.5); 2.327 (1.1); 1.351 (0.3); 1.233 (1.3); 1.189 (2.4); 1.119 (2.5); 0.000 (6.6) |
| 46 | | 1.54 | $^1$H-NMR (400.0 MHz, d$_6$-DMSO): δ = 9.478 (2.0); 9.463 (4.1); 9.447 (2.0); 9.374 (4.9); 9.189 (6.7); 9.184 (12.4); 9.172 (11.8); 9.167 (6.7); 8.847 (3.4); 8.837 (3.3); 8.583 (2.7); 8.578 (3.7); 8.573 (2.7); 8.563 (3.0); 8.558 (4.0); 8.553 (2.7); 8.311 (0.3); 7.699 (3.2); 7.687 (3.2); 7.680 (3.1); 7.667 (2.9); 4.233 (1.3); 4.216 (1.5); 4.208 (4.0); 4.192 (4.1); 4.184 (4.3); 4.168 (4.1); 4.160 (1.7); 4.144 (1.5); 4.107 (0.3); 4.094 (0.4); 3.955 (1.3); 3.902 (16.0); 3.547 (0.5); 3.508 (0.7); 3.346 (618.3); 3.170 (5.7); 2.682 (0.7); 2.678 (1.3); 2.673 (1.8); 2.669 (1.3); 2.526 (4.9); 2.513 (102.4); 2.509 (214.9); 2.504 (300.2); 2.500 (221.5); 2.495 (103.8); 2.340 (0.5); 2.335 (1.1); 2.331 (1.6); 2.326 (1.1); 1.249 (0.4); 1.232 (0.8); 0.000 (8.1) |
| 47 | | 1.90 | $^1$H-NMR (400.0 MHz, d$_6$-DMSO): δ = 9.488 (1.0); 9.473 (1.9); 9.457 (0.9); 9.257 (3.9); 9.201 (16.0); 8.880 (3.5); 8.873 (3.6); 8.536 (1.2); 8.530 (1.6); 8.525 (1.1); 8.513 (1.2); 8.506 (1.5); 8.501 (1.1); 4.234 (0.6); 4.218 (0.7); 4.210 (1.8); 4.194 (1.9); 4.186 (2.0); 4.170 (1.8); 4.162 (0.7); 4.146 (0.6); 3.902 (7.6); 3.341 (184.8); 3.334 (195.9); 3.169 (0.5); 2.677 (0.6); 2.672 (0.9); 2.668 (0.6); 2.525 (2.7); 2.512 (52.7); 2.508 (107.6); 2.503 (148.5); 2.499 (111.1); 2.494 (54.0); 2.334 (0.6); 2.330 (0.8); 2.326 (0.6); 1.234 (0.4); 0.000 (5.8) |
| 48 | | 1.20 | $^1$H-NMR (400.0 MHz, d$_6$-DMSO): δ = 9.362 (1.8); 8.997 (3.0); 8.992 (3.7); 8.945 (3.8); 8.940 (3.2); 8.844 (1.2); 8.833 (1.2); 8.573 (0.9); 8.567 (1.3); 8.563 (1.0); 8.553 (1.0); 8.547 (1.4); 8.543 (1.0); 7.697 (1.1); 7.685 (1.2); 7.677 (1.1); 7.665 (1.1); 3.902 (4.2); 3.608 (16.0); 3.424 (0.6); 3.353 (185.0); 3.347 (193.9); 3.170 (0.8); 2.673 (0.6); 2.669 (0.4); 2.526 (1.4); 2.509 (66.8); 2.504 (94.1); 2.500 (71.7); 2.335 (0.4); 2.331 (0.5); 2.326 (0.4); 1.233 (0.4); 0.000 (2.7) |
| 49 | | 1.54 | $^1$H-NMR (400.0 MHz, d$_6$-DMSO): δ = 9.245 (3.0); 9.026 (3.2); 9.021 (3.9); 8.962 (3.9); 8.957 (3.5); 8.875 (2.6); 8.868 (2.8); 8.523 (0.9); 8.517 (1.2); 8.512 (1.0); 8.499 (1.0); 8.493 (1.2); 8.488 (0.9); 3.902 (5.6); 3.607 (16.0); 3.354 (200.7); 3.346 (249.7); 3.170 (0.4); 2.678 (0.5); 2.673 (0.7); 2.669 (0.5); 2.526 (2.1); 2.513 (38.5); 2.508 (80.5); 2.504 (112.9); 2.499 (86.6); 2.495 (43.4); 2.335 (0.5); 2.331 (0.6); 2.326 (0.5); 1.234 (0.8); 0.000 (3.4) |
| 50 | | 1. 45 | $^1$H-NMR (400.0 MHz, d$_6$-DMSO): δ = 9.382 (2.0); 9.209 (1.1); 9.193 (2.3); 9.185 (4.9); 9.180 (7.3); 9.159 (6.3); 9.154 (4.4); 8.854 (1.4); 8.845 (1.4); 8.582 (1.3); 8.577 (1.9); 8.573 (1.4); 8.562 (1.5); 8.557 (2.0); 8.553 (1.4); 7.701 (1.6); 7.689 (1.6); 7.682 (1.6); 7.669 (1.5); 3.902 (16.0); 3.853 (1.3); 3.837 (1.3); 3.818 (2.6); 3.802 (2.6); 3.783 (1.4); 3.767 (1.3); 3.509 (0.4); 3.349 (364.2); 3.344 (447.4); 3.341 (452.3); 3.176 (0.8); 3.163 (0.8); 2.677 (1.0); 2.673 (1.4); 2.668 (1.1); 2.664 (0.5); 2.526 (3.6); 2.521 (5.4); 2.513 (80.5); 2.508 (172.3); 2.504 (243.6); 2.499 (179.6); 2.495 (84.0); 2.340 (0.4); 2.335 (0.9); 2.330 (1.3); 2.326 (1.0); 1.727 (4.3); 1.679 (9.7); 1.632 (4.8); 0.000 (5.0) |

TABLE 2-continued

Analytical data for the compounds reported

| Ex. No. | LogP[a] | logP[b] | 1H-NMR [σ (ppm)] or LC-MS [m/z] |
|---|---|---|---|
| 51 | 1.80 | | ¹H-NMR (400.0 MHz, d₆-DMSO): δ =9.348 (0.4); 9.343 (0.4); 9.256 (8.0); 9.242 (0.9); 9.222 (2.2); 9.206 (4.4); 9.201 (6.9); 9.196 (12.5); 9.188 (11.9); 9.183 (5.9); 8.878 (7.2); 8.872 (7.3); 8.534 (2.4); 8.528 (3.3); 8.523 (2.4); 8.511 (2.5); 8.504 (3.2); 8.499 (2.3); 8.316 (0.3); 4.428 (0.5); 4.410 (0.5); 4.110 (0.4); 4.098 (0.4); 3.958 (0.4); 3.902 (14.3); 3.854 (2.2); 3.839 (2.2); 3.819 (4.5); 3.803 (4.4); 3.784 (2.4); 3.768 (2.3); 3.598 (0.4); 3.559 (0.4); 3.528 (0.5); 3.508 (0.7); 3.490 (0.6); 3.341 (647.7); 3.176 (2.2); 3.163 (2.1); 2.677 (1.6); 2.672 (2.3); 2.668 (1.6); 2.594 (0.4); 2.588 (0.4); 2.525 (6.1); 2.512 (127.9); 2.508 (267.9); 2.503 (375.8); 2.499 (283.5); 2.494 (138.3); 2.335 (1.5); 2.330 (2.0); 2.326 (1.5); 1.728 (7.3); 1.680 (16.0); 1.633 (8.0); 1.405 (0.4); 1.388 (0.9); 1.370 (0.4); 1.244 (0.3); 1.233 (0.5); 0.008 (0.4); 0.000 (11.4) |
| 52 | 1.39 | | ¹H-NMR (400.0 MHz, d₆-DMSO): δ = 9.365 (1.2); 9.153 (2.3); 9.148 (2.8); 9.101 (2.7); 9.096 (2.4); 8.981 (0.5); 8.967 (1.0); 8.953 (0.5); 8.843 (0.9); 8.831 (0.8); 8.574 (0.7); 8.568 (1.0); 8.564 (0.7); 8.554 (0.7); 8.548 (1.0); 8.544 (0.8); 7.695 (0.8); 7.683 (0.8); 7.676 (0.8); 7.664 (0.8); 3.902 (4.0); 3.556 (0.8); 3.540 (1.6); 3.522 (1.6); 3.507 (0.9); 3.356 (130.8); 3.349 (200.4); 2.724 (1.7); 2.706 (2.5); 2.689 (1.6); 2.678 (0.4); 2.673 (0.5); 2.669 (0.3); 2.526 (1.2); 2.513 (24.8); 2.509 (53.4); 2.504 (76.2); 2.500 (58.4); 2.495 (28.7); 2.331 (0.4); 2.326 (0.3); 2.128 (16.0); 0.000 (2.5) |
| 53 | 1.72 | | ¹H-NMR (400.0 MHz, d₆-DMSO): δ = 9.248 (2.1); 9.169 (2.2); 9.164 (2.8); 9.130 (2.5); 9.124 (2.1); 8.991 (0.5); 8.977 (1.0); 8.962 (0.5); 8.875 (1.9); 8.868 (2.0); 8.524 (0.6); 8.518 (0.9); 8.513 (0.7); 8.501 (0.7); 8.495 (0.9); 8.490 (0.6); 3.902 (4.2); 3.558 (0.8); 3.542 (1.6); 3.524 (1.6); 3.508 (0.9); 3.348 (170.0); 2.725 (1.8); 2.706 (2.6); 2.689 (1.7); 2.678 (0.4); 2.673 (0.5); 2.669 (0.4); 2.526 (1.2); 2.513 (27.8); 2.509 (58.7); 2.504 (82.4); 2.500 (61.3); 2.495 (29.3); 2.335 (0.3); 2.331 (0.5); 2.326 (0.3); 2.128 (16.0); 0.000 (1.9) |
| 54 | 0.84 | | ¹H-NMR (400.0 MHz, d₆-DMSO): δ = 9.372 (1.9); 9.152 (3.4); 9.147 (4.5); 9.125 (1.7); 9.115 (4.8); 9.109 (4.2); 8.849 (1.3); 8.838 (1.3); 8.576 (1.0); 8.571 (1.4); 8.567 (1.1); 8.556 (1.1); 8.551 (1.5); 8.547 (1.1); 7.698 (1.2); 7.686 (1.2); 7.678 (1.2); 7.666 (1.1); 3.955 (0.6); 3.902 (8.0); 3.777 (0.9); 3.760 (2.4); 3.745 (2.5); 3.729 (1.2); 3.455 (2.2); 3.438 (4.0); 3.421 (1.9); 3.344 (186.2); 3.336 (242.0); 3.176 (0.6); 3.162 (0.6); 3.075 (16.0); 2.677 (0.6); 2.672 (0.8); 2.668 (0.6); 2.543 (0.6); 2.526 (2.1); 2.512 (47.9); 2.508 (101.9); 2.503 (144.1); 2.499 (111.8); 2.334 (0.6); 2.330 (0.8); 2.325 (0.6); 0.000 (3.8) |
| 55 | 1.12 | | ¹H-NMR (601.6 MHz, d₆-DMSO): δ = 9.254 (1.8); 9.252 (2.8); 9.194 (0.8); 9.185 (1.7); 9.177 (4.0); 9.173 (5.2); 9.161 (5.1); 9.158 (3.3); 8.876 (3.0); 8.872 (3.0); 8.527 (1.0); 8.524 (1.2); 8.523 (1.2); 8.520 (1.0); 8.512 (1.0); 8.508 (1.3); 8.507 (1.2); 8.504 (1.0); 7.953 (0.5); 3.769 (1.0); 3.758 (2.5); 3.748 (2.5); 3.737 (1.2); 3.454 (2.1); 3.442 (3.9); 3.431 (1.9); 3.324 (361.5); 3.281 (0.4); 3.076 (16.0); 2.986 (0.5); 2.891 (4.0); 2.7313 (3.2); 2.7307 (3.1); 2.689 (0.5); 2.617 (1.3); 2.614 (1.8); 2.611 (1.3); 2.523 (3.2); 2.520 (4.2); 2.517 (4.3); 2.508 (97.1); 2.505 (201.1); 2.502 (270.3); 2.499 (198.0); 2.496 (95.1); 2.389 (1.3); 2.386 (1.7); 2.383 (1.3); 0.937 (0.4); 0.000 (7.3) |
| 56 | 3.14 | | ¹H-NMR (400.0 MHz, d₆-DMSO): δ = 10.867 (7.7); 9.395 (4.2); 9.284 (6.7); 9.278 (9.8); 9.257 (9.3); 9.252 (6.8); 8.855 (3.0); 8.846 (3.0); 8.602 (2.2); 8.597 (3.1); 8.593 (2.3); 8.582 (2.4); 8.577 (3.4); 8.573 (2.3); 8.313 (0.4); 8.277 (6.2); 8.032 (2.9); 8.030 (2.8); 8.009 (3.2); 7.708 (2.8); 7.696 (2.8); 7.688 (2.7); 7.676 (2.6); 7.603 (3.1); 7.583 (6.6); 7.563 (4.4); 7.507 (4.3); 7.487 (2.7); 4.108 (0.8); 4.095 (0.8); 4.083 (0.3); 3.902 (16.0); |

TABLE 2-continued

Analytical data for the compounds reported

| Ex. No. | LogP[a] | logP[b] | 1H-NMR [σ (ppm)] or LC-MS [m/z] |
|---|---|---|---|
| | | | 3.508 (0.5); 3.495 (0.4); 3.346 (476.4); 3.340 (619.0); 3.176 (6.2); 3.163 (6.1); 2.677 (1.3); 2.672 (1.7); 2.668 (1.3); 2.664 (0.7); 2.526 (4.7); 2.512 (103.2); 2.508 (217.0); 2.503 (304.9); 2.499 (228.7); 2.494 (110.1); 2.335 (1.2); 2.330 (1.7); 2.326 (1.2); 1.249 (0.3); 0.008 (0.4); 0.000 (12.2); −0.009 (0.4) |
| 57 | 3.53 | | $^1$H-NMR (400.0 MHz, $d_6$-DMSO): δ = 10.872 (8.7); 9.298 (6.5); 9.293 (10.8); 9.277 (16.0); 8.887 (6.9); 8.880 (7.1); 8.555 (2.2); 8.549 (3.3); 8.544 (2.4); 8.532 (2.3); 8.525 (3.3); 8.521 (2.3); 8.308 (0.3); 8.273 (7.1); 8.025 (3.4); 8.004 (3.7); 7.605 (3.2); 7.585 (7.0); 7.565 (4.6); 7.509 (5.1); 7.490 (3.2); 3.902 (15.3); 3.705 (0.4); 3.657 (0.4); 3.603 (0.6); 3.508 (1.4); 3.361 (1440.1); 3.174 (0.6); 2.678 (1.6); 2.674 (2.2); 2.670 (1.6); 2.582 (0.4); 2.544 (1.6); 2.509 (266.9); 2.505 (367.0); 2.500 (281.7); 2.336 (1.5); 2.331 (2.0); 1.233 (0.6); 0.000 (7.6) |
| 58 | 2.54 | | $^1$H-NMR (601.6 MHz, $d_6$-DMSO): δ = 11.037 (1.3); 9.317 (7.8); 9.313 (14.4); 9.306 (16.0); 9.302 (8.6); 9.278 (8.6); 8.887 (8.8); 8.883 (10.4); 8.833 (0.9); 8.829 (0.8); 8.825 (0.9); 8.554 (2.8); 8.551 (3.7); 8.547 (2.8); 8.539 (3.0); 8.536 (3.8); 8.532 (2.6); 8.452 (8.0); 8.270 (1.6); 8.189 (0.8); 8.176 (0.9); 8.160 (4.1); 8.147 (4.3); 8.145 (4.3); 8.022 (0.8); 8.007 (0.8); 7.760 (4.0); 7.746 (8.2); 7.733 (4.8); 7.646 (5.2); 7.634 (4.1); 7.596 (0.7); 7.583 (1.5); 7.569 (0.9); 7.505 (1.0); 7.493 (0.8); 3.322 (411.9); 2.614 (2.3); 2.611 (1.7); 2.541 (1.0); 2.523 (4.5); 2.520 (5.8); 2.517 (6.8); 2.505 (256.7); 2.502 (334.0); 2.499 (250.5); 2.386 (2.0); 1.231 (0.6); 0.000 (7.3) |
| 59 | 1.65 | | $^1$H-NMR (400.0 MHz, $d_6$-DMSO): δ = 9.231 (6.6); 8.861 (5.8); 8.854 (6.1); 8.761 (8.3); 8.508 (1.9); 8.503 (2.6); 8.485 (1.9); 8.480 (2.6); 8.475 (1.8); 3.902 (16.0); 3.508 (0.4); 3.342 (396.2); 3.338 (410.6); 3.176 (0.7); 3.164 (0.7); 2.677 (1.1); 2.672 (1.5); 2.668 (1.2); 2.548 (0.6); 2.525 (4.3); 2.512 (90.4); 2.508 (185.6); 2.503 (257.8); 2.499 (197.1); 2.335 (1.2); 2.330 (1.5); 2.325 (1.2); 2.199 (0.5); 2.143 (0.6); 2.130 (0.6); 2.112 (0.6); 2.074 (0.4); 1.249 (0.3); 1.235 (0.3); 0.969 (4.6); 0.008 (0.4); 0.000 (10.5) |
| I-a-1 | | 1.95 | $^1$H-NMR (400.0 MHz, $d_6$-DMSO): δ = 9.339 (8.2); 9.337 (8.7); 9.333 (8.6); 9.332 (8.2); 9.046 (15.3); 9.040 (16.0); 8.842 (15.8); 8.836 (15.1); 8.830 (7.6); 8.827 (7.8); 8.818 (7.7); 8.814 (7.5); 8.548 (4.4); 8.544 (5.4); 8.543 (5.3); 8.538 (4.3); 8.528 (4.7); 8.524 (5.4); 8.523 (5.8); 8.518 (4.4); 8.318 (0.4); 7.679 (5.3); 7.677 (5.4); 7.667 (5.2); 7.665 (5.3); 7.659 (5.2); 7.657 (5.1); 7.647 (5.0); 7.645 (5.0); 3.757 (1.1); 3.329 (112.8); 2.678 (0.5); 2.674 (0.7); 2.669 (0.5); 2.527 (1.9); 2.514 (39.9); 2.509 (80.5); 2.505 (105.7); 2.500 (75.9); 2.496 (35.9); 2.336 (0.5); 2.331 (0.7); 2.327 (0.5); 0.146 (0.7); 0.008 (5.9); 0.000 (157.7); −0.009 (5.5); −0.150 (0.7) |
| I-j-1 | | | LC-MS: m/z 272 [M + H$^+$] |
| I-j-2 | | | LC-MS: m/z 290 [M + H$^+$] |
| I-s-1 | | | LC-MS: m/z 229 [M + H$^+$] |
| I-s-2 | | | LC-MS: m/z 247 [M + H$^+$] |

Biological Examples

*Myzus persicae*—Spray Test

Solvent: 78 parts by weight of acetone
1.5 parts by weight of dimethylformamide
Emulsifier: alkylaryl polyglycol ether To produce a suitable active ingredient formulation, 1 part by weight of active ingredient is dissolved with the specified parts by weight of solvent and made up with water containing an emulsifier concentration of 1000 ppm until the desired concentration is attained. To produce further test concentrations, the formulation is diluted with emulsifier-containing water.

Discs of Chinese cabbage leaves (*Brassica pekinensis*) infested by all stages of the green peach aphid (*Myzus persicae*) are sprayed with an active ingredient formulation of the desired concentration.

After 6 days, the efficacy in % is determined. 100% means that all the aphids have been killed; 0% means that no aphids have been killed.

In this test, for example, the following compounds from the preparation examples show an efficacy of 100% at an application rate of 500 g/ha: 2, 4, 6, 7, 9, 19, 22, 30, 41, 42, 43, 44

In this test, for example, the following compounds from the preparation examples show an efficacy of 90% at an application rate of 500 g/ha: 13, 16, 17, 18, 20, 23, 25, 26, 31, 32, 39, 45, 48, 49

*Tetranychus urticae*—Spray Test, OP-Resistant

Solvent: 78.0 parts by weight of acetone
1.5 parts by weight of dimethylformamide
Emulsifier: alkylaryl polyglycol ether To produce a suitable active ingredient formulation, 1 part by weight of active ingredient is dissolved with the specified parts by weight of solvent and made up with water containing an emulsifier concentration of 1000 ppm until the desired concentration is attained. To produce further test concentrations, the formulation is diluted with emulsifier-containing water.

Discs of bean leaves (*Phaseolus vulgaris*) infested with all stages of the greenhouse red spider mite (*Tetranychus urticae*) are sprayed with an active ingredient formulation of the desired concentration.

After 6 days, the efficacy in % is determined. 100% means that all the spider mites have been killed; 0% means that no spider mites have been killed.

In this test, for example, the following compounds from the preparation examples show an efficacy of 90% at an application rate of 500 g/ha: 22

*Phaedon cochleariae*—Spray Test

Solvent: 78.0 parts by weight of acetone
1.5 parts by weight of dimethylformamide
Emulsifier: alkylaryl polyglycol ether To produce a suitable active ingredient formulation, 1 part by weight of active ingredient is dissolved with the specified parts by weight of solvent and made up with water containing an emulsifier concentration of 1000 ppm until the desired concentration is attained. To produce further test concentrations, the formulation is diluted with emulsifier-containing water.

Discs of Chinese cabbage leaves (*Brassica pekinensis*) are sprayed with an active ingredient preparation of the desired concentration and, after drying, populated with larvae of the mustard beetle (*Phaedon cochleariae*).

After 7 days, the efficacy in % is determined. 100% means that all the beetle larvae have been killed; 0% means that no beetle larvae have been killed.

In this test, for example, the following compounds from the preparation examples show an efficacy of 83% at an application rate of 500 g/ha: 39

*Myzus persicae*—Spray Test

Solvent: 7 parts by weight of dimethylformamide
Emulsifier: alkylaryl polyglycol ether To produce a suitable active ingredient formulation, 1 part by weight of active ingredient is dissolved with the specified parts by weight of solvent and made up with water containing an emulsifier concentration of 1000 ppm until the desired concentration is attained. To produce further test concentrations, the formulation is diluted with emulsifier-containing water. If the addition of ammonium salts or/and penetrants is required, these are each added in a concentration of 1000 ppm to the formulation solution.

Bell pepper plants (*Capsicum annuum*) severely infested with the green peach aphid (*Myzus persicae*) are treated by spraying with the active ingredient formulation in the desired concentration.

After 6 days, the kill in % is determined. 100% means that all of the aphids have been killed; 0% means that none of the aphids have been killed.

In this test, for example, the following compounds from the preparation examples show an efficacy of 100% at an application rate of 4 ppm: 21.

The invention claimed is:
1. A compound of formula (I),

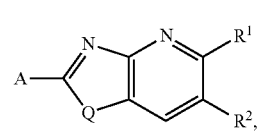

wherein
A is the (A-a) radical

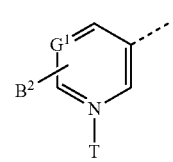

wherein the broken line denotes the bond to the carbon atom of the bicyclic system of the formula (I),
$G^1$ is $C-B^1$,
$B^1$ is hydrogen or fluorine,
$B^2$ is hydrogen,
T is oxygen or an electron pair,
Q is sulphur,
$R^1$ is hydrogen,
$R^2$ is a B radical selected from the group consisting of

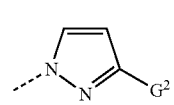

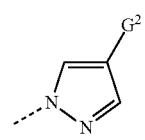

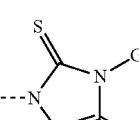

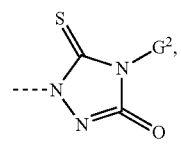

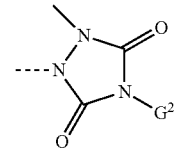

-continued

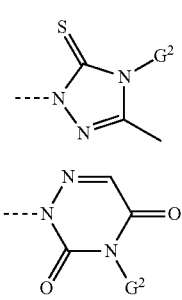
(B-46)

(B-47)

wherein the broken line denotes the bond to the carbon atom of the bicyclic system of the formula (I), or $R^2$ is a radical of formula

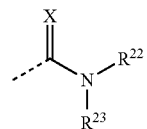

wherein the broken line denotes the bond to the carbon atom of the bicyclic system of the formula (I), or $R^2$ is a radical of formula

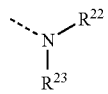

wherein the broken line denotes the bond to the carbon atom of the bicyclic system of the formula (I), in which $G^2$ is a radical selected from the group consisting of hydrogen, $C_1$-$C_4$-alkyl, halo-$C_1$-$C_4$-alkyl, $C_1$-$C_4$-alkoxy, halo-$C_1$-$C_4$-alkoxy, $C_1$-$C_4$-alkylthio and $C_1$-$C_4$-haloalkylthio, and in the case that $R^2$ is the radical of formula

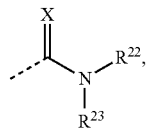

$R^{22}$ is the D radical

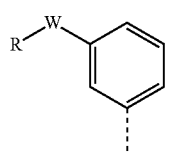
(D-2)

wherein

R is optionally mono-, di-, tri-, tetra- or penta-fluorine- or -chlorine-substituted $C_1$-$C_4$-alkyl, W is a radical from the group of S, SO and $SO_2$, $R^{23}$ is hydrogen or $C_1$-$C_6$-alkyl, and in the case that $R^2$ is the radical of formula

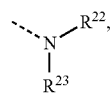

$R^{22}$ is phenyl which is optionally fluorine-, chlorine- or bromine-substituted, and $R^{23}$ is hydrogen or $C_1$-$C_6$-alkyl.

2. The compound of formula (I) according to claim 1, wherein $B^1$ is hydrogen.

3. The compound of formula (I) according to claim 1, wherein $B^1$ is fluorine.

4. The compound of formula (I) according to claim 1, wherein $R^2$ is

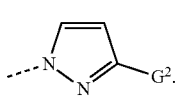
(B-1)

5. The compound of formula (I) according to claim 1, wherein $R^2$ is

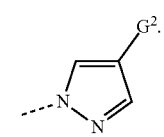
(B-2)

6. The compound of formula (I) according to claim 1, wherein $R^2$ is

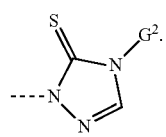
(B-41)

7. The compound of formula (I) according to claim 1, wherein $R^2$ is

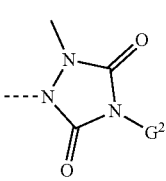
(B-42)

8. The compound of formula (I) according to claim 1, wherein $R^2$ is (B-43)

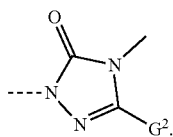

9. The compound of formula (I) according to claim 1, wherein R² is (B-46)

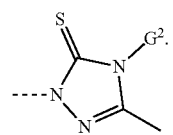

10. The compound of formula (I) according to claim 1, wherein R² is (B-47)

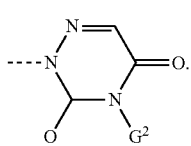

11. The compound of formula (I) according to claim 1, wherein R² is

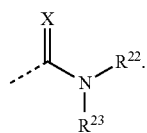

12. The compound of formula (I) according to claim 1, wherein R² is

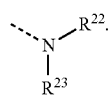

13. The compound of formula (I) according to claim 7, wherein

B¹ is hydrogen,

T is an electron pair, and

G² is methyl.

14. A composition comprising a content of at least one compound of formula (I) according to claim 1 and one or more extenders and/or surfactants.

15. The composition according to claim 14, wherein said extenders are selected from the group consisting of water, polar and nonpolar organic chemical liquids selected from classes of aromatic and non-aromatic hydrocarbons, alcohols, polyols, ketons, esters, (poly)ethers, simple and substituted amines, amides, lactams, lactones, sulphones, and sulphoxides; and wherein said surfactants are selected from the group consisting of salts of polyacrylc acid, salts of lignosulphonic acid, salts of phenolsulphonic acid, salts of napththalenesulphonic acid, polycondensates of ethylene oxide with fatty alcohols or with fatty acids or with fatty amines or with substituted phenols, salts of sulphosuccinic estesr, taurine derivatives, phosphoric esters of polyethoxylated alcohols or phenols, fatty acid esters of polyols, and derivatives of compounds containing sulphates, sulphonates, phosphates, protein hydrosylates, lignosulphite waste liquors, and methylcellulose.

16. A method for controlling pests, comprising applying a compound of formula (I) according to claim 1 to said pests and/or a habitat thereof.

17. The method according to claim 16, wherein said pests are selected from the group consisting of insects, arachnids, helminths, nematodes, and molluscs.

18. A compound of the formula

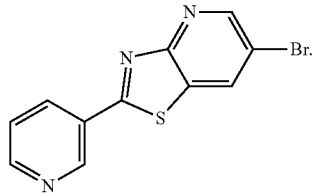 [SMILES: Brc1cnc2nc(-c3cccnc3)sc2c1]

* * * * *